US007795256B2

(12) United States Patent
Alexander et al.

(10) Patent No.: US 7,795,256 B2
(45) Date of Patent: Sep. 14, 2010

(54) THIENO-PYRIDINONE DERIVATIVES AS KINASE INHIBITORS

(75) Inventors: Rikki Peter Alexander, Buckinghamshire (GB); Jeremy Martin Davis, Wokingham (GB); Martin Clive Hutchings, Wokingham (GB); Victoria Elizabeth Laing, Kingston-upon-Thames (GB); Graham Peter Trevitt, Slough (GB)

(73) Assignee: UCB Pharma S.A., Brussels (BE)

( * ) Notice: Subject to any disclaimer, the term of this patent is extended or adjusted under 35 U.S.C. 154(b) by 1134 days.

(21) Appl. No.: 10/576,731

(22) PCT Filed: Oct. 22, 2004

(86) PCT No.: PCT/GB2004/004490

§ 371 (c)(1),
(2), (4) Date: Apr. 20, 2006

(87) PCT Pub. No.: WO2005/042540

PCT Pub. Date: May 12, 2005

(65) Prior Publication Data

US 2007/0078131 A1  Apr. 5, 2007

(30) Foreign Application Priority Data

Oct. 24, 2003 (GB) ................... 0324902.6
Dec. 19, 2003 (GB) ................... 0329490.7
Feb. 10, 2004 (GB) ................... 0402918.7
Jul. 29, 2004 (GB) ................... 0416934.8

(51) Int. Cl.
*A61K 31/5377* (2006.01)
*A61K 31/496* (2006.01)
*A61K 31/4365* (2006.01)
*C07D 495/04* (2006.01)

(52) U.S. Cl. ............... 514/233.8; 514/253; 514/254; 514/301; 544/127; 544/362; 546/114

(58) Field of Classification Search ........... 546/114; 514/301

See application file for complete search history.

(56) References Cited

U.S. PATENT DOCUMENTS

| 6,169,092 | B1 | 1/2001 | Bräunlich et al. ......... 514/258 |
| 6,180,792 | B1 | 1/2001 | Furuya et al. | |
| 2006/0004025 | A1 | 1/2006 | Brookings et al. | |
| 2006/0025428 | A1 | 2/2006 | Brookings et al. | |
| 2006/0247269 | A1 | 11/2006 | Brookings et al. | |
| 2007/0099894 | A1 | 5/2007 | Langham | |

FOREIGN PATENT DOCUMENTS

| DE | 285 356 A5 | 6/1989 |
| GB | 0 402 918 | 12/1933 |
| GB | 0 416 934 | 9/1934 |
| GB | 0 324 902 | 2/1980 |
| WO | WO 99/64400 A1 | 12/1999 |
| WO | WO 03/033502 A1 | 4/2003 |
| WO | WO 2004/014920 A1 | 2/2004 |
| WO | WO 2005/042540 A1 | 5/2005 |

OTHER PUBLICATIONS

Vippagunta et al., "Crystalline Solid", Advanced Drug Delivery Reviews 48 (2001) 3-26.*
Guillory (in Brittain ed.), Polymorphism, etc., NY: Marcel Dekker, Inc., 1999, 1-2, 183-226.*
Adams, J.L., et al., "p38 MAP kinase: molecular target for the inhibition of pro-inflammatory cytokines," *Progress in Medicinal Chemistry*, King, F.D., et al. (Eds.), Elsevier Science, 2001, vol. 38, 1-60.
Adhikari, R., et al., "An adventitious synthesis of 2,2'-dipyrryl disulfides," Australian J. Chem., 1999, 52, 63-67.
Albright, J.D., et al., "The use of α-(Aryl)- morpholineacetonitriles (masked acyl anion equivalents) in 1,4-additions to αβ-unsaturated esters and nitriles. A versatile synthetic route to 6-aryl-3-(2H)pyridazinones," J. Heterocycl. Chem., 1978, 15, 881-892.
Allen, M., et al., "Deficiency of the stress kinase p38α results in embryonic lethality: characterization of the kinase dependence of stress responses of enzyme-deficient embryonic stem cells," J. Exp. Med., 2000, 191, 859-869.
Badger, A.M., et al., "Pharmacological profile of SB 203580, a selective inhibitor of cytokine suppressive binding protein/p38 kinase, in animal models of arthritis, bone resorption, endotoxin shock and immune function," J. Pharmacol. Exp. Ther., 1996, 279(3), 1453-1461.
Cohen, P., "The search for physiological substrates of MAP and SAP inases in mammalian cells," Trends Cell Biol., 1997, 7, 353-361.
Dinarello, C.A., "An update on human interleukin-1:from molecular biology to clinical relevance," *J. Clinical Immunology*, 1985, 5(5), 287-297.
Doza, Y.N., et al., "Activation of the MAP kinase homologue RK requires the phosphorylation of Thr-180 and Tyr-182 and both resides are phosphorylated in chemically stressed KB cells," FEBS Lett., 1995, 364, 223-228.
Enslen, H., et al., "SelectiNe activation of p38 mitogen-activated protein (MAP) kinase isoforms by the MA.P kinase kinases MKK3 and MKK6," J. Biol. Chem., 1998, 273(3), 1741-1748.
Griswold, D.E., et al., "Pharmacology of cytokine suppressive anti-inflammatory drug binding protein (CSBP), a novel stress-induced kinase," Pharmacol. Commun., 1996, 7, 323-329.
Hale, K.K., et al., "Differential expression and activation of p38 mitogen-activated protein kinase α, β, γ, and δ in inflammatory cell lineages," J. Immun., 1999, 162, 4246-4252.
Hunter, T., "Protein kinase classification," *Methods in Enzymology* (*Protein Kinase Classification*), Hunter, T., et al. (Eds.), Academic Press, San Diego, 1991, vol. 200, 3-37.
Jiang, Y., et al., "Characterization of the structure and function of a new mitogen-activated protein kinase (p38β)," J. Biol. Chem., 1996, 271, 17920-17926.

(Continued)

*Primary Examiner*—Patricia L Morris
(74) *Attorney, Agent, or Firm*—McDonnell Boehnen Hulbert & Berghoff LLP

(57) ABSTRACT

A series of thieno[2,3-b]pyridin-6(7H)-one derivatives, substituted in the 3-position by an arylcarbonyl or heteroarylcarbonyl moiety, being inhibitors of p38 MAP kinase, are accordingly of use in medicine, for example in the treatment and/or prevention of immune or inflammatory disorders.

9 Claims, No Drawings

OTHER PUBLICATIONS

Kotlyarov, A., et al., "MAPKAP kinase 2 is essential for LPS-induced TNF-α biosynthesis," Nature Cell Biol., 1999, 1, 94-97.

Lee, J.C., et al., "A protein kinase involved in the regulation of inflammatory cytokine biosynthesis," Nature (London), 1994, 372, 739-746.

Lee, J.C., et al., "Inhibition of monocyte IL-1 production by the anti-inflammatory compound, SK&F 86002," Int. J. Immunopharm., 1988, 10(7), 835-843.

Lee, J.C., et al., "Bicyclic imidazoles as a novel class of cytokine biosynthesis inhibitors," Annals N.Y. Acad. Sci., 1993, 696, 149-170.

Mandrup-Poulsen, T., β-cell apoptosis stimuli and signaling, Diabetes, 2001, 50(Suppl. 1), 558-563.

McDonnell, P.C., et al., "Localization of the human stress responsive MAP kinase-like CSAIDs binding protein (CSBP) gene to chromosome 6p21.3/21.2," Genomics, 1995, 28, 301-302.

Sabauste, M.C., et al., "Infection of a human respiratory epithellal cell line with rhinovirus; Induction of cytokine release and modulation of susceptibility to infection by cytokine exposure," J. Clin. Invest., 1995, 96, 549-557.

Sont, J.K., et al., "Fully automated assessment of inflammatory cell counts and cytokine expression in bronchial tissue," Am. J. Respir. Crit. Care Med., 2003, 167, 1496-1503.

Spurlock, L.A., et al., "The nature of the carbonium ion. VIII., Cycloalkyl cations from thiocyanate isomerizations," J. Org. Chem., 1972, 1162-1168.

Takekawa, M., et al., "A family of stress-inducible GADD45-like proteins mediate activation of the stress-responsive MTK1/MEKK4 MAPKKK," Cell, 1998, 95, 521-530.

Teran, L.M., et al., "Role of nasal interleukin-8 in neutrophil recruitment and activation in children with virus-induced asthma," Am. J. Respir. Crit. Care Med., 1997, 155, 1362-1366.

Turner, R.B., et al., "Association between interleukin-8 concentration in nasal secretions and severity of symptoms of experimental rhinovirus colds," Clin. Infec. Dis., 1998, 26, 840-846.

Zhu, Z., et al., "Rhinovirus stimulation of interleukin-6 in vivo and in vitro," J. Clin. Invest., 1996, 97(2), 421-430.

* cited by examiner

THIENO-PYRIDINONE DERIVATIVES AS KINASE INHIBITORS

This invention relates to a series of substituted thieno[2,3-b]pyridin-6(7H)-one derivatives, to compositions containing them, to processes for their preparation and to their use in medicine.

Immune and inflammatory responses involve a variety of cell types with control and co-ordination of the various interactions occurring via both cell-cell contacts (e.g. integrin interactions with their receptors) and by way of intercellular signalling molecules. A large number of different signalling molecules are involved including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., *Methods in Enzymology* (*Protein Kinase Classification*), p. 3, Hunter, T. and Sefton, B. M. eds., vol. 200, Academic Press, San Diego, 1991].

One sub-class of serine/threonine kinases is the mitogen activated protein (MAP) kinases of which there are at least three families which differ in the sequence and size of the activation loop [Adams, J. L. et al., *Progress in Medicinal Chemistry*, pp. 1-60, King, F. D. and Oxford, A. W. eds., vol. 38, Elsevier Science, 2001]: the extracellular regulated kinases (ERKs); the c-Jun $NH_2$ terminal kinases or stress activated kinases (JNKs or SAP kinases); and the p38 MAP kinases, which have a threonine-glycine-tyrosine (TGY) activation motif. Both the JNKs and p38 MAP kinases (p38 MAPKs) are primarily activated by stress stimuli including, but not limited to, proinflammatory cytokines, e.g. tumour necrosis factor (TNF) and interleukin-1 (IL-1), ultraviolet light, endotoxin and chemical or osmotic shock.

Four isoforms of p38 MAPK have been described (p38α/β/γ/δ). The human p38α enzyme was initially identified as a target of cytokine-suppressive anti-inflammatory drugs (CSAIDs) and the two isoenzymes found were initially termed CSAID binding protein-1 and -2 (CSBP-1 and CSBP-2 respectively) [Lee, J. C. et al., *Nature* (London), 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al., *Genomics*, 1995, 29, 301-2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However, in monocytes and macrophages p38α is the predominant kinase activity [Lee, J. C., ibid; Jing, Y. et al., *J. Biol. Chem.*, 1996, 271, 10531-34; Hale, K. K. et al., *J. Immun.*, 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 MAPK homologues and splice variants contain a 12 amino acid activation loop that includes a Thr-Gly-Tyr (TGY) motif. Dual phosphorylation of both Thr-180 and Tyr-182 in the TGY motif by a dual specificity upstream kinase is essential for the activation of p38 MAPK and results in a >1000-fold increase in specific activity of these enzymes [Doza, Y. N. et al., *FEBS Lett.*, 1995, 364, 7095-8012]. This dual phosphorylation is effected by MKK6 and, under certain conditions, the related enzyme MKK3 [Enslen, H. et al., *J. Biol. Chem.*, 1998, 273, 1741-48]. MKK3 and MKK6 belong to a family of enzymes termed MAPKK (mitogen activated protein kinase kinase) which are in turn activated by MAPKKK (mitogen activated kinase kinase kinase), otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of MAPKKs. MEKK4/MTK1 is thought to be activated by several GADD-45-like genes that are induced in response to environmental stimuli and which eventually lead to p38 MAPK activation [Takekawa, M. and Saito, H., *Cell*, 1998, 95, 521-30]. TAK1 has been shown to activate MKK6 in response to transforming growth factor-β (TGF-β). TNF-stimulated activation of p38 MAPK is believed to be mediated by the recruitment of TRAF2 (TNF receptor associated factor) and the Fas adaptor protein, Daxx, which results in the activation of ASK1 and subsequently p38 MAPK.

Several substrates of p38 MAPK have been identified including other kinases [e.g. MAPK activated protein kinase 2/3/5 (MAPKAP 2/3/5), p38 MAPK regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)], transcription factors [e.g. activating transcription factor 2/6 (ATF2/6), monocyte-enhancer factor-2A/C (MEF2A/C), C/EBP homologous protein (CHOP), Elk1 and Sap-1a1] and other substrates [e.g. cPLA2, p47phox].

MAPKAP K2 is activated by p38 MAPK in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited L[Kotlyarov, A. et al., *Nature Cell Biol.*, 1999, 1, 94-7]. Further, MAPKAP K2 from embryonic stem cells from p38α null mice was not activated in response to stress and these cells did not produce IL-6 in response to IL-1 [Allen, M. et al., *J. Exp. Med.*, 2000, 191, 859-69]. These results indicate that MAPKAP K2 is not only essential for TNF and IL-1 production but also for signalling induced by cytokines. In addition, MAPKAP K2/3 phosphorylate and thus regulate heat shock proteins HSP 25 and HSP 27 which are involved in cytoskeletal reorganization.

Several small molecule inhibitors of p38 MAPK have been reported which inhibit IL-1 and TNF synthesis in human monocytes at concentrations in the low μM range [Lee, J. C. et al., *Int. J. Immunopharm.*, 1988, 10, 835] and exhibit activity in animal models which are refractory to cyclooxygenase inhibitors [Lee, J. C. et al., *Annals N.Y. Acad. Sci.*, 1993, 696, 149]. In addition, these small molecule inhibitors are known to decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by such small molecule inhibitors of p38 MAPK [Cohen, P., *Trends Cell Biol.*, 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resorption diseases, reperfusion injury, graft vs. host reaction, allograft rejection, adult respiratory distress syndrome, chronic pulmonary inflammatory disease, silicosis, pulmonary sarcoidosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition, IL-1 has been linked to diabetes and pancreatic β cell destruction [Dinarello, C. A., *J. Clinical Immunology*, 1985, 5, 287-97; Mandrup-Poulsen, T., *Diabetes*, 2001, 50, 558-563].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis, which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte-derived cytokines as important and critical inflammatory mediators is well documented. The inhibition of these cytokines has been shown or would be expected to be of benefit in controlling, alleviating or reducing many of these disease states.

The central position that p38 MAPK occupies within the cascade of signalling molecules mediating extracellular to intracellular signalling, and its influence over not only IL-1, TNF and IL-8 production but also the synthesis and/or action of other proinflammatory proteins (e.g. IL-6, GM-CSF, COX-2, collagenase and stromelysin), make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 MAP kinase inhibitors [Adams, ibid; Badger et al., *J. Pharmacol. Ex. Ther.*, 1996, 279, 1453-61; Griswold et al., *Pharmacol. Commun.*, 1996, 7, 323-29].

Copending international patent application no. PCT/GB03/03501, published on 19 Feb. 2004 as WO 2004/014920, describes a series of 5-6 fused ring bicyclic heteroaromatic compounds which are stated to be potent and selective inhibitors of p38 MAP kinase and thus of use in the prophylaxis and treatment of immune or inflammatory disorders.

The present invention provides a class of compounds which are potent and selective inhibitors of p38 MAP kinase, especially p38α, p38β and p38β2, and splice variants thereof. The compounds in accordance with the present invention are thus of use in medicine, for example in the prophylaxis and treatment of immune or inflammatory disorders.

In addition, the compounds according to the present invention may be used as pharmacological standards for use in the development of new biological tests and in the search for new pharmacological agents. Thus, the compounds according to this invention may be useful as radioligands in assays for detecting compounds capable of binding to the human p38 MAPK enzyme.

The present invention provides a compound of formula (I), or a pharmaceutically acceptable salt or solvate thereof:

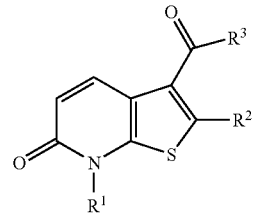

(I)

wherein $R^1$ represents $(C_{3-7}$ cycloalkyl)methyl, aryl or heteroaryl any of which groups may be optionally substituted by one or more substituents;

$R^2$ represents hydrogen, nitro, cyano, $-CO_2R^a$, $-CONR^bR^c$, $-NR^bR^c$, $-NR^dCOR^a$, $-NR^dCO_2R^a$, $-NR^dCONR^bR^c$, $-NR^dSO_2R^a$ or $-NR^dCONHNHSO_2R^a$;

$R^3$ represents an optionally substituted aryl or heteroaryl group;

$R^a$ represents hydrogen, $C_{1-6}$ alkyl [optionally substituted by amino, $C_{1-6}$ alkylamino or di($C_{1-6}$)alkylamino] or $C_{3-7}$ heterocycloalkyl (optionally substituted by $C_{1-6}$ alkyl);

$R^b$ represents hydrogen, $C_{1-6}$ alkyl [optionally substituted by hydroxy, amino, $C_{1-6}$ alkylamino, di($C_{1-6}$)alkylamino or $C_{3-7}$ heterocycloalkyl], $C_{2-6}$ alkenyl, $C_{3-7}$ cycloalkyl [optionally substituted by amino, $C_{1-6}$ alkylamino or di($C_{1-6}$)alkylamino] or $C_{3-7}$ heterocycloalkyl (optionally substituted by $C_{1-6}$ alkyl); and $R^c$ represents hydrogen or $C_{1-6}$ alkyl; or $R^b$ and $R^c$, when taken together with the nitrogen atom to which they are attached, represent azetidin-1-yl [optionally substituted by hydroxy, amino, $C_{1-6}$ alkylamino or di($C_{1-6}$) alkylamino], pyrrolidin-1-yl [optionally substituted by hydroxy, hydroxymethyl, amino, $C_{1-6}$ alkylamino or di($C_{1-6}$) alkylamino], piperidin-1-yl [optionally substituted by hydroxy, amino, $C_{1-6}$ alkylamino or di($C_{1-6}$)alkylamino], piperazin-1-yl (optionally substituted by $C_{1-6}$ alkyl) or morpholin-4-yl; and $R^d$ represents hydrogen or $C_{1-6}$ alkyl.

The present invention additionally provides a compound of formula (I) as depicted above, or a pharmaceutically acceptable salt or solvate thereof, wherein $R^b$ represents hydrogen, $C_{1-6}$ alkyl [optionally substituted by hydroxy, amino, $C_{1-6}$ alkylamino, di($C_{1-6}$)alkylamino or $C_{3-7}$ heterocycloalkyl], $C_{2-6}$ alkenyl or $C_{3-7}$ heterocycloalkyl (optionally substituted by $C_{1-6}$ alkyl); and $R^1$, $R^2$, $R^3$, $R^a$, $R^c$, $R^b/R^c$ and $R^d$ are as defined above.

The present invention also provides a compound of formula (I) as depicted above, or a pharmaceutically acceptable salt or solvate thereof, wherein $R^a$ represents hydrogen, $C_{1-6}$ alkyl or $C_{3-7}$ heterocycloalkyl (optionally substituted by $C_{1-6}$ alkyl);

$R^b$ represents hydrogen, $C_{1-6}$ alkyl [optionally substituted by hydroxy, amino, $C_{1-6}$ alkylamino, di($C_{1-6}$)alkylamino or $C_{3-7}$ heterocycloalkyl], $C_{2-6}$ alkenyl or $C_{3-7}$ heterocycloalkyl (optionally substituted by $C_{1-6}$ alkyl); and $R^1$, $R^2$, $R^3$, $R^c$, $R^b/R^c$ and $R^d$ are as defined above.

The present invention further provides a compound of formula (I) as depicted above, or a pharmaceutically acceptable salt or solvate thereof, wherein $R^2$ represents hydrogen, cyano, $-CO_2R^a$, $-CONR^bR^c$, $-NR^bR^c$, $-NR^dCOR^a$, $NR^dCO_2R^a$, $-NR^dCONR^bR^c$, $-NR^dSO_2R^a$ or $-NR^dCONHNHSO_2R^a$;

$R^a$ represents hydrogen, $C_{1-6}$ alkyl or $C_{3-7}$ heterocycloalkyl (optionally substituted by $C_{1-6}$ alkyl);

$R^b$ represents hydrogen, $C_{1-6}$ alkyl [optionally substituted by hydroxy, amino, $C_{1-6}$ alkylamino, di($C_{1-6}$)alkylamino or $C_{3-7}$ heterocycloalkyl], $C_{2-6}$ alkenyl or $C_{3-7}$ heterocycloalkyl (optionally substituted by $C_{1-6}$ alkyl); and $R^1$, $R^3$, $R^c$, $R^b/R^c$ and $R^d$ are as defined above.

The compounds of formula (I) as defined above are generically encompassed within the scope of copending international patent application no. PCT/GB03/03501, published on 19 Feb. 2004 as WO 2004/014920. However, there is no specific disclosure in that application of the precisely-defined series of thieno[2,3-b]pyridin-6(7H)-one derivatives as represented by formula (I) above.

The groups $R^1$ and $R^3$ in the compounds of formula (I) above may be unsubstituted, or substituted by one or more substituents. Typically, $R^1$ and/or $R^3$ will be unsubstituted, or substituted by one or two substituents. Possible substituents on $R^1$ and/or $R^3$ include halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, $C_{1-6}$ alkylamino, di($C_{1-6}$)-alkylamino, aminocarbonyl and $C_{2-6}$ alkoxycarbonyl. Suitable substituents on $R^1$ and/or $R^3$ include halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, aminocarbonyl and $C_{2-6}$ alkoxycarbonyl. Representative substituents on $R^1$ and/or $R^3$ include halogen, cyano, $C_{1-6}$ alkyl, trifluoromethyl, $C_{1-6}$ alkoxy, difluoromethoxy, trifluoromethoxy and di($C_{1-6}$)alkylamino. Particular substituents on $R^1$ and/or $R^3$ include halogen, cyano, $C_{1-6}$ alkyl, trifluoromethyl, $C_{1-6}$ alkoxy, difluoromethoxy and trifluoromethoxy. Illustrative substituents on $R^1$ and/or $R^3$ include halogen, cyano, $C_{1-6}$ alkyl, trifluoromethyl, $C_{1-6}$ alkoxy and trifluoromethoxy. Typical substituents on $R^1$ and/or $R^3$ include halogen, cyano, $C_{1-6}$ alkyl, trifluoromethyl and $C_{1-6}$ alkoxy. Detailed substituents on $R^1$ and/or $R^3$ include halogen, $C_{1-6}$ alkyl and $C_{1-6}$ alkoxy.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds according to the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched $C_{2-6}$ alkenyl groups, for example $C_{2-4}$ alkenyl groups. Typical examples include vinyl, allyl and dimethylallyl groups.

Suitable cycloalkyl groups include groups containing from 3 to 7 carbon atoms. Particular cycloalkyl groups include cyclopropyl, cyclobutyl, cyclopentyl and cyclohexyl.

A typical ($C_{3-7}$ cycloalkyl)methyl group is cyclopropylmethyl.

Particular aryl groups include phenyl and naphthyl, especially phenyl.

Suitable $C_{3-7}$ heterocycloalkyl groups include azetidinyl, pyrrolidinyl, piperidinyl, piperazinyl, morpholinyl and thiomorpholinyl groups.

Suitable heteroaryl groups include furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, pyridinyl, quinolinyl, isoquinolinyl, pyridazinyl, pyrimidinyl and pyrazinyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)-enol ($CH=CHOH$) tautomers. Formula (I) and the formulae depicted hereinafter are intended to represent all individual tautomers and all possible mixtures thereof, unless stated or shown otherwise.

Suitably, $R^1$ represents ($C_{3-7}$ cycloalkyl)methyl or aryl, either of which groups may be optionally substituted by one or more substituents.

In one embodiment of the compounds according to the invention, $R^1$ represents a ($C_{3-7}$ cycloalkyl)methyl group, especially cyclopropylmethyl.

In a favoured embodiment, $R^1$ represents an optionally substituted phenyl group, in particular unsubstituted, mono-substituted or disubstituted phenyl, especially unsubstituted or monosubstituted phenyl. In one aspect of this embodiment, $R^1$ represents unsubstituted phenyl. In another aspect of this embodiment, $R^1$ represents mono-substituted phenyl. In a further aspect of this embodiment, $R^1$ represents disubstituted phenyl.

In another embodiment, $R^1$ represents an optionally substituted heteroaryl group. In one aspect of this embodiment, $R^1$ represents an optionally substituted pyridinyl group, in particular unsubstituted, monosubstituted or disubstituted pyridinyl, typically unsubstituted or monosubstituted pyridinyl, especially unsubstituted pyridinyl (e.g. pyridin-3-yl).

Examples of typical substituents on the group $R^1$ include fluoro, chloro, cyano, nitro, methyl, trifluoromethyl, hydroxy, methoxy, trifluoromethoxy, methanesulphonyl, amino, methylamino, dimethylamino, aminocarbonyl, formyl and methoxycarbonyl.

Examples of suitable substituents on the group $R^1$ include fluoro, chloro, cyano, nitro, methyl, trifluoromethyl, hydroxy, methoxy, trifluoromethoxy, methanesulphonyl, amino, aminocarbonyl, formyl and methoxycarbonyl.

Illustrative substituents on $R^1$ include halogen, $C_{1-6}$ alkyl and di($C_{1-6}$)alkylamino, especially fluoro, chloro, methyl or dimethylamino. Particular substituents on $R^1$ include halogen and $C_{1-6}$ alkyl, typically fluoro, chloro or methyl, especially chloro or methyl. A particular substituent on $R^1$ is halogen, typically fluoro or chloro, especially chloro. A specific substituent on $R^1$ is fluoro. Another substituent on $R^1$ is $C_{1-6}$ alkyl, especially methyl. A further substituent on $R^1$ is di($C_{1-6}$)alkylamino, especially dimethylamino.

Suitable values of $R^1$ include cyclopropylmethyl, phenyl, fluorophenyl (especially 2-fluorophenyl or 4-fluorophenyl), chlorophenyl (especially 2-chlorophenyl), difluorophenyl (especially 2,6-difluorophenyl), methylphenyl (especially 4-methylphenyl), pyridinyl (especially pyridin-3-yl) and dimethylamino-pyridinyl [especially 6-(dimethylamino)pyridin-3-yl]. Typical values of $R^1$ include cyclopropylmethyl, phenyl, fluorophenyl (especially 2-fluorophenyl), chlorophenyl (especially 2-chlorophenyl), methylphenyl (especially 4-methylphenyl), pyridinyl (especially pyridin-3-yl) and dimethylamino-pyridinyl [especially 6-(dimethylamino)pyridin-3-yl]. Representative values of $R^1$ include cyclopropylmethyl, phenyl, chlorophenyl (especially 2-chlorophenyl), methylphenyl (especially 4-methylphenyl) and pyridinyl (especially pyridin-3-yl). Illustrative values of $R^1$ include cyclopropylmethyl, phenyl, chlorophenyl (especially 2-chlorophenyl) and methylphenyl (especially 4-methylphenyl). Detailed values of $R^1$ include cyclopropylmethyl, phenyl and chlorophenyl (especially 2-chlorophenyl).

One particular value of $R^1$ is phenyl. Another particular value of $R^1$ is 2,6-difluorophenyl.

Suitably, $R^a$ represents hydrogen, $C_{1-6}$ alkyl or $C_{3-7}$ heterocycloalkyl.

In one embodiment, $R^a$ represents hydrogen. In another embodiment, $R^a$ represents unsubstituted $C_{1-6}$ alkyl, especially methyl, ethyl or tert-butyl. In another embodiment, $R^a$ represents $C_{1-6}$ alkyl substituted by amino, especially aminomethyl, 1-aminoethyl or 2-aminoethyl. In another embodiment, $R^a$ represents $C_{1-6}$ alkyl substituted by $C_{1-6}$ alkylamino, especially methylaminomethyl. In another embodiment, $R^a$ represents $C_{1-6}$ alkyl substituted by di($C_{1-6}$)alkylamino, especially dimethylaminomethyl. In a further embodiment, $R^a$ represents unsubstituted $C_{3-7}$ heterocycloalkyl, especially pyrrolidinyl (in particular pyrrolidin-2-yl) or piperidinyl (in particular piperidin-4-yl). In an additional embodiment, $R^a$ represents $C_{3-7}$ heterocycloalkyl substituted by $C_{1-6}$ alkyl, especially methylpyrrolidinyl (in particular 1-methylpyrrolidin-2-yl), methylpiperidinyl (in particular 1-methylpiperidin-4-yl) or ethylpiperidinyl (in particular 1-ethylpiperidin-4-yl). Selected values of $R^a$ include hydrogen, methyl, aminomethyl, methylaminomethyl, dimethylaminomethyl, ethyl, 1-aminoethyl, 2-aminoethyl, tert-butyl, pyrrolidinyl (especially pyrrolidin-2-yl), methylpyrrolidinyl (especially 1-methylpyrrolidin-2-yl), piperidinyl (especially piperidin-4-yl), methylpiperidinyl (especially 1-methylpiperidin-4-yl) and ethylpiperidinyl (especially 1-ethylpiperidin-4-yl). Typical values of $R^a$ include hydrogen, methyl, ethyl, tert-butyl, piperidinyl (especially piperidin-4-yl), methylpiperidinyl (especially 1-methylpiperidin-4-yl) and ethylpiperidinyl (especially 1-ethylpiperidin-4-yl). Suitable values of $R^a$ include hydrogen, methyl, ethyl, tert-butyl, piperidinyl (especially piperidin-4-yl) and methylpiperidinyl (especially 1-methylpiperidin-4-yl). Particular values of $R^a$ include hydrogen, methyl, ethyl, tert-butyl and piperidinyl (especially piperidin-4-yl).

In a representative embodiment, $R^b$ represents hydrogen, $C_{1-6}$ alkyl [optionally substituted by hydroxy, di($C_{1-6}$)alkylamino or $C_{3-7}$ heterocycloalkyl], $C_{2-6}$ alkenyl, $C_{3-7}$ cycloalkyl (optionally substituted by amino) or $C_{3-7}$ heterocycloalkyl (optionally substituted by $C_{1-6}$ alkyl). In an illustrative embodiment, $R^b$ represents hydrogen, $C_{1-6}$ alkyl [optionally substituted by hydroxy, di($C_{1-6}$)alkylamino or $C_{3-7}$ heterocycloalkyl], $C_{2-6}$ alkenyl or $C_{3-7}$ heterocycloalkyl (optionally substituted by $C_{1-6}$ alkyl). Typically, $R^b$ represents hydrogen, $C_{1-6}$ alkyl (optionally substituted by hydroxy or $C_{3-7}$ heterocycloalkyl), $C_{2-6}$ alkenyl or $C_{3-7}$ heterocycloalkyl (optionally substituted by $C_{1-6}$ alkyl). Suitably, $R^b$ represents hydrogen, $C_{1-6}$ alkyl (optionally substituted by hydroxy), $C_{2-6}$ alkenyl or $C_{3-7}$ heterocycloalkyl (optionally substituted by $C_{1-6}$ alkyl).

In one embodiment, $R^b$ represents hydrogen. In another embodiment, $R^b$ represents unsubstituted $C_{1-6}$ alkyl, especially methyl. In a further embodiment, $R^b$ represents $C_{1-6}$ alkyl substituted by hydroxy, especially 2-hydroxyethyl, 2-hydroxy-2-methylpropyl or 1-hydroxy-2-methylprop-2-yl. In one more embodiment, $R^b$ represents $C_{1-6}$ alkyl substituted by di($C_{1-6}$)alkylamino, especially 2,2-dimethyl-3-(dimethylamino)-propyl. In a still further embodiment, $R^b$ represents $C_{1-6}$ alkyl substituted by $C_{3-7}$ heterocycloalkyl (e.g. azetidinyl, pyrrolidinyl or piperidinyl, particularly pyrrolidinyl or piperidinyl), especially azetidinylmethyl (in particular azetidin-3-ylmethyl), pyrrolidinylethyl [in particular 2-(pyrrolidin-1-yl)ethyl] or piperidinylethyl [in particular 2-(piperidin-1-yl)ethyl]. In a yet further embodiment, $R^b$ represents $C_{2-6}$ alkenyl, especially allyl. In one other embodiment, $R^b$ represents $C_{3-7}$ cycloalkyl substituted by amino, especially trans-4-aminocyclohexyl. In an additional embodiment, $R^b$ represents $C_{3-7}$ heterocycloalkyl, which may be unsubstituted or substituted by $C_{1-6}$ alkyl (e.g. methyl, ethyl or isopropyl, particularly methyl or ethyl).

Apposite values of $R^b$ include hydrogen, methyl, 2-hydroxyethyl, 2-hydroxy-2-methylpropyl, 1-hydroxy-2-methylprop-2-yl, 2,2-dimethyl-3-(dimethylamino)-propyl, azetidinylmethyl (especially azetidin-3-ylmethyl), pyrrolidinylethyl [especially 2-(pyrrolidin-1-yl)ethyl], piperidinylethyl [especially 2-(piperidin-1-yl)ethyl], allyl, aminocyclohexyl (especially trans-4-aminocyclohexyl), azetidinyl (especially azetidin-3-yl), methylazetidinyl (especially 1-methylazetidin-3-yl), ethylazetidinyl (especially 1-ethylazetidin-3-yl), isopropylazetidinyl (especially 1-isopropylazetidin-3-yl), pyrrolidinyl (especially pyrrolidin-3-yl), methylpyrrolidinyl (especially 1-methylpyrrolidin-3-yl), ethylpyrrolidinyl (especially 1-ethylpyrrolidin-3-yl), isopropylpyrrolidinyl (especially 1-isopropylpyrrolidin-3-yl), piperidinyl (e.g. piperidin-3-yl or piperidin-4-yl, especially piperidin-3-yl), methylpiperidinyl (e.g. 1-methylpiperidin-3-yl or 1-methylpiperidin-4-yl, especially 1-methylpiperidin-4-yl), ethylpiperidinyl (especially 1-ethylpiperidin-4-yl) and isopropylpiperidinyl (especially 1-isopropylpiperidin-4-yl).

Detailed values of $R^b$ include hydrogen, methyl, 2-hydroxyethyl, 2-hydroxy-2-methylpropyl, 1-hydroxy-2-methylprop-2-yl, 2,2-dimethyl-3-(dimethylamino)-propyl, azetidinylmethyl (especially azetidin-3-ylmethyl), pyrrolidinylethyl [especially 2-(pyrrolidin-1-yl)ethyl], piperidinylethyl [especially 2-(piperidin-1-yl)ethyl], allyl, azetidinyl (especially azetidin-3-yl), methylazetidinyl (especially 1-methylazetidin-3-yl), ethylazetidinyl (especially 1-ethylazetidin-3-yl), isopropylazetidinyl (especially 1-isopropylazetidin-3-yl), pyrrolidinyl (especially pyrrolidin-3-yl), methylpyrrolidinyl (especially 1-methylpyrrolidin-3-yl), ethylpyrrolidinyl (especially 1-ethylpyrrolidin-3-yl), piperidinyl (e.g. piperidin-3-yl or piperidin-4-yl, especially piperidin-3-yl) and methylpiperidinyl (especially 1-methylpiperidin-3-yl or 1-methylpiperidin-4-yl). Illustrative values of $R^b$ include hydrogen, methyl, 2-hydroxy-2-methylpropyl, 1-hydroxy-2-methylprop-2-yl, piperidinylethyl [especially 2-(piperidin-1-yl)ethyl], pyrrolidinylethyl [especially 2-(pyrrolidin-1-yl)ethyl], allyl, azetidinyl (especially azetidin-3-yl), methylazetidinyl (especially 1-methylazetidin-3-yl), ethylpyrrolidinyl (especially 1-ethylpyrrolidin-3-yl) and piperidinyl (especially piperidin-3-yl). Suitable values of $R^b$ include hydrogen, methyl, 2-hydroxy-2-methylpropyl, 1-hydroxy-2-methylprop-2-yl, piperidinylethyl [especially 2-(piperidin-1-yl)ethyl], allyl and ethylpyrrolidinyl (especially 1-ethylpyrrolidin-3-yl). Typical values of $R^b$ include hydrogen, methyl, 2-hydroxy-2-methylpropyl, 1-hydroxy-2-methylprop-2-yl, allyl and ethylpyrrolidinyl (especially 1-ethylpyrrolidin-3-yl).

In one particular embodiment, $R^b$ represents 1-methylazetidin-3-yl. In another particular embodiment, $R^b$ represents 1-methylpiperidin-4-yl.

In one embodiment, $R^c$ represents hydrogen. In another embodiment, $R^c$ represents $C_{1-6}$ alkyl, especially methyl. Suitable values of $R^c$ include hydrogen and methyl.

In the alternative, $R^b$ and $R^c$, when taken together with the nitrogen atom to which they are attached, ideally represent azetidin-1-yl [optionally substituted by amino or di($C_{1-6}$)alkylamino], pyrrolidin-1-yl [optionally substituted by hydroxy, hydroxymethyl, amino, $C_{1-6}$ alkylamino or di($C_{1-6}$)alkylamino], piperidin-1-yl (optionally substituted by amino), piperazin-1-yl (optionally substituted by $C_{1-6}$ alkyl) or morpholin-4-yl. Alternatively, $R^b$ and $R^c$, when taken together with the nitrogen atom to which they are attached, typically represent azetidin-1-yl, pyrrolidin-1-yl (optionally substituted by hydroxy or hydroxymethyl), piperidin-1-yl, piperazin-1-yl (optionally substituted by $C_{1-6}$ alkyl) or morpholin-4-yl. Similarly, $R^b$ and $R^c$, when taken together with the nitrogen atom to which they are attached, suitably represent azetidin-1-yl, pyrrolidin-1-yl (optionally substituted by hydroxymethyl), piperidin-1-yl, piperazin-1-yl (optionally substituted by $C_{1-6}$ alkyl) or morpholin-4-yl.

In a detailed embodiment, $R^b$ and $R^c$, when taken together with the nitrogen atom to which they are attached, represent azetidin-1-yl, aminoazetidin-1-yl (especially 3-aminoazetidin-1-yl), dimethylamino-azetidin-1-yl [especially 3-(dimethylamino)azetidin-1-yl], pyrrolidin-1-yl, hydroxypyrrolidin-1-yl (especially 3-hydroxypyrrolidin-1-yl), hydroxymethyl-pyrrolidin-1-yl [especially 2-(hydroxymethyl)pyrrolidin-1-yl], aminopyrrolidin-1-yl (especially 3-aminopyrrolidin-1-yl), isopropylamino-pyrrolidin-1-yl [especially 3-(isopropylamino)pyrrolidin-1-yl], dimethylamino-pyrrolidin-1-yl [especially 3-(dimethylamino)pyrrolidin-1-yl], piperidin-1-yl, aminopiperidin-1-yl (especially 4 aminopiperidin-1-yl), methyl-piperazin-1-yl (especially 4-methylpiperazin-1-yl) or morpholin-4-yl. In a typical embodiment, $R^b$ and $R^c$, when taken together with the nitrogen atom to which they are attached, represent azetidin-1-yl, pyrrolidin-1-yl, hydroxypyrrolidin-1-yl (especially 3-hydroxypyrrolidin-1-yl), hydroxymethyl-pyrrolidin-1-yl [especially 2-(hydroxymethyl)pyrrolidin-1-yl], piperidin-1-yl, methyl-piperazin-1-yl (especially 4-methylpiperazin-1-yl) or morpholin-4-yl. In an alternative embodiment, $R^b$ and $R^c$, when taken together with the nitrogen atom to which they are attached, represent azetidin-1-yl, pyrrolidin-1-yl, hydroxymethyl-pyrrolidin-1-yl [especially 2-(hydroxymethyl)pyrrolidin-1-yl], piperidin-1-yl, methyl-piperazin-1-yl (especially 4-methylpiperazin-1-yl) or morpholin-4-yl.

In one embodiment, $R^d$ represents hydrogen. In another embodiment, $R^d$ represents $C_{1-6}$ alkyl, especially methyl. Typically, $R^d$ is hydrogen.

Apposite values of $R^2$ include hydrogen, nitro, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, (azetidin-3-yl)methylamino, 2-(pyrrolidin-1-yl)ethylamino, 2-(piperidin-1-yl)ethylamino, 2,2-dimethyl-3-(dimethylamino)propylamino, trans-(4-aminocyclohexyl)amino, azetidin-3-ylamino, 1-methylazetidin-3-ylamino, 1-ethylazetidin-3-ylamino, 1-isopropylazetidin-3-ylamino, pyrrolidin-3-ylamino, 1-methylpyrrolidin-3-ylamino, 1-isopropylpyrrolidin-3-ylamino, piperidin-3-ylamino, piperidin-4-ylamino, 1-methylpiperidin-3-ylamino, 1-methylpiperidin-4-ylamino, 1-ethylpiperidin-4-ylamino, 1-isopropylpiperidin-4-ylamino, dimethylamino, azetidin-1-yl, 3-aminoazetidin-1-yl, 3-(dimethylamino)azetidin-1-yl, 3-hydroxypyrrolidin-1-yl, 3-(dimethylamino)pyrrolidin-1-yl, piperidin-1-yl, 4 aminopiperidin-1-yl, morpholin-4-yl, acetylamino, aminomethylcarbonylamino, (methylamino)methylcarbonylamino, (dimethylamino)methylcarbonylamino, (1-aminoethyl)carbonylamino, (2-aminoethyl)carbonylamino, pyrrolidin-2-ylcarbonylamino, (1-methylpyrrolidin-2-yl)carbonylamino, piperidin-4-ylcarbonylamino, (1-methylpiperidin-4-yl)carbonylamino, (1-ethylpiperidin-4-yl)carbonylamino, tert-butoxycarbonylamino, aminocarbonylamino, (2-hydroxyethyl)aminocarbonylamino, (2-hydroxy-2-methylpropyl)aminocarbonylamino, (1-hydroxy-2-methylprop-2-yl)aminocarbonylamino, dimethylaminocarbonylamino, allylaminocarbonylamino, (pyrrolidin-3-yl)aminocarbonylamino, (1-methylpyrrolidin-3-yl)aminocarbonylamino, (1-ethylpyrrolidin-3-yl)aminocarbonylamino, azetidin-1-ylcarbonylamino, 3-hydroxypyrrolidin-1-ylcarbonylamino, 2-(hydroxymethyl)pyrrolidin-1-ylcarbonylamino, 3-aminopyrrolidin-1-ylcarbonylamino, 3-(isopropylamino)pyrrolidin-1-ylcarbonylamino, 3-(dimethylamino)pyrrolidin-1-ylcarbonylamino, (4-methylpiperazin-1-yl)carbonylamino, methanesulphonylamino and methanesulphonylhydrazinylcarbonylamino.

Selected values of $R^2$ include hydrogen, nitro, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1- ylcarbonyl, 2-(hydroxy-methyl)pyrrolidin-1-ylcarbonyl, morpholin-4-ylcarbonyl, amino, (azetidin-3-yl)methylamino, 2-(pyrrolidin-1-yl)ethylamino, 2-(piperidin-1-yl)ethylamino, 2,2-dimethyl-3-(dimethylamino)propylamino, azetidin-3-ylamino, 1-methylazetidin-3-ylamino, 1-ethylazetidin-3-ylamino, 1-isopropylazetidin-3-ylamino, pyrrolidin-3-ylamino, 1-methylpyrrolidin-3-ylamino, piperidin-3-ylamino, piperidin-4-ylamino, 1-methyl-piperidin-3-ylamino, 1-methylpiperidin-4-ylamino, di-methylamino, azetidin-1-yl, 3-aminoazetidin-1-yl, 3-(dimethylamino)azetidin-1-yl, 3-hydroxypyrrolidin-1-yl, 3-(dimethylamino)pyrrolidin-1-yl, piperidin-1-yl, 4-aminopiperidin-1-yl, morpholin-4-yl, acetylamino, aminomethylcarbonylamino, (methylamino)methylcarbonylamino, (dimethylamino)methylcarbonylamino, (1-aminoethyl)carbonylamino, (2-aminoethyl)carbonylamino, pyrrolidin-2-ylcarbonylamino, (1-methylpyrrolidin-2-yl)carbonylamino, piperidin-4-ylcarbonylamino, (1-methylpiperidin-4-yl)carbonylamino, (1-ethylpiperidin-4-yl)carbonylamino, tert-butoxycarbonylamino, aminocarbonylamino, (2-hydroxyethyl)aminocarbonylamino, (2-hydroxy-2-methylpropyl)aminocarbonylamino, (1-hydroxy-2-methylprop-2-yl)aminocarbonylamino, dimethylaminocarbonylamino, allylaminocarbonylamino, (pyrrolidin-3-yl)aminocarbonylamino, (1-methylpyrrolidin-3-yl)aminocarbonylamino, (1-ethylpyrrolidin-3-yl)aminocarbonylamino, azetidin-1-ylcarbonylamino, 3-hydroxypyrrolidin-1-ylcarbonylamino, 2-(hydroxymethyl)pyrrolidin-1-ylcarbonylamino, 3-aminopyrrolidin-1-ylcarbonylamino, 3-(isopropylamino)pyrrolidin-1-ylcarbonylamino, 3-(dimethylamino)pyrrolidin-1-ylcarbonylamino, (4-methylpiperazin-1-yl)carbonylamino, methanesulphonylamino and methanesulphonylhydrazinylcarbonylamino.

Detailed values of $R^2$ include hydrogen, nitro, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, 2-(pyrrolidin-1-yl)ethylamino, 2-(piperidin-1-yl)ethylamino, azetidin-3-ylamino, 1-methylazetidin-3-ylamino, piperidin-3-ylamino, dimethylamino, azetidin-1-yl, 3-hydroxypyrrolidin-1-yl, piperidin-1-yl, acetylamino, piperidin-4-ylcarbonylamino, (1-methylpiperidin-4-yl)carbonylamino, (1-ethylpiperidin-4-yl)carbonylamino, tert-butoxycarbonylamino, aminocarbonylamino, (2-hydroxy-2-methylpropyl)aminocarbonylamino, (1-hydroxy-2-methylprop-2-yl)aminocarbonylamino, dimethylaminocarbonylamino, allylaminocarbonylamino, (1-ethylpyrrolidin-3-yl)amino-carbonylamino, azetidin-1-ylcarbonylamino, 3-hydroxypyrrolidin-1-ylcarbonylamino, 2-(hydroxymethyl)pyrrolidin-1-ylcarbonylamino, (4-methylpiperazin-1-yl)carbonylamino, methanesulphonylamino and methanesulphonylhydrazinylcarbonylamino.

Suitable values of $R^2$ include hydrogen, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, 2-(pyrrolidin-1-yl)ethylamino, 2-(piperidin-1-yl)ethylamino, azetidin-3-ylamino, 1-methylazetidin-3-ylamino, piperidin-3-ylamino, dimethylamino, azetidin-1-yl, 3-hydroxypyrrolidin-1-yl, piperidin-1-yl, acetylamino, piperidin-4-ylcarbonylamino, (1-methylpiperidin-4-yl)carbonylamino, (1-ethylpiperidin-4-yl)carbonylamino, tert-butoxycarbonylamino, aminocarbonylamino, (2-hydroxy-2-methylpropyl)aminocarbonylamino, dimethylaminocarbonylamino, allylaminocarbonylamino, (1-ethylpyrrolidin-3-yl)aminocarbonylamino, azetidin-1-ylcarbonylamino, 2-(hydroxymethyl)pyrrolidin-1-ylcarbonylamino, (4-methylpiperazin-1-yl)carbonylamino, methanesulphonylamino and methanesulphonylhydrazinylcarbonylamino.

Illustrative values of $R^2$ include hydrogen, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, 2-(piperidin-1-yl)ethylamino, dimethylamino, azetidin-1-yl, 3-hydroxypyrrolidin-1-yl, piperidin-1-yl, acetylamino, piperidin-4-ylcarbonylamino, (1-methylpiperidin-4-yl)carbonylamino, tert-butoxycarbonylamino, aminocarbonylamino, (2-hydroxy-2-methylpropyl)aminocarbonylamino, dimethylaminocarbonylamino, allylaminocarbonylamino, (1-ethylpyrrolidin-3-yl)aminocarbonylamino, azetidin-1-ylcarbonylamino, 2-(hydroxymethyl)pyrrolidin-1-ylcarbonyl-amino, (4-methylpiperazin-1-yl)carbonylamino, methanesulphonylamino and methanesulphonylhydrazinylcarbonylamino.

Representative values of $R^2$ include hydrogen, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, dimethylamino, azetidin-1-yl, piperidin-1-yl, acetylamino, piperidin-4-ylcarbonylamino, (1-methylpiperidin-4-yl)carbonylamino, tert-butoxycarbonylamino, aminocarbonylamino, (2-hydroxy-2-methylpropyl)aminocarbonylamino, dimethylaminocarbonylamino, allylaminocarbonylamino, (1-ethylpyrrolidin-3-yl)amino-carbonylamino, azetidin-1-ylcarbonylamino, 2-(hydroxymethyl)pyrrolidin-1-ylcarbonyl-amino, (4-methylpiperazin-1-yl)carbonylamino, methanesulphonylamino and methanesulphonylhydrazinylcarbonylamino.

Typical values of $R^2$ include hydrogen, cyano, carboxy, ethoxycarbonyl, aminocarbonyl, methylaminocarbonyl, (1-hydroxy-2-methylprop-2-yl)aminocarbonyl, dimethylaminocarbonyl, azetidin-1-ylcarbonyl, pyrrolidin-1-ylcarbonyl, 2-(hydroxymethyl)pyrrolidin-1-ylcarbonyl, morpholin-4-ylcarbonyl, amino, dimethylamino, azetidin-1-yl, piperidin-1-yl, acetylamino, piperidin-4-ylcarbonylamino, tert-butoxycarbonylamino, aminocarbonylamino, (2-hydroxy-2-methylpropyl)aminocarbonylamino, dimethylaminocarbonylamino, allylaminocarbonylamino, (1-ethylpyrrolidin-3-yl)aminocarbonylamino, azetidin-1-ylcarbonylamino, 2-(hydroxymethyl)pyrrolidin-1-ylcarbonylamino, (4-methylpiperazin-1-yl)carbonylamino, methanesulphonylamino and methanesulphonylhydrazinylcarbonylamino.

In a specific embodiment, $R^2$ represents —$NR^bR^c$ in which $R^b$ and $R^c$ are as defined above.

One particular value of $R^2$ is 1-methylazetidin-3-ylamino. Another particular value of $R^2$ is 1-methylpiperidin-4-ylamino.

Selected values for the substituent $R^3$ include phenyl, pyridinyl, pyridazinyl, pyrimidinyl, pyrazinyl, thienyl, thiazolyl, isothiazolyl, pyrrolyl, pyrazolyl, imidazolyl, triazolyl and tetrazolyl, any of which groups may be optionally substituted by one or more substituents.

In a favoured embodiment, $R^3$ represents an optionally substituted phenyl group, in particular unsubstituted, monosubstituted or disubstituted phenyl.

In another embodiment, $R^3$ represents optionally substituted pyridinyl, especially unsubstituted or monosubstituted pyridin-2-yl.

In a further embodiment, $R^3$ represents optionally substituted thienyl, especially unsubstituted or monosubstituted thien-2-yl.

In an additional embodiment, $R^3$ represents optionally substituted thiazolyl, especially unsubstituted or monosubstituted thiazol-2-yl.

Examples of typical substituents on the group $R^3$ include fluoro, chloro, bromo, cyano, nitro, methyl, trifluoromethyl, hydroxy, methoxy, ethoxy, difluoromethoxy, trifluoromethoxy, methanesulphonyl, amino, aminocarbonyl and methoxycarbonyl. Examples of suitable substituents on the group $R^3$ include fluoro, chloro, cyano, nitro, methyl, trifluoromethyl, hydroxy, methoxy, ethoxy, difluoromethoxy, trifluoromethoxy, methanesulphonyl, amino, aminocarbonyl and methoxycarbonyl.

Examples of illustrative substituents on $R^3$ include fluoro, chloro, bromo, cyano, methyl, trifluoromethyl, methoxy, ethoxy, difluoromethoxy and trifluoromethoxy. Examples of representative substituents on $R^3$ include fluoro, chloro, bromo, cyano, methyl, trifluoromethyl, methoxy, ethoxy and trifluoromethoxy. Examples of suitable substituents on $R^3$ include fluoro, chloro, cyano, methyl, trifluoromethyl and ethoxy. Examples of typical substituents on $R^3$ include fluoro, chloro, methyl, trifluoromethyl and ethoxy. Examples of individual substituents on $R^3$ include fluoro, chloro, methyl and ethoxy.

Particular values of $R^3$ include phenyl, fluorophenyl, difluorophenyl, chlorophenyl, (chloro)(fluoro)phenyl, bromophenyl, cyanophenyl, methylphenyl, (fluoro)(methyl)phenyl, dimethylphenyl, trifluoromethyl-phenyl, methoxyphenyl, (ethoxy)(methyl)phenyl, difluoromethoxy-phenyl, trifluoromethoxy-phenyl, pyridinyl, methylpyridinyl, thienyl and thiazolyl.

Specific values of $R^3$ include phenyl, fluorophenyl, difluorophenyl, chlorophenyl, (chloro)(fluoro)phenyl, bromophenyl, cyanophenyl, methylphenyl, (fluoro)(methyl)phenyl, dimethylphenyl, trifluoromethyl-phenyl, methoxyphenyl, (ethoxy)(methyl)phenyl, difluoromethoxy-phenyl, trifluoromethoxy-phenyl, methylpyridinyl and thienyl.

Selected values of $R^3$ include phenyl, fluorophenyl, difluorophenyl, chlorophenyl, (chloro)(fluoro)phenyl, bromophenyl, cyanophenyl, methylphenyl, (fluoro)(methyl)-phenyl, dimethylphenyl, trifluoromethyl-phenyl, methoxyphenyl, (ethoxy)(methyl)-phenyl, trifluoromethoxy-phenyl and methylpyridinyl. Suitable values of $R^3$ include phenyl, difluorophenyl, chlorophenyl, (chloro)-(fluoro)phenyl, cyanophenyl, methylphenyl, (fluoro)(methyl)phenyl, trifluoromethylphenyl, (ethoxy)(methyl)phenyl and methylpyridinyl.

Typical values of $R^3$ include phenyl, difluorophenyl, chlorophenyl, (chloro)(fluoro)phenyl, methylphenyl, (fluoro)(methyl)phenyl, trifluoromethylphenyl, (ethoxy)(methyl)phenyl and methylpyridinyl.

Detailed values of $R^3$ include phenyl, difluorophenyl, chlorophenyl, (chloro)-(fluoro)phenyl, methylphenyl, (fluoro)(methyl)phenyl, (ethoxy)(methyl)phenyl and methylpyridinyl.

One particular value of $R^3$ is phenyl. Another particular value of $R^3$ is (fluoro)(methyl)phenyl.

A particular sub-class of compounds according to the invention is represented by the compounds of formula (IIA), and pharmaceutically acceptable salts and solvates thereof:

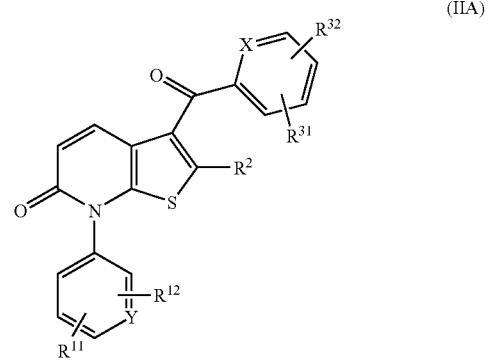

(IIA)

wherein
X represents CH or N;
Y represents CH or N;
$R^{11}$, $R^{12}$, $R^{31}$ and $R^{32}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, $C_{1-6}$ alkylamino, di($C_{1-6}$)alkylamino, aminocarbonyl or $C_{2-6}$ alkoxycarbonyl; and
$R^2$ is as defined above.

In one embodiment, X is CH.
In another embodiment, X is N.
In one embodiment, Y is CH.
In another embodiment, Y is N.

Ideally, $R^{11}$, $R^{12}$, $R^{31}$ and $R^{32}$ independently represent hydrogen, fluoro, chloro, bromo, cyano, nitro, methyl, trifluoromethyl, hydroxy, methoxy, ethoxy, difluoromethoxy, trifluoromethoxy, methanesulphonyl, amino, methylamino, dimethylamino, aminocarbonyl or methoxycarbonyl.

In one embodiment of the compounds of formula (IIA) above, $R^{11}$, $R^{12}$, $R^{31}$ and $R^{32}$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, aminocarbonyl or $C_{2-6}$ alkoxycarbonyl.

Typically, $R^{11}$, $R^{12}$, $R^{31}$ and $R^{32}$ independently represent hydrogen, fluoro, chloro, bromo, cyano, nitro, methyl, trifluoromethyl, hydroxy, methoxy, ethoxy, difluoromethoxy, trifluoromethoxy, methanesulphonyl, amino, aminocarbonyl or methoxycarbonyl.

Suitably, $R^{11}$, $R^{12}$, $R^{31}$ and $R^{32}$ independently represent hydrogen, fluoro, chloro, cyano, nitro, methyl, trifluoromethyl, hydroxy, methoxy, ethoxy, difluoromethoxy, trifluoromethoxy, methanesulphonyl, amino, aminocarbonyl or methoxycarbonyl.

In a detailed embodiment, $R^{11}$, $R^{12}$, $R^{31}$ and $R^{32}$ independently represent hydrogen, halogen, cyano, $C_{1-6}$ alkyl, trifluoromethyl, $C_{1-6}$ alkoxy, difluoromethoxy, trifluoromethoxy or di($C_{1-6}$)alkylamino. Suitable values of $R^{11}$, $R^{12}$, $R^{31}$ and $R^{32}$ include hydrogen, fluoro, chloro, bromo, cyano, methyl, trifluoromethyl, methoxy, ethoxy, difluoromethoxy, trifluoromethoxy and dimethylamino.

In a particular embodiment, $R^{11}$, $R^{12}$, $R^{31}$ and $R^{32}$ independently represent hydrogen, halogen, cyano, $C_{1-6}$ alkyl, trifluoromethyl, $C_{1-6}$ alkoxy, difluoromethoxy or trifluoromethoxy. Suitable values of $R^{11}$, $R^{12}$, $R^{31}$ and $R^{32}$ include hydrogen, fluoro, chloro, bromo, cyano, methyl, trifluoromethyl, methoxy, ethoxy, difluoromethoxy and trifluoromethoxy.

Representatively, $R^{11}$, $R^{12}$, $R^{31}$ and $R^{32}$ independently represent hydrogen, halogen, cyano, $C_{1-6}$ alkyl, trifluoromethyl, $C_{1-6}$ alkoxy or trifluoromethoxy. Suitable values of $R^{11}$, $R^{12}$, $R^{31}$ and $R^{32}$ include hydrogen, fluoro, chloro, bromo, cyano, methyl, trifluoromethyl, methoxy, ethoxy and trifluoromethoxy.

Illustratively, $R^{11}$, $R^{12}$, $R^{31}$ and $R^{32}$ independently represent hydrogen, halogen, cyano, $C_{1-6}$ alkyl, trifluoromethyl or $C_{1-6}$ alkoxy. Suitable values of $R^{11}$, $R^{12}$, $R^{31}$ and $R^{32}$ include hydrogen, fluoro, chloro, cyano, methyl, trifluoromethyl and ethoxy.

Typically, $R^{11}$, $R^{12}$, $R^{31}$ and $R^{32}$ independently represent hydrogen, halogen, $C_{1-6}$ alkyl or $C_{1-6}$ alkoxy. Particular values of $R^{11}$, $R^{12}$, $R^{31}$ and $R^{32}$ include hydrogen, fluoro, chloro, methyl and ethoxy.

Selected values of $R^{11}$ include hydrogen, halogen, $C_{1-6}$ alkyl and di($C_{1-6}$)alkylamino. Suitable values of $R^{11}$ include hydrogen, halogen and $C_{1-6}$ alkyl. Particular values of $R^{11}$ include hydrogen and halogen. In one embodiment, $R^{11}$ is hydrogen. In another embodiment, $R^{11}$ represents halogen, e.g. fluoro or chloro, especially chloro. In a specific embodiment, $R^{11}$ represents fluoro. In a further embodiment, $R^{11}$ represents $C_{1-6}$ alkyl, especially methyl. In an additional embodiment, $R^{11}$ represents di($C_{1-6}$)alkylamino, especially dimethylamino.

Particular values of $R^{12}$ include hydrogen and halogen. In one embodiment, $R^{12}$ is hydrogen. In another embodiment, $R^{12}$ represents halogen, e.g. fluoro.

Typically, $R^{12}$ is hydrogen.

Individual values of $R^{31}$ include hydrogen, halogen, cyano, $C_{1-6}$ alkyl, trifluoromethyl, $C_{1-6}$ alkoxy, difluoromethoxy and trifluoromethoxy. Itemised values of $R^{31}$ include hydrogen, fluoro, chloro, bromo, cyano, methyl, trifluoromethyl, methoxy, ethoxy, difluoromethoxy and trifluoromethoxy.

Illustrative values of $R^{31}$ include hydrogen, halogen, cyano, $C_{1-6}$ alkyl, trifluoromethyl, $C_{1-6}$ alkoxy and trifluoromethoxy. Selected values of $R^{31}$ include hydrogen, fluoro, chloro, bromo, cyano, methyl, trifluoromethyl, methoxy, ethoxy and trifluoromethoxy.

Suitable values of $R^{31}$ include hydrogen, halogen, cyano, $C_{1-6}$ alkyl and trifluoromethyl. Particular values of $R^{31}$ include hydrogen, fluoro, chloro, cyano, methyl and trifluoromethyl.

Typical values of $R^{31}$ include hydrogen, halogen, $C_{1-6}$ alkyl and trifluoromethyl. Detailed values of $R^{31}$ include hydrogen, fluoro, chloro, methyl and trifluoromethyl.

Representative values of $R^{31}$ include hydrogen, halogen and $C_{1-6}$ alkyl. Specific values of $R^{31}$ include hydrogen, fluoro, chloro and methyl.

Typical values of $R^{32}$ include hydrogen, halogen, $C_{1-6}$ alkyl and $C_{1-6}$ alkoxy. Detailed values of $R^{32}$ include hydrogen, fluoro, methyl and ethoxy. In one embodiment, $R^{32}$ is hydrogen. In another embodiment, $R^{32}$ is fluoro. In a further embodiment, $R^{32}$ is methyl.

Suitable values of $R^{32}$ include hydrogen, halogen and $C_{1-6}$ alkoxy. Particular values of $R^{32}$ include hydrogen, fluoro and ethoxy.

Another subclass of compound according to the invention is represented by the compounds of formula (IIB), and pharmaceutically acceptable salts and solvates thereof:

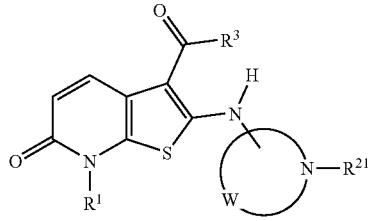

wherein

W represents the residue of an azetidine, pyrrolidine or piperidine ring;

$R^{21}$ represents hydrogen or $C_{1-6}$ alkyl; and $R^1$ and $R^3$ are as defined above.

In one embodiment, W represents the residue of an azetidine ring, especially an azetidin-3-yl ring.

In another embodiment, W represents the residue of a pyrrolidine ring, especially a pyrrolidin-3-yl ring.

In a further embodiment, W represents the residue of a piperidine ring. In one aspect of this embodiment, W represents the residue of a piperidin-3-yl ring. In another aspect of this embodiment, W represents the residue of a piperidin-4-yl ring.

Appositely, W represents the residue of an azetidin-3-yl or piperidin-4-yl ring.

Suitably, W represents the residue of an azetidin-3-yl or piperidin-3-yl ring.

Typically, $R^{21}$ represents hydrogen, methyl, ethyl or isopropyl, especially hydrogen or methyl. In one embodiment, $R^{21}$ is hydrogen. In another embodiment, $R^{21}$ is methyl. In an additional embodiment, $R^{21}$ is ethyl. In a further embodiment, $R^{21}$ is isopropyl.

Particularly useful compounds of the invention include each of the compounds described in the accompanying Examples, and pharmaceutically acceptable salts and solvates thereof.

Compounds according to the invention are potent and selective inhibitors of p38 MAP kinases, including isoforms and splice variants thereof. More specifically, the compounds of the invention are inhibitors of p38α, p38β and p38β2. The ability of the compounds to act in this way may be simply determined by employing tests such as those described hereinbelow.

The compounds of formula (I) are of use in modulating the activity of p38 MAP kinases and in particular are of use in the prophylaxis and treatment of any p38 MAP kinase mediated diseases or disorders in a human or other mammal. The invention extends to such a use and to the use of the compounds for the manufacture of a medicament for treating such diseases or disorders. Furthermore, the invention extends to the administration to a human of an effective amount of a p38 MAPK inhibitor for treating any such disease or disorder.

The invention also extends to the prophylaxis or treatment of any disease or disorder in which p38 MAP kinase plays a role including conditions caused by excessive or unregulated pro-inflammatory cytokine production, including for example excessive or unregulated TNF, IL-1, IL-6 and IL-8 production in a human or other mammal. The invention extends to such a use and to the use of the compounds for the manufacture of a medicament for treating such cytokine-mediated diseases or disorders. Furthermore, the invention extends to the administration to a human of an effective amount of a p38 MAPK inhibitor for treating any such disease or disorder.

Diseases or disorders in which p38 MAP kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs host disease and psoriasis.

The invention further extends to the particular autoimmune disease rheumatoid arthritis.

Inflammatory diseases which may be prevented or treated include but are not limited to asthma, allergies, respiratory distress syndrome, and acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastatic melanoma and multiple myeloma.

Neurodegenerative diseases which may be prevented or treated include but are not limited to Parkinson's disease, Alzheimer's disease, cerebral ischemias and neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 MAPK inhibitors of this invention exhibit inhibition of expression of inducible pro-inflammatory proteins such as prostaglandin endoperoxidase synthetase-2, otherwise known as cyclooxygenase-2 (COX-2), and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular, these inflammatory mediators have been implicated in pain, such as in the sensitization of pain receptors, or edema. Accordingly, additional p38 MAPK-mediated conditions which may be prevented or treated include edema, analgesia, fever and pain such as neuromuscular pain, headache, dental pain, arthritis pain and pain caused by cancer.

As a result of their p38 MAPK inhibitory activity, compounds of the invention have utility in the prevention and treatment of diseases associated with cytokine production including but not limited to those diseases associated with TNF, IL-1, IL-6 and IL-8 production.

TNF-mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoidosis, bone resportion disease, reperfusion injury, graft vs host reaction, allograft rejections, fever and myalgias due to infection, cachexia secondary to infection, AIDS, ARC or malignancy, keloid formation, scar tissue formation, Crohn's disease, ulcerative colitis, pyresis, and viral infections such as HIV, CMV, influenza and herpes; veterinary viral infections such as lentivirus infections, including but not limited to equine infectious anemia virus, caprine arthritis virus, visna virus or maedi virus; and retrovirus infections, including feline immunodeficiency virus, bovine immunodeficiency virus and canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF-inhibiting compounds of the invention. Such viruses include, but are not limited to, HIV-1, HIV-2 and HIV-3, Cytomegalovirus (CMV), influenza, adenovirus and the herpes group of viruses such as Herpes zoster and Herpes simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al., *Clin. Infec. Dis.*, 1997, 26, 840; Grunberg et al., *Am. J. Crit. Care Med.*, 1997, 155, 1362; Zhu et al., *J. Clin. Invest.*, 1996, 97, 421]. It has also been demonstrated in vitro that infection of pulmonary epithelial cells (which represent the primary site of infection by HRV) with HRV results in production of IL-6 and IL-8 [Sabauste et al., *J. Clin. Invest.*, 1995, 96, 549]. Therefore, p38 MAPK inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus.

For the prophylaxis or treatment of a p38 MAPK or pro-inflammatory cytokine mediated disease the compounds according to the invention may be administered to a human or mammal as pharmaceutical compositions, and according to a further aspect of the invention there is provided a pharmaceutical composition which comprises a compound of formula (I) in association with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fngicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds according to the invention may be prepared by a process which comprises oxidizing a compound of formula (III):

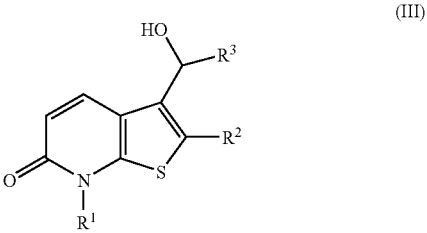

(III)

wherein $R^1$, $R^2$ and $R^3$ are as defined above.

Oxidation of compound (III) may be conveniently carried out by treatment with an oxidizing agent such as manganese dioxide, typically at room temperature in a solvent such as dichloromethane.

The compounds of formula (III) may be prepared by reacting an aldehyde of formula $R^3$—CHO with a compound of formula (IV):

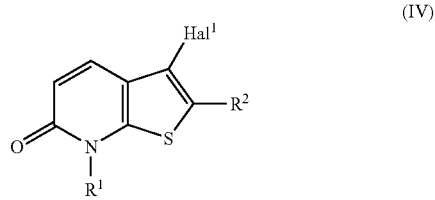

(IV)

wherein $R^1$, $R^2$ and $R^3$ are as defined above, and $Hal^1$ represents a halogen atom, e.g. bromo.

The reaction is conveniently effected by treating compound (IV) with a strong base, e.g. n-butyllithium or tert-butyllithium, followed by addition of the aldehyde of formula R³—CHO, typically in an inert solvent such as tetrahydrofuran.

Alternatively, the compounds according to the invention may be obtained directly from the reaction between R³—CHO and compound (IV) by a process which comprises treating the reactants with a strong base, e.g. sodium hydride, in the presence of 1-ethyl-3-methyl-1H-imidazolium chloride, typically in a dipolar aprotic solvent such as N,N-dimethylformamide.

The intermediates of formula (IV) may be prepared from the corresponding amine of formula (V):

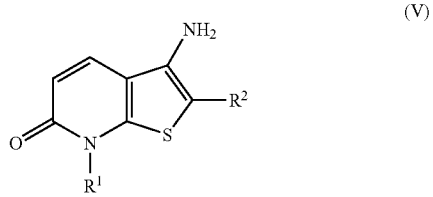

wherein R¹ and R² are as defined above; by diazotisation followed by halogen exchange.

Diazotisation may be conveniently effected by treating compound (V) with a nitrite, e.g. tert-butyl nitrite. Halogen exchange may be conveniently accomplished by reaction with a copper halide, e.g. copper(II) bromide. Advantageously, both procedures may be carried out in situ, typically in an inert solvent such as acetonitrile.

The intermediates of formula (V) wherein R² represents cyano may be prepared by reacting a compound of formula Hal²-CH₂—CN with a compound of formula (VI):

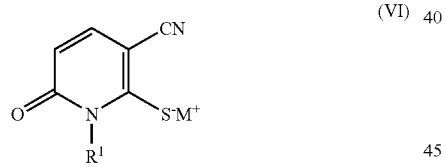

wherein R¹ is as defined above, M⁺ represents an alkali metal cation, and Hal² represents a halogen atom, e.g. chloro.

The alkali metal cation M⁺ is suitably a sodium or potassium cation, especially Na⁺.

The reaction is conveniently performed at an elevated temperature in a suitable solvent, e.g. acetonitrile.

The intermediates of formula (VI) may be prepared by reacting 1,3-dimethyluracil with a compound of formula (VII):

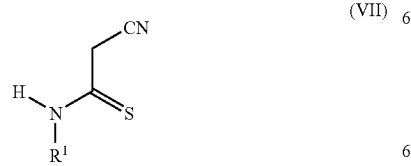

wherein R¹ is as defined above; in the presence of an alkali metal alkoxide MOAlk, in which M is as defined above, and Alk represents $C_{1-6}$ alkyl, e.g. methyl.

The reaction is conveniently effected in a suitable solvent, for example a $C_{1-4}$ alkanol such as methanol or ethanol, or mixtures thereof, at an elevated temperature, for example the reflux temperature of the solvent(s) employed.

In an alternative procedure, the intermediates of formula (IV) wherein R¹ represents optionally substituted aryl or heteroaryl may be prepared by reacting a boronic acid derivative of formula $R^{1a}$—B(OH)₂ with a compound of formula (VIII):

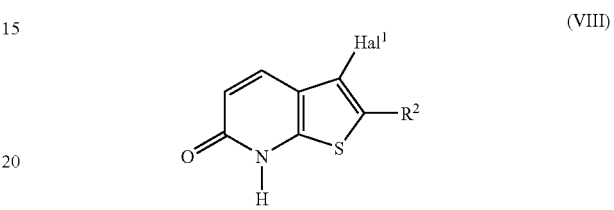

wherein R² and Hal¹ are as defined above, and $R^{1a}$ represents aryl or heteroaryl, which may be optionally substituted by one or more substituents (as defined above for R¹).

The reaction is conveniently accomplished by mixing the reagents with a copper salt, e.g. copper(II) acetate, typically in the presence of pyridine, in a suitable solvent such as dichloromethane.

In a further procedure, the intermediates of formula (IV) wherein R¹ represents optionally substituted ($C_{3-7}$ cycloalkyl)methyl may be prepared by treating a compound of formula (VIII) as defined above with a strong base, e.g. sodium hydride; followed by reaction with a compound of formula L-$R^{1b}$, in which L represents a leaving group, and $R^{1b}$ represents ($C_{3-7}$ cycloalkyl)methyl, which may be optionally substituted by one or more substituents (as defined above for R¹).

The reaction is conveniently effected in a dipolar aprotic solvent, e.g. N,N-dimethylformamide.

The intermediates of formula (VIII) may be prepared by treating a compound of formula (IX):

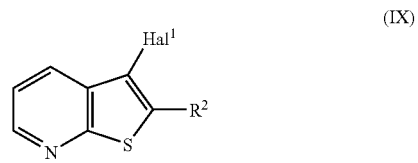

wherein R² and Hal¹ are as defined above; with an oxidising agent; and subsequently rearranging the N-oxide derivative thereby obtained to the required compound of formula (VIII) by treatment with trifluoroacetic anhydride.

The oxidising agent employed to convert compound (IX) to the corresponding N-oxide derivative may suitably be a peracid such as 3-chloroperoxybenzoic acid. The reaction is conveniently accomplished by stirring in a solvent such as dichloromethane, typically at room temperature.

The trifluoroacetic anhydride-mediated rearrangement of the N-oxide derivative to compound (VIII) is conveniently carried out in a dipolar aprotic solvent such as N,N-dimethylformamide, typically at a temperature in the region of 0° C.

The intermediates of formula (IX) may be prepared from the corresponding amine of formula (X):

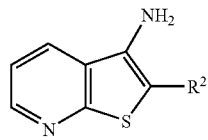

(X)

wherein $R^2$ is as defined above; by diazotisation followed by halogen exchange; under conditions analogous to those described above for the conversion of compound (V) into compound (IV).

The intermediates of formula (X) in which $R^2$ is an electron-withdrawing group, for example cyano or —$CO_2R^a$, may be prepared by reacting 2-chloro-3-cyanopyridine with a compound of formula $R^{2a}$—$CH_2$—SH wherein $R^{2a}$ represents an electron-withdrawing group, e.g. cyano or —$CO_2R^a$, in which $R^a$ is as defined above. The reaction is conveniently effected in the presence of a base such as sodium carbonate, in a suitable solvent, for example a $C_{1-4}$ alkanol such as ethanol, typically at the reflux temperature of the solvent employed.

The compounds according to the invention may also be prepared by a process which comprises hydrolysing a compound of formula (XI):

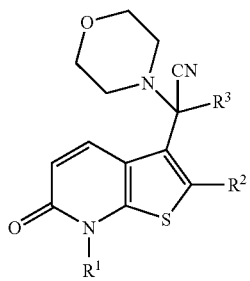

(XI)

wherein $R^1$, $R^2$ and $R^3$ are as defined above.

Hydrolysis of compound (XI) may conveniently be effected at an elevated temperature under acidic conditions, e.g. by treatment with aqueous ethanolic HCl or aqueous acetic acid. Alternatively, hydrolysis may be accomplished by heating in the presence of copper(II) sulphate in a suitable solvent, e.g. aqueous N,N-dimethylformamide.

The intermediates of formula (XI) may be prepared by reacting a compound of formula (IV) as defined above with a compound of formula (XII):

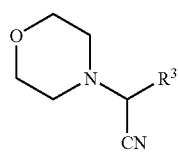

(XII)

wherein $R^3$ is as defined above.

The reaction is conveniently effected in the presence of a strong base, e.g. sodium hydride, typically in a dipolar aprotic solvent such as N,N-dimethylformamide.

The intermediates of formula (XII) may be prepared by the procedure described in *J. Heterocycl. Chem.*, 1978, 15, 881, or by methods analogous thereto.

The compounds according to the invention wherein $R^2$ represents amino (—$NH_2$) may be prepared by a process which comprises reducing a compound of formula (XIII):

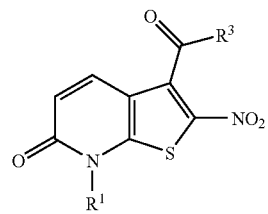

(XIII)

wherein $R^1$ and $R^3$ are as defined above.

As will be appreciated, the compounds of formula (XIII) correspond to compounds of formula (I) as defined above wherein $R^2$ represents nitro.

Reduction of the nitro group in compound (XIII) may conveniently be effected by treatment with iron powder in an acidic medium, e.g. aqueous ethanolic HCl or aqueous acetic acid. Alternatively, the nitro group in compound (XIII) may be reduced by treatment with tin (II) chloride; or by treatment with hydrogen in the presence of a conventional hydrogenation catalyst, e.g. palladium on charcoal.

In an alternative approach, the compounds according to the invention wherein $R^2$ represents —$NR^aR^b$ and at least one of $R^a$ and $R^b$ is other than hydrogen may be prepared directly from the appropriate compound of formula (XIII) as defined above by reaction thereof with the appropriate compound of formula H—$NR^aR^b$. The reaction is conveniently effected at an elevated temperature and pressure, ideally in a microwave apparatus.

The intermediates of formula (XIII) may be prepared by hydrolysing a compound of formula (XIV):

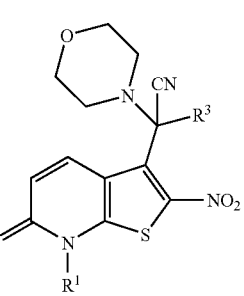

(XIV)

wherein $R^1$ and $R^3$ are as defined above; under conditions analogous to those described above for the hydrolysis of compound (XI).

The intermediates of formula (XIV) may be prepared by reacting a compound of formula (XII) as defined above with a compound of formula (XV):

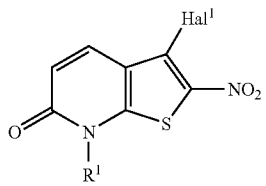

wherein $R^1$ and $Hal^1$ are as defined above; under conditions analogous to those described above for the reaction between compounds (IV) and (XII).

Alternatively, the intermediates of formula (XIII) may be obtained directly by reacting a compound of formula $R^3$—CHO with compound (XV) by a process which comprises treating the reactants with a strong base, e.g. sodium hydride, in the presence of 1-ethyl-3-methyl-1H-imidazolium chloride, typically in a dipolar aprotic solvent such as N,N-dimethylformamide.

The intermediates of formula (XV) may be prepared from the corresponding amine of formula (XVI):

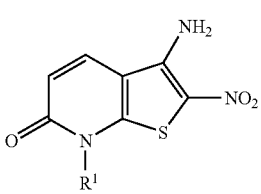

wherein $R^1$ and $R^2$ are as defined above; by diazotisation followed by halogen exchange; under conditions analogous to those described above for the conversion of compound (V) into compound (IV).

The intermediates of formula (XVI) may be prepared by reacting a compound of formula $Hal^3$-$CH_2$—$NO_2$, wherein $Hal^3$ represents a halogen atom, e.g. bromo, with a compound of formula (VI) as defined above. The reaction is conveniently performed at an elevated temperature in a suitable solvent, e.g. acetonitrile, optionally in the presence of a base, e.g. potassium carbonate.

Where they are not commercially available, the starting materials of formula (VII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^2$ represents cyano may be converted into the corresponding compound wherein $R^2$ represents amido (—$CONH_2$) by treatment with a strong base such as sodium hydroxide, typically in refluxing aqueous ethanol. Similarly, a compound of formula (I) wherein $R^2$ represents —$CO_2R^a$, in which $R^a$ is other than hydrogen, may be converted into the corresponding compound in which $R^2$ is carboxy (—$CO_2H$) by treatment with a strong base such as sodium hydroxide, typically in refluxing aqueous ethanol. A compound of formula (I) wherein $R^2$ represents —$CO_2H$ may be decarboxylated to the corresponding compound wherein $R^2$ is hydrogen by treatment with a strong mineral acid, e.g. concentrated hydrochloric acid. A compound of formula (I) wherein $R^2$ represents —$CO_2H$ may be converted into the corresponding compound wherein $R^2$ represents —$CONR^aR^b$ by reaction with an amine of formula H—$NR^aR^b$ in the presence of a condensing agent such as EDC (vide infra), a triazole additive such as HOBT (vide infra) and a morpholine derivative such as NMM (vide infra). A compound of formula (I) wherein $R^2$ represents —$CO_2H$ may be converted into the corresponding compound wherein $R^1$ represents —$NHCO_2R^a$ by treatment with diphenylphosphoryl azide at an elevated temperature in the presence of the requisite alcohol of formula $R^a$—OH and an organic base such as triethylamine. A compound of formula (I) wherein $R^2$ represents tert-butoxycarbonylamino may be converted into the corresponding compound wherein $R^2$ is amino (—$NH_2$) by treatment with a strong organic acid such as trifluoroacetic acid. A compound of formula (I) wherein $R^2$ represents —$NH_2$ may be converted into the corresponding compound wherein $R^2$ represents halogen, e.g. bromo, by diazotisation followed by halogen exchange, under conditions analogous to those described above for the conversion of compound (V) into compound (IV); the resulting halo derivative may in turn be converted into the corresponding compound wherein $R^2$ represents —$NR^aR^b$, in which $R^a$ and/or $R^b$ is other than hydrogen, by reaction with the appropriate amine of formula H—$NR^aR^b$ in the presence of a transition metal catalyst such as tris(dibenzylideneacetone)palladium (0), ideally in the presence of a ligand such as BINAP (vide infra) and a base such as caesium carbonate, typically at an elevated temperature in a suitable solvent, e.g. toluene. A compound of formula (I) wherein $R^2$ represents —$NH_2$ may be converted into the corresponding compound wherein $R^2$ represents —$NHCOR^a$ by reaction with an acid anhydride of formula $(R^aCO)_2O$, suitably in the presence of an acylation catalyst such as 4-dimethylaminopyridine. Alternatively, a compound of formula (I) wherein $R^2$ represents —$NH_2$ may be converted into the corresponding compound wherein $R^2$ represents —$NHCOR^a$ by reaction with a carboxylic acid of formula $R^aCO_2H$ in the presence of a condensing agent such as EDC, a triazole additive such as HOBT and a morpholine derivative such as NMM. A compound of formula (I) wherein $R^2$ represents —$NH_2$ may be converted into the corresponding compound wherein $R^2$ represents —NHCOCl by treatment with phosgene, typically in the presence of an organic amine such as triethylamine; the resulting compound may in turn be converted into the corresponding compound wherein $R^2$ represents —$NHCONR^aR^b$ by reaction with the appropriate amine of formula H—$NR^aR^b$. Similarly, a compound of formula (I) wherein $R^2$ represents —$NH_2$ may be converted into the corresponding compound wherein $R^2$ represents —NHCOCl by treatment with phosgene, as before; the resulting compound may in turn be converted into the corresponding compound wherein $R^2$ represents —$NHCONHNHSO_2R^a$ by reaction with the appropriate hydrazine derivative of formula $R^aSO_2NHNH_2$. A compound of formula (I) wherein $R^2$ represents tert-butoxycarbonylamino may be converted into the corresponding compound wherein $R^2$ represents —$N(SO_2R^a)[CO_2C(CH_3)_3]$ by treatment with a strong base, e.g. sodium bis(trimethylsilyl)amide, and then with the appropriate sulphonyl halide derivative, for instance a sulphonyl chloride derivative of formula $R^aSO_2Cl$; the resulting compound may in turn be converted into the corresponding compound wherein $R^2$ represents —$NHSO_2R^a$ by deprotection using a strong organic acid such as trifluoroacetic acid. A compound of formula (I) wherein $R^2$ incorporates a primary or secondary amine moiety may be alkylated on the amino nitrogen atom by treatment with paraformaldehyde or a $C_{1-6}$ alkyl aldehyde, e.g. acetaldehyde, or a ketone, e.g. acetone, in the presence of a reducing agent such as sodium cyanoborohydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed, J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the invention. All temperatures are in ° C. The following abbreviations are used:

NMM—N-methylmorpholine;
EtOAc—ethyl acetate;
MeOH—methanol;
BOC—tert-butoxycarbonyl;
DCM—dichloromethane;
AcOH—acetic acid;
DMF—N,N-dimethylformamide;
EtOH—ethanol;
DMSO—dimethylsulphoxide;
iPr—isopropyl;
Et$_2$O—diethyl ether;
Me—methyl;
THF—tetrahydrofuran;
h—hour;
MCPBA—3-chloroperoxybenzoic acid;
r.t.—room temperature;
EDC—1-[3-(dimethylamino)propyl]-3-ethylcarbodiimide hydrochloride;

HOBT—1-hydroxybenzotriazole hydrate;
BINAP—2,2'-bis(diphenylphosphino)-1,1'-binaphthyl;
m.p.—melting point;
aq—aqueous;
sat.—saturated;
DMAP—4-(dimethylamino)pyridine;
EDTA—ethylenediaminetetraacetic acid, disodium salt.

All NMRs were obtained either at 300 MHz or 400 MHz.

Compounds were named with the aid of ACD Labs Name (v. 6.0) supplied by Advanced Chemical Development, Toronto, Canada.

LCMS retention times (RT) quoted were generated on a Hewlett Packard 1100 LC/MS using the following method: Phenomenex Luna 3μ C$_{18}$(2) 50×4.6 mm column; mobile phase A=0.1% formic acid in water; mobile phase B=0.1% formic acid in MeCN; flow rate of 0.9 mlmin$^{-1}$; column temperature 40° C.

Gradient:

| Time (min) | % B |
|---|---|
| Initial | 5 |
| 2.0 | 95 |
| 3.0 | 95 |
| 5.0 | 5 |
| 5.5 | end |

Where stated alternative LCMS conditions (Conditions B) were used: LCMS retention times (RT) quoted were generated on a Hewlett Packard 1100/ThermoFinnigan LCQ Duo LC/MS system using Electrospray ionisation and the following LC method: Phenomenex Luna 5μ C$_{18}$(2) 100×4.6 mm column; mobile phase A=0.08% formic acid in water; mobile phase B=0.08% formic acid in MeCN; flow rate of 3.0 mlmin$^{-1}$; column temperature 35° C.

Gradient:

| Time (min) | % B |
|---|---|
| 0.00 | 5 |
| 4.40 | 95 |
| 5.30 | 95 |
| 5.32 | 5 |
| 6.50 | 5 |

INTERMEDIATE 1

Ethyl 3-aminothieno[2,3-b]pyridine-2-carboxylate

A mixture of 2-chloro-3-cyanopyridine (330 g, 2.38 mol), ethyl 2-mercaptoacetate (361.2 g, 3.01 mol), sodium carbonate (265 g, 2.5 mol) and EtOH (1.2 l) was heated to reflux for 4.5 h. The reaction mixture was then cooled to ambient temperature and added to water (15 l). The resulting slurry was stirred for 0.5 h then filtered. The filter cake was washed with two portions of water (2×2.5 l). The solids were then dried to constant weight under vacuum at 45° C. to yield the title compound as a brown solid (493 g, 93%). $\delta_H$ (CDCl$_3$) 8.68 (1H, dd, J 4.7, 1.2 Hz), 7.93 (1H, dd, J 8.5, 1.2 Hz), 7.29 (1H, dd, J 8.5, 4.7 Hz), 5.90 (2H, br), 4.38 (2H, q, J 7.0 Hz), 1.40 (3H, t, J 7.0 Hz). LCMS RT 2.9 minutes, 223 (M+H)$^+$.

INTERMEDIATE 2

Ethyl 3-bromothieno[2,3-b]pyridine-2-carboxylate

Intermediate 1 (363.6 g, 1.64 mol) was added in portions over two hours to a mixture of copper(II) bromide (403.3 g, 1.81 mol), tert-butyl nitrite (220.6 g, 2.15 mol) and acetonitrile (3.6 l) with stirring and maintaining a temperature of between 20 and 25° C. The mixture was then stirred at 20° C. for 2 hours before it was slowly added to 2M HCl(aq) (4.2 l). The reaction mixture slurry was filtered and the solids were washed with water (500 ml). The combined filtrate was extracted with ethyl acetate (8 l) and this ethyl acetate solution was washed with 2M HCl(aq) (2.2 l). The filtered solids were also dissolved in ethyl acetate (6 l) and this solution was washed twice with 2M HCl(aq) (4.4 l and 2.2 l). The combined ethyl acetate solutions were washed with 2M HCl(aq) (2.2 l) and water (2×2l), dried (MgSO$_4$), filtered and concentrated in vacuo to give a solid residue. This was broken up and dried to constant weight under vacuum at 45° C. to yield the title compound as a brown solid (458.5 g, 98%). $\delta_H$ (DMSO-d$_6$) 8.89 (1H, d, J 4.7 Hz), 8.47 (1H, d, J 8.6 Hz), 7.71 (1H, dd, J 8.6, 4.7 Hz), 4.46 (2H, q, J 7.2 Hz), 1.40 (3H, t, J 7.2 Hz). LCMS RT 3.8 minutes, 288 (M+H)$^+$.

INTERMEDIATE 3

Ethyl 3-bromothieno[2,3-b]pyridine-2-carboxylate N-oxide

MCPBA (240 g @ 70%=168 g, 0.97 mol) was added portionwise over 0.5 h to a slurry of Intermediate 2 (214 g, 0.747 mol) in DCM (2140 ml) under nitrogen and the mixture then stirred at room temperature for 18 h. The reaction mixture was quenched with water (800 ml) and pH adjusted to 8.5 with 10% w/v sodium carbonate solution (1250 ml). The basic aqueous layer was removed and the organic layer washed with water until pH 7. The organic layer was concentrated in vacuo and the crude title product was recovered as a tan solid. The crude product was purified by slurrying in tert-butyl methyl ether (600 ml) for 1 h at 0-5° C. to give the title compound (174 g, 77%). $\delta_H$ (CDCl$_3$) 8.44 (1H, dd, J 6.2, 0.8 Hz), 7.87 (1H, dd, J 8.3, 0.8 Hz), 7.48 (1H, dd, J 8.3, 6.2 Hz), 4.49 (2H, q, J 7.1 Hz), 1.48 (3H, t, J 7.1 Hz). LCMS (ES$^+$) RT 2.61 minutes, 302 (M+H)$^+$.

INTERMEDIATE 4

Ethyl 3-bromo-6-oxo-6,7-dihydrothieno[2,3-b]pyridine-2-carboxylate

Trifluoroacetic anhydride (3.49 g, 2.36 ml, 16.6 mmol) was added to a mixture of Intermediate 3 (500 mg, 1.66 mmol) and DMF (10 ml) at 0° C. under nitrogen. After stirring for 16 h the volatiles were removed in vacuo and the residue co-evaporated with toluene (2×20 ml). The crude material was then extracted with EtOAc (2×100 ml). The EtOAc extracts were dried (MgSO$_4$) and concentrated in vacuo. The crude product was purified by slurrying in toluene (10 ml) to give the title compound as a beige solid (260 mg, 52%). $\delta_H$ (DMSO-d$_6$) 12.20 (1H, br s), 7.75 (1H, d, J 9.0 Hz), 6.50 (1H, d, J 9.0 Hz), 4.15 (2H, q, J 7.1 Hz), 1.12 (3H, t, J 7.1 Hz). LCMS (ES$^+$) RT 2.86 minutes, 302 (M+H)$^+$.

INTERMEDIATE 5

Ethyl 3-bromo-6-oxo-7-phenyl-6,7-dihydrothieno[2,3-b]pyridine-2-carboxylate

A mixture of Intermediate 4 (302 mg, 1.00 mmol), copper (II) acetate (278 mg, 1.50 mmol), phenylboronic acid (488 mg, 4.00 mmol), DCM (5 ml) and pyridine (158 mg, 2.00 mmol) was stirred at room temperature for 18 h with the exclusion of moisture. The reaction was then diluted with DCM (50 ml), washed with 2M HCl(aq) (50 ml) and the aqueous re-extracted with DCM (50 ml). The combined organics were then washed with water (50 ml), dried (MgSO$_4$) and concentrated in vacuo. The crude product was purified by trituration with MeOH (12 ml), to give the title compound as a beige solid (270 mg, 72%). $\delta_H$ (CDCl$_3$) 7.82 (1H, d, J 8.5 Hz), 7.70-7.62 (3H, m), 7.54-7.42 (2H, m), 6.70 (1H, d, J 8.5 Hz), 4.15 (2H, q, J 7.1 Hz), 1.14 (3H, t, J 7.1 Hz). LCMS (ES$^+$) RT 3.75 minutes, 378 (M+H)$^+$. m.p. 201.6-206.0° C.

INTERMEDIATE 6

Sodium 3-cyano-6-oxo-1-phenyl-1,6-dihydropyridine-2-thiolate

A solution of sodium methoxide in MeOH (30 wt %, 202.2 g) was added to absolute EtOH (360 ml) followed by 1,3-dimethyluracil (75 g) and 2-cyano-N-phenyl-thioacetamide (Adhikari et al., *Australian J. Chem.*, 1999, 52, 63-67) (90 g). The resulting mixture was heated at reflux for 8 h and then allowed to cool to ambient temperature overnight. The reaction mixture was then cooled to +5° C. and maintained at this temperature for at least an hour when the product was recovered by filtration. The filter cake was washed with cold (+5° C.) absolute ethanol (450 ml) and then dried to constant weight under vacuum at 45° C. to give the title compound as a pale pink solid (130.0 g). The product thus obtained contained residual EtOH and MeOH, estimated at 12.2 wt % by $^1$H NMR, corresponding to a corrected yield of 114.1 g. $\delta_H$ (DMSO-d$_6$) 7.32 (2H, m), 7.27-7.18 (1H, m), 7.16 (1H, d, J 9.1 Hz), 6.92 (2H, m), 5.63 (1H, d, J 9.1 Hz). LCMS (Conditions B) (ES$^+$) RT 2.43 minutes, 229 (M+H)$^+$.

INTERMEDIATE 7

3-Amino-6-oxo-7-phenyl-6,7-dihydrothieno[2,3-b]pyridine-2-carbonitrile

A mixture of Intermediate 6 (100 g, 0.4 mol) and chloroacetonitrile (30.4 ml, 0.48 mol) in acetonitrile (500 ml) was heated at reflux for 2 h. The mixture was cooled, initially to 40° C. when water (300 ml) was added, and then to +10° C. The reaction was maintained at +10° C. for at least 1 h, then the product was recovered by filtration. The filter cake was washed with cold (+10° C.) water (500 ml) followed by a cold (+10° C.) mixture of acetonitrile and water (1:1, 300 ml). The product was dried under vacuum at 50° C. to constant weight to give the title compound as an off-white solid (100.9 g, 94%). $\delta_H$ (DMSO-d$_6$) 7.90 (1H, d, J 9.6 Hz), 7.46-7.33 (3H, m), 7.25 (2H, m), 6.95 (2H, br s), 6.35 (1H, d, J 9.6 Hz). LCMS (Conditions B) (ES+) RT 2.69 minutes, 268 (M+H)+.

INTERMEDIATE 8

3-Bromo-6-oxo-7-phenyl-6,7-dihydrothieno[2,3-b]pyridine-2-carbonitrile

Intermediate 7 (20 g, 75 mmol) was added portionwise to a mixture of anhydrous copper(II) bromide (23.4 g, 105 mmol) and tert-butyl nitrite (14.8 ml, 125 mmol) in acetonitrile (600 ml) at room temperature at such a rate as to keep the internal temperature below 25° C. The addition took approximately 1 hour. After a further 0.5 h the reaction mixture was poured onto 1M HCl (500 ml) and the mixture extracted with dichloromethane (2×400 ml). The combined organic extracts were then washed with 1M HCl (3×300 ml), dried (MgSO$_4$) and evaporated in vacuo. The resulting crude product was then recrystallised from methyl isobutyl ketone (700 ml). The product was dried under vacuum at 50° C. to constant weight to give the title compound as a light brown solid (15.14 g, 61%). $\delta_H$ (CDCl$_3$) 7.75 (1H, d, J 8.5 Hz), 7.55-7.70 (3H, m), 7.35 (2H, m), 6.80 (1H, d, J 8.5 Hz). LCMS (Conditions B) (ES+) RT 3.54 minutes, no parent ion observed.

INTERMEDIATE 9

Ethyl 3-bromo-7-(cyclopropylmethyl)-6-oxo-6,7-dihydrothieno[2,3-b]pyridine-2-carboxylate Sodium hydride (60% in mineral oil, 3.27 g, 81.4 mmol) was added in portions to a solution of Intermediate 4 (22.3 g, 74 mmol) in DMF (300 ml) at 0° C. The mixture was stirred at r.t. for 30 minutes then cyclopropylmethyl bromide (10 g, 74 mmol) was added slowly. On complete addition the mixture was heated at 60° C. overnight. The reaction was cooled to r.t., DMF was removed in vacuo and the residue partitioned between EtOAc and brine. The organic phase was dried (MgSO$_4$) and concentrated in vacuo. Purification by column chromatography (silica, 0% to 10% EtOAc in DCM) gave the title compound as a yellow solid (12.5 g, 47%). $\delta_H$ (CDCl$_3$) 7.57 (1H, d, J 9.5 Hz), 6.47 (1H, d, J 9.5 Hz), 4.22 (2H, q, J 7.0 Hz), 3.87 (2H, d, J 7.1 Hz), 1.26-1.19 (4H, m), 0.43-0.37 (4H, m). LCMS (ES+) RT 3.80 minutes, 357 (M+H)+.

INTERMEDIATE 10

3-Amino-7-(2-chlorophenyl)-6-oxo-6,7-dihydrothieno[2,3-b]pyridine-2-carbonitrile Acetonitrile (10 ml) was added to a solution of sodium bis(trimethylsilyl)amide (100 ml, 1.0M in THF, 100 mmol) in THF (50 ml) at −78° C. to give a thick white precipitate. 2-Chlorophenyl isothiocyanate (7.72 g, 45.45 mmol) was added to give a brown solution. The mixture was allowed to warm to r.t. over 1 h then diluted with EtOH (50 ml). 1,3-Dimethyluracil (6.4 g, 45 mmol) was added and the mixture heated at reflux for 24 h. Volatiles were removed in vacuo and the residue dissolved in acetonitrile (100 ml). Chloroacetonitrile (2.85 ml, 45 mmol) was added and the mixture heated at 50° C. for 1 h, a second charge of chloroacetonitrile (2.85 ml, 45 mmol) was added and heating continued for 1.5 h. Some of the acetonitrile (~50 ml) was removed in vacuo and water was added to precipitate the product. The brown solid was filtered off, washed with water (50 ml) and Et$_2$O (50 ml) and dried to give the title compound as a brown solid (14.3 g, quantitative). $\delta_H$ (DMSO-d$_6$) 8.10 (1H, d, J 9.7 Hz), 7.75-7.73 (1H, m), 7.65-7.54 (3H, m), 7.14 (2H, br s, Hz), 6.54 (1H, d, J 9.7 Hz). LCMS (ES+) RT 2.97 minutes, 302 (M+H)+.

INTERMEDIATE 11

3-Bromo-7-(2-chlorophenyl)-6-oxo-6,7-dihydrothieno[2,3-b]pyridine-2-carbonitrile Intermediate 10 (1.17 g, 3.88 mmol) was suspended in acetonitrile (20 ml). Copper(II) bromide (953 mg, 4.27 mmol) was added, followed by tert-butyl nitrite (0.64 ml, 5.43 mmol). The mixture was stirred at r.t. for 3 h then partitioned between 2M HCl(aq) (100 ml) and EtOAc (100 ml). The organic layer was washed with 2M HCl(aq) (50 ml), 2M NaOH(aq) (50 ml) and water (25 ml), dried (Na$_2$SO$_4$) and concentrated in vacuo. Purification by column chromatography (silica, 0 to 5% EtOAc in DCM) gave the title compound as a pale brown solid (980 mg, 67%). $\delta_H$ (CDCl$_3$) 7.70 (1H, d, J 9.7 Hz), 7.61 (1H, dd, J 1.7, 7.7 Hz), 7.52-7.44 (2H, m), 7.34 (1H, dd, J 1.7, 7.7 Hz), 6.70 (1H, d, J 9.7 Hz). LCMS (ES+) RT 3.56 minutes, 365 (M+H)+.

INTERMEDIATE 12

Ethyl 3-[hydroxy(3-methylphenyl methyl]-6-oxo-7-phenyl-6,7-dihydrothieno[2,3-b]pyridine-2-carboxylate A solution of Intermediate 5 (5.0 g, 13.0 mmol) in THF (500 ml) was cooled to −110° C. under nitrogen and n-BuLi (6.4 ml of a 2.5M solution in hexanes, 16 mmol) was added slowly. A solution of 3-methylbenzaldehyde (2.38 g, 20 mmol) in THF (5 ml) was added, the reaction mixture was warmed to −50° C. and NaHCO$_3$(aq) (500 ml) added. The mixture was extracted with DCM (3×100 ml). The combined organic extracts were dried (MgSO$_4$) and concentrated in vacuo. The crude product was purified by chromatography (silica, 0-30% EtOAc in DCM) to give the title compound as a light tan solid (2.84 g, 52%). $\delta_H$ (CDCl$_3$) 7.86 (1H, d, J 9.8 Hz), 7.56-7.47 (3H, m), 7.33 (2H, d, J 7.1 Hz), 7.18-7.11 (4H, m), 7.02 (1H, d, J 7.1 Hz), 6.57 (1H, s), 6.53 (1H, d, J 9.8 Hz), 4.20 (2H, q, J 7.1 Hz), 2.28 (3H, s), 1.21 (3H, t, J 7.1 Hz). LCMS (ES+) RT 3.61 minutes, 420 (M+H)+.

INTERMEDIATE 13

3-[Hydroxy(3-methylphenyl)methyl]-6-oxo-7-phenyl-6,7-dihydrothieno[2,3-b]pyridine-2-carbonitrile Intermediate 8 (520 mg, 1.57 mmol) was dissolved in THF (30 ml) and cooled to −100° C. n-BuLi (0.70 ml of 2.5M solution in hexanes, 1.7 mmol) was added dropwise. The red solution was stirred at −100° C. for 30 minutes before the addition of a solution of 3-methylbenzaldehyde (0.28 ml, 2.34 mmol) in THF (10 ml). The reaction mixture was allowed to warm to −30° C. before addition of water (50 ml). The aqueous layer was extracted with DCM (2×100 ml) and the combined organic extracts dried (MgSO$_4$) and concentrated in vacuo. The crude product was purified by chromatography (silica, 10-20% EtOAc in DCM) to give the title compound as a white solid (163 mg, 28%). $\delta_H$ (CDCl$_3$) 7.90 (1H, d, J 9.7 Hz), 7.55-7.45 (3H, m), 7.30-7.18 (5H, m), 7.05

(1H, m), 6.51 (1H, d, J 9.7 Hz), 6.13 (1H, d, J 3.2 Hz), 2.96 (1H, d, J 3.2 Hz), 2.11 (3H, s). LCMS (ES$^+$) RT 3.38 minutes, 373 (M+H)$^+$.

INTERMEDIATE 14

2-Bromo-3-(3-methylbenzoyl)-7-phenylthieno[2,3-b]pyridin-6(7H)-one

Example 4 (700 mg, 1.94 mmol) was dissolved in acetonitrile (10 ml). Copper(II) bromide (499 mg, 2.14 mmol) was added to the reaction mixture at r.t., followed by dropwise addition of a solution of tert-butyl nitrite (0.28 ml, 2.3 mmol) in acetonitrile (5 ml). The solution was stirred for 4 h and then poured into 2M HCl(aq) (100 ml). The aqueous layer was extracted with DCM (2×100 ml) and the combined organic layers combined, dried (MgSO$_4$) and the solvent removed in vacuo. The crude product was partially purified by chromatography on silica (0-20% EtOAc in DCM) to give the title compound as a brown solid (250 mg of 75% pure material by LC, 23% yield). RT 4.83 minutes. This intermediate was typically used without further purification in subsequent reactions.

INTERMEDIATE 15

Ethyl 3-[hydroxy(phenyl)methyl]-6-oxo-7-phenyl-6,7-dihydrothieno[2,3-b]pyridine-2-carboxylate From Intermediate 5 and benzaldehyde by the method of Intermediate 12. Off-white solid. $\delta_H$ (CDCl$_3$) 7.96 (1H, d, J 10 Hz), 7.52-7.70 (3H, m), 7.25-7.50 (7H, m), 6.69 (1H, s), 6.62 (1H, d, J 10 Hz), 4.29 (2H, q, J 7 Hz), 1.36 (3H, t, J 7 Hz). LCMS (ES$^+$) RT 3.56 minutes, 406 (+H)$^+$.

INTERMEDIATE 16 tert-Butyl(3-benzoyl-6-oxo-7-phenyl-6,7-dihydrothieno[2,3-b]pyridin-2-yl)(methylsulfonyl)carbamate A solution of Example 12 (100 mg, 0.22 mmol) in THF (5 ml) was cooled to −78° C. under nitrogen and sodium bis(trimethylsilyl)amide (0.24 ml of a 1.0M solution in THF, 0.24 mmol) was added slowly. The reaction mixture was warmed to r.t., methanesulphonyl chloride (0.25 mg, 0.22 mmol) was added, and the mixture stirred at r.t. for 18 h. 2M HCl(aq) (10 ml) was added, and the mixture was extracted with DCM (3×10 ml). The combined organic extracts were dried (MgSO$_4$) and concentrated in vacuo. The crude product was taken on to the next step. LCMS (ES$^+$) RT 3.59 minutes, 525 (M+H)$^+$.

INTERMEDIATE 17 tert-Butyl[3-(3-methylbenzoyl)-6-oxo-7-phenyl-6,7-dihydrothieno[2,3-b]pyridin-2-yl](methylsulfonyl)carbamate From Example 3 by the method of Intermediate 16. Dark yellow solid. LCMS (ES) RT 3.75 minutes, 539 (M+H)$^+$.

INTERMEDIATE 18

Benzyl 3-[({[3-(3-methylbenzoyl)-6-oxo-7-phenyl-6,7-dihydrothieno[2,3-b]pyridin-2-yl]amino}carbonyl)amino]pyrrolidine-1-carboxylate From Example 4 and 3-aminopyrrolidine 1-carboxylic acid benzyl ester (242 mg, 1.1 mmol), by the method of Example 20, to give the title compound as a yellow solid (258 mg, 77%). LCMS (ES$^+$) RT 3.66 minutes, 607 (M+H)$^+$.

INTERMEDIATE 19

3-[Hydroxy(phenyl methyl]-6-oxo-7-phenyl-6,7-dihydrothieno[2,3-b]pyridine-2-carbonitrile Intermediate 8 (520 mg, 1.57 mmol) was dissolved in THF (30 ml) and cooled to −100° C. n-BuLi (2.5M in hexanes, 0.75 ml, 1.9 mmol) was added dropwise with the internal temperature kept below −95° C. The red solution was stirred at −100° C. for 30 minutes before the addition of a solution of benzaldehyde (0.24 ml, 2.4 mmol) in THF (10 ml). The reaction mixture was allowed to warm to room temperature before addition of water (50 ml). The aqueous layer was extracted with DCM (2×100 ml) and the combined organic extracts dried (MgSO$_4$) and concentrated in vacuo. The crude product was purified by chromatography on silica (10-20% EtOAc in DCM) to give the title compound as a white solid (140 mg, 25%). $\delta_H$ (CDCl$_3$) 7.90 (1H, d, J 9.8 Hz), 7.57-7.23 (10H, m), 6.52 (1H, d, J 9.8 Hz), 6.18 (1H, d, J 3.7 Hz), 2.89 (1H, br s). LCMS (ES$^+$) RT 3.24 minutes, 359 (M+H)$^+$.

INTERMEDIATE 20

Ethyl 7-(cyclopropylmethyl)-3-[hydroxy(phenyl)methyl]-6-oxo-6,7-dihydrothieno[2,3-b]pyridine-2-carboxylate A solution of Intermediate 9 (1.0 g, 2.81 mmol), and benzaldehyde (0.45 ml, 4.22 mmol) in anhydrous THF (100 ml) under nitrogen was cooled to −78° C. tert-Butyllithium (3.47 ml, 1.7M in pentane, 5.9 mmol) was added dropwise and the red solution allowed to stir at −78° C. for one hour. The solution was allowed to warm to −10° C. before the reaction was quenched by the addition of 10% aqueous ammonium chloride solution (250 ml). The mixture was extracted with DCM (3×100 ml), the organics washed with brine (2×200 ml), dried (MgSO$_4$), filtered and the solvents removed in vacuo. The crude residue was purified by chromatography on silica (0-15% EtOAc in DCM) to give the title compound as an off-white solid (452 mg, 42%). $\delta_H$ (CDCl$_3$) 7.77 (1H, d, J 9.7 Hz), 7.34-7.32 (2H, m), 7.28-7.22 (2H, m), 7.20-7.17 (1H, m), 6.57 (1H, d, J 8.1 Hz), 6.44 (1H, d, J 9.7 Hz), 4.63 (1H, d, J 8.1 Hz), 4.33-4.22 (2H, m), 3.97 (2H, d, J 7.2 Hz), 1.35-1.28 (1H, m), 1.31 (3H, t, J 7.1 Hz), 0.54-0.48 (4H, m). LCMS (ES$^+$) RT 3.59 minutes, 384 (M+H)$^+$.

INTERMEDIATE 21

7-(2-Chlorophenyl)-3-[hydroxy(phenyl)methyl]-6-oxo-6,7-dihydrothieno[2,3-b]pyridine 2-carbonitrile From Intermediate 11 (5 g, 13.7 mmol) and benzaldehyde (2.1 ml, 21 mmol) by the method of Intermediate 13. White solid (363 mg, 7%). $\delta_H$ (CDCl$_3$) 7.90 (1H, d, J 9.8 Hz), 7.60-7.58 (1H, m), 7.49-7.41 (4H, m), 7.37-7.27 (4H, m), 6.52 (1H, d, J 9.8 Hz), 6.19 (1H, s). LCMS (ES$^+$) RT 3.73 minutes, 393 (M+H)$^+$.

INTERMEDIATE 22

3-[(3-Chlorophenyl)(hydroxy)methyl]-6-oxo-7-phenyl-6,7-dihydrothieno[2,3-b]pyridine-2-carbonitrile From Intermediate 8 (250 mg, 0.75 mmol) and 3-chlorobenzaldehyde (0.12 ml, 1.13 mmol) by the method of Intermediate 13. White solid (224 mg, 76%). $\delta_H$ (CDCl$_3$) 7.83 (1H, d, J 9.8 Hz), 7.55-7.46 (4H, m), 7.38 (1H, s) 7.28-7.20 (5H, m), 6.48 (1H, d, J 9.8 Hz), 6.06 (1H, s). LCMS (ES$^+$) RT 3.48 minutes, 393 (M+H)$^+$.

INTERMEDIATE 23

3-(3-Chlorobenzoyl)-6-oxo-7-phenyl-6,7-dihydrothieno[2,3-b]pyridine-2-carbonitrile From Intermediate 22 (224 mg, 0.57 mmol) and manganese(IV)oxide (191 mg, 2.2 mmol) by the method of Example 5. White solid (53 mg, 24%). $\delta_H$ (CDCl$_3$) 7.82-7.81 (1H, m), 7.73-7.68 (2H, m), 7.62-7.52 (4H, m) 7.43 (1H, t, J 7.9 Hz), 7.37-7.34 (2H, m), 6.66 (1H, d, J 9.8 Hz). LCMS (ES$^+$) RT 3.67 minutes, 391 (M+H)$^+$.

INTERMEDIATE 24

Ethyl 3-[(3-chlorophenyl)(hydroxy)methyl]-6-oxo-7-phenyl-6,7-dihydrothieno[2,3-b]pyridine-2-carboxylate From Intermediate 5 (5.0 g, 13 mmol) and 3-chlorobenzaldehyde (1.7 ml, 15 mmol) by the method of Intermediate 12 to give the title compound as an off-white solid (1.8 g, 40%). $\delta_H$(MeOD-d$_3$) 8.02 (1H, d, J 9.7 Hz), 7.48-7.38 (3H, m), 7.31 (1H, s), 7.23-7.16 (3H, m), 7.10-7.00 (2H, m), 6.83 (1H, s), 6.29 (1H, d, J 9.7 Hz), 4.09 (2H, q, J 7.1 Hz), 1.07 (3H, t, J 7.1 Hz). LCMS (ES$^+$) RT 3.70 minutes, 440 (M+H)$^+$.

INTERMEDIATE 25

3-[(2,4-Difluorophenyl)(hydroxy)methyl]-6-oxo-7-phenyl-6,7-dihydrothieno[2,3-b]pyridine-2-carbonitrile From Intermediate 8 (250 mg, 0.75 mmol) and 2,4-difluorobenzaldehyde (0.12 ml, 1.13 mmol) by the method of Intermediate 13. White solid (41 mg, 14%). $\delta_H$ (CDCl$_3$) 7.84 (1H, d, J 9.7 Hz), 7.56-7.28 (9H, m), 6.56 (1H, d, J 9.7 Hz), 6.36 (1H, br s). LCMS (ES$^+$) RT 3.30 minutes, 395 (M+H)$^+$.

INTERMEDIATE 26

3-(2,4-Difluorobenzoyl)-6-oxo-7-phenyl-6,7-dihydrothieno[2,3-b]pyridine-2-carbonitrile From Intermediate 25 (41 mg, 0.10 mmol) and manganese(IV) oxide (41 mg, 0.47 mmol) by the method of Example 5. White solid (14 mg, 36%). $\delta_H$ (CDCl$_3$) 7.95 (1H, d, J 9.8 Hz), 7.75-7.70 (1H, m), 7.60-7.51 (3H, m), 7.37-7.34 (2H, m), 7.04-6.99 (1H, m), 6.91-6.85 (1H, m), 6.70 (1H, d, J 9.8 Hz). LCMS (ES$^+$) RT 3.55 minutes, 393 (M+H)$^+$.

INTERMEDIATE 27

3-[(4-Fluoro-3-methylphenyl)(hydroxy)methyl]-6-oxo-7-phenyl-6,7-dihydrothieno[2,3-b]pyridine-2-carbonitrile From Intermediate 8 (250 mg, 0.75 mmol) and 4-fluoro-3-methylbenzaldehyde (0.14 ml, 1.13 mmol) by the method of Intermediate 13. White solid (138 mg, 47%). $\delta_H$ (CDCl$_3$) 7.87 (1H, d, J 9.8 Hz), 7.57-7.41 (3H, m), 7.30-7.28 (2H, m), 7.23-7.19 (3H, m), 6.96 (1H, t, J 8.8 Hz), 6.53 (1H, d, J 9.7 Hz), 6.13 (1H, s), 2.22 (3H, s). LCMS (ES$^+$) RT 3.46 minutes, 391 (M+H)$^+$.

INTERMEDIATE 28

3-(4-Fluoro-3-methylbenzoyl)-6-oxo-7-phenyl-6,7-dihydrothieno[2,3-b]pyridine-2-carbonitrile From Intermediate 27 (138 mg, 0.35 mmol) and manganese(IV) oxide (138 mg, 1.6 mmol) by the method of Example 5. White solid (89 mg, 65%). $\delta_H$ (CDCl$_3$) 7.75-7.51 (6H, m), 7.37-7.34 (2H, m), 7.08 (1H, t, J 8.8 Hz), 6.64 (1H, d, J 9.7 Hz), 2.29 (3H, s). LCMS (ES$^+$) RT 3.68 minutes, 389 (M+H)$^+$.

INTERMEDIATE 29

Ethyl 3-[(4-fluoro-3-methylphenyl)(hydroxy)methyl]-6-oxo-7-phenyl-6,7-dihydrothieno[2,3-b]pyridine-2-carboxylate From Intermediate 5 and 4-fluoro-3-methylbenzaldehyde by the method of Intermediate 12. LC RT 3.58 minutes.

INTERMEDIATE 30

3-[(3-Chloro-4-fluorophenyl)(hydroxy)methyl]-6-oxo-7-phenyl-6,7-dihydrothieno[2,3-b]pyridine-2-carbonitrile From Intermediate 8 (250 mg, 0.75 mmol) and 3-chloro-4-fluorobenzaldehyde (179 mg, 1.13 mmol) by the method of Intermediate 13. White solid (182 mg, 59%). LCMS (ES$^+$) RT 3.64 minutes, 411 (M+H)$^+$.

INTERMEDIATE 31

3-(3-Chloro-4-fluorobenzoyl)-6-oxo-7-phenyl-6,7-dihydrothieno[2,3-b]pyridine-2-carbonitrile From Intermediate 30 (182 mg, 0.44 mmol) and manganese(I) oxide (182 mg, 2.1 mmol) by the method of Example 5. White solid (22 mg, 12%). $\delta_H$ (CDCl$_3$) 7.94 (1H, dd, J 2.2, 6.9 Hz), 7.76-7.72 (2H, m), 7.61-7.54 (3H, m), 7.37-7.35 (2H, m), 7.25 (1H, t, J 8.4 Hz), 6.68 (1H, d, J 9.7 Hz). LCMS (ES$^+$) RT 3.71 minutes, 409 (M+H)$^+$.

INTERMEDIATE 32

Ethyl 3-[hydroxy(6-methylpyridin-2-yl)methyl]-6-oxo-7-phenyl-6,7-dihydrothieno[2,3-b]pyridine-2-carboxylate From Intermediate 5 (5.0 g, 13.3 mmol) and 6-methyl-2-pyridinecarboxaldehyde (2.42 g, 2.0 mmol) by the method of Intermediate 12. White solid (2.30 g, 42%). $\delta_H$ (CDCl$_3$) 7.82

(1H, d, J 9.8 Hz), 7.51-7.46 (4H, m), 7.29 (2H, m), 7.02 (2H, t, J 7.0 Hz), 6.89 (1H, s), 6.41 (1H, d, J 9.8 Hz), 6.01 (1H, br s), 4.32-4.19 (2H, m), 2.57 (3H, s), 1.25 (3H, t, J 7.0 Hz). LCMS (ES$^+$) RT 2.86 minutes, 421 (M+H)$^+$.

INTERMEDIATE 33

Ethyl 3-[(6-methylpyridin-2-yl)carbonyl]-6-oxo-7-phenyl-6,7-dihydrothieno[2,3-b]pyridine-2-carboxylate From Intermediate 32 (2.30 g, 5.5 mmol) and manganese (IV) oxide (2.30 g, 26 mmol) by the method of Example 1. White solid (1.80 g, 79%) $\delta_H$ (CDCl$_3$) 7.95 (1H, d, J 7.6 Hz), 7.72 (1H, t, J 7.6 Hz), 7.58-7.48 (4H, m), 7.40-7.32 (2H, m), 7.26 (1H, d, J 7.6 Hz), 6.58 (1H, d, J 9.7 Hz), 3.91 (2H, q, J 7.1 Hz), 2.43 (3H, s), 0.89 (3H, t, J 7.1 Hz). LCMS (ES$^+$) RT 3.51 minutes, 419 (M+H)$^+$.

INTERMEDIATE 34

3-[(6-Methylpyridin-2-yl)carbonyl]-6-oxo-7-phenyl-6,7-dihydrothieno[2,3-b]pyridine-2-carboxylic acid From Intermediate 33 (2.30 g, 5.5 mmol) and 0.25M sodium hydroxide(aq) (17 ml, 4.3 mmol) by the method of Example 2. White solid. $\delta_H$ (DMSO-d$_6$) 7.89 (1H, t, J 7.7 Hz), 7.82-0.78 (1H, m), 7.73-7.61 (3H, m), 7.59-7.52 (3H, m), 7.46 (1H, d, J 7.4 Hz), 6.49 (1H, d, J 9.5 Hz), 2.49 (3H, s). LCMS (ES$^+$) RT 2.86 minutes, 391 (M+1)$^+$.

INTERMEDIATE 35 tert-Butyl{3-[(6-methylpyridin-2-yl)carbonyl]-6-oxo-7-phenyl-6,7-dihydrothieno[2,3-b]pyridin-2-yl}carbamate From Intermediate 34 (1.67 g, 4.3 mmol) and diphenylphosphoryl azide (1.3 g, 4.7 mmol) by the method of Example 3. Yellow solid (1.15 g, 58%). $\delta_H$ (CDCl$_3$) 12.35 (1H, s), 7.83-7.75 (2H, m), 7.53-7.44 (3H, m), 7.37-7.23 (3H, m), 7.26 (1H, d, J 9.8 Hz), 6.41 (1H, d, J 9.8 Hz), 2.58 (3H, s), 1.43 (9H, s). LCMS (ES$^+$) RT 4.00 minutes, 462 (M+H)$^+$.

INTERMEDIATE 36

3-Benzoyl-2-bromo-7-phenylthieno[2,3-b]pyridin-6 (7H)-one

A suspension of Example 13 (2.84 g, 8.20 mmol) in acetonitrile (50 ml) at 0° C. was treated with tert-butyl nitrite (1.50 ml, 12.3 mmol). The suspension was diluted with a mixture of acetonitrile and THF (40 ml, 1:1 mixture) and was stirred at 0° C. for 10 minutes, followed by slow addition of copper(II) bromide (2.20 g, 9.84 mmol) in minimal acetonitrile. The reaction was stirred at 0° C. for 5 minutes. The reaction was quenched by addition of 2M HCl(aq) (200 ml) and the aqueous extracted with DCM (2×200 ml). The combined organic extracts were washed with brine, dried (MgSO$_4$) and concentrated in vacuo. Purification by column chromatography (silica, 2-40% EtOAc in DCM) gave the title compound as an orange-brown solid (140 mg, 4%). $\delta_H$ (CDCl$_3$) 9.85 (2H, d, J 7.6 Hz), 7.36-7.62 (9H, m), 6.53 (1H, d, J 9.6 Hz). LCMS (ES$^+$) RT 3.70 minutes, 410 $^{79}$Br(M+H)$^+$ and 412 $^{81}$Br(M+H)$^+$.

INTERMEDIATE 37

Ethyl 3-{hydroxy[3-(trifluoromethyl)phenyl]methyl}-6-oxo-7-phenyl-6,7-dihydrothieno[2,3-b]pyridine-2-carboxylate From Intermediate 5 (5.0 g, 13.2 mmol), n-BuLi (5.8 ml of 2.5 M in hexanes, 14.5 mmol) and 3-(trifluoromethyl)benzaldehyde (1.9 ml, 14.5 mmol) in THF (450 ml) by the method of Intermediate 12. The crude product was purified by chromatography (silica, 5 -20% EtOAc in DCM) to give the title compound as a white solid (4.02 g, 64%). $\delta_H$ (CDCl$_3$) 7.83 (1H, d, J 9.8 Hz), 7.70 (1H, s), 7.58-7.47 (5H, m), 7.41-7.33 (3H, m), 6.65 (1H, d, J 7.9 Hz), 6.55 (1H, d, J 9.8 Hz), 4.48 (2H, d, J 7.9 Hz), 4.21 (1H, q, J 7.1 Hz), 1.21 (3H, t, J 7.1 Hz). LCMS (ES$^+$) RT 3.83 minutes, 474 (M+H)$^+$.

INTERMEDIATE 38

Ethyl 6-oxo-7-phenyl-3-[3-(trifluoromethyl)benzoyl]-6,7-dihydrothieno[2,3-b]pyridine-2-carboxylate From Intermediate 37 (3.90 g, 7.61 mmol) and activated manganese(IV) oxide (6.0 g, 69.0 mmol) in DCM (50 ml) by the method of Example 1. The crude product was purified by chromatography (silica, 5-10% EtOAc in DCM) to give the title compound as an off-white solid (3.28 g, 84%). $\delta_H$ (CDCl$_3$) 8.12 (1H, s), 7.97 (1H, d, J 7.3 Hz), 7.81 (1H, d, J 7.3 Hz), 7.61-7.54 (4H, m), 7.44-7.38 (3H, m), 6.58 (1H, d, J 9.7 Hz), 3.99 (2H, q, J 7.1 Hz), 0.92 (3H, t, J 7.1 Hz). LCMS (ES$^+$) RT 3.98 minutes, 472 (M+H)$^+$.

INTERMEDIATE 39

6-Oxo-7-phenyl-3-[3-(trifluoromethyl)benzoyl]-6,7-dihydrothieno[2,3-b]pyridine-2-carboxylic acid From Intermediate 38 (3.30 g, 7.02 mmol) and 1M NaOH (aq) (10 ml, 10 mmol) in ethanol/water (50 ml/10 ml) by the method of Example 2. Filtration gave the title compound as a white solid (2.97 g, 95%). $\delta_H$ (CDCl$_3$) 8.19 (1H, s), 8.13-8.06 (1H, m), 7.81-7.86 (1H, m), 7.75-7.61 (7H, m), 6.59 (1H, d, J 9.6 Hz). LCMS (ES$^+$) RT 3.36 minutes, 444 (M+H)$^+$.

INTERMEDIATE 40 tert-Butyl{6-oxo-7-phenyl-3-[3-(trifluoromethyl) benzoyl]-6,7-dihydrothieno[2,3-b]pyridin-2-yl}carbamate From Intermediate 39 (2.97 g, 6.70 mmol), diphenylphosphoryl azide (1.59 ml, 7.37 mmol) and triethylamine (1.03 ml, 7.37 mmol) in 2-methyl-2-propanol (100 ml) by the method of Example 3. The crude product was purified by chromatography (Silica, 2-12% EtOAc in DCM) to give the title compound as a yellow solid (3.18 g, 92%). $\delta_H$ (CDCl$_3$) 8.10-7.98 (3H, m), 7.84-7.69 (4H, m), 7.56 (2H, d, J 6.7 Hz), 6.94 (1H, d, J 9.7 Hz), 6.54 (1H, d, J 9.7 Hz), 1.65 (9H, s). LCMS (ES$^+$) RT 4.68 minutes, 515 (M+H)$^+$.

INTERMEDIATE 41 tert-Butyl 4-[({6-oxo-7-phenyl-3-[3-(trifluoromethyl)benzoyl]-6,7-dihydrothieno[2,3-b]pyridin-2-yl}amino)carbonyl]piperidine-1-carboxylate A mixture of Example 57 (500 mg, 1.13 mmol), NMM (0.87 ml, 7.9 mmol), HOBT (410 mg, 3.03 mmol), EDC (581 mg, 3.03 mmol) and BOC-isonipecotic acid (694 mg, 3.03 mmol) in DMF (8 ml) was heated at 80° C. for 3 days. The reaction was cooled and partitioned between NaHCO$_3$ (aq) and DCM, the organic phase washed with 2M HCl (aq), dried (MgSO$_4$) and concentrated in vacuo. The crude product was purified by chromatography (silica, 10% EtOAc in DCM) to give the title compound as a yellow solid (780 mg, 94%). LCMS (ES$^+$) RT 4.46 minutes, 626 (M+1)$^+$.

INTERMEDIATE 42 tert-Butyl 4-({[3-(3-chlorobenzoyl)-6-oxo-7-phenyl-6,7-dihydrothieno[2,3-b]pyridin-2-yl]amino}carbonyl)piperidine-1-carboxylate From Example 45 (170 mg, 0.48 mmol), NMM (0.32 ml, 2.9 mmol), HOBT (148 mg, 1.10 mmol), EDC (210 mg, 1.10 mmol) and BOC-isonipecotic acid (252 mg, 1.10 mmol) in DMF (4 ml) by the method of Intermediate 41. The cmde product was purified by chromatography (silica, 10% EtOAc in DCM) to give the title compound as a yellow solid (210 mg, 72%). LCMS (ES$^+$) RT 4.43 minutes, 592 (M+H)$^+$.

INTERMEDIATE 43 tert-Butyl 3-[(3-benzoyl-6-oxo-7-phenyl-6,7-dihydrothieno[2,3-b]pyridin-2-yl)amino]piperidine-1-carboxylate From Intermediate 36 (800 mg, 1.9 mmol) and 3-amino-1-N—BOC-piperidine following the method of Example 55. The title compound was obtained as a yellow solid (237 mg, 22%). LCMS (ES$^+$) RT 3.81 minutes, 530 (M+H)$^+$.

INTERMEDIATE 44 tert-Butyl 3-[(3-benzoyl-6-oxo-7-phenyl-6,7-dihydrothieno[2,3-b]pyridin-2-yl)amino]azetidine-1-carboxylate From Intermediate 36 (930 mg, 2.2 mmol) and 3-aminoazetidine-1-carboxylic acid tert-butyl ester (460 mg, 2.7 mmol) by the method of Example 55. The title compound was obtained as a yellow solid. $\delta_H$ (DMSO-d$_6$) 9.30 (1H, br m), 7.66-7.60 (8H, m), 7.56-7.55 (2H, m), 6.34 (1H, d, J 9.8 Hz), 6.24 (1H, d, J 9.7 Hz), 4.16-4.09 (1H, m), 4.09-4.02 (2H, m), 3.85-3.84 (2H, m), 1.36 (9H, s). LCMS (ES$^+$) RT 3.64 minutes, 502 (M+H)$^+$.

INTERMEDIATE 45

3-Amino-2-nitro-7-phenylthieno[2,3-b]pyridin-6(7H)-one

A mixture of Intermediate 6 (2.09 g, 8 mmol) and bromonitromethane (1.16 ml, 16 mmol) in acetonitrile (40 ml) was heated at 40° C. for 2 h. Water (20 ml) was added to the solution and the mixture was cooled in an ice bath. The precipitate was filtered off and dried in vacuo to give the title compound as a yellow solid (1.22 g, 53%). $\delta_H$ (DMSO-d$_6$) 8.86 (2H, br s), 8.25 (1H, d, J 9.7 Hz), 7.66-7.59 (3H, m), 7.52-7.50 (2H, m), 6.60 (1H, d, J 9.7 Hz). LCMS (ES$^+$) RT 2.69 minutes, 288 (M+H)$^+$.

INTERMEDIATE 46

3-Bromo-2-nitro-7-phenylthieno[2,3-b]pyridin-6(7H)-one

From Intermediate 45 (1.19 g, 4.0 mmol) and tert-butyl nitrite (577 mg, 5.6 mmol), by the method of Intermediate 8, to give the title compound as a yellow solid (974 mg, 69%). $\delta_H$ (CDCl$_3$) 7.78 (1H, d, J 9.8 Hz), 7.58-7.54 (3H, m), 7.33-7.30 (2H, m), 6.73 (1H, d, J 9.8 Hz). LCMS (ES$^+$) RT 3.53 minutes, 353 (M+H)$^+$.

INTERMEDIATE 47

3-(3-Methoxybenzoyl)-2-nitro-7-phenylthieno[2,3-b]pyridine-6(7H)-one

A mixture of (3-methoxyphenyl)(morpholin-4-yl)acetonitrile (*J. Heterocycl. Chem.*, 1978, 15, 881) (1.0 g, 3.9 mmol) and sodium hydride (256 mg of 60% in mineral oil, 6.4 mmol) was stirred in DMF (10 ml) at r.t. for 1 h. The reaction was cooled to 0° C. and a solution of Intermediate 46 (1.15 g, 3.2 mmol) in DMF (30 ml) was added dropwise. The reaction was stirred at r.t. for 3 h. The mixture was poured onto iced water (100 ml) containing AcOH (10 ml). The precipitate was filtered off, and the filtrate was extracted with DCM (2×200 ml), dried (MgSO$_4$), and concentrated in vacuo. The solid and concentrated filtrate were combined and dried in vacuo. The crude product was suspended in EtOH (40 ml) and 2M HCl (aq) (40 ml) and the reaction was heated to reflux for 4 h. The mixture was poured onto iced water and the precipitate was filtered off and dried in vacuo. The crude product was purified by chromatography (silica, 0-5% EtOAc in DCM) to give the title compound as a yellow solid (500 mg, 32%). $\delta_H$ (CDCl$_3$) 7.72-7.63 (3H, m), 7.55-7.54 (1H, m), 7.49-7.36 (5H, m), 7.25-7.22 (1H, m), 6.71 (1H, d, J 9.7 Hz), 3.92 (3H, s). LCMS (ES$^+$) RT 3.62 minutes, 407 (M+H)$^+$.

INTERMEDIATE 48

3-(2-Chlorobenzoyl)-2-nitro-7-phenylthieno[2,3-b]pyridin-6(7H)-one

From (2-chlorophenyl)(morpholin-4-yl)acetonitrile (*J. Heterocycl. Chem.*, 1978, 15, 881) (1.0 g, 3.8 mmol) and Intermediate 46 (1.12 g, 3.2 mmol) by the method of Intermediate 47 to give the title compound as a yellow solid (311 mg, 31%). $\delta_H$ (CDCl$_3$) 7.84-7.47 (10H, m), 6.71 (1H, d, J 9.8 Hz). LCMS (ES$^+$) RT 3.72 minutes, 412 (M+H)$^+$.

INTERMEDIATE 49

(3-Chloro-4-fluorophenyl)(morpholin-4-yl)(2-nitro-6-oxo-7-phenyl-6,7-dihydrothieno[2,3-b]pyridin-3-yl)acetonitrile A mixture of (3-chloro-4-fluorophenyl)(morpholin-4-yl)acetonitrile (*J. Heterocycl. Chem.*, 1978, 15, 881) (700 mg, 2.75 mmol) and sodium hydride (183 mg of ~60% in mineral oil, 4.58 mmol) was stirred in DMF (10 ml) at r.t. for 1 h. The reaction was cooled to 0° C. and a solution of Intermediate 46 (806 mg, 2.29 mmol) in DMF (10 ml) was added dropwise.

The reaction was stirred at r.t. for 3 h. The mixture was poured onto iced water (100 ml) containing AcOH (10 ml). The precipitate was filtered off, and the filtrate was extracted with DCM (2×200 ml), dried (MgSO$_4$), and concentrated in vacuo. The solid obtained and concentrated filtrate were combined and dried in vacuo. The crude product was purified by chromatography (silica, 0-10% EtOAc in DCM) to give the title compound as a yellow solid (456 mg, 38%). LCMS (ES$^+$) RT 3.89 minutes, 525 (M+M)$^+$.

INTERMEDIATE 50

3-Cyano(morpholin-4-yl)(2-nitro-6-oxo-7-phenyl-6, 7-dihydrothieno[2,3-b]pyridin-3-yl)methyl]benzonitrile From (3-cyanophenyl)(morpholin-4-yl)acetonitrile (*J. Heterocycl. Chem.*, 1978, 15, 881) (830 mg, 3.65 mmol) and Intermediate 46 (1.06 g, 3.04 mmol) by the method of Intermediate 49. The title compound was obtained as a yellow solid (523 mg, 24%). LCMS (ES$^+$) RT 3.52 minutes, 498 (M+H)$^+$.

INTERMEDIATE 51

(2-Fluorophenyl)(morpholin-4-yl)(2-nitro-6-oxo-7-phenyl-6,7-dihydrothieno[2,3-b]pyridin-3-yl)acetonitrile From (2-fluorophenyl)(morpholin-4-yl)acetonitrile (*J. Heterocycl. Chem.*, 1978, 15, 881) (785 mg, 3.2 mmol) and Intermediate 46 (947 mg, 2.7 mmol) by the method of Intermediate 49. The title compound was obtained as a yellow solid (949 mg, 71%). LCMS (ES$^+$) RT 3.57 minutes, 491 (M+H)$^+$.

INTERMEDIATE 52

(4-Chlorophenyl)(morpholin-4-yl)(2-nitro-6-oxo-7-phenyl-6,7-dihydrothieno[2,3-b]pyridin-3-yl)acetonitrile From (4-chlorophenyl)(morpholin-4-yl)acetonitrile (*J. Heterocycl. Chem.*, 1978, 15, 881) (698 mg, 2.7 mmol) and Intermediate 46 (791 g, 2.2 mmol) by the method of Intermediate 49. The title compound was obtained as a yellow solid (692 mg, 62%). LCMS (ES$^+$) RT 3.90 minutes, 507 (M+H)$^+$.

INTERMEDIATE 53

(4-Fluorophenyl)(morpholin-4-yl)(2-nitro-6-oxo-7-phenyl-6,7-dihydrothieno[2,3-b]pyridin-3-yl)acetonitrile From (4-fluorophenyl)(morpholin-4-yl)acetonitrile (*J. Heterocycl. Chem.*, 1978, 15, 881) (1.0 g, 4.1 mmol) and Intermediate 46 (1.21 g, 3.4 mmol) by the method of Intermediate 49. The title compound was obtained as a yellow solid (633 mg, 38%). LCMS (ES$^+$) RT 3.64 minutes, 491 (M+H)$^+$.

INTERMEDIATE 54

(3-Bromophenyl)(morpholin-4-yl)(2-nitro-6-oxo-7-phenyl-6,7-dihydrothieno[2,3-b]pyridin-3-yl)acetonitrile From (3-bromophenyl)(morpholin-4-yl)acetonitrile (*J. Heterocycl. Chem.*, 1978, 15, 881) (1.0 g, 3.0 mmol) and Intermediate 46 (965 mg, 2.7 mmol) by the method of Example 49. The title compound was obtained as a yellow solid (692 mg, 46%). LCMS (ES$^+$) RT 3.83 minutes, 555 (+H)$^+$.

INTERMEDIATE 55

3-(2,4-Difluorobenzoyl)-2-nitro-7-phenylthieno[2,3-b]pyridin-6(7H)-one

From Intermediate 46 and (2,4-difluorophenyl)(morpholin-4-yl)acetonitrile (*J. Heterocycl. Chem.*, 1978, 15, 881) by the method of Intermediate 47 to give the title compound as a yellow solid. δ$_H$ (DMSO-d$_6$) 8.06 (1H, dt, J 6.4, 8.6 Hz), 7.65-7.53 (3H, m), 7.43 (1H, d, J 9.7 Hz), 7.40-7.35 (2H, m), 7.03 (1H, dt, J 2.3, 8.6 Hz), 6.80 (1H, dq, J 2.3, 8.5 Hz), 6.64 (1H, d, J 9.7 Hz). LC RT 3.74 minutes.

INTERMEDIATE 56

3-(3,4-Dimethylbenzoyl)-2-nitro-7-phenylthieno[2,3-b]pyridin-6(7R)-one

Intermediate 46 (1.37 g, 3.9 mmol) and 3,4-dimethylbenzaldehyde (0.65 g, 5.0 mmol) were dissolved in DMF (20 ml). 1-Ethyl-3-methyl-1H-imidazolium chloride (114 mg, 0.7 mmol) and sodium hydride (261 mg of a 60% suspension in mineral oil, 6.5 mmol) were added and the solution stirred at r.t. for 2 h. The solution was poured onto ice and 2M HCl (aq) (20 ml) and extracted with DCM (2×200 ml). The organic layers were combined, washed with brine (2×200 ml), dried (MgSO$_4$), and the solvent removed in vacuo. The crude product was purified by chromatography (silica, 0-5% EtOAc in DCM) to give the title compound as a yellow solid (565 mg, 36%). δ$_H$ DMSO-d$_6$) 7.76-7.57 (8H, m), 7.36 (1H, d, J 7.8 Hz), 6.64 (1H, d, J 9.7 Hz), 2.33 (3H, s), 2.31 (3H, s). LCMS (ES$^+$) RT 3.82 minutes, 405 (M+H)$^+$.

INTERMEDIATE 57

3-(2-Methoxybenzoyl)-2-nitro-7-phenylthieno[2,3-b]pyridin-6(7H)-one

From Intermediate 46 and 2-methoxybenzaldehyde by the method of Intermediate 56. The title compound was obtained a yellow solid. δ$_H$ (DMSO-d$_6$) 7.93 (1H, dd, J 1.9, 7.8 Hz), 7.75-7.65 (7H, m), 7.22-7.15 (2H, m), 6.66 (1H, d, J 9.7 Hz), 3.68 (3H, s).

INTERMEDIATE 58

2-[(2-Nitro-6-oxo-7-phenyl-6,7-dihydrothieno[2,3-b]pyridin-3-yl)carbonyl]benzonitrile From Intermediate 46 and 2-cyanobenzaldehyde by the method of Intermediate 56. The title compound was obtained as a yellow solid. δ$_H$ (DMSO-d$_6$) 8.18 (1H, d, J 7.5 Hz), 7.97-7.57 (9H, m), 6.72 (1H, d, J 9.7 Hz).

INTERMEDIATE 59

Ethyl 3-bromo-6-oxo-7-(pyridin-3-yl)-6,7-dihydrothieno[2,3-b]pyridine-2-carboxylate Intermediate 4 (6.13 g, 20.3 mmol), 3-pyridylboronic acid (5 g, 40.7 mmol) and copper(II) acetate (3.68 g, 20.3 mmol) were suspended in DCM (300 ml) and pyridine (9.64 g, 122 mmol) added. The mixture was allowed to stir for seven days with an air purge through the reaction mixture. The reaction was diluted with DCM (500 ml), and washed with successive portions of copper(II) sulphate (aq), EDTA (aq) and brine (×3). The organic phase was dried (MgSO$_4$), filtered and the solvents removed in vacuo. The crude was purified by column chromatography (silica, 0-50% EtOAc in DCM) to give the title compound as a white solid (657 mg, 8.5%). $\delta_H$ (CDCl$_3$) 8.84 (1H, dd, J 1.5, 4.8 Hz), 8.73 (1H, d, J 2.0 Hz), 7.89 (1H, d, J 9.7 Hz), 7.83-7.79 (1H, m), 7.62-7.58 (1H, m), 6.75 (1H, d, J 9.7 Hz), 4.35 (2H, q, J 7.1 Hz), 1.36 (3H, t, J 7.1 Hz). LCMS (ES$^+$) RT 3.17 minutes, 380 (M+H, Br$^{79}$)$^+$, 382 (M+H, Br$^{81}$)$^+$.

INTERMEDIATE 60

Ethyl 3-[hydroxy(phenyl)methyl]-6-oxo-7-(pyridin-3-yl)-6,7-dihydrothieno[2,3-b]pyridine-2-carboxylate A solution of Intermediate 59 (500 mg, 1.32 mmol) and benzaldehyde (212 mg, 2.0 mmol) in dry THF (50 ml) was cooled to −78° C. under nitrogen. tert-Butyllithium (1.55 ml, 1.7 M solution in pentane, 2.64 mmol) was added dropwise and the resultant mixture allowed to stir at −78° C. for 3 h. The reaction was warmed to −15° C. for 1 h before quenching by addition of sat. ammonium chloride (aq) (200 ml). The mixture was extracted with EtOAc (3×150 ml). The combined organic fractions were washed with brine, dried (MgSO$_4$), filtered and the solvents removed in vacuo. The crude residue was purified by column chromatography (silica, 10-20% EtOAc in DCM) to give the title compound as an off-white solid (325 mg, 61%). LCMS (ES$^+$) RT 2.74 minutes, 407 (M+H)$^+$.

INTERMEDIATE 61

Ethyl 3-benzoyl-6-oxo-7-(pyridin-3-yl)-6,7-dihydrothieno[2,3-b]pyridine-2-carboxylate Intermediate 60 (300 mg, 0.74 mmol) was dissolved in DCM and activated manganese(IV) oxide (500 mg) added. The mixture was stirred at r.t. for 18 h. The reaction mixture was filtered and the solvents removed in vacuo. The crude was purified by column chromatography (silica, 30% EtOAc in DCM) to give the title compound as a white solid (65 mg, 22%). $\delta_H$ (CDCl$_3$) 8.87 (1H, dd, J 1.5, 5.0 Hz), 8.80 (1H, d, j 2.1 Hz), 7.94-7.85 (3H, m), 7.70-7.60 (2H, m), 7.56-7.50 (3H, m), 6.65 (1H, d, J 9.7 Hz), 4.09 (2H, q, J 7.1 Hz), 1.01 (3H, t, J 7.1 Hz). LCMS (ES$^+$) RT 2.90 minutes, 405 (M+H)$^+$.

INTERMEDIATE 62 tert-Butyl[3-benzoyl-6-oxo-7-(pyridin-3-yl)-6,7-dihydrothieno[2,3-b]pyridin-2-yl]carbamate Intermediate 61 (65 mg, 0.16 mmol), 0.275M NaOH (aq) (0.6 ml, 0.17 mmol) and EtOH (5 ml) were heated at 60° C. for 4 h. LC analysis confirmed hydrolysis of the ester (single peak at 2.77 minutes RT). The solvents were removed in vacuo and the crude residue suspended in 2-methyl-2-propanol (10 ml). Diphenylphosphoryl azide (50 mg, 0.18 mmol) and triethylamine (0.026 ml, 0.18 mmol) were added and the mixture heated to 90° C. for 4 h. The reaction was cooled to r.t. and the volatiles removed in vacuo. The title compound was used in the subsequent deprotection without further purification. LCMS (ES$^+$) RT 3.68 minutes, 448 (M+H)$^+$.

INTERMEDIATE 63

Ethyl 3-bromo-7-(4-methylphenyl-6-oxo-6,7-dihydrothieno[2,3-b]pyridine-2-carboxylate From Intermediate 4 and 4-methylphenylboronic acid by the method of Intermediate 5. $\delta_H$ (CDCl$_3$) 7.85 (1H, d, J 9.6 Hz), 7.51-7.48 (1H, m), 7.38-7.27 (1H, m), 7.29 (2H, br m), 6.75 (1H, d, J 9.6 Hz), 4.34 (2H, q, J 7.1 Hz), 2.46 (3H, s), 1.35 (3H, t, J 7.1 Hz). LCMS (ES$^+$) RT 3.865 minutes, 393 (M+H)$^+$.

INTERMEDIATE 64

Ethyl 3-[hydroxy(phenyl)methyl]-7-(4-methylphenyl)-6-oxo-6,7-dihydrothieno[2,3-b]pyridine-2-carboxylate From Intermediate 63 (5 g, 12.7 mmol) and benzaldehyde (1.92 ml, 19 mmol) by the method of Intermediate 12 to give the title compound as a white solid (1.28 g, 24%). LCMS (ES$^+$) RT 3.75 minutes, 420 (M+H)$^+$.

INTERMEDIATE 65

Ethyl 3-benzoyl-7-(4-methylphenyl)-6-oxo-6,7-dihydrothieno[2,3-b]pyridine-2-carboxylate From Intermediate 64 (1.28 g, 3.05 mmol) and activated manganese(IV) oxide (1.28 g of ~85%, 12.9 mmol) by the method of Example 1 to give the title compound as a white solid (237 mg, 19%). LCMS (ES$^+$) RT 3.94 minutes, 418 (M+M)$^+$.

INTERMEDIATE 66

3-Benzoyl-7-(4-methylphenyl)-6-oxo-6,7-dihydrothieno[2,3-b]pyridine-2-carboxylic acid From Intermediate 65 (237 mg, 0.56 mmol) and 0.25M NaOH (aq) (2.27 ml, 0.56 mmol) by the method of Example 2 to give the title compound as a white solid (145 mg, 68%). $\delta_H$ (DMSO-d$_6$) 7.92-7.89 (2H, m), 7.78 (1H, t, J 7.4 Hz), 7.66-7.53 (7H, m), 6.59 (1H, d, J 9.6 Hz), 2.51 (3H, s). LCMS (ES$^+$) RT 3.33 minutes, 390 (M+H)$^+$.

INTERMEDIATE 67 tert-Butyl[3-benzoyl-7-(4-methylphenyl)-6-oxo-6,7-dihydrothieno[2,3-b]pyridin-2-yl]carbamate From Intermediate 66 (145 mg, 0.37 mmol) and diphenylphosphoryl azide (112 mg, 0.41 mmol) by the method of Example 3 to give the title compound as a yellow solid (80 mg, 47%). $\delta_H$ (CDCl$_3$) 10.65 (1H, s), 7.59-7.53 (3H, m), 7.44 (2H, t, J 7.7 Hz), 7.30 (2H, d, J 8.2 Hz), 7.20 (2H, d, J 8.2 Hz), 6.77 (1H, d, J 9.7 Hz), 6.30 (1H, d, J 9.7 Hz), 2.37 (3H, s), 1.42 (9H, s). LCMS (ES$^+$) RT 4.86 minutes, 461 (M+H)$^+$.

INTERMEDIATE 68

2-Nitro-7-phenyl-3-[4-(trifluoromethyl)benzoyl]thieno[2,3-b]pyridin-6(7H)-one

From Intermediate 46 (2.0 g, 5.7 mmol) and α,α,α-trifluoro-p-tolualdehyde (1.21 g, 7.0 mmol) by the method of Intermediate 56 to give the title compound as a yellow solid (929 mg, 37%). $\delta_H$ (DMSO-$d_6$) 8.18 (2H, d, J 8.1 Hz), 7.98 (2H, d, J 8.3 Hz), 7.75-7.64 (6H, m), 6.68 (1H, d, J 9.7 Hz). LCMS (ES$^+$) RT 3.89 minutes, 445 (M+H)$^+$.

INTERMEDIATE 69

4-[(2-Nitro-6-oxo-7-phenyl-6,7-dihydrothieno[2,3-b]pyridine-3-yl)carbonyl]benzonitrile From Intermediate 46 (2.0 g, 5.7 mmol) and 4-cyanobenzaldehyde (890 mg, 6.8 mmol) by the method of Intermediate 56 to give the title compound as a yellow solid (1.5 g, 66%). $\delta_H$ (DMSO-$d_6$) 8.44-8.00 (4H, m), 7.75-7.65 (6H, m), 6.68 (1H, d, J 9.7 Hz).

INTERMEDIATE 70

3-(4-Methoxybenzoyl)-2-nitro-7-phenylthieno[2,3-b]pyridin-6(7H)-one

From Intermediate 46 (2.0 g, 5.7 mmol) and 4-methoxybenzaldehyde (930 mg, 6.8 mmol) by the method of Intermediate 56 to give the title compound as a yellow solid (600 mg, 26%).

INTERMEDIATE 71

2-Nitro-7-phenyl-3-[4-(trifluoromethoxy)benzoyl]thieno[2,3-b]pyridin-6(7H)-one

From Intermediate 46 (2.0 g, 5.7 mmol) and 4-trifluoromethoxybenzaldehyde (1.33 g, 7.0 mmol) by the method of Intermediate 56 to give the title compound as a yellow solid (1.47 g, 57%). $\delta_H$ (DMSO-4) 8.12 (2H, d, J 8.8 Hz), 7.72-7.58 (7H, m), 7.49 (1H, d, J 8.1 Hz), 6.67 (1H, d, J 9.7 Hz). LCMS (ES$^+$) RT 3.90 minutes, 461 (M+H)$^+$.

INTERMEDIATE 72

3-(2-Methylbenzoyl)-2-nitro-7-phenylthieno[2,3-b]pyridin-6(7H)-one

From Intermediate 46 (2.0 g, 5.7 mmol) and o-tolualdehyde (841 mg, 7.0 mmol) by the method of Intermediate 56 to give the title compound as a yellow solid (530 mg, 24%). $\delta_H$ (DMSO-$d_6$) 7.74-7.59 (8H, m), 7.49 (1H, d, J 7.8 Hz), 7.33 (1H, t, J 7.7 Hz), 6.78 (1H, d, J 9.7 Hz), 2.71 (3H, s). LCMS (ES$^+$) RT 3.75 minutes, 391 (M+H)$^+$.

INTERMEDIATE 73

3-(4-Methylbenzoyl)-2-nitro-7-phenylthieno[2,3-b]pyridin-6(7H)-one

From Intermediate 46 (2.0 g, 5.7 mmol) and p-tolualdehyde (841 mg, 7.0 mmol) by the method of Intermediate 56 to give the title compound as a yellow solid (681 mg, 31%). $\delta_H$ (DMSO-$d_6$) 7.85 (2H, d, J 8.1 Hz), 7.74-7.59 (6H, m), 7.42 (2H, d, J 8.1 Hz), 6.65 (1H, d, J 9.7 Hz), 2.43 (3H, s). LCMS (ES$^+$) RT 3.71 minutes, 391 (M+H)$^+$.

INTERMEDIATE 74

2-Nitro-7-phenyl-3-[2-(trifluoromethyl)benzoyl]thieno[2,3-b]pyridin-6(7H)-one

From Intermediate 46 (2.0 g, 5.7 mmol) and 2-trifluoromethylbenzaldehyde (1.21 g, 7.0 mmol) by the method of Intermediate 56 to give the title compound as a yellow solid (1.01 g, 41%). LCMS (ES$^+$) RT 3.72 minutes, 445 (M+1)$^+$.

INTERMEDIATE 75

3-[3-(Difluoromethoxy)benzoyl]-2-nitro-7-phenylthieno[2,3-b]pyridin-6(7H)-one

From Intermediate 46 (2.0 g, 5.7 mmol) and 3-difluoromethoxybenzaldehyde (1.2 g, 6.8 mmol) by the method of Intermediate 56 to give the title compound as a yellow solid (800 mg, 32%). $\delta_H$ DMSO-$d_6$) 7.82-7.58 (10H, m), 7.41 (1H, t, J 73.6 Hz), 6.67 (1H, d, J 9.7 Hz). LCMS (ES$^+$) RT 3.61 minutes, 443 (M+H)$^+$.

INTERMEDIATE 76

2-Nitro-7-phenyl-3-(2-thienylcarbonyl)thieno[2,3-b]pyridin-6(7H)-one

From Intermediate 46 (2.04 g, 5.8 mmol) and (2-thienyl)(morpholin-4-yl)-acetonitrile (1.45 g, 6.9 mmol) by the method of Intermediate 47 to give the title compound as a yellow solid (559 mg, 25%). LCMS (ES$^+$) RT 3.48 minutes, 383 (M+H)$^+$.

INTERMEDIATE 77

3-[4-(Difluoromethoxy)benzoyl]-2-nitro-7-phenylthieno[2,3-b]pyridin-6(7H)-one

From Intermediate 46 (2.0 g, 5.7 mmol) and 4-difluoromethoxybenzaldehyde (1.2 g, 6.8 mmol) by the method of Intermediate 56 to give the title compound as a yellow solid (1000 mg, 40%). $\delta_H$ (DMSO-$d_6$) 8.05 (2H, m), 7.77-7.72 (6H, m), 7.48 (1H, t, J 73.6 Hz), 7.37 (2H, m), 6.66 (1H, d, J 9.7 Hz). LCMS (ES$^+$) RT 3.60 minutes, 443 (M+H)$^+$.

INTERMEDIATE 78

3-[2-(Difluoromethoxy)benzoyl]-2-nitro-7-phenylthieno[2,3-b]pyridin-6(7H)-one

From Intermediate 46 (2.0 g, 5.7 mmol) and 2-difluoromethoxybenzaldehyde (1.2 g, 6.8 mmol) by the method of Intermediate 56 to give the title compound as a yellow solid (960 mg, 38%). $\delta_H$ (DMSO-$d_6$) 8.02 (1H, dd, J 1.8, 7.5 Hz), 7.84-7.58 (7H, m), 7.51-7.45 (1H, m), 7.36 (1H, d, J 7.9 Hz), 7.22 (1H, t, J 76.3 Hz), 6.70 (1H, d, J 9.8 Hz). LCMS (ES$^+$) RT 3.57 minutes, 443 (M+H)$^+$.

INTERMEDIATE 79

3-Amino-7-(cyclopropylmethyl)-2-nitrothieno[2,3-b]pyridin-6(7H)-one

A mixture of (isothiocyanatomethyl)cyclopropane (3.3 g, 31.13 mmol) (*J. Org. Chem.*, 1972, 37, 1162-1168) and acetonitrile (4 ml) was dissolved in dry THF (50 ml) and cooled to −78° C. under a nitrogen atmosphere. A solution of sodium bis(trimethylsilyl)amide in THF (1.0M, 66 ml, 66 mmol) was added over 10 min and the reaction mixture then allowed to warm to r.t. over 2 h. EtOH (50 ml) and N,N-dimethyluracil (4.8 g, 34.2 mmol) were added and the mixture heated to reflux for 24 h. The mixture was cooled and concentrated in vacuo. The residue was dissolved in acetonitrile (50 ml) and bromonitromethane (7.30 g, 46.7 mmol) was added. The mixture was heated to 55° C. for 18 h then cooled to r.t. and diluted with ice/water (100 ml). The resulting solid was isolated by filtration to give the title compound as a brown solid (3.3 g, 40%). $\delta_H$ (CDCl$_3$) 7.52 (1H, d, J 9.6 Hz), 6.87 (2H, br s), 6.58 (1H, d, J 9.6 Hz), 3.96 (2H, d, J 7.2 Hz), 1.40-1.33 (1H, m), 0.62-0.51 (4H, m). LCMS (ES$^+$) RT 2.92 minutes, 266.0 (M+H)$^+$.

INTERMEDIATE 80

3-Bromo-7-(cyclopropylmethyl)-2-nitrothieno[2,3-b]pyridin-6(7H)-one

A mixture of Intermediate 79 (2.9 g, 10.9 mmol) and copper(II) bromide (3.0 g, 13.1 mmol) was suspended in dry acetonitrile (50 ml). The flask was covered with foil to keep its contents in the dark and tert-butyl nitrite (2.2 ml, 16.4 mmol) added. The mixture was stirred at r.t. overnight before quenching with 2M HCl (250 ml). The mixture was then extracted with DCM (300 ml), dried (Na$_2$SO$_4$) and concentrated in vacuo. The crude product was purified by chromatography (silica, DCM) to give the title compound as a yellow solid (2.34 g, 65%). $\delta_H$ (CDCl$_3$) 7.76 (1H, d, J 9.6 Hz), 6.70 (1H, d, J 9.6 Hz), 4.03 (2H, d, J 7.2 Hz), 1.40-1.32 (1H, m), 0.66-0.54 (4H, m). LCMS (ES$^+$) RT 3.57 minutes, 353.0 (M+Na)$^+$.

INTERMEDIATE 81

7-(Cyclopropylmethyl)-3-(4-fluoro-3-methylbenzoyl)-2-nitrothieno[2,3-b]pyridin-6(7H)-one From Intermediate 80 (3.47 g, 10.58 mmol) and 4-fluoro-3-methylbenzaldehyde (1.86 g, 13.22 mmol) by the method of Intermediate 56 to give the title compound as a yellow solid (891 mg, 22%). $\delta_H$ (CDCl$_3$) 7.79-7.77 (1H, m), 7.68-7.65 (1H, m), 7.34 (1H, d, J 9.6 Hz), 7.10 (1H, t, J 8.7 Hz), 6.60 (1H, d, J 9.6 Hz), 4.08 (2H, d, J 7.1 Hz), 2.33 (3H, s), 1.44-1.38 (1H, m), 0.70-0.58 (4H, m). LCMS (ES$^+$) RT 3.82 minutes, 409.9 (M+H)$^+$.

INTERMEDIATE 82

3-Amino-7-(2-chlorophenyl)-2-nitrothieno[2,3-b]pyridin-6(7H)-one

A mixture of (2-chlorophenyl)isothiocyanate (23.1 g, 136 mmol) and acetonitrile (30 ml) was dissolved in dry THF (200 ml) and cooled to −78° C. under a nitrogen atmosphere. A solution of sodium bis(trimethylsilyl)amide in THF (1.0M, 300 ml, 300 mmol) was added over 10 min and the reaction mixture then stirred with warming to r.t. over 2 h. Ethanol (250 ml) and N,N-dimethyluracil (19.4 g, 136 mmol) were added and the mixture heated to reflux for 24 h. The mixture was cooled and concentrated in vacuo to leave a thick brown oil. The residue was dissolved in acetonitrile (200 ml) and bromonitromethane (23.0 g, 164 mmol) added. The mixture was heated to 55° C. for 18 h then cooled to r.t. and diluted with ice/water (800 ml). The resultant solid was isolated by filtration to give a hard black solid. This was then purified by treatment with hot acetone/water (3:1, 300 ml). Cooling and filtration gave the title compound as a pale orange solid (18.0 g, 41%). $\delta_H$ (DMSO-d$_6$) 8.78-8.52 (2H, br s), 8.31 (1H, d, J 9.7 Hz), 7.83-7.50 (4H, m), 6.64 (1H, d, J 9.7 Hz). LCMS (ES$^+$) RT 3.02 minutes, 322 (M+H)$^+$

INTERMEDIATE 83

3-Bromo-7-(2-chlorophenyl)-2-nitrothieno[2,3-b]pyridin-6(7H)-one

A mixture of Intermediate 82 (10.0 g, 31.1 mmol) and copper(II) bromide (7.65 g, 34.2 mmol) was suspended in dry acetonitrile (200 ml). The flask was covered with foil to keep the contents in the dark and tert-butyl nitrite (5.20 ml, 43.5 mmol) added. The mixture was stirred at r.t. for 5 h before quenching with 2M HCl (300 ml). The mixture was then extracted with DCM (300 ml), dried (Na$_2$SO$_4$) and concentrated in vacuo. The crude product was purified by chromatography (silica, DCM) to give the title compound as a yellow solid (8.0 g, 67%). $\delta_H$ (CDCl$_3$) 7.90 (1H, d, J 9.8 Hz), 7.74-7.71 (1H, m), 7.64-7.54 (2H, m), 7.46-7.43 (1H, m), 6.82 (1H, d, J 9.8 Hz). LCMS (ES$^+$) RT 3.67 minutes, 407 (M+Na)$^+$.

INTERMEDIATE 84 tert-Butyl 4-({[3-benzoyl-7-(2-chlorophenyl)-6-oxo-6,7-dihydrothieno[2,3-b]pyridin-2-yl]amino}carbonyl)piperidine-1-carboxylate N-Boc-DL-isonipecotic acid (482 mg, 2.10 mmol), EDC (402 mg, 2.10 mmol) and NMM (0.231 ml, 2.10 mmol) were dissolved in dry DMF (15 ml). Example 42 (400 mg, 1.05 mmol) and DMAP (12 mg, 0.1 mmol) were then added and the mixture stirred at 50° C. for 7 days. The mixture was then partitioned between EtOAc (100 ml) and sat. brine (250 ml). The organic extract was washed with further sat. brine (100 ml), dried (Na$_2$SO$_4$) and concentrated in vacuo. The crude product was purified by chromatography (silica, 15% EtOAc, 85% DCM) to give the title compound as a yellow solid (310 mg, 50%). $\delta_H$ (DMSO-d$_6$) 11.93 (1H, br s), 7.72-7.45 (9H, m), 6.97 (1H, d, J 9.7 Hz), 6.44 (1H, d, J 9.7 Hz), 4.17-4.15 (2H, m), 2.88-2.81 (2H, m), 2.60-2.56 (1H m), 2.00-1.97 (2H, m), 1.73-1.69 (2H, m), 1.48 (9H, s). LCMS (ES$^+$) RT 3.98 minutes, 592.0 (M+H)$^+$.

INTERMEDIATE 85

2-Nitro-7-phenyl-3-[2-(trifluoromethoxy)benzoyl]thieno[2,3-b]pyridin-6(7H)-one

From Intermediate 46 and o-trifluoromethoxybenzaldehyde by the method of Intermediate 56 to give the title compound as a yellow solid. LCMS (ES$^+$) RT 3.77 minutes, 461 (M+H)$^+$.

INTERMEDIATE 86

3-(3-Fluorobenzoyl)-2-nitro-7-phenylthieno[2,3-b]pyridin-6(7H)-one

From Intermediate 46 and m-fluorobenzaldehyde by the method of Intermediate 56 to give the title compound as a yellow solid. LCMS (ES$^+$) RT 3.60 minutes, 395 (M+H)$^+$.

INTERMEDIATE 87

2-Nitro-7-phenyl-3-(1,3-thiazol-2-ylcarbonyl)thieno[2,3-b]pyridin-6(7H)-one

From Intermediate 46 and morpholin-4-yl(1,3-thiazol-2-yl)acetonitrile by the method of Intermediate 47 to give the title compound as a yellow solid. LCMS (ES$^+$) RT 3.40 minutes, 406 (M+Na)$^+$.

INTERMEDIATE 88

2-Nitro-7-phenyl-3-(pyridin-2-ylcarbonyl)thieno[2,3-b]pyridin-6(7H)-one

From Intermediate 46 and 2-pyridinecarboxaldehyde by the method of Intermediate 56 to give the title compound as a yellow solid. LCMS (ES$^+$) RT 3.39 minutes, 378 (M+H)$^+$.

INTERMEDIATE 89

7-(2-Chlorophenyl)-3-(3-methylbenzoyl)-2-nitrothieno[2,3-b]pyridin-6(7H)-one

From Intermediate 83 (2.0 g, 5.19 mmol) and m-tolualdehyde (0.735 ml, 6.22 mmol) by the method of Intermediate 56 to give the title compound as a yellow solid (240 mg, 11%). $\delta_H$ (DMSO-d$_6$) 7.91-7.82 (3H, m), 7.79-7.68 (4H, m), 7.61 (1H, d, J 7.6 Hz), 7.50 (1H, t, J 7.6 Hz), 6.70 (1H, d, J 9.7 Hz), 2.41 (3H, s). LCMS (ES$^+$) RT 3.80 minutes, 425 (M+H)$^+$.

INTERMEDIATE 90

3-Amino-7-(2-fluorophenyl)-2-nitrothieno[2,3-b]pyridin-6(7H)-one

From (2-fluorophenyl)isothiocyanate (24.25 g, 158 mmol) by the method of Intermediate 82 to give the title compound as a brown solid (38.75 g, 80%). $\delta_H$ (DMSO-d$_6$) 9.00 (2H, br s), 8.30 (1H, d, J 9.7 Hz), 7.75-7.67 (2H, m), 7.60-7.54 (1H, m), 7.51-7.45 (1H, m), 6.63 (1H, d, J 9.7 Hz). LCMS (ES$^+$) RT 2.89 minutes, 306 (M+H)$^+$.

INTERMEDIATE 91

3-Bromo-7-(2-fluorophenyl)-2-nitrothieno[2,3-b]pyridin-6(7H)-one

From Intermediate 90 (19.7 g, 64.52 mmol) by the method of Intermediate 83 to give the title compound as a yellow solid (19.0 g, 80%). $\delta_H$ (DMSO-d$_6$) 8.05 (1H, d, J 9.8 Hz), 7.86-7.70 (2H, m), 7.67-7.64 (1H, m), 7.60-7.54 (1H, m), 6.86 (1H, d, J 9.8 Hz). LCMS (ES$^+$) RT 3.512 minutes, 393 (M+Na)$^+$.

INTERMEDIATE 92

3-Benzoyl-7-(2-fluorophenyl)-2-nitrothieno[2,3-b]pyridin-6(7H)-one

From Intermediate 91 (2.50 g, 7.42 mmol) and benzaldehyde (0.940 ml, 9.27 mmol) by the method of Intermediate 56 to give the title compound as a yellow solid (370 mg, 13%). $\delta_H$ (DMSO-d$_6$) 8.00-7.97 (2H, m), 7.89-7.53 (8H, m), 6.69 (1H, d, J 9.7 Hz). LCMS (ES$^+$) RT 3.59 minutes, 395 (M+H)$^+$.

INTERMEDIATE 93

3-(4-Fluoro-3-methylbenzoyl)-7-(2-fluorophenyl)-2-nitrothieno[2,3-b]pyridin-6(7H)-one From Intermediate 91 (5.38 g, 14.57 mmol) and 4-fluoro-3-methylbenzaldehyde (2.26 ml, 18.21 mmol) by the method of Intermediate 56 to give the title compound as a yellow solid (850 mg, 14%). $\delta_H$ (DMSO-d$_6$) 8.04 (1H, m), 7.94-7.78 (3H, m), 7.75-7.58 (3H, m), 7.41 (1H, t, J 9 Hz), 6.73 (1H, d, J 9.7 Hz), 2.36 (3H, s). LCMS (ES$^+$) RT 3.77 minutes, 449 (M+Na)$^+$.

INTERMEDIATE 94

7-(2-Fluorophenyl)-3-(3-methylbenzoyl)-2-nitrothieno[2,3-b]pyridin-6(7H)-one

From Intermediate 91 (2.57 g, 6.77 mmol) and 3-methylbenzaldehyde (1.07 ml, 8.8 mmol) by the method of Intermediate 56 to give the title compound as a yellow solid (360 mg, 13%). $\delta_H$ (DMSO-d$_6$) 7.91-7.50 (9H, m), 6.72 (1H, d, J 9.7 Hz), 2.44 (3H, s). LCMS (ES$^+$) RT 3.72 minutes, 431 (M+Na)$^+$.

INTERMEDIATE 95

2-Chloro-5-isothiocyanatopyridine

A mixture of 5-amino-2-chloropyridine (5.0 g, 38.11 mmol) and thiophosgene (3.6 ml, 45.73 mmol) in DCM (75 ml) and water (35 ml) was stirred at r.t. for 18 h. The organic phase was dried (Na$_2$SO$_4$) and evaporated in vacuo to give the title compound as an off-white solid (6.6 g, 95%). $\delta_H$ (CDCl$_3$) 8.35 (1H, dd, J 0.5, 2.2 Hz), 7.54 (1H, dd, J 2.2, 8.5 Hz), 7.40 (1H, dd, J 0.5, 8.5 Hz). LCMS (ES$^+$) RT 3.61 minutes, 171 (M+H)$^+$.

INTERMEDIATE 96

Sodium 6'-chloro-5-cyano-2-oxo-2H-1,3'-bipyridine-6-thiolate

From Intermediate 95 (6.6 g, 38.74 mmol) by the method of Intermediate 6 to give the title compound, LCMS RT 1.17 minutes, contaminated with sodium 5-cyano-6'-ethoxy-2-oxo-2H-1,3'-bipyridine-6-thiolate.

INTERMEDIATE 97

3-Amino-7-(6-chloropyridin-3-yl)-2-nitrothieno[2,3-b]pyridin-6(7H)-one

From Intermediate 96 by the method of Intermediate 7 to give the title compound, LCMS (ES$^+$) RT 2.79 minutes, 323 (M+H)$^+$, contaminated with 3-amino-7-(6-ethoxypyridin-3-yl)-2-nitrothieno[2,3-b]pyridin-6(7H)-one, LCMS (ES$^+$) RT 2.97 minutes, 333 (M+H)$^+$.

INTERMEDIATE 98

3-Bromo-7-(6-chloropyridin-3-yl)-2-nitrothieno[2,3-b]pyridin-6(7R)-one

From Intermediate 97 by the method of Intermediate 46 to give the title compound as a yellow solid, LCMS (ES$^+$) RT 3.35 minutes, 386 (M+H)$^+$, contaminated with 3-bromo-7-(6-ethoxypyridin-3-yl)-2-nitrothieno[2,3-b]pyridin-6(7R)-one, LCMS (ES$^+$) RT 3.548 minutes, 398 (M+Na)$^+$.

INTERMEDIATE 99

3-Benzoyl-7-(6-chloropyridin-3-yl)-2-nitrothieno[2,3-b]pyridin-6(7H)-one

From Intermediate 98 (2.0 g, ~4.6 mmol) and morpholin-4-yl(phenyl)acetonitrile (650 mg, 3.2 mmol) by the method of Intermediate 47 to give the title compound, LCMS (ES$^+$) RT 3.50 minutes, 434 (M+Na)$^+$, contaminated with 3-benzoyl-7-(6-ethoxypyridin-3-yl)-2-nitrothieno[2,3-b]pyridin-6(7H)-one, LCMS (ES$^+$) RT 3.66 minutes, 422 (M+H)$^+$.

INTERMEDIATE 100

2-Amino-3-benzoyl-7-(6-chloropyridin-3-yl)thieno[2,3-b]pyridin-6(7H)-one

From Intermediate 99 (680 mg, ~1.5 mmol) by the method of Example 69 to give the title compound as a pale-orange solid (110 mg), LCMS (ES$^+$) RT 2.96 minutes, 382 (M+H)$^+$, contaminated with 2-amino-3-benzoyl-7-(6-ethoxypyridin-3-yl)thieno[2,3-b]pyridin-6(7H)-one, LCMS (ES$^+$) RT 3.09 minutes, 392 (M+H)$^+$.

INTERMEDIATE 101 tert-Butyl{2-[(3-benzoyl-6-oxo-7-phenyl-6,7-dihydrothieno[2,3-b]pyridin-2-yl(amino]-2-oxoethyl}carbamate From Example 13 (500 mg, 1.44 mmol) and N—BOC-glycine (505 mg, 2.88 mmol) by the method of Intermediate 41 to give the title compound as a yellow solid (160 mg, 22%). $\delta_H$ (DMSO-d$_6$) 11.40 (1H, s), 7.75-7.43 (10H, br m), 7.00 (1H, d, J 9.7 Hz), 6.39 (1H, d, J 9.7 Hz), 3.74 (2H, d J 5.9 Hz), 1.36 (9H, s). LCMS (ES$^+$) RT 3.43 minutes, 504 (M+H)$^+$.

INTERMEDIATE 102 tert-Butyl{2-[(3-benzoyl-6-oxo-7-phenyl-6,7-dihydrothieno[2,3-b]pyridin-2-yl)amino]-2-oxoethyl}methylcarbamate From Example 13 (440 mg, 1.27 mmol) and N—BOC-sarcosine (480 mg, 2.54 mmol) by the method of Intermediate 41 to give the title compound as a yellow solid (486 mg, 74%). $\delta_H$ (DMSO-d$_6$) (rotamers observed) 11.24 (0.5H, br s), 11.16 (0.5H, br s), 7.77-7.51 (10H, m), 7.11-7.08 (1H, m), 6.40 (1H, d, J 9.6 Hz), 4.05-4.02 (2H, br m), 2.80 (1.5H, br s), 2.27 (1.5H, br s), 1.37 (4.5H, br s), 1.27 (4.5H, br s). LCMS (ES$^+$) RT 3.62 minutes, 518 (M+H)$^+$.

INTERMEDIATE 103 tert-Butyl{(1S)-2-[(3-benzoyl-6-oxo-7-phenyl-6,7-dihydrothieno[2,3-b]pyridin-2-yl)amino]-1-methyl-2-oxoethyl}carbamate Carbonyl diimidazole (140 mg, 0.87 mmol) was added to a solution of N—BOC-L-alanine (164 mg, 0.87 mmol) in DMF (2 ml) and the mixture stirred at r.t. for 0.5 h. A solution of Example 13 (150 mg, 0.43 mmol) in DMF (3 ml) was added and the mixture stirred at r.t. overnight. The solvent was removed in vacuo and the residue partitioned between DCM and NaHCO$_3$(aq). The organic phase was dried (MgSO$_4$) and concentrated in vacuo. Purification by column chromatography (silica, 0 to 20% EtOAc in DCM) gave the title compound as a yellow solid (185 mg, 83%). $\delta_H$ (DMSO-d$_6$) 11.44 (1H, br s), 7.73-7.50 (10H, br m), 7.05 (1H, d, J 9.7 Hz), 6.39 (1H, d, J 9.7 Hz), 4.10-4.05 (1H, br m), 1.35 (9H, b s), 1.14 (3H, d, J 6.1 Hz). LCMS (ES$^+$) RT 3.54 minutes, 518 (M+H)$^+$.

INTERMEDIATE 104 tert-Butyl{3-[(3-benzoyl-6-oxo-7-phenyl-6,7-dihydrothieno[2,3-b]pyridin-2-yl)amino]-3-oxopropyl}carbamate From Example 13 (500 mg, 1.44 mmol) and N—BOC-β-alanine (547 mg, 2.89 mmol) by the method of Intermediate 103 to give the title compound as a yellow solid (360 mg, 48%). $\delta_H$ (DMSO-d$_6$) 10.90 (1H, s), 7.77 (2H, d, J 7.8 Hz), 7.72-7.50 (8H, m), 7.20 (1H, d, J 9.7 Hz), 6.80 (1H, br s), 6.41 (1H, d, J 9.7 Hz), 3.09-3.06 (2H, br m), 2.46-2.43 (2H, br m), 1.33 (9H, s). LCMS (ES$^+$) RT 3.46 minutes, 518 (M+H)$^+$.

INTERMEDIATE 105 tert-Butyl 4-({[3-benzoyl-7-(cyclopropylmethyl)-6-oxo-6,7-dihydrothieno[2,3-b]pyridin-2-yl]amino}carbonyl)piperidine-1-carboxylate From Example 40 (300 mg, 0.92 mmol) and N—BOC-DL-isonipecotic acid (424 mg, 1.84 mmol) by the method of Intermediate 41 to give the title compound as a yellow solid (90 mg, 18%). $\delta_H$ (CDCl$_3$) 11.85 (1H, s), 7.65-7.61 (3H, m), 7.53-7.48 (2H, m), 6.83 (1H, d, J 9.6 Hz), 6.33 (1H, d, J 9.6 Hz), 4.21-4.12 (2H, m), 4.10-4.08 (2H, d, J 7.1 Hz), 3.95-3.85 (1H, m), 2.90-2.81 (2H, m), 2.66-2.57 (1H, m), 2.05-2.00 (2H, m), 1.84-1.67 (2H, m), 1.46 (9H, s), 0.57-0.53 (4H, m). LCMS (ES$^+$) RT 3.98 minutes, 536 (M+H)$^+$.

INTERMEDIATE 106 tert-Butyl 4-({[3-(4-fluoro-3-methylbenzoyl)-7-(2-fluorophenyl)-6-oxo-6,7-dihydrothieno[2,3-b]pyridin-2-yl]amino}carbonyl)piperidine-1-carboxylate From Example 133 (293 mg, 0.74 mmol) and N—BOC-DL-isonipecotic acid (340 mg, 1.44 mmol) by the method of Intermediate 41 to give the title compound as a yellow solid (326 mg, 80%). $\delta_H$ (DMSO-d$_6$) 10.96 (1H, s), 7.80-7.69 (4H, m), 7.65-7.60 (1H, m(, 7.54-7.50 (1H, m, 7.46 (1H, d, J 9.6 Hz), 7.39 -7.34 (1H, m), 6.52 (1H, d, J 9.6 Hz),3.88-3.84 (2H, m), 2.75-2.60 (2H, m), 2.50 (1H, obscured by DMSO), 2.34 (3H, s), 1.62-1.58 (2H, m), 1.42 (9H, s), 1.32-1.29 (2H, m). LCMS (ES$^+$) RT 4.08 minutes, 608 (M+H)$^+$.

INTERMEDIATE 107 tert-Butyl 4-({[3-(4-fluoro-3-methylbenzoyl)-6-oxo-7-phenyl-6,7-dihydrothieno[2,3-b]pyridin-2-yl]amino}carbonyl piperidine-1-carboxylate From Example 50 and N—BOC-DL-isonipecotic acid by the method of Intermediate 103 to give the title compound as a yellow solid. LCMS (ES$^+$) RT 3.99 minutes, 590 (M+H)$^+$.

INTERMEDIATE 108 tert-Butyl(2S)-2-{[(3-benzoyl-6-oxo-7-phenyl-6,7-dihydrothieno[2,3-b]pyridin-2-yl)amino]carbonyl}pyrrolidine-1-carboxylate From Example 13 (500 mg, 1.44 mmol) and N—BOC-L-proline (622 mg, 2.89 mmol) by the method of Intermediate 41 to give the title compound as a yellow solid (268 mg, 34%). $\delta_H$ (CDCl$_3$) 11.98 (1H, br s), 7.70-7.51 (8H, br m), 7.43 (2H, d, J 6.9 Hz), 6.94 (1H, d, J 9.7 Hz), 6.43 (1H, d, J 9.7 Hz), 4.51-4.35 (1H, br m), 3.70-3.43 (2H, br m), 2.25-2.19 (2H, br m), 1.96-1.92 (2H, br m), 1.62-1.45 (9H, br m). LCMS (ES$^+$) RT 3.75 minutes, 544 (M+H)$^+$.

INTERMEDIATE 109 tert-Butyl(2R)-2-{[(3-benzoyl-6-oxo-7-phenyl-6,7-dihydrothieno[2,3-b]pyridin-2-yl)amino]carbonyl}pyrrolidine-1-carboxylate From Example 13 (500 mg, 1.44 mmol) and N—BOC-D-proline (622 mg, 2.89 mmol) by the method of Intermediate 103 to give the title compound as a yellow solid (770 mg, 98%). $\delta_H$ (CDCl$_3$) 11.98 (1H, br s), 7.70-7.41 (10H, br m), 6.94 (1H, d, J 9.7 Hz), 6.42 (1H, d, J 9.7 Hz), 4.52-4.35 (1H, br m), 3.70-3.40 (2H, br m), 2.35-2.20 (2H, br m), 2.06-1.92 (2H, br m), 1.65-1.40 (9H, br m). LCMS (ES$^+$) RT 3.75 minutes, 544 (M+H)$^+$.

INTERMEDIATE 110 tert-Butyl(3R)-3-({[(3-benzoyl-6-oxo-7-phenyl-6,7-dihydrothieno[2,3-b]pyridin-2-yl)amino]carbonyl}amino)pyrrolidine-1-carboxylate From Example 13 (1.0 g, 2.9 mmol) and tert-butyl(3R)-3-aminopyrrolidine-1-carboxylate (997 mg, 5.8 mmol) by the method of Example 20 to give the title compound as a yellow solid (1.34 g, 83%). $\delta_H$ (DMSO-d$_6$) 10.72 (1H, s), 8.27 (1H, d, J 6.3 Hz), 7.71-7.55 (8H, m), 7.49-7.47 (2H, m), 6.71 (1H, d, J 9.7 Hz), 6.26 (1H, d, J 9.7 Hz), 4.06 (1H, br s), 3.41-3.27 (3H, m), 3.11-3.05 (1H, m), 2.10-1.90 (1H, m), 1.76-1.74 (1H, m), 1.38 (9H, s). LCMS (ES$^+$) RT 3.58 minutes, 559 (M+H)$^+$.

INTERMEDIATE 111

N-(3-Benzoyl-6-oxo-7-phenyl-6,7-dihydrothieno[2,3-b]pyridin-2-yl)-N'-[(3R)-pyrrolidin 3-yl]urea hydrochloride From Intermediate 110 (1.34 g, 2.4 mmol) by the method of Example 61 to give a yellow solid (200 mg) which was then treated with HCl in 1,4-dioxane to give, after filtration, the title compound as a yellow solid (152 mg, 70%). $\delta_H$ (DMSO-d$_6$) 10.76 (1H, s), 9.23 (1H, br s), 9.20 (1H, br s), 8.39 (1H, d, J 5.6 Hz), 7.71-7.47 (10H, m), 6.72 (1H, d, J 9.7 Hz), 6.27 (1H, d, J 9.7 Hz), 4.17-4.15 (1H, m), 3.39-3.28 (3H, m), 3.08-2.95 (1H, m), 2.18-2.06 (1H, m), 1.87-1.77 (1H, m). LCMS (ES$^+$) RT 2.20 minutes, 459 (M+H)$^+$.

INTERMEDIATE 112 tert-Butyl(3S)-3-({[(3-benzoyl-6-oxo-7-phenyl-6,7-dihydrothieno[2,3-b]pyridin-2-yl)amino]carbonyl}amino)pyrrolidine-1-carboxylate From Example 13 (800 mg, 2.3 mmol) and tert-butyl(3S)-3-aminopyrrolidine-1-carboxylate (860 mg, 4.6 mmol) by the method of Example 20 to give the title compound as a yellow solid (587 mg, 46%). $\delta_H$ DMSO-d$_6$) 10.70 (1H, s), 8.27 (1H, d, J 6.1 Hz), 7.70-7.52 (8H, m), 7.47 (2H, d, J 6.6 Hz), 6.71 (1H, d, J 9.7 Hz), 6.26 (1H, d, J 9.7 Hz), 4.06 (1H, br s), 3.82-3.76 (1H, m), 3.73-3.26 (2H, m), 3.08-3.00 (1H, m), 2.02-1.90 (1H, m), 1.78-1.67 (1H, m), 1.38 (9H, s). LCMS (ES$^+$) RT 3.57 minutes, 559 (M+H)$^+$.

INTERMEDIATE 113 tert-Butyl((3R)-1-{[(3-benzoyl-6-oxo-7-phenyl-6,7-dihydrothieno[2,3-b]pyridin-2-yl)amino]carbonyl}pyrrolidin-3-yl)carbamate From Example 13 (500 mg, 1.44 mmol) and tert-butyl (3R)-pyrrolidin-3-ylcarbamate (536 mg, 2.88 mmol) by the method of Example 20 to give the title compound as a bright yellow solid (606 mg, 75%). $\delta_H$ (DMSO-d$_6$) 10.91 (1H, br s), 7.67-7.48 (10H, m), 7.19 (1H, br s), 6.91 (1H, d, J 9.7 Hz), 6.32 (1H, d, J 9.7 Hz), 4.05-3.95 (1H, br m), 3.45-3.37 (3H, br m), 3.25-3.15 (1H, br m), 2.11-2.01 (1H, br m), 1.88-1.77 (1H, br m), 1.38-1.35 (9H, br m). LCMS (ES$^+$) RT 3.53 minutes, 559 (M+H)$^+$.

INTERMEDIATE 114 tert-Butyl((3S)-1-{[(3-benzoyl-6-oxo-7-phenyl-6,7-dihydrothieno[2,3-b]pyridin-2-yl)amino]carbonyl}pyrrolidin-3-yl)carbamate From Example 13 (500 mg, 1.44 mmol) and tert-butyl(3S)-pyrrolidin-3-ylcarbamate (536 mg, 2.88 mmol) by the method of Example 20 to give the title compound as a bright yellow solid (620 mg, 77%). $\delta_H$ (DMSO-d$_6$) 10.91 (1H, br s), 7.67-7.48 (10H, m), 7.18 (1H, br s), 6.92 (1H, d, J 9.7 Hz), 6.33 (1H, d, J 9.7 Hz), 4.03-3.98 (1H, br m), 3.45-3.36 (3H, br m), 3.20-3.10 (1H, br m), 2.10-2.00 (1H, br m), 1.85-1.75 (1H, br m), 1.37-1.34 (9H, br m). LCMS (ES$^+$) RT 3.53 minutes, 559 (M+H)$^+$.

INTERMEDIATE 115 tert-Butyl(3R)-3-[({[3-(4-fluoro-3-methylbenzoyl)-6-oxo-7-phenyl-6,7-dihydrothieno[2,3-b]pyridin-2-yl]amino}carbonyl)amino]pyrrolidine-1-carboxylate From Example 50 (1.0 g, 2.6 mmol) and tert-butyl(3R)-3-aminopyrrolidine-1-carboxylate (160 mg, 1.80 mmol) by the method of Example 20 to give the title compound as a yellow solid (1.35 g, 88%). $\delta_H$ (DMSO-$d_6$) 10.58 (1H, s), 8.22 (1H, d, J 6.0 Hz), 7.68-7.46 (7H, m), 7.32 (1H, t, J 8.0 Hz), 6.83 (1H, d, J 9.7 Hz), 6.30 (1H, d, J 9.7 Hz), 4.05 (1H, br s), 3.41-3.22 (3H, m), 3.07-3.04 (1H, m), 2.32 (3H, s), 2.08-1.93 (1H, m) 1.80-1.67 (1H, m), 1.39 (9H, s) LCMS (ES$^+$) RT 3.72 minutes, 591 (M+H)$^+$.

INTERMEDIATE 116 tert-Butyl 4-[(3-benzoyl-6-oxo-7-phenyl-6,7-dihydrothieno[2,3-b]pyridin-2-yl)amino]piperidine-1-carboxylate From Intermediate 36 (274 mg, 0.66 mmol) and tert-butyl 4-aminopiperidine-1-carboxylate (159 mg, 0.79 mmol) by the method of Example 55 to give the title compound as a yellow solid (123 mg, 35%). $\delta_H$ (CDCl$_3$) 9.72 (1H, d, J 8.3 Hz), 7.57-7.32 (10H, m), 6.63 (1H, d, J 9.7 Hz), 6.23 (1H, d, J 9.7 Hz), 3.89-3.85 (2H, br m), 3.20-3.17 (1H, br m), 2.94-2.87 (2H, br m), 1.93-1.90 (2H, br m), 1.44-1.40 (2H, br m), 1.38 (9H, s). LCMS (ES$^+$) RT 3.81 minutes, 530 (M+H)$^+$.

INTERMEDIATE 117 tert-Butyl(3R)-3-[(3-benzoyl-6-oxo-7-phenyl-6,7-dihydrothieno[2,3-b]pyridin-2-yl)amino]pyrrolidine-1-carboxylate From Intermediate 36 (800 mg, 1.95 mmol) and tert-butyl (3R)-3-aminopyrrolidine-1-carboxylate (402 mg, 2.34 mmol) by the method of Example 55 to give the title compound as a yellow solid (680 mg, 68%). $\delta_H$ (DMSO-$d_6$) 9.34 (1H, d, J 8.0 Hz), 7.67-7.48 (10H, m), 6.62 (1H, d, J 9.7 Hz), 6.24 (1H, d, J 9.7 Hz), 4.01-3.90 (1H, m), 3.54-3.49 (1H, m), 3.20 (1H, dd, J 4.4, 11.0 Hz), 2.20-2.05 (1H, m), 1.95-1.90 (1H, m), 1.38 (9H, s), 1.31-1.24 (1H, m), 1.16-1.11 (1H, m). LCMS (ES$^+$) RT 3.67 minutes, 516 (M+H)$^+$.

INTERMEDIATE 118 tert-Butyl(3S-3-[(3-benzoyl-6-oxo-7-phenyl-6,7-dihydrothieno[2,3-b]pyridin-2-yl)amino]pyrrolidine-1-carboxylate From Intermediate 36 (1.0 g, 2.4 mmol) and tert-butyl(3S)-3-aminopyrrolidine-1-carboxylate (540 mg, 2.9 mmol) by the method of Example 55 to give the title compound as a brown solid (1.0 g, 83%). LCMS (ES$^+$) RT 3.72 minutes, 516 (M+H)$^+$.

INTERMEDIATE 119 tert-Butyl[1-(3-benzoyl-6-oxo-7-phenyl-6,7-dihydrothieno[2,3-b]pyridin-2-yl)azetidin-3-yl]carbamate From Intermediate 36 (1.0 g, 2.4 mmol) and azetidin-3-ylcarbamic acid tert-butyl ester (499 mg, 2.9 mmol) by the method of Example 55 to give the title compound as a yellow solid (1.0 g, 84%). $\delta_H$ (DMSO-$d_6$) 7.73-7.71 (2H, m), 7.66-7.49 (9H, m), 7.39 (1H, d, J 9.6 Hz), 6.39 (1H, d, J 9.6 Hz), 4.19-4.18 (1H, m), 3.74 (2H, t, J 8.1 Hz), 3.44 (2H, dd, J 5.8, 8.3 Hz), 1.32 (9H, s). LCMS (ES$^+$) RT 3.51 minutes, 502 (M+H)$^+$.

INTERMEDIATE 120 tert-Butyl[1-(3-benzoyl-6-oxo-7-phenyl-6,7-dihydrothieno[2,3-b]pyridin-2-yl)piperidin-4-yl]carbamate From Intermediate 36 (1.0 g, 2.4 mmol) and tert-butyl piperidin-4-ylcarbamate (580 mg, 2.9 mmol) by the method of Example 55 to give the title compound as a yellow solid (359 mg, 28%). LCMS (ES$^+$) RT 3.74 minutes, 530 (M+H)$^+$.

INTERMEDIATE 121 tert-Butyl 3-{[(3-benzoyl-6-oxo-7-phenyl-6,7-dihydrothieno[2,3-b]pyridin-2-yl)amino]methyl}azetidine-1-carboxylate From Intermediate 36 (1.0 g, 2.4 mmol) and tert-butyl 3-(aminomethyl)azetidine-1-carboxylate (536 mg, 2.8 mmol) by the method of Example 55 to give the title compound as a yellow solid (494 mg, 40%). $\delta_H$ (DMSO-$d_6$) 9.44 (1H, t, J 6.0 Hz), 7.66-7.47 (10H, m), 6.56 (1H, d, J 9.7 Hz), 6.21 (1H, d, J 9.7 Hz), 3.85 (2H, t, J 8.0 Hz), 3.55-3.50 (2H, m), 3.43 (2H, t, J 6.6 Hz), 2.82-2.77 (1H, m), 1.34 (9H, s). LCMS (ES$^+$) RT 3.58 minutes, 516 (M+H)$^+$.

INTERMEDIATE 122

2-Bromo-3-(4-fluoro-3-methylbenzoyl)-7-phenylthieno[2,3-b]pyridin-6(7H)-one

From Example 50 (4.95 g, 1.3 mmol) by the method of Intermediate 36 to give the title compound as a pink solid (2.35 g, 41%). $\delta_H$ (DMSO-$d_6$) 7.89 (1H, d, J 7.3 Hz), 7.79-7.74 (1H, m), 7.69-7.55 (6H, m), 7.37 (1H, t, J 9.0 Hz), 6.52 (1H, d, J 9.6 Hz), 2.32 (3H, s). LCMS (ES$^+$) RT 4.01 minutes, 443 (M+H)$^+$.

INTERMEDIATE 123

2-Bromo-3-(3-methylbenzoyl)-7-phenylthieno[2,3-b]pyridin-6(7H)-one

From Example 4 (3.67 g, 1.0 mmol) by the method of Intermediate 36 to give the title compound as a pink solid (1.44 g, 34%). $\delta_H$ (DMSO-$d_6$) 7.72-7.46 (9H, m), 7.48 (1H, t, J 7.6 Hz), 6.51 (1H, d, J 9.6 Hz), 2.40 (3H, s). LCMS (ES$^+$) RT 3.92 minutes, 425 (M+H)$^+$.

INTERMEDIATE 124 tert-Butyl 3-{[3-(4-fluoro-3-methylbenzoyl)-6-oxo-7-phenyl-6,7-dihydrothieno[2,3-b]pyridin-2-yl]amino}azetidine-1-carboxylate From Intermediate 122 (850 mg, 1.92 mmol) and tert-butyl 3-aminoazetidine-1-carboxylate (397 mg, 2.31 mmol) by the method of Example 55 to give the title compound as a brown solid (606 mg, 59%). $\delta_H$ (DMSO-$d_6$) 9.10 (1H, d, J 7.7 Hz), 7.67-7.60 (4H, m), 7.58-7.43 (3H, m), 7.29 (1H, t, J 9.0 Hz), 6.82 (1H, d, J 9.7 Hz), 6.30 (1H, d, J 9.7 Hz), 4.17-4.03 (3H, m), 3.83-3.79 (2H, m), 2.31 (3H, s), 1.36 (9H, s). LCMS (ES+) RT 3.810 minutes, 534 (M+H)+.

INTERMEDIATE 125 tert-Butyl 4-{[3-(4-fluoro-3-methylbenzoyl)-6-oxo-7-phenyl-6,7-dihydrothieno[2,3-b]pyridin-2-yl]amino}piperidine-1-carboxylate From Intermediate 122 (1.2 g, 2.7 mmol) and tert-butyl 4-aminopiperidine-1-carboxylate (649 mg, 3.2 mmol) by the method of Example 55 to give the title compound as a yellow solid (1.29 g, 85%). $\delta_H$ (DMSO-$d_6$) 9.31 (1H, d, J 8.9 Hz), 7.67-7.55 (3H, m), 7.51-7.46 (3H, m), 7.43-7.38 (1H, m), 7.31-7.25 (1H, t, J 9.0 Hz), 6.71 (1H, d, J 9.7 Hz), 6.26 (1H, d, J 9.7 Hz), 3.81-3.77 (2H, br m), 3.39-3.35 (1H, br m), 2.97-2.82 (2H, br m), 2.30 (3H, s), 1.86-1.83 (2H, br m), 1.49-1.34 (11H, m). LCMS (ES+) RT 4.04 minutes, 562 (M+H)+.

INTERMEDIATE 126 tert-Butyl(3R)-3-{[3-(4-fluoro-3-methylbenzoyl)-6-oxo-7-phenyl-6,7-dihydrothieno[2,3-b]pyridin-2-yl]amino}pyrrolidine-1-carboxylate From Intermediate 122 (1.0 g, 2.3 mmol) and tert-butyl (3R)-3-aminopyrrolidine-1-carboxylate (514 mg, 2.8 mmol) by the method of Example 55 to give the title compound as a yellow solid (642 mg, 51%). $\delta_H$ (DMSO-$d_6$) 9.12 (1H, d, J 7.9 Hz), 7.67-7.41 (7H, m), 7.28 (1H, t, J 9.0 Hz), 6.79 (1H, d, J 9.7 Hz), 6.29 (1H, d, J 9.7 Hz), 4.01-3.89 (1H, m), 3.53-3.47 (1H, m), 3.28 (2H, m), 3.18 (1H, dd, J 4.4, 11.0 Hz), 2.50 (3H, s), 2.11-2.09 (1H, m), 1.99-1.93 (1H, m), 1.38 (9H, s). LCMS (ES+) RT 3.88 minutes, 548 (M+H)+.

INTERMEDIATE 127 tert-Butyl(3S)-3-{[3-(4-fluoro-3-methylbenzoyl)-6-oxo-7-phenyl-6,7-dihydrothieno[2,3-b]pyridin-2-yl]amino}pyrrolidine-1-carboxylate From Intermediate 122 (1.40 g, 3.00 mmol) and tert-butyl (3S)-3-amino-pyrrolidine-1-carboxylate (670 mg, 3.60 mmol) by the method of Example 55 to give the title compound as a yellow solid (1.24 g, 72%). $\delta_H$ (DMSO-$d_6$) 9.12 (1H, d, J 7.9 Hz), 7.67-7.41 (7H, m), 7.32-7.26 (1H, m), 6.80 (1H, d, J 9.7 Hz), 6.29 (1H, d, J 9.7 Hz), 4.00-3.95 (1H, br m), 3.53-3.47 (1H, br m), 3.30-3.28 (2H, br m), 3.19 (1H, dd, J 11.0, 4.4 Hz), 2.30 (3H, s), 2.12-2.06 (1H, br m), 1.98-1.90 (1H, br m), 1.38 (9H, s). LCMS (ES) RT 3.85 minutes, 548 (M+H)+.

INTERMEDIATE 128 tert-Butyl 4-{[3-(3-methylbenzoyl)-6-oxo-7-phenyl-6,7-dihydrothieno[2,3-b]pyridin-2-yl]amino}piperidine-1-carboxylate From Intermediate 123 (800 mg, 1.88 mmol) and tert-butyl 4-aminopiperidine-1-carboxylate (452 mg, 2.26 mmol) by the method of Example 55 to give the title compound as a yellow solid (1.05 g, 100%). $\delta_H$ (DMSO-$d_6$) 9.44 (1H, d, J 8.9 Hz), 7.66-7.58 (3H, m), 7.50-7.47 (2H, m), 7.43-7.41 (2H, m), 7.34-7.30 (2H, m), 6.59 (1H, d, J 9.7 Hz), 6.22 (1H, d, J 9.7 Hz), 3.81-3.78 (2H, br m), 3.42-3.38 (1H, br m), 2.94-2.86 (2H, br m), 2.38 (3H, s), 1.87-1.85 (2H, br m), 1.45-1.39 (11H, m). LCMS (ES+) RT 3.98 minutes, 544 (M+H)+.

INTERMEDIATE 129 tert-Butyl 3-{[3-(3-methylbenzoyl)-6-oxo-7-phenyl-6,7-dihydrothieno[2,3-b]pyridin-2-yl]amino}azetidine-1-carboxylate From Intermediate 123 (1.41 g, 3.3 mmol) and tert-butyl 3-aminoazetidine-1-carboxylate (671 mg, 3.9 mmol) by the method of Example 55 to give the title compound as a yellow solid (757 mg, 45%). $\delta_H$ (DMSO-$d_6$) 9.27 (1H, d, J 7.6 Hz), 7.67-7.30 (9H, m), 6.67 (1H, d, J 9.7 Hz), 6.24 (1H, d, J 9.7 Hz), 4.20-4.12 (1H, m), 4.09-4.02 (2H, m), 3.85-3.80 (2H, m), 2.49 (3H, s), 1.36 (9H, s). LCMS (ES+) RT 3.75 minutes, 516 (M+H)+.

INTERMEDIATE 130 tert-Butyl(3R)-3-[(3-benzoyl-6-oxo-7-phenyl-6,7-dihydrothieno[2,3-b]pyridin-2-yl)amino]piperidine-1-carboxylate From Intermediate 36 (1.00 g, 2.4 mmol) and tert-butyl (3R)-3-aminopiperidine-1-carboxylate (561 mg, 2.8 mmol) by the method of Example 55 to give the title compound as a yellow solid (892 mg, 70%). $\delta_H$ (DMSO-$d_6$) 9.60 (1H, d, J 7.2 Hz), 7.79-7.37 (10H, m), 6.56 (1H, d, J 9.7 Hz), 6.22 (1H, d, J 9.7 Hz), 3.68-3.50 (1H, m), 3.30-2.73 (3H, m), 1.89-1.79 (1H, m), 1.72-1.35 (3H, m), 1.25-1.20 (10H, m). LCMS (ES+) RT 3.78 minutes, 530 (M+H)+.

INTERMEDIATE 131 tert-Butyl(3S)-3-[(3-benzoyl-6-oxo-7-phenyl-6,7-dihydrothieno[2,3-b]pyridin-2-yl)amino]piperidine-1-carboxylate From Intermediate 36 (1.00 g, 2.4 mmol) and tert-butyl (3S)-3-aminopiperidine-1-carboxylate (561 mg, 2.8 mmol) by the method of Example 55 to give the title compound as a yellow solid (710 mg, 56%). $\delta_H$ (DMSO-$d_6$) 9.60 (1H, d, J 7.3 Hz), 7.70-7.35 (10H, m), 6.56 (1H, d, J 9.7 Hz), 6.22 (1H, d, J 9.7 Hz), 3.69-3.51 (1H, m), 3.29-3.16 (3H, m), 1.95-1.80 (1H, m), 1.72-1.48 (3H, m), 1.25-1.18 (10H, m). LCMS (ES+) RT 3.77 minutes, 530 (M+H)+.

INTERMEDIATE 132 tert-Butyl{trans-4-[(3-benzoyl-6-oxo-7-phenyl-6,7-dihydrothieno[2,3-b]pyridin-2-yl)amino]cyclohexyl}carbamate From Intermediate 36 and tert-butyl(trans-4-aminocyclohexyl)carbamate by the method of Example 55. Used in next step without further purification.

INTERMEDIATE 133 tert-Butyl(3S)-3-{[3-(3-methylbenzoyl)-6-oxo-7-phenyl-6,7-dihydrothieno[2,3-b]pyridin-2-yl]amino}pyrrolidine-1-carboxylate From Intermediate 123 (1.57 g, 3.70 mmol) and tert-butyl (3S)-3-aminopyrrolidine-1-carboxylate (828 mg, 4.45 mmol) by the method of Example 55. Purification by column chromatography (silica, 0%-20% EtOAc in DCM) gave the title compound as a yellow solid (1.33 g, 68%). $\delta_H$ (DMSO-$d_6$) 9.30 (1H, d, J 8.0 Hz), 7.67-7.30 (9H, m), 6.66 (1H, d, J 9.7 Hz), 6.25 (1H, d, J 9.7 Hz), 4.02-3.95 (2H, br m), 3.54-3.49 (1H, br m), 3.35-3.18 (2H, br m), 2.38 (3H, s), 2.15-2.05 (1H, br m), 2.00-1.93 (1H, br m), 1.38 (9H, s). LCMS (ES$^+$) RT 3.81 minutes, 530 (M+H)$^+$.

INTERMEDIATE 134

3-Benzoyl-2-bromo-7-(cyclopropylmethyl thieno[2,3-b]pyridin-6(7H)-one

From Example 40 (2.37 g, 7.31 mmol) by the method of Intermediate 36 to give the title compound as a brown solid (1.29 g, 46%). $\delta_H$ (DMSO-$d_6$) 7.88-7.85 (H, m), 7.79-7.72 (1H, m), 7.62-7.50 (2H, m), 7.47 (1H, d, J 9.5 Hz), 6.43 (1H, d, J 9.5 Hz), 3.99 (2H, d, J 7.1 Hz), 1.38-1.29 (1H, m), 0.61-0.47 (4H, m). LCMS (ES$^+$) RT 3.80 minutes, 388 (M+H)$^+$.

INTERMEDIATE 135 tert-Butyl 3-{[3-benzoyl-7-(cyclopropylmethyl)-6-oxo-6,7-dihydrothieno[2,3-b]pyridin-2-yl]amino}azetidine-1-carboxylate From Intermediate 134 (1.12 g, 2.89 mmol) and tert-butyl 3-aminoazetidine-1-carboxylate by the method of Example 55 to give the title compound as a yellow solid (901 mg, 65%). $\delta_H$ (DMSO-$d_6$) 9.27 (1H, d, J 7.4 Hz), 7.60-7.52 (5H, m), 6.57 (1H, d, J 9.6 Hz), 6.16 (1H, d, J 9.6 Hz), 4.41-4.32 (1H, m), 4.24-4.20 (2H, m), 3.98-3.92 (4H, m), 1.40 (9H, s), 1.29-1.09 (1H, m), 0.53-0.47 (4H, m). LCMS (ES$^+$) RT 3.71 minutes, 480 (M+H)$^+$.

INTERMEDIATE 136

2-Bromo-7-(cyclopropylmethyl)-3-(4-fluoro-3-methylbenzoyl)thieno[2,3-b]pyridin-6(7H)-one From Example 115 (2.15 g, 6.04 mmol) by the method of Intermediate 36 to give the title compound as a brown solid (1.37 g, 54%). $\delta_H$ (DMSO-$d_6$) 7.88-7.83 (1H, m), 7.78-7.71 (1H, m), 7.49 (1H, d, J 9.5 Hz), 7.35 (1H, t, J 9.0 Hz), 6.44 (1H, d, J 9.5 Hz), 3.99 (2H, d, J 7.0 Hz), 2.31 (3H, s), 1.42-1.24 (1H, m), 0.63-0.45 (4H, m). LCMS (ES$^+$) RT 4.06 minutes, 420 (M+H)$^+$.

INTERMEDIATE 137 tert-Butyl 3-{[7-(cyclopropylmethyl)-3-(4-fluoro-3-methylbenzoyl)-6-oxo-6,7-dihydrothieno[2,3-b]pyridin-2-yl]amino}azetidine-1-carboxylate From Intermediate 136 (1.38 g, 3.27 mmol) and tert-butyl 3-aminoazetidine-1-carboxylate by the method of Example 55 to give the title compound as a yellow solid (880 mg, 53%). $\delta_H$ (DMSO-$d_6$) 9.04 (1H, d, J 7.2 Hz), 7.51 (1H, d, J 7.6 Hz), 7.45-7.40 (1H, m), 7.26 (1H, t, J 9.0 Hz), 6.72 (1H, d, J 9.6 Hz), 6.21 (1H, d, J 9.7 Hz), 4.35-4.29 (1H, m), 3.20 (2H, t, J 8.0 Hz), 3.94-3.88 (4H, m), 2.28 (3H, s), 1.39 (9H, s), 1.33-1.18 (1H, m), 0.56-0.45 (4H, m). LCMS (ES$^+$) RT 3.88 minutes, 512 (M+H)$^+$.

INTERMEDIATE 138

2-Bromo-3-(3-methoxybenzoyl)-7-phenylthieno[2,3-b]pyridin-6(7H)-one

From Example 69 by the method of Intermediate 36 to give the title compound as a purple solid. $\delta_H$ (CDCl$_3$) 7.67-7.39 (9H, m), 7.29-7.20 (1H, m), 6.61 (1H, d, J 9.7 Hz), 3.98 (3H, s). LCMS (ES$^+$) RT 3.73 minutes, 442 (M+H)$^+$.

INTERMEDIATE 139

2-Bromo-3-(3-chloro-4-fluorobenzoyl)-7-phenylthieno[2,3-b]pyridin-6(7H)-one

From Example 71 by the method of Intermediate 36 to give the title compound as a purple solid. $\delta_H$ (CDCl$_3$) 8.01 (1H, dd, J 2.1, 7.0 Hz), 7.83 (1H, m), 7.67-7.56 (4H, m), 7.45 (2H, m), 7.30 (1H, t, J 8.4 Hz), 6.64 (1H, d, J 9.7 Hz). LCMS (ES$^+$) RT 4.04 minutes, 462 (M+H)$^+$.

INTERMEDIATE 140

Sodium 3-cyano-1-(2,6-difluorophenyl)-6-oxo-1,6-dihydropyridine-2-thiolate

A solution of sodium bis(trimethylsilyl)amide (351 ml of a 1M solution in THF, 351 mmol) in THF (150 ml) was cooled to –78° C. and acetonitrile (30 ml) was added. After 20 min, 2,6-difluorophenyl isothiocyanate (30.0 g, 175.5 mmol) was added slowly over 5 min. The reaction mixture was allowed to warm slowly to r.t. over 2 h. EtOH (100 ml) was added followed by 1,3-dimethyluracil (27.0 g, 193.5 mmol) and the mixture heated to reflux for 18 h. After cooling, the mixture was concentrated in vacuo to a volume of approx. 150 ml and EtOH (75 ml) was added. This mixture was cooled and Et$_2$O (approx. 750 ml) was added slowly to give a pale yellow precipitate. The solid was filtered off, washed with Et$_2$O (2×100 ml) then dried to give the title compound as a yellow/pale brown solid (49.0 g, 86%). $\delta_H$ (DMSO-$d_6$) 7.43-7.33 (1H, m), 7.23 (1H, d, J 9.2 Hz), 7.13-7.06 (2H, m), 5.64 (1H, d, J 9.2 Hz). LCMS (ES$^+$) RT 7.0 minutes, 265 (M+H)$^+$.

INTERMEDIATE 141

3-Amino-7-(2,6-difluorophenyl)-2-nitrothieno[2,3-b]pyridin-6(7H)-one

A mixture of Intermediate 140 (15.0 g, 52.4 mmol), bromonitromethane (15 ml of a 40% solution in toluene, 78.6 mmol) and K$_2$CO$_3$ (7.24 g, 52.4 mmol) in acetonitrile (150 ml) was heated at 55° C. overnight. The bulk of the solvent was removed in vacuo and the residue poured into ice/water (400 ml). The resulting solid was filtered off and dried to give the title compound as a yellow solid (13.74 g, 81%). $\delta_H$ (DMSO-$d_6$) 9.40-8.60 (2H, m), 8.37 (1H, d, J 9.8 Hz), 7.86-7.80 (1H, m), 7.56-7.50 (2H, m), 6.70 (1H, d, J 9.8 Hz). LCMS (ES$^+$) RT 2.991 minutes, 324 (M+H)$^+$.

INTERMEDIATE 142

3-Bromo-7-(2,6-difluorophenyl)-2-nitrothieno[2,3-b]pyridin-6(7H)-one

From Intermediate 141 (13.45 g, 41.6 mmol) by the method of Intermediate 36 to give the title compound as a yellow solid (10.79 g, 67%). $\delta_H$ (DMSO-$d_6$) 8.09 (1H, d, J 9.8 Hz), 7.90-7.83 (1H, m), 7.60-7.56 (2H, m), 6.88 (1H, d, J 9.8 Hz). LCMS (ES$^+$) RT 3.62 minutes, 388 (M+H)$^+$.

INTERMEDIATE 143

[7-(2,6-Difluorophenyl)-2-nitro-6-oxo-6,7-dihydrothieno[2,3-b]pyridin-3-yl]morpholin-4-yl)phenylacetonitrile From Intermediate 142 (5.0 g, 12.9 mmol) and morpholin-4-yl(phenyl)acetonitrile by the method of Intermediate 49 to give the title compound as a yellow solid (5.42 g, 82%). LCMS (ES$^+$) RT 3.69 minutes, 509 (M+H)$^+$.

INTERMEDIATE 144

3-Benzoyl-7-(2,6-difluorophenyl)-2-nitrothieno[2,3-b]pyridin-6(7H)-one

Copper(II) sulphate (6.81 g, 42.0 mmol) suspended in water (25 ml) was added to a solution of Intermediate 143 (5.42 g, 10.0 mmol) in DMF (100 ml), and the mixture was heated at 50° C. for 16 h. The mixture was poured into iced water (300 ml) and the precipitate was filtered off to give a yellow solid which was suspended in NH$_4$Cl (aq) (90 ml) with NH$_3$ (aq) (100 ml) and the resulting precipitate filtered off and dried in vacuo. The crude product was purified by chromatography (silica, 100% DCM), to give the title compound as a yellow solid (3.55 g, 86%). $\delta_H$ (DMSO-$d_6$) 8.02 (2H, d, J 7.6 Hz), 7.98-7.87 (1H, m), 7.80-7.77 (2H, m), 7.61-7.58 (4H, m), 6.74 (1H, d, J 9.7 Hz). LCMS (ES$^+$) RT 3.57 minutes, 413 (M+H)$^+$.

INTERMEDIATE 145

3-Benzoyl-2-bromo-7-(2,6-difluorophenyl)thieno[2,3-b]pyridin-6(7H)-one

The reaction of Example 226 (2.1 g, 5.46 mmol) by the method of Intermediate 36 gave the title compound as a brown solid (918 mg, 38%). $\delta_H$ (DMSO-$d_6$) 7.93-7.90 (2H, m), 7.87-7.26 (7H, m), 6.60 (1H, d, J 9.7 Hz). LCMS (ES$^+$) RT 3.77 minutes, 446 (M+H)$^+$.

INTERMEDIATE 146 tert-Butyl 3-{[3-benzoyl-7-(2,6-difluorophenyl)-6-oxo-6,7-dihydrothieno[2,3-b]pyridin-2-yl]amino}azetidine-1-carboxylate From Intermediate 145 (918 mg, 2.06 mmol) and tert-butyl 3-aminoazetidine-1-carboxylate by the method of Example 55 to give the title compound as a yellow solid (800 mg, 73%). $\delta_H$ (DMSO-$d_6$) 9.32 (1H, d, J 7.8 Hz), 7.83-7.73 (1H, m), 7.64-7.41 (7H, m), 6.75 (1H, d, J 9.8 Hz), 6.32 (1H, d, J 9.8 Hz), 4.22-4.02 (3H, m), 3.88-3.84 (2H, m), 1.36 (9H, s). LCMS (ES$^+$) RT 3.71 minutes, 538 (M+)$^+$.

INTERMEDIATE 147

[7-(2,6-Difluorophenyl)-2-nitro-6-oxo-6,7-dihydrothieno[2,3-b]pyridin-3-yl](4-fluoro-3-methylphenyl)morpholin-4-ylacetonitrile From Intermediate 142 (8.6 g, 22.0 mmol) and 4-fluoro-3-methylphenyl)(morpholin-4-yl)acetonitrile by the method of Intermediate 49 to give the title compound as a brown solid (9.62 g, 81%). LCMS (ES$^+$) RT 3.87 minutes, 541 (M+H)$^+$.

INTERMEDIATE 148

7-(2,6-Difluorophenyl)-3-(4-fluoro-3-methylbenzoyl)-2-nitrothieno[2,3-b]pyridin-6(7H)-one From Intermediate 147 (9.62 g, 17.8 mmol) by the method of Intermediate 144 to give the title compound as a yellow solid (4.31 g, 54%). $\delta_H$ (DMSO-$d_6$) 8.03 (1H, dd, J 1.6, 7.2 Hz), 7.94-7.85 (2H, m), 7.77 (1H, d, J 9.8 Hz), 7.60 (2H, t, J 8.6 Hz), 7.36 (1H, t, J 9.0 Hz), 6.75 (1H, d, J 9.8 Hz), 2.32 (3H, s). LCMS (ES$^+$) RT 3.83 minutes, 445 (M+H)$^+$.

INTERMEDIATE 149

2-Bromo-7-(2,6-difluorophenyl)-3-(4-fluoro-3-methylbenzoyl)thieno[2,3-b]pyridin-6(7H)-one From Example 229 (1.24 g, 3.0 mmol) by the method of Intermediate 36 to give the title compound as a brown solid (440 mg, 31%). $\delta_H$ (DMSO-$d_6$) 7.94-7.77 (4H, m), 7.56-7.51 (2H, m), 7.40-7.33 (1H, m), 6.60 (1H, d, J 9.7 Hz), 2.33 (3H, d, J 1.6 Hz). LCMS (ES$^+$) RT 4.14 minutes, 478 (M+H)$^+$.

INTERMEDIATE 150

3-Benzoyl-2-bromo-7-(4-methylphenyl)thieno[2,3-b]pyridin-6(7H)-one

From Example 83 (1.61 g, 4.47 mmol) by the method of Intermediate 36 to give the title compound as a brown solid (957 mg, 51%). $\delta_H$ (DMSO-$d_6$) 7.90-7.87 (2H, m), 7.78-7.70 (1H, m), 7.63-7.54 (3H, m), 7.45-7.37 (4H, m), 6.49 (1H, d, J 9.6 Hz), 2.43 (3H, s). LCMS (ES$^+$) RT 3.93 minutes, 425 (M+H)$^+$.

INTERMEDIATE 151 tert-Butyl 3-{[3-benzoyl-7-(4-methylphenyl)-6-oxo-6,7-dihydrothieno[2,3-b]pyridin-2-yl]amino}azetidine-1-carboxylate From Intermediate 150 (957 mg, 2.26 mmol) and tert-butyl 3-aminoazetidine-1-carboxylate by the method of Example 55 to give the title compound as a yellow solid (557 mg, 48%). $\delta_H$ (DMSO-$d_6$) 9.31 (1H, d, J 7.6 Hz), 7.63-7.51 (5H, m), 7.42 (2H, d, J 8.1 Hz), 7.34 (2H, d, J 8.4 Hz), 6.63 (1H, d, J 9.7 Hz), 6.22 (1H, d, J 9.7 Hz), 4.21-4.07 (3H, m), 3.85-3.81 (2H, m), 2.42 (3H, s), 1.36 (9H, s). LCMS (ES$^+$) RT 3.72 minutes, 516 (M+H)$^+$.

INTERMEDIATE 152

Sodium 3-cyano-1-(4-methylphenyl)-6-oxo-1,6-dihydropyridine-2-thiolate

From 4-methylphenyl isothiocyanate (25.0 g, 170 mmol) by the method of Intermediate 140 to give the title compound as beige solid (33.7 g, 75%). $\delta_H$ (DMSO-$d_6$) 7.16-7.13 (3H, m), 6.81 (2H, dd, J 1.7, 6.4 Hz), 5.62 (1H, d, J 9.1 Hz), 2.32 (3H, s). LCMS (ES$^+$) RT 4.17 minutes.

INTERMEDIATE 153

3-Amino-7-(4-methylphenyl)-2-nitrothieno[2,3-b]pyridin-6(7H)-one

From Intermediate 152 (20.0 g, 76.0 mmol) and bromonitromethane by the method of Intermediate 141 to give the title compound as a yellow solid (16.25 g, 71%). $\delta_H$ (DMSO-$d_6$) 8.80 (2H, br s), 8.23 (1H, d, J 9.7 Hz), 7.44-7.31 (4H, m), 6.57 (1H, d, J 9.7 Hz), 2.42 (3H, s). LCMS (ES$^+$) RT 3.65 minutes, 302 (M+H)$^+$.

INTERMEDIATE 154

3-Bromo-7-(4-methylphenyl)-2-nitrothieno[2,3-b]pyridin-6(7H)-one

From Intermediate 153 (16.25 g, 54.0 mmol) by the method of Intermediate 36 to give the title compound as a yellow solid (12.98 g, 66%). $\delta_H$ (DMSO-$d_6$) 7.96 (1H, d, J 9.7 Hz), 7.49-7.43 (4H, m), 6.77 (1H, d, J 9.7 Hz), 2.44 (3H, s). LCMS (ES$^+$) RT 3.65 minutes, 367 (M+H)$^+$.

INTERMEDIATE 155

(4-Fluoro-3-methylphenyl)[7-(4-methylphenyl)-2-nitro-6-oxo-6,7-dihydrothieno[2,3-b]pyridin-3-yl]morpholin-4-ylacetonitrile From Intermediate 154 (5.98 g, 16.0 mmol) and (4-fluoro-3-methylphenyl)-(morpholin-4-yl)acetonitrile by the method of Intermediate 49 to give the title compound as a yellow solid (7.65 g, 92%). LCMS (FS$^+$) RT 3.94 minutes, 519 (M+H)$^+$.

INTERMEDIATE 156

3-(4-Fluoro-3-methylbenzoyl)-7-(4-methylphenyl)-2-nitrothieno[2,3-b]pyridin-6(7H)-one From Intermediate 155 (7.65 g, 14.8 mmol) by the method of Intermediate 144 to give the title compound as a yellow solid (4.64 g, 74%). $\delta_H$ (DMSO-$d_6$) 7.96 (1H, d, J 7.1 Hz), 7.84-7.33 (7H, m), 6.64 (1H, d, J 9.7 Hz), 2.47 (3H, s), 2.46 (3H, s). LCMS (ES$^+$) RT 3.89 minutes, 423 (M+H)$^+$.

INTERMEDIATE 157

2-Bromo-3-(4-fluoro-3-methylbenzoyl)-7-(4-methylphenyl thieno[2,3-b]pyridin-6(7H)-one From Example 234 (1.67 g, 4.26 mmol) by the method of Intermediate 36 to give the title compound as a brown solid (959 mg, 49%). $\delta_H$ (DMSO-$d_6$) 7.88 (1H, dd, J 1.6, 7.4 Hz), 7.78-7.73 (1H, m), 7.57 (1H, d, J 9.6 Hz), 7.47-7.33 (5H, m), 6.50 (1H, d, J 9.6 Hz), 2.43 (3H, s), 2.32 (3H, s). LCMS (ES$^+$) RT 4.26 minutes, 456 (M+H)$^+$.

INTERMEDIATE 158 tert-Butyl 3-{[3-(4-fluoro-3-methylbenzoyl)-7-(4-methylphenyl)-6-oxo-6,7-dihydrothieno[2,3-b]pyridin-2-yl]amino}azetidine-1-carboxylate From Intermediate 157 (959 mg, 2.10 mmol) and tert-butyl 3-aminoazetidine-1-carboxylate by the method of Example 55 to give the title compound as a yellow solid (824 mg, 72%). $\delta_H$ (DMSO-$d_6$) 9.12 (1H, d, J 7.7 Hz), 7.54 (1H, d, J 6.0 Hz), 7.47-7.41 (3H, m), 7.35-7.27 (3H, m), 6.79 (1H, d, J 9.7 Hz), 6.28 (1H, d, J 9.7 Hz), 4.22-4.13 (1H, m), 4.08-4.06 (2H, m), 3.83-3.81 (2H, m), 2.51 (3H, s), 2.42 (3H, s), 1.36 (9H, s). LCMS (ES$^+$) RT 3.93 minutes, 548 (M+H)$^+$.

INTERMEDIATE 159

Sodium 3-cyano-1-(4-fluorophenyl)-6-oxo-1,6-dihydropyridine-2-thiolate

From 4-fluorophenyl isothiocyanate (25.0 g, 163 mmol) by the method of Intermediate 140 to give the title compound as pale yellow solid (34.6 g, 72%). $\delta_H$ (DMSO-$d_6$) 7.17-7.12 (2H, m), 7.70 (1H, d, J 9.1 Hz), 7.00-6.95 (2H, m), 5.65 (1H, d, J 9.1 Hz).

INTERMEDIATE 160

3-Amino-7-(4-fluorophenyl)-2-nitrothieno[2,3-b]pyridin-6(7H)-one

From Intermediate 159 (28.0 g, 94.7 mmol) and bromonitromethane by the method of Intermediate 141 to give the title compound as a yellow solid (24.8 g, 86%). $\delta_H$ (DMSO-$d_6$) 8.81 (2H, br s), 8.25 (1H, d, J 9.7 Hz), 7.64-7.57 (2H, m), 7.50-7.43 (2H, m), 6.59 (1H, d, J 9.7 Hz). LCMS (ES$^+$) RT 2.90 minutes, 306 (M+H)$^+$.

INTERMEDIATE 161

3-Bromo-7-(4-fluorophenyl)-2-nitrothieno[2,3-b]pyridin-6(7H)-one

From Intermediate 160 (24.5 g, 80.3 mmol) by the method of Intermediate 36 to give the title compound as a yellow solid (26.6 g, 90%). $\delta_H$ (DMSO-$d_6$) 7.97 (1H, d, J 9.7 Hz), 7.70-7.64 (2H, m), 7.57-7.50 (2H, m), 6.79 (1H, d, J 9.7 Hz). LCMS (ES$^+$) RT 3.46 minutes, 369 (M+H)$^+$.

INTERMEDIATE 162

[7-(4-Fluorophenyl)-2-nitro-6-oxo-6,7-dihydrothieno[2,3-b]pyridin-3-yl](morpholin-4-yl)phenylacetonitrile From Intermediate 161 (14.34 g, 39 mmol) and morpholin-4-yl(phenyl)-acetonitrile by the method of Intermediate 49 to give the title compound as a black solid (19.6 g) used in the next step without purification. LCMS (ES$^+$) RT 3.64 minutes, 491 (M+H)$^+$.

INTERMEDIATE 163

3-Benzoyl-7-(4-fluorophenyl)-2-nitrothieno[2,3-b]pyridin-6(7H)-one

From Intermediate 162 (19.6 g crude material) by the method of Intermediate 144 to give the title compound as a yellow solid (3.0 g, 20% over 2 steps from Intermediate 161). $\delta_H$ (DMSO-$d_6$) 7.97-7.94 (2H, m), 7.81-7.71 (3H, m), 7.65-7.53 (5H, m), 6.66 (1H, d, J 9.7 Hz). LCMS (ES$^+$) RT 3.56 minutes, 395 (M+H)$^+$.

INTERMEDIATE 164

(4-Fluoro-3-methylphenyl)[7-(4-fluorophenyl)-2-nitro-6-oxo-6,7-dihydrothieno[23-b]pyridin-3-yl]morpholin-4-ylacetonitrile From Intermediate 161 (12.3 g, 33.0 mmol) and (4-fluoro-3-methylphenyl)(morpholin-4-yl)acetonitrile by the method of Intermediate 49 to give the title compound as a brown solid (13.37 g, 78%). LCMS (ES$^+$) RT 3.79 minutes, 523 (M+H)$^+$.

INTERMEDIATE 165

3-(4-Fluoro-3-methylbenzoyl)-7-(4-fluorophenyl)-2-nitrothieno[2,3-b]pyridin-6(7H)-one From Intermediate 164 (13.37 g, 26.0 mmol) by the method of Intermediate 144 gave the title compound as a yellow solid (4.2 g, 40%). $\delta_H$ (DMSO-$d_6$) 7.97 (1H, dd, J 1.6, 7.3 Hz), 7.86-7.81 (1H, m), 7.76-7.71 (2H, m), 7.64-7.53 (3H, m), 7.37 (1H, t, J 9.0 Hz), 6.65 (1H, d, J 9.7 Hz), 2.31 (3H, s). LCMS (ES$^+$) RT 3.75 minutes, 427 (M+H)$^+$.

INTERMEDIATE 166

3-Benzoyl-2-bromo-7-(4-fluorophenyl)thieno[2,3-b]pyridin-6(7H)-one

From Example 238 (1.90 g, 5.20 mmol) by the method of Intermediate 36 to give the title compound as an orange solid (1.07 g, 48%). $\delta_H$ (DMSO-$d_6$) 7.90-7.87 (2H, m), 7.78-7.39 (8H, m), 6.51 (1H, d, J 9.6 Hz). LCMS (ES$^+$) RT 3.76 minutes, 428 (M+H)$^+$.

INTERMEDIATE 167

2-Bromo-3-(4-fluoro-3-methylbenzoyl)-7-(4-fluorophenyl)thieno[2,3-b]pyridin-6(7H)-one From Example 237 (3.36 g, 8.48 mmol) by the method of Intermediate 36 to give the title compound as a brown solid (2.19 g, 56%). $\delta_H$ (DMSO-$d_6$) 7.89-7.87 (1H, m), 7.82-7.73 (1H, m), 7.69-7.64 (2H, m), 7.58 (1H, d, J 9.6 Hz), 7.54-7.47 (2H, m), 7.37 (1H, t, J 9.0 Hz), 6.51 (1H, d, J 9.6 Hz), 2.32 (3H, s). LCMS (ES$^+$) RT 4.02 minutes, 460 (M+H)$^+$.

INTERMEDIATE 168 tert-Butyl 3-{[7-(2,6-difluorophenyl)-3-(4-fluoro-3-methylbenzoyl)-6-oxo-6,7-dihydrothieno[2,3-b]pyridin-2-yl]amino}azetidine-1-carboxylate From Intermediate 149 (1.13 g, 2.37 mmol) and tert-butyl 3-aminoazetidine-1-carboxylate by the method of Example 55 to give the title compound as a yellow solid (929 mg, 69%). $\delta_H$ (DMSO-$d_6$) 9.10 (1H, d, J 7.6 Hz), 7.82-7.72 (1H, m), 7.59-7.45 (4H, m), 7.29 (1H, t, J 9.0 Hz), 6.92 (1H, d, J 9.8 Hz), 6.37 (1H, d, J 9.8 Hz), 4.21-4.07 (3H, m), 3.85-3.81 (2H, m), 2.31 (3H, s), 1.36 (9H, s). LCMS (ES$^+$) RT 3.91 minutes, 570 (M+H)$^+$.

EXAMPLE 1

Ethyl 3-(3-methylbenzoyl)-6-oxo-7-phenyl-6,7-dihydrothieno[2,3-b]pyridine-2-carboxylate A mixture of Intermediate 12 (5.69 g, 13 mmol) and activated manganese(IV) oxide (5.69 g of ~85%, 55 mmol) was stirred in DCM (100 ml) at r.t. for 18 h. The mixture was filtered through a short pad of Celite® and the filtrate concentrated in vacuo. The crude product was purified by chromatography (silica, 0-20% EtOAc in DCM) to give the title compound as a white solid (4.23 g, 78%). $\delta_H$ (CDCl$_3$) 7.66 (1H, s), 7.59-7.49 (4H, m), 7.42-7.36 (4H, m), 7.31-7.27 (1H, m), 6.56 (1H, d, J 9.6 Hz), 4.00 (2H, q, J 7.1 Hz), 2.34 (3H, s), 0.92 (3, t, J 7.1 Hz). LCMS (ES$^+$) RT 3.80 minutes, 418 (M+H)$^+$.

EXAMPLE 2

3-(3-Methylbenzoyl)-6-oxo-7-phenyl-6,7-dihydrothieno[2,3-b]pyridine-2-carboxylic acid A mixture of Example 1 (4.23 g, 10 mmol) and 0.25M NaOH(aq) (48 ml, 12 mmol) in EtOH (100 ml) was heated at reflux for 1 h. The solution was cooled to r.t. and the solvent removed in vacuo. The residue was dissolved in water (ca. 10 ml) and poured into 2M HCl(aq) (200 ml). The precipitate was filtered and dried in vacuo to give the title compound as a white solid (3.17 g, 81%). $\delta_H$ (DMSO-$d_6$) 7.64-7.53 (7H, m), 7.48-7.43 (2H, m), 7.39 (1H, t, J 7.6 Hz), 6.49 (1H, d, J 9.6 Hz), 2.32 (3H, s). LCMS (ES$^+$) RT 3.19 minutes, 390 (M+H)$^+$.

EXAMPLE 3 tert-Butyl[3-(3-methylbenzoyl)-6-oxo-7-phenyl-6,7-dihydrothieno[2,3-b]pyridin-2-yl]carbamate A mixture of Example 2 (4.7 g, 12.0 mmol), diphenylphosphoryl azide (3.63 g, 13 mmol) and triethylamine (1.31 g, 13 mmol) in 2-methyl-2-propanol (100 ml) was heated at 90° C. for 3 h. The reaction was cooled to r.t. and NaHCO$_3$(aq) (200 ml) added. The mixture was extracted with DCM (3×100 ml). The combined organic extracts were dried (MgSO$_4$) and concentrated in vacuo. The crude product was purified by chromatography (silica, 10% EtOAc in DCM) to give the title compound as a yellow solid (5.4 g, 90%). $\delta_H$ (CDCl$_3$) 10.6 (1H, s), 7.62-7.46 (3H, m), 7.40-7.29 (6H, m), 6.81 (1H, d, J 9.7 Hz), 6.36 (1H, d, J 9.7 Hz), 2.37 (3H, s), 1.42 (9H, s). LCMS (ES$^+$) RT 4.44 minutes, 461 (M+H)$^+$.

EXAMPLE 4

2-Amino-3-(3-methylbenzoyl)-7-phenylthieno[2,3-b]pyridin-6(7H)-one

Trifluoroacetic acid (20 ml) was added to a solution of Example 3 (5.4 g, 11.0 mmol) in DCM (20 ml) and stirred at r.t. for 5 h. NaHCO$_3$(aq) (200 ml) was added to the reaction, and the mixture extracted with DCM (3×100 ml). The combined organic extracts were dried (MgSO$_4$) and concentrated in vacuo. The crude product was purified by chromatography (silica, 10% THF in DCM) to give the title compound as a yellow solid (3.0 g, 76%). $\delta_H$ (CDCl$_3$) 7.52-7.45 (3H, m), 7.33-7.30 (6H, m), 6.72 (1H, d, J 9.6 Hz), 6.33 (1H, d, J 9.6 Hz), 2.35 (3H, s). LCMS (ES$^+$) RT 3.11 minutes, 361 (M+H)$^+$.

EXAMPLE 5

3-(3-Methylbenzoyl)-6-oxo-7-phenyl-6,7 dihydrothieno[2,3-b]pyridine-2-carbonitrile A mixture of Intermediate 13 (150 mg, 0.40 mmol) and manganese dioxide (300 mg, 3.4 mmol) was stirred in DCM (30 ml) at r.t. for 18 h. The solution was filtered through a short pad of Celite® and the solvent removed in vacuo. The crude product was purified by chromatography on silica (0-10% EtOAc in DCM) to give the title compound as a white solid (130 mg, 88%). $\delta_H$ (CDCl$_3$) 7.80 (1H, d, J 9.8 Hz), 7.76 (1H, s), 7.72-7.60 (4H, m), 7.58-7.43 (4H, m), 6.74 (1H, d, J 9.8 Hz), 2.48 (3H, s). LCMS (ES) RT 3.59 minutes, 371 (+H)$^+$.

EXAMPLE 6

3-(3-Methylbenzoyl)-6-oxo-7-phenyl-6,7-dihydrothieno[2,3-b]pyridine-2-carboxamide A mixture of Example 5 (127 mg, 0.34 mmol) and 0.25M sodium hydroxide(aq) (1.36 ml, 0.34 mmol) was heated to reflux in EtOH (20 ml) for 45 minutes. The solution was cooled to room temperature, 2M HCl(aq) (100 ml) added and the aqueous extracted with DCM (2×100 ml). The combined DCM extracts were dried (MgSO$_4$) and concentrated in vacuo. The crude product was purified by chromatography on silica (0-10% EtOAc in DCM) to give the title compound as a white solid (125 mg, 95%). $\delta_H$ (CDCl$_3$) 7.70 (1H, br s), 7.59-7.32 (8H, m), 7.05 (1H, d, J 9.7 Hz), 6.44 (1H, d, J 9.7 Hz), 2.37 (3H, s). LCMS (ES$^+$) RT 3.00 minutes, 389 (M+H)$^+$.

EXAMPLE 7

2-(Azetidin-1-ylcarbonyl)-3-(3-methylbenzoyl)-7-phenylthieno[2,3-b]pyridin-6(7H)-one Example 2 (300 mg, 0.77 mmol) was dissolved in DCM (10 ml). NMM (0.25 ml, 2.3 mmol), EDC (177 mg, 0.92 mmol), HOBT (124 mg, 0.92 mmol) and azetidine hydrochloride (107 mg, 1.16 mmol) were added sequentially. The solution was stirred at room temperature for 18 h before being partitioned between DCM (100 ml) and aqueous NaHCO$_3$. The aqueous layer was extracted with DCM (2×100 ml) and the combined organic layers were washed with 2M HCl(aq), dried (MgSO$_4$) and concentrated in vacuo. The crude product was purified by chromatography on silica (0-20% EtOAc in DCM) to give the title compound as a white solid (110 mg, 34%). $\delta_H$ (CDCl$_3$) 7.68 (1H, s), 7.62-7.27 (9H, m), 6.56 (1H, d, J 9.7 Hz), 3.92 (4H, br s), 2.33 (3H, s), 2.09 (2H, m). LCMS (ES$^+$) RT 3.28 minutes, 429 (M+H)$^+$.

EXAMPLE 8

3-(3-Methylbenzoyl)-7-phenyl-2-(piperidin-1-yl)thieno[2,3-b]pyridin-6(7H)-one

Intermediate 14 (100 mg of 75% pure material, 18 mmol) was dissolved in toluene (5 ml). Cs$_2$CO$_3$ (108 mg, 0.33 mmol), tris(dibenzylideneacetone)dipalladium(0) (11 mg, 0.012 mmol), BINAP (15 mg, 0.024 mmol) and piperidine (0.029 ml, 0.29 mmol) were added sequentially. The mixture was heated at reflux for 18 h, cooled to room temperature and poured into water (100 ml). The aqueous mixture was extracted with DCM (2×100 ml), the combined organic extracts dried (MgSO$_4$) and the solvent removed in vacuo. The crude product was purified by chromatography on silica (5-20% EtOAc in DCM) to give the title compound as a yellow solid (22 mg, 29%). $\delta_H$ (DMSO-d$_6$) 7.87 (1H, d, J 9.6 Hz), 7.67-7.32 (9H, m), 6.53 (1H, d, J 9.6 Hz), 2.74 (4H, m), 2.37 (3H, s), 1.25-0.96 (6H, m). LCMS (ES$^+$) RT 4.30 minutes, 429 (M+H)$^+$.

EXAMPLE 9

3-(3-Methylbenzoyl)-7-phenylthieno[2,3-b]pyridin-6(7H)-one

Example 2 (100 mg, 0.26 mmol) was dissolved in 1,4-dioxane (5 ml) and HCl (conc.) (1 ml) added. The solution was heated in a microwave (180° C., 200 psi) for 5 minutes. The cooled solution was poured into DCM (100 ml) and washed with aqueous NaHCO$_3$. The organic layer was dried (MgSO$_4$) and concentrated in vacuo to give a crude product which was purified by chromatography on silica (0-20% EtOAc in DCM) to give the title compound as a white solid (12 mg, 12%). $\delta_H$ (DMSO-d$_6$) 8.25 (1H, d, J 9.6 Hz), 7.73 (1H, s), 7.63-7.38 (9H, m), 6.57 (1H, d, J 9.6 Hz), 2.34 (3H, s). LCMS (ES$^+$) RT 3.65 mutes, 346, (M+H)$^+$.

EXAMPLE 10

Ethyl 3-benzoyl-6-oxo-7-phenyl-6,7-dihydrothieno[2,3-b]pyridine-2-carboxylate

From Intermediate 15 by the method of Example 1. White solid. $\delta_H$ (CDCl$_3$) 7.84-7.78 (2H, m), 7.59-7.51 (4H, m), 7.44-7.37 (5H, m), 6.56 (1H, d, J 9.6 Hz), 3.99 (2H, q, J 7.1 Hz), 0.90 (3H, t, J 7.1 Hz). LCMS (ES$^+$) RT 3.62 minutes, 404 (M+H)$^+$.

EXAMPLE 11

3-Benzoyl-6-oxo-7-phenyl-6,7-dihydrothieno[2,3-b]pyridine-2-carboxylic acid

A mixture of Example 10 (3.0 g, 7.4 mmol) and 0.25M sodium hydroxide(aq) (29 ml, 7.4 mmol) was stirred in EtOH (150 ml) and heated at reflux for 1 h. The solution was cooled to r.t. and the solvent removed in vacuo. The residue was dissolved in water (ca. 10 ml) and poured into 2M HCl(aq) (200 ml). The precipitate was filtered and dried in vacuo to give the title compound as a white solid (1.89 g, 68%). $\delta_H$ (DMSO-d$_6$) 7.91-7.89 (2H, m), 7.79-7.58 (9H, m), 6.60 (1H, d, J 9.6 Hz). LCMS (ES$^+$) RT 3.06 minutes, 376 (M+H)$^+$.

EXAMPLE 12 tert-Butyl(3-benzoyl-6-oxo-7-phenyl-6,7-dihydrothieno[2,3-b]pyridin-2-yl)carbamate From Example 11 (1.46 g, 3.9 mmol), diphenylphosphoryl azide (1.17 g, 4.3 mmol) and triethylamine (0.43 g, 4.3 mmol) in 2-methyl-2-propanol (30 ml), by the method of Example 3, to give the title compound as a yellow solid (1.5 g, 84%). $\delta_H$ (CDCl$_3$) 10.66 (1H, s), 7.60-7.43 (8H, m), 7.33 (2H, d, J 7.4 Hz), 6.80 (1H, d, J 9.7 Hz), 6.36 (1H, d, J 9.7 Hz), 1.42 (9H, s). LCMS (ES$^+$) RT 4.07 minutes, 447 (M+H)$^+$.

EXAMPLE 13

2-Amino-3-benzoyl-7-phenylthieno[2,3-b]pyridin-6(7H)-one

From Example 12 by the method of Example 4. Yellow solid. $\delta_H$ (DMSO-d$_6$) 8.29 (2H, br s), 7.70-7.50 (10H, m), 6.60 (1H, d, J 9.6 Hz), 6.23 (1H, d, J 9.6 Hz). LCMS (ES$^+$) RT 3.016 minutes, 347 (M+H)$^+$.

EXAMPLE 14

N-(3-Benzoyl-6-oxo-7-phenyl-6,7-dihydrothieno[2,3-b]pyridin-2-yl)acetamide

To a solution of Example 13 (270 mg, 0.78 mmol) in DMF (10 ml) 4-dimethylaminopyridine (~10 mg, catalytic) was added. Acetic anhydride (0.074 ml, 0.78 mmol) premixed in DMF (~1 ml) was added to the reaction mixture and stirred at r.t. for 18 h. NaHCO$_3$(aq) (20 ml) was added, and the mixture was extracted with DCM (2×20 ml). The combined organic extracts were dried (MgSO$_4$) and concentrated in vacuo. The crude product was purified by chromatography (silica, 20-40% EtOAc in DCM), to give the title compound as a yellow solid (123 mg, 41%). $\delta_H$ (DMSO-d$_6$) 10.98 (1H, s), 7.78-7.75 (2H, m), 7.70-7.50 (8H, m) 7.17 (1H, d, J 9.6 Hz), 6.40 (1H, d, J 9.6 Hz), 2.02 (3H, s). LCMS (ES$^+$) RT 3.26 minutes, 389 (M+H)$^+$.

EXAMPLE 15

N-[3-(3-Methylbenzoyl)-6-oxo-7-phenyl-6,7-dihydrothieno[2,3-b]pyridin-2-yl]acetamide From Example 4 by the method of Example 14. Yellow solid. $\delta_H$ (DMSO-d$_6$) 11.03 (1H, br s), 7.76-7.48 (9H, m), 7.24 (1H, d, J 9.7 Hz), 6.47 (1H, d, J 9.7 Hz), 2.46 (3H, s), 2.10 (3H, s). LCMS (ES$^+$) RT 3.42 minutes, 403 (M+H)$^+$.

EXAMPLE 16

N-(3-Benzoyl-6-oxo-7-phenyl-6,7-dihydrothieno[2,3-b]pyridin-2-yl)methanesulfonamide Trifluoroacetic acid (5 ml) was added to a solution of Intermediate 16 (100 mg, 1.90 mmol) in DCM (5 ml) and stirred at r.t. for 5 h. NaHCO$_3$(aq) (50 ml) was added to the reaction, and the mixture was extracted with DCM (3×10 ml). The combined organic extracts were dried (MgSO$_4$) and concentrated in vacuo. The crude product was purified by chromatography (silica, 20% THF in DCM) to give the title compound as a yellow solid (11 mg, 14%). $\delta_H$ (CDCl$_3$) 10.12 (1H, s), 7.67-7.45 (8H, m), 7.33 (2H, d, J 7.8 Hz), 6.89 (1H, d, J 9.7 Hz), 6.42 (1H, d, J 9.7 Hz), 2.99 (3H, s). LCMS (ES$^+$) RT 3.11 minutes, 425 (M+H)$^+$.

EXAMPLE 17

N-[3-(3-Methylbenzoyl)-6-oxo-7-phenyl-6,7-dihydrothieno[2,3-b]pyridin-2-yl]methanesulfonamide From Intermediate 17 by the method of Example 16. Yellow solid. $\delta_H$ (CDCl$_3$) 10.07 (1H, s), 7.56-7.32 (9H, m), 6.89 (1H, d, J 9.7 Hz), 6.36 (1H, d, J 9.7 Hz), 2.99 (3H, s), 2.38 (3H, s). LCMS (ES$^+$) RT 3.22 minutes, 439 (M+H)$^+$.

EXAMPLE 18

2-(Azetidin-1-yl)-3-(3-methylbenzoyl)-7-phenylthieno[2,3-b]pyridin-6(7H)-one

From Intermediate 14 and azetidine by the method of Example 8. Yellow solid. $\delta_H$ (CDCl$_3$) 7.58-7.44 (5H, m), 7.39-7.23 (5H, m), 6.39 (1H, d, J 9.7 Hz), 3.66 (4H, t, J 7.4 Hz), 2.35 (3H, s), 2.22 (2H, m). LCMS (ES$^+$) RT 3.55 minutes, 401 (M+H)$^+$.

EXAMPLE 19

N-(3-Benzoyl-6-oxo-7-phenyl-6,7-dihydrothieno[2,3-b]pyridin-2-yl)piperidine-4-carboxamide Example 13 (500 mg, 1.45 mmol) was dissolved in DCM (10 ml). NMM (1.0 ml, 8.7 mmol), HOBT (470 mg, 3.4 mmol), EDC (670 mg, 3.4 mmol) and BOC-isonipecotic acid (740 mg, 3.4 mmol) were added sequentially. The solution was heated at reflux for 48 h, cooled to room temperature and poured into DCM (250 ml). The aqueous was sequentially washed with NaHCO$_3$ (sat. aq) (100 ml) and cold 2M HCl(aq) (100 ml). The organic layer was dried (MgSO$_4$) and the solvent removed in vacuo. The crude product was purified by chromatography on silica (10-30% EtOAc in DCM to give a yellow solid (350 mg, 42%). This intermediate was dissolved in DCM (20 ml) and TFA (10 ml) was added. The reaction was stirred at room temperature for 20 h before being poured into cold NaHCO$_3$ (sat. aq) (500 ml) (CAUTION). The product was extracted with DCM (2×250 ml), the combined organic layers dried (MgSO$_4$) and the solvent removed in vacuo to give the title compound as a yellow solid (262 mg, 94%). $\delta_H$ (DMSO-d$_6$) 7.61-7.33 (12H, m), 7.28 (1H, d), 2.87 (2H, m), 2.54 (2H, t, J 10.5 Hz), 2.23 (1H, m), 1.45 (2H, m), 1.30 (2H, m). LCMS (ES$^+$) RT 2.27 minutes, 458 (M+H)$^+$.

EXAMPLE 20

N'-(3-Benzoyl-6-oxo-7-phenyl-6,7-dihydrothieno[2,3-b]pyridin-2-yl)-N,N-dimethylurea A solution of phosgene (0.188 ml, 0.32 mmol) in DCM (10 ml) was cooled to −30° C. under nitrogen. Triethylamine (0.088 ml, 0.64 mmol) and Example 13 (100 mg, 0.29 mmol) were added, and the reaction mixture stirred at −30° C. for 0.5 h. Dimethylamine (0.29 ml of a 2.0M solution in THF, 0.58 mmol) was added and the mixture was warmed to r.t. and stirred for 18 h. Water (10 ml) was added, and the mixture was extracted with DCM (2×10 ml). The combined organic extracts were dried (MgSO$_4$) and concentrated in vacuo. The crude product was purified by chromatography (silica, 5% THF in DCM) to give the title compound as a yellow solid (55 mg, 46%). $\delta_H$ (CDCl$_3$) 11.95 (1H, s), 7.82-7.43 (8H, m), 7.37-7.31 (2H, m), 6.79 (1H, d, J 9.7 Hz), 6.38 (1H, d, J 9.7 Hz), 3.02 (6H, s). LCMS (ES$^+$) RT 3.36 minutes, 418 (M+H)$^+$.

EXAMPLE 21

N-(2-Hydroxy-2-methylpropyl)-N'-[3-(3-methylbenzoyl)-6-oxo-7-phenyl-6,7-dihydrothieno[2,3-b]pyridin-2-yl]urea From Example 4 and 1-amino-2-methylpropan-2-ol hydrochloride (137 mg, 1.1 mmol), by the method of Example 20, to give the title compound as a yellow solid (174 mg, 66%). $\delta_H$ (CDCl$_3$) 11.22 (1H, s), 7.51-7.42 (3H, m), 7.35-7.29 (6H, m), 6.73 (1H, d, J 9.7 Hz), 6.31 (1H, d, J 9.7 Hz), 5.82 (1H, br s), 3.15 (2H, d, J 5.9 Hz), 2.34 (3H, s), 1.14 (6H, s), 0.80-0.75 (1H, m). LCMS (ES$^+$) RT 3.12 minutes, 476 (M+H)$^+$.

EXAMPLE 22

4-Methyl-N-[3-(3-methylbenzoyl)-6-oxo-7-phenyl-6,7-dihydrothieno[2,3-b]pyridin-2-yl]piperazine-1-carboxamide From Example 4 and 1-methylpiperazine (0.12 ml, 1.1 mmol), by the method of Example 20, to give the title compound as a yellow solid (238 mg, 88%). $\delta_H$ (CDCl$_3$) 12.34 (1H, s), 7.69-7.60 (3H, m), 7.55-7.47 (6H, m), 6.97 (1H, d, J 9.7 Hz), 6.48 (1H, d, J 9.7 Hz), 4.28 (2H, m), 4.05 (2H, m), 3.60 (2H, m), 2.89 (5H, s), 2.53 (3H, s). LCMS (ES$^+$) RT 2.28 minutes, 487 (M+H)$^+$.

EXAMPLE 23

N-[3-(3-Methylbenzoyl)-6-oxo-7-phenyl-6,7-dihydrothieno[2,3-b]pyridin-2-yl]urea

From Example 4 and ammonia(aq) (0.07 ml, 4.1 mmol), by the method of Example 20, to give the title compound as a yellow solid (80 mg, 36%). $\delta_H$ (CDCl$_3$) 10.58 (1H, s), 7.59-7.50 (3H, m), 7.42-7.37 (6H, m), 7.10 (1H, br s), 6.67 (1H, d, J 9.7 Hz), 6.19 (1H, d, J 9.7 Hz), 2.33 (3H, s). LCMS (ES$^+$) RT 3.01 minutes, 404 (M+H)$^+$.

EXAMPLE 24

N,N-Dimethyl-N'-[3-(3-methylbenzoyl)-6-oxo-7-phenyl-6,7-dihydrothieno[2,3-b]pyridin-2-yl]urea From Example 4 and dimethylamine (0.55 ml of a 2.0M solution in THF, 1.1 mmol), by the method of Example 20, to give the title compound as a yellow solid (59 mg, 25%). $\delta_H$ (CDCl$_3$) 11.94 (1H, s), 7.52-7.45 (3H, m), 7.38-7.32 (6H, m), 6.80 (1H, d, J 9.7 Hz), 6.30 (1H, d, J 9.7 Hz), 3.02 (6H, s), 2.33 (3H, s). LCMS (ES$^+$) RT 3.51 minutes, 432 (M+H)$^+$.

EXAMPLE 25

N-[3-(3-Methylbenzoyl)-6-oxo-7-phenyl-6,7-dihydrothieno[2,3-b]pyridin-2-yl]azetidine-1-carboxamide From Example 4 and azetidine hydrochloride (102 mg, 1.1 mmol), by the method of Example 20, to give the title compound as a yellow solid (157 mg, 64%). $\delta_H$ (CDCl$_3$) 11.24 (1H, s), 7.52-7.42 (3H, m), 7.37-7.30 (6H, m), 6.78 (1H, d, J 9.7 Hz), 6.29 (1H, d, J 9.7 Hz), 4.09 (4H, t, J 7.6 Hz), 2.36-2.27 (5H, m). LCMS (ES$^+$) RT 3.52 minutes, 444 (M+H)$^+$.

EXAMPLE 26

N-Allyl-N'-[3-(3-methylbenzoyl)-6-oxo-7-phenyl-6,7-dihydrothieno[2,3-b]pyridin-2-yl]urea From Example 4 and allylamine (0.08 ml, 1.1 mmol), by the method of Example 20, to give the title compound as a yellow solid (120 mg, 49%). $\delta_H$ (CDCl$_3$) 11.32 (1H, s), 7.52-7.42 (3H, m), 7.36-7.29 (6H, m), 6.73 (1H, d, J 9.7 Hz), 6.30 (1H, d, J 9.7 Hz), 5.80-5.71 (1H, m), 5.21-5.08 (3H, m), 3.79 (2H, t, J 5.7 Hz), 2.36 (3H, s). LCMS (ES$^+$) RT 3.49 minutes, 444 (M+H)$^+$.

EXAMPLE 27

(2R)-2-(Hydroxymethyl)-N-[3-(3-methylbenzoyl)-6-oxo-7-phenyl-6,7-dihydrothieno[2,3-b]pyridin-2-yl]pyrrolidine-1-carboxamide From Example 4 and (R)-(−)-2-pyrrolidinemethanol (0.11 ml, 1.1 mmol), by the method of Example 20, to give the title compound as a yellow solid (89 mg, 33%). $\delta_H$ (CDCl$_3$) 11.73 (1H, s), 7.53-7.44 (3H, m), 7.38-7.32 (6H, m), 6.80 (1H, d, J 9.7 Hz), 6.30 (1H, d, J 9.7 Hz), 4.05 (1H, br s), 3.66-3.54 (4H, m), 2.37 (3H, s), 2.04-1.91 (3H, m), 1.81-1.78 (1H, m), 1.18 (1H, s). LCMS (ES$^+$) RT 3.31 minutes, 488 (M+H)$^+$.

EXAMPLE 28

N-(1-Ethylpyrrolidin-3-yl)-N'-[3-(3-methylbenzoyl)-6-oxo-7-phenyl-6,7-dihydrothieno[2,3-b]pyridin-2-yl]urea To a solution of Intermediate 18 (258 mg, 0.43 mmol) in EtOH (20 ml) palladium (4.5 mg, 10 wt % on carbon powder, 0.043 mmol) was added. The reaction was placed under an atmosphere of nitrogen and stirred at r.t. for 18 h. The solution was filtered through a short pad of Celite® and the solvent removed in vacuo. The crude product was purified by preparative HPLC to give the title compound as a yellow solid (6.8 mg, 3%). $\delta_H$ (DMSO-d$_6$) 10.72 (1H, s), 8.29 (1H, d, J 5.8 Hz), 7.87-7.58 (3H, m), 7.50-7.41 (6H, m), 6.73 (1H, d, J 9.7 Hz), 6.27 (1H, d, J 9.7 Hz), 4.08 (1H, br s), 2.87 (2H, br s) 2.67-2.62 (4H, m), 2.40 (3H, s), 2.17-2.13 (1H, m), 1.64-1.59 (1H, m), 1.07 (3H, t, J 7.1 Hz). LCMS (ES$^+$) RT 2.33 minutes, 501 (M+H)$^+$.

EXAMPLE 29

N-[3-(3-Methylbenzoyl)-6-oxo-7-phenyl-6,7-dihydrothieno[2,3-b]pyridin-2-yl]-2-(methylsulfonyl)hydrazinecarboxamide From Example 4 and methanesulfonyl hydrazine (121 mg, 1.1 mmol), by the method of Example 20, to give the title compound as a yellow solid (10 mg, 4%). $\delta_H$ (DMSO-d$_6$) 9.98 (1H, br s), 9.77 (1H, br s), 7.78-7.70 (3H, m), 7.61-7.54 (6H, m), 6.90 (1H, d, J 9.7 Hz), 6.41 (1H, d, J 9.7 Hz), 3.11 (3H, br s), 2.50 (3H, s). LCMS (ES$^+$) RT 3.00 minutes, 497 (M+H)$^+$.

EXAMPLE 30

3-Benzoyl-N-methyl-6-oxo-7-phenyl-6,7-dihydrothieno[2,3-b]pyridine-2-carboxamide From Example 11 with methylamine hydrochloride, by the method of Example 7. White solid. $\delta_H$ (CDCl$_3$) 7.82 (2H, m), 7.70-7.19 (8H, m), 7.02 (1H, d, J 9.7 Hz), 6.41 (1H, d, J 9.7 Hz), 2.76 (3H, d, J 4.8 Hz). LCMS (ES$^+$) RT 3.07 minutes, 389 (M+H)$^+$.

EXAMPLE 31

2-(Azetidin-1-ylcarbonyl)-3-benzoyl-7-phenylthieno[2,3-b]pyridin-6(7H)-one

From Example 11 with azetidine hydrochloride, by the method of Example 7. White solid. $\delta_H$ (DMSO-d$_6$) 7.54 (2H, m), 7.66-7.46 (9H, m), 6.50 (1H, d, J 9.8 Hz), 3.90 (4H, br s), 2.44 (2H, m). LCMS (ES$^+$) RT 3.14 minutes, 415 (M+H)$^+$.

EXAMPLE 32

3-Benzoyl-N-(1,1-dimethyl-2-hydroxyethyl-6-oxo-7-phenyl-6,7-dihydrothieno[2,3-b]pyridine-2-carboxamide From Example 11 with 1,1-dimethyl-2-hydroxyethylamine, by the method of Example 7. White solid. $\delta_H$ (CDCl$_3$) 7.81 (2H, m), 7.64-7.34 (8H, m), 7.10 (1H, d, J 9.7 Hz), 6.25 (1H, d, J 9.7 Hz), 3.44 (2H, s), 1.14 (6H, s). LCMS (ES$^+$) RT 3.13 minutes, 447 (M+H)$^+$.

EXAMPLE 33

3-Benzoyl-N,N-dimethyl-6-oxo-7-phenyl-6,7-dihydrothieno[2,3-b]pyridine-2-carboxamide From Example 11 with dimethylamine, by the method of Example 7. White solid. $\delta_H$ (CDCl$_3$) 7.84-7.76 (2H, m), 7.57-7.35 (9H, m), 6.63 (1H, d, J 9.7 Hz), 2.58 (6H, s). LCMS (ES$^+$) RT 3.11 minutes, 403 (M+H)$^+$.

EXAMPLE 34

3-Benzoyl-2-{[(2S)-2-(hydroxymethyl)pyrrolidin-1-yl]carbonyl}-7-phenylthieno[2,3-b]pyridin-6(7H)-one From Example 11 with (S)-prolinol, by the method of Example 7. White solid. BH (DMSO-d$_6$) 7.83-7.52 (11H, m), 6.63 (1H, d, J 9.7 Hz), 3.70 (1H, m), 3.40-3.29 (2H, m), 3.09 (1H, m), 2.78 (1H, m), 1.75 (4H, m). LCMS (ES$^+$) RT 2.96 minutes, 459 (M+H)$^+$.

EXAMPLE 35

3-Benzoyl-2-(morpholin-4-ylcarbonyl)-7-phenylthieno[2,3-b]pyridin-6(7H)-one

From Example 11 with morpholine, by the method of Example 7. White solid. $\delta_H$ (CDCl$_3$) 7.82 (2H, m), 7.58 (1H, d, J 9.7 Hz), 7.46-7.15 (8H, m), 6.51 (1H, d, J 9.7 Hz), 3.22 (4H, m), 3.01 (4H, m). LCMS (ES$^+$) RT 3.09 minutes, 445 (M+H)$^+$.

EXAMPLE 36

3-Benzoyl-7-phenyl-2-pyrrolidin-1-ylcarbonyl thieno[2,3-b]pyridin-6(7H)-one

From Example 11 with pyrrolidine, by the method of Example 7. White solid. $\delta_H$ (CDCl$_3$) 7.82 (2H, m), 7.74 (1H, d, J 9.7 Hz), 7.59-7.37 (8H, m), 6.61 (1H, d, J 9.7 Hz), 3.10 (4H, br s), 1.63 (4H, br s). LCMS (ES$^+$) RT 3.22 minutes, 429 (M+H)$^+$.

EXAMPLE 37

3-Benzoyl-6-oxo-7-phenyl-6,7-dihydrothieno[2,3-b]pyridine-2-carbonitrile

From Intermediate 19 by the method of Example 5. White solid. $\delta_H$ (CDCl$_3$) 7.83 (2H, m), 7.70 (1H, d, J 9.7 Hz), 7.67-7.48 (6H, m), 7.36 (2H, m), 6.64 (1H, d, J 9.7 Hz). LCMS (ES$^+$) RT 3.43 minutes, 357 (M+H)$^+$.

EXAMPLE 38

3-Benzoyl-6-oxo-7-phenyl-6,7-dihydrothieno[2,3-b]pyridine-2-carboxamide

From Example 37 by the method of Example 6. White solid. $\delta_H$ (CDCl$_3$) 7.80 (2H, m), 7.67-7.35 (8H, m), 7.04 (1H, d, J 9.7 Hz), 6.45 (1H, d, J 9.7 Hz). LCMS (ES$^+$) RT 2.86 minutes, 375 (M+H)$^+$.

EXAMPLE 39

Ethyl 3-benzoyl-7-(cyclopropylmethyl)-6-oxo-6,7-dihydrothieno[2,3-b]pyridine-2-carboxylate From Intermediate 20 by the method of Example 1. White solid. $\delta_H$ (DMSO-d$_6$) 7.88 (2H, m), 7.76 (1H, tt, J 1.2, 6.2 Hz), 7.61 (2H, m), 7.54 (1H, d, J 9.5 Hz), 6.55 (1H, d, J 9.5 Hz), 4.12 (4H, m), 1.43 (1H, m), 1.02 (3H, t, J 7.1 Hz), 0.60 (4H, m). LCMS (ES$^+$) RT 3.71 minutes, 382 (M+H)$^+$.

EXAMPLE 40

2-Amino-3-benzoyl-7-(cyclopropylmethyl)thieno[2,3-b]pyridin-6(7H)-one

From Example 39 by the method of Examples 2, 3 and 4 (intermediates taken on without purification). Yellow solid. $\delta_H$ (DMSO-d$_6$) 8.36 (2H, m), 7.65-7.48 (5H, m), 6.48 (1H, d, J 9.6 Hz), 6.30 (1H, d, J 9.6 Hz), 3.90 (2H, d, J 7.0 Hz), 1.30-1.21 (1H, m), 0.55-0.44 (4H, m). LCMS (ES$^+$) RT 2.93 minutes, 325 (M+H)$^+$.

EXAMPLE 41

3-Benzoyl-7-(2-chlorophenyl)-6-oxo-6,7-dihydrothieno[2,3-b]pyridine-2-carbonitrile From Intermediate 21 (333 mg, 0.93 mmol) and manganese(IV) oxide (333 mg, 3.3 mmol) by the method of Example 5. White solid (102 mg, 30%). $\delta_H$ (CDCl$_3$) 7.86-7.84 (2H, m), 7.74 (1H, d, J 9.8 Hz), 7.67-7.63 (2H, m), 7.54-7.46 (4H, m), 7.41-7.38 (1H, m), 6.65 (1H, d, J 9.8 Hz). LCMS (ES$^+$) RT 3.57 minutes, 391 (M+H)$^+$.

EXAMPLE 42

2-Amino-3-benzoyl-7-(2-chlorophenyl)thieno[2,3-b]pyridin-6(7H)-one

Example 41 (91 mg, 0.23 mmol) was suspended in EtOH (10 ml), 0.25M NaOH (1.8 ml) added and the solution heated to reflux for 60 h. The reaction was cooled to room temperature and the solvent removed in vacuo. The solid residue was taken up in water (10 ml) and poured into 2M HCl (50 ml). The precipitate formed was filtered and dried in vacuo to give a white solid (35 mg, 37%). This crude intermediate was converted to the title compound by the methods of Examples 3 and 4. Yellow solid. $\delta_H$ (DMSO-$d_6$) 8.30 (2H, m), 7.83 (1H, dd, J 1.8, 7.1 Hz), 7.72-7.53 (8H, m), 6.62 (1H, d, J 9.7 Hz), 6.24 (1H, d, J 9.7 Hz). LCMS (ES$^+$) RT 3.18 minutes, 381 (M+H)$^+$.

EXAMPLE 43

3-(3-Chlorobenzoyl)-6-oxo-7-phenyl-6,7-dihydrothieno[2,3-b]pyridine-2-carboxamide From Intermediate 23 (53 mg, 0.136 mmol) and 0.25M sodium hydroxide(aq) (0.27 ml, 0.07 mmol) by the method of Example 6. White solid (20 mg, 36%). $\delta_H$ (DMSO-$d_6$) 8.43 (2H, s), 7.70-7.66 (6H, m), 7.63-7.56 (4H, m), 6.55 (1H, d, J 9.6 Hz). LCMS (ES$^+$) RT 3.08 minutes, 409 (M+H)$^+$.

EXAMPLE 44

Ethyl 3-(3-chlorobenzoyl)-6-oxo-7-phenyl-6,7-dihydrothieno[2,3-b]pyridine-2-carboxylate From Intermediate 24 by the method of Example 1. White solid. $\delta_H$ (DMSO-$d_6$) 7.79 (1H, d, J 1.8 Hz), 7.73-7.68 (2H, m), 7.64-7.50 (7H, m), 6.50 (1H, d, J 9.7 Hz), 3.95 (2H, q, J 7.1 Hz), 0.87 (3H, t, J 7.1 Hz). LCMS (ES$^+$) RT 3.82 minutes, 438 (M+H)$^+$.

EXAMPLE 45

2-Amino-3-(3-chlorobenzoyl)-7-phenylthieno[2,3-b]pyridin-6(7H)-one

From Example 44 by the methods of Examples 2, 3 and 4 (intermediates used crude). Yellow solid. $\delta_H$ (DMSO-$d_6$) 8.46 (2H, m), 7.83-7.59 (9H, m), 6.76 (1H, d, J 9.7 Hz), 6.37 (1H, d, J 9.7 Hz). LCMS (ES$^+$) RT 3.21 minutes, 381 (M+H)$^+$.

EXAMPLE 46

N-[3-(3-Chlorobenzoyl-6-oxo-7-phenyl-6,7-dihydrothieno[2,3-b]pyridin-2-yl]acetamide From Example 45 by the method of Example 14. Yellow solid. $\delta_H$ (DMSO-$d_6$) 13.70 (1H, s), 7.70-7.41 (9H, m), 7.21 (1H, d, J 9.6 Hz), 6.36 (1H, d, J 9.6 Hz), 1.94 (3H, s). MS (ES$^+$) RT 3.42 minutes, 423 (M+H)$^+$.

EXAMPLE 47

3-(2,4-Difluorobenzoyl)-6-oxo-7-phenyl-6,7-dihydrothieno[2,3-b]pyridine-2-carboxamide From Intermediate 26 (14 mg, 0.036 mmol) and 0.25M sodium hydroxide(aq) (0.07 ml, 0.02 mmol) by the method of Example 6. White solid (6 mg, 41%). $\delta_H$ (DMSO-$d_6$) 8.51 (2H, s), 7.82-7.76 (1H, m), 7.70-7.52 (6H, m), 7.40-7.34 (1H, m), 7.22 (1H, dt, J 2.2, 8.4 Hz), 6.57 (1H, d, J 9.6 Hz). LCMS (ES$^+$) RT 2.94 minutes, 411 (M+H)$^+$.

EXAMPLE 48

3-(4-Fluoro-3-methylbenzoyl)-6-oxo-7-phenyl-6,7-dihydrothieno[2,3-b]pyridine-2-carboxamide From Intermediate 28 (89 mg, 0.23 mmol) and 0.25M sodium hydroxide(aq) (0.44 ml, 0.11 mmol) by the method of Example 6. White solid (28 mg, 30%). $\delta_H$ (CDCl$_3$) 7.84 (1H, dd, J 1.7, 7.4 Hz), 7.76-7.65 (6H, m), 7.58 (1H, d, J 9.6 Hz), 7.34 (1H, t, J 9.0 Hz), 6.59 (1H, d, J 9.6 Hz), 2.35 (3H, s). LCMS (ES$^+$) RT 3.08 minutes, 407 (M+H)$^+$.

EXAMPLE 49

Ethyl 3-(4-fluoro-3-methylbenzoyl)-6-oxo-7-phenyl-6,7-dihydrothieno[2,3-b]pyridine-2-carboxylate From Intermediate 29 by the method of Example 1. White solid. $\delta_H$ (DMSO-$d_6$) 7.80 (1H, dd, J 1.7, 7.3 Hz), 7.67-7.52 (7H, m), 7.27 (1H, t, J 8.9 Hz), 6.51 (1H, d, J 9.7 Hz), 3.97 (2H, q, J 7.1 Hz), 2.24 (3H, s), 0.90 (3H, t, J 7.1 Hz). LCMS (ES$^+$) RT 3.77 minutes, 436 (M+H)$^+$.

EXAMPLE 50

2-Amino-3-(4-fluoro-3-methylbenzoyl)-7-phenylthieno[2,3-b]pyridin-6(7H)-one

From Example 49 by the methods of Examples 2, 3 and 4. Obtained as a 1:1 mixture with Example 51. Purification by preparative HPLC gave the title compound as a yellow solid. $\delta_H$ (DMSO-$d_6$) 8.37 (2H, m), 7.89-7.62 (7H, m), 7.51 (1H, m), 6.94 (1H, d, J 9.7 Hz), 6.47 (1H, d, J 9.7 Hz), 2.74 (3H, s). LCMS (ES$^+$) RT 3.17 minutes, 379

EXAMPLE 51

2-Amino-3-(4-ethoxy-3-methylbenzoyl)-7-phenylthieno[2,3-b]pyridin-6(7H)-one

From Example 49 by the methods of Examples 2, 3 and 4. Obtained as a 1:1 mixture with Example 50. Purification by preparative HPLC gave the title compound as a tan solid. $\delta_H$ (DMSO-$d_6$) 7.63 (2H, m), 7.43-7.14 (7H, m), 6.79 (1H, m), 6.62 (1H, d, J 9.7 Hz), 6.00 (1H, d, J 9.7 Hz), 3.89 (2H, q, J 6.9 Hz), 1.97 (3H, s), 1.16 (3H, t, J 6.9 Hz). LCMS (ES$^+$) RT 3.38 minutes, 405 (M+H)$^+$.

EXAMPLE 52

3-(3-Chloro-4-fluorobenzoyl)-6-oxo-7-phenyl-6,7-dihydrothieno[2,3-b]pyridine-2-carboxamide From Intermediate 31 (22 mg, 0.054 mmol) and 0.25M sodium hydroxide(aq) (0.11 ml, 0.27 mmol) by the method of Example 6. White solid (4 mg, 17%). $\delta_H$ (DMSO-$d_6$) 8.50 (2H, s), 7.94 (1H, dd, J 2.0, 7.1 Hz), 7.79-7.50 (8H, m), 6.54 (1H, d, J 9.6 Hz). LCMS (ES$^+$) RT 3.12 minutes, 427 (M+H)$^+$.

EXAMPLE 53

2-Amino-3-[(6-methylpyridin-2-yl)carbonyl]-7-phenylthieno[2,3-b]pyridin-6(7H)-one From Intermediate 35 (1.15 g, 2.5 mmol) and trifluoroacetic acid (5 ml), by the method of Example 4, to give the title compound as a yellow solid (646 mg, 72%). $\delta_H$ (CDCl$_3$) 7.75

(1H, t, J 7.7 Hz), 7.56-7.51 (1H, m), 7.50-7.42 (3H, m) 7.31-7.28 (3H, m), 7.01 (2H, s), 6.67 (1H, d, J 9.7 Hz), 6.27 (1H, d, J 9.7 Hz), 2.53 (3H, s). LCMS (ES$^+$) RT 3.69 minutes, 362 (M+H)$^+$.

EXAMPLE 54

N-{3-[(6-Methylpyridin-2-yl)carbonyl]-6-oxo-7-phenyl-6,7-dihydrothieno[2,3-b]pyridin-2-yl}acetamide From Example 53 (100 mg, 0.27 mmol) and acetic anhydride (0.026 ml, 0.27 mmol) by the method of Example 14. Yellow solid (66 mg, 60%). $\delta_H$ (CDCl$_3$) 12.11 (1H, s), 7.81 (1H, t, J 7.7 Hz), 7.67 (1H, d, J 7.7 Hz), 7.54-7.45 (3H, m), 7.37-7.31 (3H, m), 6.85 (1H, d, J 9.7 Hz), 6.37 (1H, d, J 9.7 Hz), 2.55 (3H, s), 2.21 (3H, s). LCMS (ES$^+$) RT 3.07 minutes, 404 (M+H)$^+$.

EXAMPLE 55

3-Benzoyl-2-(dimethylamino)-7-phenylthieno[2,3-b]pyridin-6(7H)-one

A mixture of Intermediate 36 (125 mg, 0.31 mmol), dimethylamine hydrochloride (30 mg, 0.37 mmol), cesium carbonate (303 mg, 0.93 mmol) and BINAP (41 mg, 0.06 mmol) in toluene (4 ml) in a Schlenk tube was degassed and tris(dibenzylideneacetone)-dipalladium(0) (29 mg, 0.03 mmol) added. The mixture was heated at 100° C. overnight. The reaction was diluted with DCM (50 ml) and washed with 2M HCl(aq) (200 ml). The organic phase was collected, dried (MgSO$_4$) and concentrated in vacuo. Purification by column chromatography (silica, 20% EtOAc in DCM) gave the title compound as a yellow-brown solid (45 mg, 39%). $\delta_H$ (DMSO-d$_6$) 7.99 (2H, dd, J 8.6, 1.6 Hz), 7.70-7.88 (9H, m), 6.64 (1H, d, J 9.6 Hz), 2.79 (6H, s). LCMS (ES$^+$) RT 3.40 minutes, 375 (M+H)$^+$.

EXAMPLE 56

3-Benzoyl-7-phenylthieno[2,3-b]pyridin-6(7H)-one

From Example 11 by the method of Example 9. Pink solid. $\delta_H$ (CDCl$_3$) 8.43 (1H, d, J 9.6 Hz), 7.75-7.76 (2H, m), 7.38-7.62 (9H, m), 6.63 (1H, d, J 9.6 Hz). LCMS (ES$^+$) RT 3.44 minutes, 332 (M+H)$^+$.

EXAMPLE 57

2-Amino-7-phenyl-3-[3-(trifluoromethyl)benzoyl]thieno[2,3-b]pyridin-6(7H)-one

From Intermediate 40 (3.15 g, 6.13 mmol) and TFA (20 ml, 260 mmol) in DCM (100 ml) by the method of Example 4. The crude product was triturated with a minimum amount of DCM to give the title compound as a bright yellow solid (1.60 g, 63%). $\delta_H$ (CDCl$_3$) 8.09 (2H, br s), 7.74 (1H, d, J 7.8 Hz), 7.63-7.61 (2H, m), 7.54 (1H, t, J 7.8 Hz), 7.43-7.30 (3H, m), 7.26-7.23 (2H, m), 6.36 (1H, d, J 9.6 Hz), 5.97 (1H, d, J 9.6 Hz). LCMS (ES$^+$) RT 3.34 minutes, 415 (M+H)$^+$.

EXAMPLE 58

N-{6-Oxo-7-phenyl-3-[3-trifluoromethyl)benzoyl]-6,7-dihydrothieno[2,3-b]pyridin-2-yl}acetamide From Example 57 (200 mg, 0.48 mmol), acetic anhydride (54 mg, 0.53 mmol) and DMAP (2.5 mg, 0.02 mmol) in DMF (5 ml) by the method of Example 14. The crude product was purified by chromatography (silica, 5-10% EtOAc in DCM) to give the title compound as a yellow solid (150 g, 68%). $\delta_H$ (CDCl$_3$) 7.90-7.78 (3H, br m), 7.64-7.47 (4H, br m), 7.36-7.33 (2H, m), 6.76 (1H, d, J 9.7 Hz), 6.36 (1H, d, J 9.7 Hz), 2.22 (3H, s). LCMS (ES$^+$) RT 3.59 minutes, 457 (M+H)$^+$.

EXAMPLE 59

N-(3-Benzoyl-6-oxo-7-phenyl-6,7-dihydrothieno[2,3-b]pyridin-2-yl)-1-methylpiperidine-4-carboxamide Example 19 (70 mg, 0.15 mmol), paraformaldehyde (22 mg, 0.76 mmol) and sodium cyanoborohydride (10 mg, 0.15 mmol) in MeOH (3 ml) were stirred at r.t. overnight. The reaction mixture was partitioned between 2M HCl (aq) and DCM, and the organic phase washed with aq. NaHCO$_3$. The organic phase was dried (MgSO$_4$) and concentrated in vacuo. The crude product was purified by chromatography (silica, 2-10% MeOH in DCM) to give the title compound as a yellow solid (9 mg, 13%). $\delta_H$ (CDCl$_3$) 7.61-7.49 (8H, In). 7.34-7.32 (2H, m), 6.84 (1H, d, J 9.7 Hz), 6.34 (1H, d, J 9.7 Hz), 2.94 (2H, br m), 2.34 (4H, br m), 1.95 (3H, br m), 1.92-1.57 (3H, br m). LCMS (ES$^+$) RT 2.20 minutes, 472 (M+H)$^+$.

EXAMPLE 60

N-(3-Benzoyl-6-oxo-7-phenyl-6,7-dihydrothieno[2,3-b]pyridin-2-yl)-1-ethylpiperidine-4-carboxamide From Example 19 (280 mg, 0.61 mmol), acetaldehyde (134 mg, 3.05 mmol) and sodium cyanoborohydride (50 mg, 0.73 mmol) in methanol (15 ml) by the method of Example 59. The crude product was purified by chromatography (silica, 1-8% MeOH in DCM) to give the title compound as a white solid (164 g, 55%). $\delta_H$ (CDCl$_3$) 10.87 (1H, br s), 7.76-7.50 (10H, m), 7.33-7.29 (1H, br m), 6.42 (1H, d, J 9.6 Hz), 2.80-2.77 (2H, br m), 2.30-2.23 (3H, br m), 1.82-1.70 (2H, br m), 1.60-1.40 (4H, br m), 0.95 (3H, t, J 7.1 Hz). LCMS (ES$^+$) RT 2.28 minutes, 486 (M+H)$^+$.

EXAMPLE 61

N-{6-Oxo-7-phenyl-3-[3-(trifluoromethyl)benzoyl]-6,7-dihydrothieno[2,3-b]pyridin-2-yl}piperidine-4-carboxamide Trifluoroacetic acid (20 ml) was added to a solution of Intermediate 41 (780 mg, 1.24 mmol) in DCM (40 ml) and the mixture stirred at r.t. overnight. NaHCO$_3$ (aq) (200 ml) was added to the reaction, and the mixture extracted with DCM (3×100 ml). The combined organic extracts were dried (MgSO$_4$) and concentrated in vacuo. The crude product was purified by chromatography (silica, 50% EtOAc in DCM to 10% MeOH in DCM) to give the title compound as a yellow solid (196 mg, 30%). $\delta_H$ (DMSO-d$_6$) 7.98-7.82 (4H, m), 7.75-7.60 (4H, m), 7.51-7.31 (2H, m), 6.46 (1H, d, J 9.6 Hz), 3.06-3.03 (2H, br m), 2.74 (2H, t, J 9.9 Hz), 2.38-2.27 (1H, br m), 1.59-1.56 (2H, m), 1.43-1.41 (2H, m). LCMS (ES$^+$) RT 2.32 minutes, 526 (M+H)$^+$.

EXAMPLE 62

N-[3-(3-Chlorobenzoyl)-6-oxo-7-phenyl-6,7-dihydrothieno[2,3-b]pyridin-2-yl]piperidine-4-carboxamide From Intermediate 42 (210 mg, 0.34 mmol) and trifluoroacetic acid (20 ml) in DCM (40 m) by the method of Example 61. The crude product was purified by chromatography (silica, 50% EtOAc in DCM to 10% MeOH in DCM) to give the title compound as a yellow solid (77 mg, 44%). $\delta_H$ (DMSO-d$_6$) 9.03 (2H, br s), 7.82-7.57 (9H, m), 7.46 (1H, d, J 9.6 Hz), 6.53 (1H, t, J 9.6 Hz), 3.27-3.23 (2H, br m), 2.92-2.84 (2H, m), 2.72-2.56 (1H, m), 1.98-1.62 (4H, m). LCMS (ES$^+$) RT 2.25 minutes, 492 (M+H)$^+$.

EXAMPLE 63

3-Benzoyl-2-[(3R)-3-hydroxypyrrolidin-1-yl]-7-phenylthieno[2,3-b]pyridin-6(7H)-one From Intermediate 36 (150 mg, 0.36 mmol) and R-(+)-3-pyrrolidinol (0.03 ml, 0.43 mmol) by the method of Example 55. The crude product was purified by chromatography (silica, 10-50% EtOAc in DCM) to give the title compound as a yellow solid (6 mg, 4%). $\delta_H$ (CDCl$_3$) 7.90-7.89 (2H, m), 7.61-7.45 (9H, m), 7.29 (1H, d, J 9.0 Hz), 6.50 (1H, br s), 4.45 (1H, br m), 3.35 (2H, br m), 3.20 (1H, br m), 2.85 (1H, br m), 2.19-2.07 (1H, br m), 2.01-1.96 (1H, br m). LCMS (ES$^+$) RT 2.84 minutes, 418 (M+H)$^+$.

EXAMPLE 64

3-Benzoyl-7-phenyl-2-{[2-(piperidin-1-yl)ethyl]amino}thieno[2,3-b]pyridin-6(7H)-one From Intermediate 36 (150 mg, 0.36 mmol) and 1-(2-aminoethyl)piperidine (0.05 ml, 0.43 mmol) by the method of Example 55. The crude product was purified by chromatography (silica, 10-50% EtOAc in DCM) to give the title compound as a yellow solid (20 mg, 11%). $\delta_H$ (CDCl$_3$) 9.52 (1H, br s), 7.54-7.36 (8H, m), 7.34-7.32 (2H, m), 6.61 (1H, d, J 9.7 Hz), 6.23 (1H, d, J 9.7 Hz), 3.18-3.17 (2H, m), 2.54-2.51 (3H, m), 2.34 (3H, br m), 1.53-1.49 (4H, m), 1.36-1.26 (2H, m). LCMS (ES$^+$) RT 2.21 minutes, 458 (M+H)$^+$.

EXAMPLE 65

3-Benzoyl-7-phenyl-2-{[2-(pyrrolidin-1-yl)ethyl]amino}thieno[2,3-b]pyridin-6(7H)-one From Intermediate 36 (430 mg, 1.04 mmol) and 1-(2-aminoethyl)pyrrolidine (0.15 ml, 1.25 mmol) by the method of Example 55. The crude product was purified by chromatography (silica, 50-100% EtOAc in DCM to give the title compound as a yellow solid (45 mg, 10%). $\delta_H$ (CDCl$_3$) 9.56 (1H, br s), 7.53-7.38 (8H, m), 7.34-7.32 (2H, m), 6.63 (1H, d, J 9.7 Hz), 6.23 (1H, d, J 9.7 Hz), 3.25-3.19 (2H, m), 2.68 (2H, t, J 6.2 Hz), 2.48 (3H, s), 1.71 (3H, s), 1.57 (2H, s). LCMS (ES$^+$) RT 2.17 minutes, 444 (M+H)$^+$.

EXAMPLE 66

3-Benzoyl-7-phenyl-2-(piperidin-3-ylamino)thieno[2,3-b]pyridin-6(7H)-one

From Intermediate 43 (237 mg, 0.44 mmol) by the method of Example 61. The crude product was purified by chromatography (silica, 10% MeOH in DCM) to give the title compound as a yellow solid (105 mg, 54%). $\delta_H$ (DMSO-d$_6$) 9.81 (1H, d, J 8.8 Hz), 7.71-7.52 (10H, m), 6.58 (1H, d, J 9.7 Hz), 6.26 (1H, d, J 9.7 Hz), 2.95 (1H, m), 2.72-2.64 (4H, m), 1.91-1.81 (1H, m), 1.67-1.61 (2H, m), 1.46-1.29 (1H, m). LCMS (ES$^+$) RT 2.25 minutes, 430 (M+H)$^+$.

EXAMPLE 67

2-(Azetidin-3-Ylamino)-3-benzoyl-7-phenylthieno[2,3-b]pyridin-6(7H)-one

From Intermediate 44 (690 mg, 1.37 mmol) by the method of Example 61. The crude product was purified by chromatography (silica, 10% MeOH in DCM) to give the title compound as a yellow solid (105 mg, 54%). $\delta_H$ (DMSO-d$_6$) 9.52 (1H, br s), 7.66-7.54 (8H, m), 7.48-7.46 (2H, m), 6.60 (1H, d, J 9.7 Hz), 6.22 (1H, d, J 9.7 Hz), 4.16-4.14 (1H, m), 3.74-3.71 (2H, m), 3.68-3.54 (2H, m). LCMS (ES$^+$) RT 2.08 minutes, 402 (M+H)$^+$.

EXAMPLE 68

3-Benzoyl-2-[(1-methylazetidin-3-yl)amino]-7-phenylthieno[2,3-b]pyridin-6(7H)-one From Example 67 (300 mg, 0.74 mmol) and paraformaldehyde (112 mg, 3.74 mmol) by the method of Example 60. The crude product was purified by chromatography (silica, 50% EtOAc in DCM) to give a yellow solid (97 mg, 31%). $\delta_H$ (CDCl$_3$) 9.90 (1H, br s), 7.56-7.39 (8H, m), 7.33-7.30 (2H, m), 6.63 (1H, d, J 9.7 Hz), 6.23 (1H, d, J 9.7 Hz), 3.89-3.80 (1H, m), 3.73-3.71 (2H, m), 2.94 (2H, t, J 6.7 Hz), 2.28 (3H, s). LCMS (ES$^+$) RT 2.18 minutes, 416 (M+1)$^+$.

EXAMPLE 69

2-Amino-3-(3-methoxybenzoyl)-7-phenylthieno[2,3-b]pyridin-6(7H)-one

Intermediate 47 (500 mg, 1.23 mmol) was suspended in a mixture of EtOH (20 ml) and 2M HCl (aq) (20 ml). Iron powder (326 mg, 6.16 mmol) was added to the solution and the mixture heated at 80° C. for 3 h. The solution was filtered hot through a short pad of Celite® and the filtrate extracted with DCM (2×200 ml). The combined organic extracts were dried (MgSO$_4$) and concentrated in vacuo. The crude product was purified by chromatography (silica, 5-20% EtOAc in DCM) to give the title compound as a yellow solid (160 mg, 35%). $\delta_H$ (DMSO-d$_6$) 8.26 (2H, d, J 4.6 Hz), 7.65-7.53 (3H, m), 7.48-7.41 (3H, m), 7.17-7.13 (1H, m), 7.07-7.04 (2H, m), 6.57 (1H, d, J 9.7 Hz), 6.18 (1H, d, J 9.7 Hz), 3.80 (3H, s). LCMS (ES$^+$) RT 3.04 minutes, 377 (M+H)$^+$.

EXAMPLE 70

2-Amino-3-(2-chlorobenzoyl)-7-phenylthieno[2,3-b]pyridin-6(7H)-one

From Intermediate 48 (311 mg, 0.76 mmol) and iron powder (211 mg, 3.79 mmol) by the method of Example 69, to give the title compound as a yellow solid (125 mg, 43%). $\delta_H$ (DMSO-d$_6$) 8.76 (2H, s), 7.91-7.40 (9H, m), 6.16 (1H, d, J 9.7 Hz), 6.10 (1H, d, J 9.7 Hz). LCMS (ES$^+$) RT 3.08 minutes, 381 (M+H)$^+$.

EXAMPLE 71

2-Amino-3-(3-chloro-4-fluorobenzoyl)-7-phenylthieno[2,3-b]pyridin-6(7H)-one

Intermediate 49 (456 mg, 0.87 mmol) was suspended in 70% AcOH (30 ml) and heated at reflux for 30 min. Iron powder (639 mg, 11.45 mmol) was added to the solution and the mixture heated at reflux for a further 2 h. The solution was filtered hot through a short pad of Celite® and the filtrate extracted with DCM (2×200 ml). The combined organic extracts were dried (MgSO$_4$) and concentrated in vacuo. The crude product was purified by chromatography (silica, 5-20% EtOAc in DCM) to give the title compound as a yellow solid (176 mg, 51%). $\delta_H$ (CDCl$_3$) 7.65 (1H, dd, J 2.0, 7.0 Hz), 7.54-7.43 (4H, m), 7.34-7.31 (2H, m), 7.21-7.16 (1H, m), 6.76 (1H, d, J 9.7 Hz), 6.70 (2H, br s), 6.33 (1H, d, J 9.7 Hz). LCMS (ES$^+$) RT 3.29 minutes, 399 (M+H)$^+$.

EXAMPLE 72

3-[(2-Amino-6-oxo-7-phenyl-6,7-dihydrothieno[2,3-b]pyridin-3-yl)carbonyl]benzonitrile From Intermediate 50 (523 mg, 1.07 mmol) and iron powder (848 mg, 15.2 mmol) by the method of Example 71. The title compound was obtained as a yellow solid (111 mg, 28%). $\delta_H$ (DMSO-d$_6$) 8.33 (2H, d, J 4.6 Hz), 8.05 (1H, dd, J 1.3, 7.7 Hz), 7.99 (1H, s) 7.85 (1H, d, J 7.8 Hz), 7.73 (1H, t, J 7.7 Hz), 7.65-7.57 (3H, m), 7.46 (2H, dd, J 1.3, 7.7 Hz), 6.57 (1H, d, J 9.6 Hz), 6.21 (1H, d, J 9.6 Hz). LCMS (ES$^+$) RT 2.91 minutes, 372 (M+H)$^+$.

EXAMPLE 73

2-Amino-3-(2-fluorobenzoyl)-7-phenylthieno[2,3-b]pyridin-6(7H)-one

From Intermediate 51 (949 mg, 1.93 mmol) and iron powder (538 mg, 9.65 mmol) by the method of Example 71. The title compound was obtained as a yellow solid (100 mg, 14%). $\delta_H$ (DMSO-d$_6$) 8.66 (2H, d, J 3.3 Hz), 7.66-7.53 (4H, m), 7.47-7.35 (5H, m), 6.35 (1H, d, J 9.6 Hz), 6.17 (1H, d, J 9.6 Hz). LCMS (ES$^+$) RT 3.01 minutes, 365 (M+H)$^+$.

EXAMPLE 74

2-Amino-3-(4-chlorobenzoyl)-7-phenylthieno[2,3-b]pyridin-6(7H)-one

From Intermediate 52 (692 mg, 1.36 mmol) and iron powder (381 mg, 6.84 mmol) by the method of Example 71. The title compound was obtained as a yellow solid (6 mg, 1%). $\delta_H$ (DMSO-d$_6$) 8.22 (2H, d, J 4.2 Hz), 7.67-7.55 (7H, m), 7.47-7.45 (2H, m), 6.68 (1H, d, J 9.7 Hz), 6.23 (1H, d, J 9.7 Hz). LCMS (ES$^+$) RT 3.20 minutes, 381 (M+H)$^+$.

EXAMPLE 75

2-Amino-3-(4-fluorobenzoyl)-7phenylthieno[2,3-b]pyridin-6(7H)-one

From Intermediate 53 (633 mg, 1.29 mmol) and iron powder (360 mg, 6.45 mmol) by the method of Example 71. The title compound was obtained as a yellow solid (131 mg, 28%). $\delta_H$ (DMSO-d$_6$) 8.14 (2H, d, J 6.6 Hz), 7.64-7.55 (5H, m), 7.47-7.45 (2H, m), 7.38-7.33 (2H, m), 6.68 (1H, d, J 9.7 Hz), 6.22 (1H, d, J 9.7 Hz). LCMS (ES$^+$) RT 3.07 minutes, 365 (M+H)$^+$.

EXAMPLE 76

2-Amino-3-(3-bromobenzoyl)-7-phenylthieno[2,3-b]pyridin-6(7H)-one

From Intermediate 54 (692 mg, 1.25 mmol) and iron powder (348 mg, 6.24 mmol) by the method of Example 71. The title compound was obtained as a yellow solid (364 mg, 68%). $\delta_H$ (DMSO-d$_6$) 8.31 (2H, d, J 4.3 Hz), 7.79 (1H, dd, J 2.0, 5.5 Hz), 7.77 (1H, s), 7.69-7.45 (7H, m), 6.60 (1H, d, J 9.7 Hz), 6.22 (1H, d, J 9.7 Hz). LCMS (ES$^+$) RT 3.28 minutes, 427 (M+H)$^+$.

EXAMPLE 77

2-Amino-3-(2,4-difluorobenzoyl)-7-phenylthieno[2,3-b]pyridin-6(7H)-one

From Intermediate 55 by the method of Example 69 to give the title compound as a yellow solid. $\delta_H$ (DMSO-d$_6$) 8.66 (2H, br s), 7.69-7.42 (7H, m), 7.30 (1H, dt, J 2.4, 8.5 Hz), 6.54 (1H, d, J 9.6 Hz), 6.27 (1H, d, J 9.6 Hz). LCMS (ES$^+$) RT 3.10 minutes, 383 (M+H)$^+$.

EXAMPLE 78

2-Amino-7-phenyl-3-[3-(trifluoromethoxy)benzoyl]thieno[2,3-b]pyridin-6(7H)-one

Morpholin-4-yl[3-(trifluoromethoxy)phenyl]acetonitrile (*J. Heterocyclic Chem.*, 1978, 15, 881) (1.0 g, 3.5 mmol) was dissolved in DMF (10 ml). The solution was cooled to 0° C. and sodium hydride (0.23 g of a 60% suspension in mineral oil, 5.8 mmol) was added. The suspension formed was stirred for 10 min after which time Intermediate 46 (1.0 g, 2.9 mmol) dissolved in DMF (30 ml) was added over 5 min. The reaction was stirred at r.t. for 3 h before being poured onto ice (200 g)/AcOH (10 ml). The product was extracted with EtOAc (2×200 ml) and the combined organic extracts washed with brine (2×200 ml), dried (MgSO$_4$) and the solvent removed in vacuo to give a brown solid. LC/MS (ES$^+$) RT 3.89 minutes, 557 (M+H)$^+$. The residue was taken up in EtOH (40 ml) and 2M HCl (aq) (40 ml) and heated to reflux for 3 h. The reaction was cooled to r.t. and poured onto ice. The yellow precipitate formed was filtered off, suspended in EtOH (20 ml) and 2M HCl (aq) (20 ml). Iron powder (182 mg, 3.3 mmol) was added and the reaction heated to reflux for 2 h. The solution was cooled to r.t., poured into brine (200 ml) and extracted with DCM (2×200 ml). The organic layers were combined, dried (MgSO$_4$) and the solvent removed in vacuo. Purification by flash column chromatography (silica, 0-40% EtOAc in DCM)

EXAMPLE 79

2-Amino-3-(3,4-dimethylbenzoyl)-7-phenylthieno[2,3-b]pyridin-6(7H)-one

From Intermediate 56 (565 mg, 1.39 mmol) and iron powder (390 mg, 6.99 mmol) by the method of Example 69. The title compound was obtained as a yellow solid (403 mg, 78%). $\delta_H$ (DMSO-$d_6$) 8.08 (2H, d, J 6.8 Hz), 7.64-7.55 (3H, m), 7.48-7.46 (2H, m), 7.33 (1H, s), 7.29-7.24 (2H, m), 6.71 (1H, d, J 9.7 Hz), 6.20 (1H, d, J 9.7 Hz), 2.32 (3H, s), 2.29 (3H, s). LCMS (ES$^+$) RT 3.29 minutes, 375 (M+H)$^+$.

EXAMPLE 80

2-Amino-3-(2-methoxybenzoyl)-7-phenylthieno[2,3-b]pyridin-6(7H)-one

From Intermediate 57 by the method of Example 69. The title compound was obtained as a yellow solid. $\delta_H$ (DMSO-$d_6$) 8.57 (2H, br s), 7.64-7.42 (6H, m), 7.25-7.15 (2H, m), 7.09 (1H, t, J 7.4 Hz), 6.30 (1H, d, J 9.7 Hz), 6.12 (1H, d, J 9.7 Hz), 3.73 (3H, s). LCMS (ES$^+$) RT 2.97 minutes, 377 (M+H)$^+$.

EXAMPLE 81

2-[(2-Amino-6-oxo-7-phenyl-6,7-dihydrothieno[2,3-b]pyridin-3-yl)carbonyl]benzonitrile From Intermediate 58 by the method of Example 69. The title compound was obtained as a red-brown solid. $\delta_H$ (DMSO-$d_6$) 8.72 (2H, br s), 8.06 (1H, dd, J 0.8, 7.7 Hz), 7.86 (1H, dt, J 1.3, 7.9 Hz), 7.77 (1H, dt, J 1.3, 7.6 Hz), 7.68-7.53 (4H, m), 7.48-7.42 (2H, m), 6.23 (1H, d, J 9.7 Hz), 6.18 (1H, d, J 9.7 Hz). LCMS (ES$^+$) RT 2.88 minutes, 371 (M+H)$^+$.

EXAMPLE 82

2-Amino-3-benzoyl-7-pyridin-3-ylthieno[2,3-b]pyridin-6(7H)-one

Crude Intermediate 62 (assumed 0.16 mmol) was dissolved in DCM (20 ml) and TFA (20 ml) added. The mixture was stirred at room temperature for 18 h. The volatiles were removed in vacuo and the crude residue azeotroped with toluene. The residue was dissolved in DCM (50 ml) and washed with sat. NaHCO$_3$ (aq) (2×100 ml). The organic layers were dried (MgSO$_4$), filtered, and the solvents removed in vacuo. Column chromatography (silica, 10-20% THF in DCM) gave the title compound as a white solid (5 mg, 9%). $\delta_H$ (DMSO-$d_6$) 8.77 (1H, d, J 4.7 Hz), 8.72 (1H, d, J 2.2 Hz), 8.27 (2H, br s), 8.04 (1H, d, J 8.1 Hz), 7.69 (1H, dd, J 4.8, 8.1 Hz), 7.62-7.53 (5H, m), 6.58 (1H, d, J 9.7 Hz), 6.21 (1H, d, J 9.7 Hz). LCMS (ES$^+$) RT 2.63 minutes, 348 (M+H)$^+$.

EXAMPLE 83

2-Amino-3-benzoyl-7-(4-methylphenyl)thieno[2,3-b]pyridin-6(7H)-one

From Intermediate 67 (80 mg, 0.17 mmol) and trifluoroacetic acid (5 ml) by the method of Example 4 to give the title compound as a yellow solid (30 mg, 49%). $\delta_H$ (DMSO-$d_6$) 8.28 (2H, d, J 6.4 Hz), 7.67-7.56 (5H, m), 7.46 (2H, d, J 8.1 Hz), 7.37 (2H, dd, J 1.7, 6.6 Hz), 6.58 (1H, d, J 9.7 Hz), 6.20 (1H, d, J 9.7 Hz), 2.47 (3H, s). LCMS (ES$^+$) RT 3.25 minutes, 361 (M+H)$^+$.

EXAMPLE 84

N-[3-Benzoyl-7-(2-chlorophenyl-6-oxo-6,7-dihydrothieno[2,3-b]pyridin-2-yl]acetamide From Example 42 (25 mg, 0.06 mmol) and acetic anhydride (6.32 mg, 0.06 mmol) by the method of Example 14 to give the title compound as a yellow solid (14 mg, 56%). $\delta_H$ (DMSO-$d_6$) 11.02 (1H, s), 7.84-7.56 (9H, m), 7.22 (1H, d, J 9.7 Hz), 6.43 (1H, d, J 9.7 Hz), 2.03 (3H, s). LCMS (ES$^+$) RT 3.37 minutes, 423 (M+H)$^+$.

EXAMPLE 85

N-[3-(3-Chloro-4-fluorobenzoyl)-6-oxo-7-phenyl-6,7-dihydrothieno[2,3-b]pyridin-2-yl]acetamide From Example 71 (43 mg, 0.10 mmol) and acetic anhydride (11 mg, 0.10 mmol) by the method of Example 14 to give the title compound as a yellow solid (25 mg, 53%). $\delta_H$ (DMSO-$d_6$) 10.92 (1H, s), 7.97-7.96 (1H, m), 7.78-7.75 (1H, m), 7.68-7.57 (4H, m), 7.51 (2H, d, J 7.3 Hz), 7.38 (1H, d, J 9.7 Hz), 6.45 (1H, d, J 9.7 Hz), 2.00 (3H, s). LCMS (ES$^+$) RT 3.45 minutes, 441 (M+H)$^+$.

EXAMPLE 86

N-[3-Benzoyl-7-(cyclopropylmethyl)-6-oxo-6,7-dihydrothieno[2,3-b]pyridin-2-yl]acetamide From Example 40 (20 mg, 0.06 mmol) and acetic anhydride (6 mg, 0.06 mmol) by the method of Example 14 to give the title compound as a yellow solid (6 mg, 26%). $\delta_H$ (DMSO-$d_6$) 11.01 (1H, s), 7.75-7.66 (3H, m), 7.55 (2H, t, J 7.7 Hz), 7.09 (1H, d, J 9.5 Hz), 6.32 (1H, d, J 9.5 Hz), 4.02 (2H, d, J 7.0 Hz), 2.08 (3H, s), 1.37-1.15 (1H, m), 0.55-0.49 (4H, m). LCMS (ES$^+$) RT 3.32 minutes, 367 (M+H)$^+$.

EXAMPLE 87

N-[3-(2-Fluorobenzoyl)-6-oxo-7-phenyl-6,7-dihydrothieno[2,3-b]pyridin-2-yl]acetamide From Example 73 (53 mg, 0.14 mmol) and acetic anhydride (15 mg, 0.14 mmol) by the method of Example 14 to give the title compound as a yellow solid (20 mg, 35%). $\delta_H$ (DMSO-$d_6$) 11.46 (1H, s), 7.82-7.73 (5H, ma), 7.71-7.45 (4H, m), 6.98 (1H, d, J 9.6 Hz), 6.44 (1H, d, J 9.6 Hz), 2.21 (3H, s). LCMS (ES$^+$) RT 3.25 minutes, 407 (M+H)$^+$.

EXAMPLE 88

N-[3-(4-Fluoro-3-methylbenzoyl)-6-oxo-7-phenyl-6,7-dihydrothieno[2,3-b]pyridin-2-yl]acetamide From Example 50 (100 mg, 0.26 mmol) and acetic anhydride (27 mg, 0.26 mmol) by the method of Example 14 to give the title compound as a yellow solid (84 mg, 77%). $\delta_H$ (DMSO-$d_6$) 10.90 (1H, s), 7.77 (1H, d, J 5.8 Hz), 7.68-7.60 (4H, m), 7.52-7.50 (2H, m), 7.34-7.26 (2H, m), 6.42 (1H, d, J 9.6 Hz), 2.31 (3H, s), 2.01 (3H, s). LCMS (ES$^+$) RT 3.39 minutes, 421 (M+H)$^+$.

EXAMPLE 89

N-[3-(4-Fluorobenzoyl)-6-oxo-7-phenyl-6,7-dihydrothieno[2,3-b]pyridin-2-yl]acetamide From Example 75 (86 mg, 0.23 mmol) and acetic anhydride (24 mg, 0.23 mmol) by the method of Example 14 to give the title compound as a yellow solid (72 mg, 76%). $\delta_H$ (DMSO-$d_6$) 10.92 (1H, s), 7.86 (2H, dd, J 5.6, 8.6 Hz), 7.68-7.61 (3H, m), 7.51 (2H, d, J 7.2 Hz), 7.40 (2H, t, J 8.6 Hz), 7.30 (1H, d, J 9.6 Hz), 6.43 (1H, d, J 9.6 Hz), 2.01 (3H, s). LCMS (ES$^+$) RT 3.27 minutes, 407 (M+H)$^+$.

EXAMPLE 90

N-[3-(3-Methoxybenzoyl)-6-oxo-7-phenyl-6,7-dihydrothieno[2,3-b]pyridin-2-yl]acetamide From Example 69 (94 mg, 0.25 mmol) and acetic anhydride (25 mg, 0.25 mmol) by the method of Example 14 to give the title compound as a yellow solid (64 mg, 61%). $\delta_H$ (DMSO-$d_6$) 11.00 (1H, s), 7.68-7.58 (3H, m), 7.53-7.46 (3H, m), 7.31-7.27 (3H, m), 7.18 (1H, d, J 9.6 Hz), 6.40 (1H, d, J 9.6 Hz), 3.82 (3H, s), 2.01 (3H, s). LCMS (ES$^+$) RT 3.29 minutes, 419 (M+H)$^+$.

EXAMPLE 91

N-[3-(3-Bromobenzoyl)-6-oxo-7-phenyl-6,7-dihydrothieno[2,3-b]pyridin-2-yl]acetamide From Example 76 (300 mg, 0.70 mmol) and acetic anhydride (71 mg, 0.70 mmol) by the method of Example 14 to give the title compound as a yellow solid (160 mg, 49%). $\delta_H$ (DMSO-$d_6$) 10.96 (1H, s), 7.90 (2H, d, J 7.7 Hz), 7.71 (1H, d, J 7.7 Hz), 7.68-7.59 (3H, m), 7.54-7.51 (3H, m), 7.30 (1H, d, J 9.6 Hz), 6.43 (1H, d, J 9.6 Hz), 2.01 (3H, s). LCMS (ES$^+$) RT 3.48 minutes, 469 (M+H)$^+$.

EXAMPLE 92

2-Amino-7-phenyl-3-[4-(trifluoromethyl)benzoyl]thieno[2,3-b]pyridin-6(7H)-one

From Intermediate 68 (929 mg, 2.09 mmol) and iron powder (584 mg, 10.46 mmol) by the method of Example 69 to give the title compound as a yellow solid (257 mg, 30%). $\delta_H$ (DMSO-$d_6$) 8.38 (2H, s), 7.90 (2H, d, J 8.1 Hz), 7.75 (2H, d, J 7.9 Hz), 7.65-7.54 (3H, m), 7.48-7.44 (2H, m), 6.57 (1H, d, J 9.6 Hz), 6.21 (1H, d, J 9.6 Hz). LCMS (ES$^+$) RT 3.32 minutes, 415 (M+H)$^+$.

EXAMPLE 93

4-[(2-Amino-6-oxo-7-phenyl-6,7-dihydrothieno[2,3-b]pyridin-3-yl)carbonyl]benzonitrile From Intermediate 69 (1.5 g, 3.7 mmol) and iron powder (1.04 g, 18.5 mmol) by the method of Example 69 to give the title compound as a red solid (670 mg, 49%). $\delta_H$ (DMSO-$d_6$) 8.43 (2H, br s), 8.00 (2H, d, J 8.2 Hz), 7.70 (2H, d, J 8.2 Hz), 7.67-7.43 (5H, m), 6.54 (1H, d, J 9.7 Hz), 6.21 (1H, d, J 9.6 Hz). LCMS (ES$^+$) RT 2.94 minutes, 372 (M+H)$^+$.

EXAMPLE 94

2-Amino-3-(4-methoxybenzoyl)-7-phenylthieno[2,3-b]pyridin-6(7H)-one

From Intermediate 70 (600 mg, 1.5 mmol) and iron powder (420 mg, 7.5 mmol) by the method of Example 69 to give the title compound as a yellow solid (60 mg, 11%). $\delta_H$ (DMSO-$d_6$) 7.89 (2H, br s), 7.65-7.44 (7H, m), 7.08-7.03 (2H, m), 6.85 (1H, d, J 9.7 Hz), 6.23 (1H, d, J 9.7 Hz), 3.86 (3H, s). LCMS (ES$^+$) RT 3.02 minutes, 377 (M+H)$^+$.

EXAMPLE 95

2-Amino-7-phenyl-3-[4-(trifluoromethoxy)benzoyl]thieno[2,3-b]pyridin-6(7H)-one

From Intermediate 71 (1.47 g, 3.0 mmol) and iron powder (892 mg, 15.0 mmol) by the method of Example 69 to give the title compound as a yellow solid (310 mg, 30%). $\delta_H$ (DMSO-$d_6$) 8.24 (2H, s), 7.70-7.44 (9H, m), 6.64 (1H, d, J 9.6 Hz), 6.21 (1H, d, J 9.6 Hz). LCMS (ES$^+$) RT 3.38 minutes, 431 (M+H)$^+$.

EXAMPLE 96

2-Amino-3-(2-methylbenzoyl)-7-phenylthieno[2,3-b]pyridin-6(7H)-one

From Intermediate 72 (530 mg, 1.36 mmol) and iron powder (379 mg, 6.79 mmol) by the method of Example 69 to give the title compound as a yellow solid (140 mg, 29%). $\delta_H$ (DMSO-$d_6$) 8.61 (2H, s), 7.61-7.55 (3H, m), 7.54-7.31 (5H, m), 7.20 (1H, d, J 6.5 Hz), 6.10 (2H, s), 2.21 (3H, s). LCMS (ES$^+$) RT 3.11 minutes, 361 (M+H)$^+$.

EXAMPLE 97

2-Amino-3-(4-methylbenzoyl)-7-phenylthieno[2,3-b]pyridin-6(7H)-one

From Intermediate 73 (681 mg, 1.75 mmol) and iron powder (487 mg, 8.73 mmol) by the method of Example 69 to give the title compound as a yellow solid (340 mg, 54%). $\delta_H$ (DMSO-$d_6$) 8.10 (2H, s), 7.65-7.54 (3H, m), 7.48-7.43 (4H, m), 7.33 (2H, d, J 8.0 Hz), 6.69 (1H, d, J 9.6 Hz), 6.20 (1H, d, J 9.6 Hz), 2.41 (3H, s). LCMS (ES$^+$) RT 3.17 minutes, 361 (M+H)$^+$.

EXAMPLE 98

2-Amino-7-phenyl-3-[2-(trifluoromethyl benzoyl]thieno[2,3-b]pyridin-6(7H)-one

From Intermediate 74 (1.01 g, 2.28 mmol) and iron powder (639 mg, 11.44 mmol) by the method of Example 69 to give the title compound as a yellow solid (145 mg, 15%). $\delta_H$ (DMSO-$d_6$) 8.70 (2H, s), 7.95 (1H, d, J 7.3 Hz), 7.84-7.76 (2H, m), 7.65-7.51 (3H, m), 7.48-7.45 (3H, m), 6.12 (1H, d, J 9.7 Hz), 5.97 (1H, d, J 9.7 Hz). LCMS (ES$^+$) RT 3.16 minutes, 415 (M+H)$^+$.

EXAMPLE 99

2-Amino-3-[3-(difluoromethoxy)benzoyl]-7-phenylthieno[2,3-b]pyridin-6(7H)-one From Intermediate 75 (800 mg, 1.8 mmol) and iron powder (500 mg, 9.0 mmol) by the method of Example 69 to give the title compound as a yellow solid (600 mg, 81%). $\delta_H$ (DMSO-$d_6$) 8.32 (1H, s), 8.31 (1H, s), 7.65-7.32 (9H, m), 7.33 (1H, t, J 63.8 Hz), 6.60 (1H, d, J 9.7 Hz), 6.20 (1H, d, J 9.7 Hz). LCMS (ES$^+$) RT 3.12 minutes, 413 (M+H)$^+$.

EXAMPLE 100

2-Amino-7-phenyl-3-(2-thienylcarbonyl thieno[2,3-b]pyridin-6(7H)-one

From Intermediate 76 (559 mg, 1.46 mmol) and iron powder (408 mg, 7.32 mmol) by the method of Example 69 to give the title compound as a yellow solid (120 mg, 23%). $\delta_H$ (DMSO-$d_6$) 7.95 (1H, dd, J 4.9, 1.1 Hz), 7.75 (2H, d, J 5.4 Hz), 7.65-7.54 (4H, m), 7.50-7.47 (2H, m), 7.30 (1H, d, J 9.6 Hz), 7.20 (1H, dd, J 3.7, 4.9 Hz), 6.32 (1H, d, J 9.6 Hz). LCMS (ES$^+$) RT 2.95 minutes, 353 (M+H)$^+$.

EXAMPLE 101

2-Amino-3-[4-(difluoromethoxy)benzoyl]-7-phenylthieno[2,3-b]pyridin-6(7H)-one From Intermediate 77 (1000 mg, 2.3 mmol) and iron powder (640 mg, 12.0 mmol) by the method of Example 69 to give the title compound as a yellow solid (450 mg, 47%). $\delta_H$ DMSO-$d_6$) 8.16 (1H, s), 8.14 (1H, s), 7.89-7.29 (9H, m), 7.40 (1H, t, J 63.6 Hz), 6.72 (1H, d, J 9.7 Hz), 6.22 (1H, d, J 9.7 Hz). LCMS (ES$^+$) RT 3.15 minutes, 413 (M+H)$^+$.

EXAMPLE 102

2-Amino-3-[2-(difluoromethoxy)benzoyl]-7-phenylthieno[2,3-b]pyridin-6(7H)-one From Intermediate 78 (960 mg, 2.2 mmol) and iron powder (620 mg, 11.0 mmol) by the method of Example 69 to give the title compound as a yellow solid (250 mg, 28%). $\delta_H$ (DMSO-$d_6$) 8.66 (2H, br s), 7.65-7.55 (4H, m), 7.46-7.39 (5H, m), 7.21 (1H, t, J 63.6 Hz), 6.22 (1H, d, J 9.8 Hz), 6.14 (1H, d, J 9.8 Hz). LCMS (ES$^+$) RT 3.05 minutes, 413 (M+H)$^+$.

EXAMPLE 103

N-{6-Oxo-7-phenyl-3-[3-(trifluoromethoxy)benzoyl]-6,7-dihydrothieno[2,3-b]pyridin-2-yl}acetamide From Example 78 (150 mg, 0.35 mmol) and acetic anhydride (0.40 ml, 0.42 mmol) by the method of Example 14 to give the title compound as a yellow solid (50 mg, 30%). $\delta_H$ (DMSO-d) 10.95 (1H, br s), 7.85-7.31 (10H, m), 6.45 (1H, d, J 9.6 Hz), 1.98 (3H, s). LCMS (ES$^+$) RT 3.55 minutes, 473 (M+H)$^+$.

EXAMPLE 104

N-[3-(3,4-Dimethylbenzoyl)-6-oxo-7-phenyl-6,7-dihydrothieno[2,3-b]pyridin-2-yl]acetamide From Example 79 (156 mg, 0.41 mmol) and acetic anhydride (43 mg, 0.41 mmol) by the method of Example 14 to give the title compound as a yellow solid (81 mg, 47%). $\delta_H$ (DMSO-$d_6$) 10.93 (1H, s), 7.69-7.60 (4H, m), 7.57-7.46 (3H, m), 7.32 (1H, d, J 7.8 Hz), 7.19 (1H, d, J 9.6 Hz), 6.39 (1H, d, J 9.6 Hz), 2.33 (3H, s), 2.30 (3H, s), 2.03 (3H, s). LCMS (ES$^+$) RT 3.50 minutes, 417 (M+H)$^+$.

EXAMPLE 105

N-[3-(2-Methoxybenzoyl)-6-oxo-7-phenyl-6,7-dihydrothieno[2,3-b]pyridin-2-yl]acetamide From Example 80 (200 mg, 0.53 mmol) and acetic anhydride (0.060 ml, 0.64 mmol) by the method of Example 14 to give the title compound as a yellow solid (200 mg, 90%). $\delta_H$ (DMSO-$d_6$) 11.81 (1H, s), 7.68-7.56 (4H, m), 7.49-7.45 (2H, m), 7.41-7.37 (1H, dd, J 1.7, 7.5 Hz), 7.24 (1H, d, J 8.3 Hz), 7.16 (1H, t, J 7.4 Hz), 6.62 (1H, d, J 9.8 Hz), 6.30 (1H, d, J 9.8 Hz), 3.71 (3H, s), 2.25 (3H, s). LCMS (ES$^+$) RT 3.26 minutes, 419 (M+H)$^+$.

EXAMPLE 106

N-[3-(2-Cyanobenzoyl)-6-oxo-7-phenyl-6,7-dihydrothieno[2,3-b]pyridin-2-yl]acetamide From Example 81 (200 mg, 0.54 mmol) and acetic anhydride (0.060 ml, 0.64 mmol) by the method of Example 14 to give the title compound as a yellow solid (120 mg, 54%). $\delta_H$ (DMSO-$d_6$) 8.10 (1H, t, J 5.7 Hz), 7.89-7.57 (6H, m), 7.55-7.46 (2H, m), 7.15 (1H, d, J 9.7 Hz), 6.41 (1H, d, J 9.7 Hz), 2.06 (3H, s). LCMS (ES$^+$) RT 3.11 minutes, 414 (M+H)$^+$.

EXAMPLE 107

N-[3-(2-Chlorobenzoyl)-6-oxo-7-phenyl-6,7-dihydrothieno[2,3-b]pyridin-2-yl]acetamide From Example 70 (59 mg, 0.15 mmol) and acetic anhydride (16 mg, 0.15 mmol) by the method of Example 14 to give the title compound as a yellow solid (28 mg, 43%). $\delta_H$ (DMSO-$d_6$) 11.85 (1H, s), 7.72-7.57 (7H, m), 7.49 (2H, d, J 6.7 Hz), 6.41 (1H, d, J 9.8 Hz), 6.33 (1H, d, J 9.8 Hz), 2.29 (3H, s). LCMS (ES$^+$) RT 3.40 minutes, 423 (M+H)$^+$.

EXAMPLE 108

N-[3-2-Methylbenzoyl)-6-oxo-7-phenyl-6,7-dihydrothieno[2,3-b]pyridin-2-yl]acetamide From Example 96 (90 mg, 0.25 mmol) and acetic anhydride (0.026 ml, 0.28 mmol) by the method of Example 14 to give the title compound as a yellow solid (48 mg, 48%). $\delta_H$ (DMSO-$d_6$) 7.67-7.35 (10H, m), 6.47 (1H, d, J 9.7 Hz), 6.28 (1H, d, J 9.7 Hz), 2.32 (3H, s), 2.22 (3H, s). LCMS (ES$^+$) RT 3.42 minutes, 403 (M+H)$^+$.

EXAMPLE 109

N-[3-(4-Methylbenzoyl)-6-oxo-7-phenyl-6,7-dihydrothieno[2,3-b]pyridin-2-yl]acetamide From Example 97 (240 mg, 0.67 mmol) and acetic anhydride (0.069 ml, 0.73 mmol) by the method of Example 14 to give the title compound as a yellow solid (50 mg, 19%). $\delta_H$ (DMSO-$d_6$) 10.94 (1H, s), 7.70-7.58 (5H, m), 7.52-7.50 (2H, m), 7.39-7.35 (2H, m), 7.21 (1H, d, J 9.7 Hz), 6.40 (1H, d, J 9.7 Hz), 2.42 (3H, s), 2.03 (3H, s). LCMS (ES$^+$) RT 3.38 minutes, 403 (M+H)$^+$.

EXAMPLE 110

N-[6-Oxo-7-phenyl-3-(2-thienylcarbonyl)-6,7-dihydrothieno[2,3-b]pyridin-2-yl]acetamide From Example 100 (60 mg, 0.17 mmol) and acetic anhydride (17 mg, 0.17 mmol) by the method of Example 14 to give the title compound as a yellow solid (30 mg, 45%). $\delta_H$ (DMSO-$d_6$) 11.02 (1H, s), 8.20 (1H, dd, J 1.1, 4.9 Hz), 7.75-7.66 (5H, m), 7.64-7.56 (2H, m), 7.30 (1H, dd, J 3.9, 4.9 Hz), 6.52 (1H, d, J 9.6 Hz), 2.06 (3H, s). LCMS (ES$^+$) RT 3.08 minutes, 395 (M+H)$^+$.

EXAMPLE 111

N-(3-Benzoyl-6-oxo-7-phenyl-6,7-dihydrothieno[2,3-b]pyridin-2-yl)-N'-(2-hydroxy-2-methylpropyl)urea From Example 13 (290 mg, 0.84 mmol) and 3-amino-2-methyl-2-propanol hydrochloride salt (211 mg, 1.68 mmol) by the method of Example 20. Purification by column chromatography (silica, 5-10% THF in DCM) gave the title compound as a yellow solid (110 mg, 28%). $\delta_H$ (DMSO-$d_6$) 10.70 (1H, s), 7.96 (1H, br m), 7.70-7.55 (8H, m), 7.50-7.47 (2H, m), 6.75 (1H, d, J 9.8 Hz), 6.26 (1H, d, J 9.8 Hz), 4.46 (1H, s), 2.99 (2H, d, J 5.6 Hz), 1.04 (6H, s). LCMS (ES$^+$) RT 3.00 minutes, 462 (M+H)$^+$.

EXAMPLE 112

N-(3-Benzoyl-6-oxo-7-phenyl-6,7-dihydrothieno[2,3-b]pyridin-2-yl)-N'-(2-hydroxy-1,1-dimethylethyl)urea From Example 13 (290 mg, 0.84 mmol) and 2-amino-2-methyl-1-propanol (150 mg, 1.68 mmol) by the method of Example 20. Purification by column chromatography (silica, 5-10% THF in DCM) gave the title compound as a yellow solid (180 mg, 47%). $\delta_H$ (CDCl$_3$) 10.64 (1H, s), 7.75-7.55 (9H, m), 7.49-7.47 (2H, m), 6.74 (1H, d, J 9.6 Hz), 6.25 (1H, d, J 9.6 Hz), 4.79-4.75 (1H, m), 3.35 (2H, d, J 5.6 Hz), 1.16 (6H, s). LCMS (ES$^+$) RT 3.15 minutes, 462 (M+H)$^+$.

EXAMPLE 113

N-(3-Benzoyl-6-oxo-7-phenyl-6,7-dihydrothieno[2,3-b]pyridin-2-yl)-4-methylpiperazine-1-carboxamide From Example 13 (290 mg, 0.84 mmol) and 1-methylpiperazine (168 mg, 1.68 mmol) by the method of Example 20. Purification by trituration with EtOAc gave the title compound as a yellow solid (310 mg, 78%). $\delta_H$ (CDCl$_3$) 8.14-7.55 (11H, m), 7.27-7.20 (1H, br m), 6.46 (1H, d, J 9.6 Hz), 3.30-3.20 (4H, br m), 2.36-2.25 (7H, br m). LCMS (ES$^+$) RT 2.20 minutes, 473 (M+H)$^+$.

EXAMPLE 114

(3R)-N-(3-Benzoyl-6-oxo-7-phenyl-6,7-dihydrothieno[2,3-b]pyridin-2-yl)-3-hydroxypyrrolidine-1-carboxamide From Example 13 (150 mg, 0.43 mmol) and (R)-(+)-3-hydroxypyrrolidine (75 mg, 0.86 mmol) by the method of Example 20 to give the title compound as a yellow solid (97 mg, 49%). $\delta_H$ (DMSO-$d_6$) 10.91 (1H, s), 7.67-7.54 (8H, m), 7.49 (2H, d, J 6.6 Hz), 6.91 (1H, d, J 9.7 Hz), 6.32 (1H, d, J 9.7 Hz), 5.02 (1H, br s), 4.29 (1H, br s), 3.37-3.35 (3H, m), 3.28-3.12 (1H, m), 1.82-1.73 (2H, m). LCMS (ES$^+$) RT 2.94 minutes, 460 (M+H)$^+$.

EXAMPLE 115

2-Amino-7-(cyclopropylmethyl)-3-(4-fluoro-3-methylbenzoyl thieno[2,3-b]pyridin-6(7H)-one From Intermediate 81 (685 mg, 1.77 mmol) and iron powder (495 mg, 8.86 mmol) by the method of Example 69 to give the title compound as a brown-yellow solid (327 mg, 52%). $\delta_H$ (CDCl$_3$) 7.49-7.46 (1H, m), 7.42-7.39 (1H, m), 7.07 (1H, t, J 8.8 Hz), 6.9-6.50 (3H, m), 6.35-6.33 (1H, m), 3.99 (2H, d, J 6.7 Hz), 2.31 (3H, s), 1.36-1.27 (1H, m), 0.59-0.53 (4H, m). LCMS (ES$^+$) RT 3.25 minutes, 357.0 (M+H)$^+$.

EXAMPLE 116

N-[7-(Cyclopropylmethyl)-3-(4-fluoro-3-methylbenzoyl)-6-oxo-6,7-dihydrothieno[2,3-b]pyridin-2-yl]acetamide From Example 115 (91.8 mg, 0.25 mmol) and acetic anhydride (0.025 ml, 0.25 mmol) by the method of Example 14 to give the title compound as a yellow solid (85 mg, 77%). $\delta_H$ (CDCl$_3$) 11.43 (1H, br s), 7.60-7.45 (2H, m), 7.13 (1H, t, J 8.8 Hz), 6.90 (1H, d, J 9.6 Hz), 6.36 (1H, d, J 9.6 Hz), 4.11 (2H, d, J 7.1 Hz), 2.34 (6H, s), 1.48-1.39 (1H, m), 0.60-0.58 (4H, m). LCMS (ES$^+$) RT 3.48 minutes, 399.0 (M+H)$^+$.

EXAMPLE 117

N-[7-(Cyclopropylmethyl)-3-(4-fluoro-3-methylbenzoyl)-6-oxo-6,7-dihydrothieno[2,3-b]pyridin-2-yl]-N'-(2-hydroxy-2-methylpropyl)urea From Example 115 (124.6 mg, 0.35 mmol) and 3-amino-2-methyl-2-propanol HCl salt (83 mg, 0.7 mmol) by the method of Example 20 to give the title compound as a yellow solid (56 mg, 34%). $\delta_H$ (CDCl$_3$) 11.03 (1H, br s), 7.41-7.32 (2H, m), 7.01 (1H, t, J 8.7 Hz), 6.75 (1H, d, J 9.5 Hz), 6.70 (1H, br s), 6.30 (1H, d, J 9.5 Hz), 4.07 (2H, d, J 7.0 Hz), 3.34 (2H, d, J 5.8 Hz), 2.90-2.40 (11H, br s), 2.26 (3H, s), 1.45-1.36 (1H, m), 1.29 (6H, s), 0.45-0.43 (4H, m). LCMS (ES$^+$) RT 3.20 minutes, 472.1 (M+H)$^+$.

EXAMPLE 118

N-[7-(Cyclopropylmethyl)-3-(4-fluoro-3-methylbenzoyl)-6-oxo-6,7-dihydrothieno[2,3-b]pyridin-2-yl]-N'-(2-hydroxy-1,1-dimethylethyl)urea From Example 115 (90.5 mg, 0.25 mmol) and 2-amino-2-methyl-1-propanol (0.051 ml, 0.50 mmol) by the method of Example 20 to give the title compound as a yellow solid (39 mg, 33%). $\delta_H$ (CDCl$_3$) 10.98 (1H, br s), 7.39-7.34 (2H, m), 7.06 (1H, t, J 8.7 Hz), 6.78 (1H, d, J 9.5 Hz), 6.31 (1H, d, J 9.5 Hz), 5.74 (1H, s), 4.06 (2H, d, J 7.1 Hz), 3.68 (2H, s), 3.48 (1H, br s), 2.30 (3H, s), 1.43-1.35 (7H, m), 0.58-0.50 (4H, m). LCMS (ES$^+$) RT 3.33 minutes, 472.0 (M+H)$^+$.

EXAMPLE 119

7-(2-Chlorophenyl)-3-(4-fluoro-3-methylbenzoyl)-2-nitrothieno[2,3-b]pyridin-6(7H)-one From Intermediate 83 (4.0 g, 10.4 mmol) and 4-fluoro-3-methylbenzaldehyde (1.79 g, 13.0 mmol) by the method of Intermediate 56 to give the title compound as a yellow solid (1.0 g, 22%). $\delta_H$ (MeOD-d$_4$) 7.95-7.93 (1H, m), 7.87-7.67 (6H, m), 7.26 (1H, t, J 9.0 Hz), 6.75 (1H, d, J 9.7 Hz), 2.37 (3H, d, J 1.9 Hz). LCMS (ES$^+$) RT 3.89 minutes, 443 (M+H)$^+$.

EXAMPLE 120

2-Amino-7-(2-chlorophenyl)-3-(4-fluoro-3-methylbenzoyl)thieno[2,3-b]pyridin-6(7H)-one Example 119 (965 mg, 2.18 mmol) was suspended in EtOH (50 ml). Iron powder (488 mg, 8.72 mmol) and 2M HCl (8.7 ml, 17.4 mmol) were added and the mixture stirred at r.t. for 5 h. Water (300 ml) was added and the mixture extracted with EtOAc (150 ml). The organic extracts were dried (Na$_2$SO$_4$) and concentrated in vacuo. The crude product was purified by trituration with EtOAc:hexane (2:1, 50 ml) to give after filtration the title compound as a yellow solid (560 mg, 62%). $\delta_H$ (DMSO-d$_6$) 8.18 (2H, br s), 7.81-7.78 (1H, m), 7.68-7.59 (3H, m), 7.51 (1H, d, J 7.1 Hz), 7.42-7.39 (1H, m), 7.31-7.26 (1H, m), 6.74 (1H, d, J 9.7 Hz), 6.26 (1H, d, J 9.7 Hz), 2.31 (3H, s). LCMS (ES$^+$) RT 3.32 minutes, 413 (M+H)$^+$.

EXAMPLE 121

N-[7-(2-Chlorophenyl)-3-(4-fluoro-3-methylbenzoyl)-6-oxo-6,7-dihydrothieno[2,3-b]pyridin-2-yl]acetamide From Example 120 (100 mg, 0.24 mmol) and acetic anhydride (0.025 ml, 0.26 mmol) by the method of Example 14 to give the title compound as a yellow solid (85 mg, 77%). $\delta_H$ (DMSO-d$_6$) 11.02 (1H, br s), 7.89-7.68 (6H, m), 7.41-7.39 (1H, m), 7.38 (1H, d, J 9.7 Hz), 6.51 (1H, d, J 9.7 Hz), 2.38 (3H, s), 2.08 (3H, s). LCMS (ES$^+$) RT 3.53 minutes, 455 (M+H)$^+$.

EXAMPLE 122

N-[3-Benzoyl-7-(2-chlorophenyl)-6-oxo-6,7-dihydrothieno[2,3-b]pyridin-2-yl]piperidine-4-carboxamide hydrochloride Intermediate 84 (270 mg, 0.45 mmol) was dissolved in 1,4-dioxane (10 ml) and 4M HCl in 1,4-dioxane (3.6 ml, 14.4 mmol) was added. The mixture was stirred at r.t. for 48 h before concentrating in vacuo. Trituration of the solid with ether (25 ml) gave, after filtration, the title compound as a yellow solid (190 mg, 79%). $\delta_H$ (DMSO-d$_6$) 11.14 (1H, br s), 9.02 (1H, br m), 8.70 (1H, br m), 7.85-7.56 (9H, m), 7.31 (1H, d, J 9.7 Hz), 6.46 (1H, d, J 9.7 Hz), 3.21-3.18 (2H, m), 2.85-2.80 (2H, m), 2.77-2.65 (1H, m), 1.79-1.73 (2H, m), 1.68-1.62 (2H, m). LCMS (ES$^+$) RT 2.30 minutes, 492 (M+H)$^+$.

EXAMPLE 123

N-[3-Benzoyl-7-(2-chlorophenyl)-6-oxo-6,7-dihydrothieno[2,3-b]pyridin-2-yl]-N'-(2-hydroxy-1,1-dimethylethyl)urea From Example 42 (280 mg, 0.74 mmol) and 2-amino-2-methyl-1-propanol (0.144 ml, 1.50 mmol) by the method of Example 20 to give the title compound as a pale brown solid (145 mg, 40%). $\delta_H$ (DMSO-d$_6$) 10.68 (1H, br s), 7.83-7.81 (1H, m), 7.78 (1H, br s), 7.70-7.57 (8H, m), 6.75 (1H, d, J 9.7 Hz), 6.28 (1H, d, J 9.7 Hz), 4.78 (1H, t, J 5.7 Hz), 3.35 (2H, appt dd, J 3.6, 5.3 Hz), 1.16 (6H, s). LCMS (ES$^+$) RT 3.24 minutes, 496 (M+H)$^+$.

EXAMPLE 124

N-[3-Benzoyl-7-(2-chlorophenyl)-6-oxo-6,7-dihydrothieno[2,3-b]pyridin-2-yl]-N'-(2-hydroxy-2-methylpropyl)urea From Example 42 (280 mg, 0.74 mmol) and 3-amino-2-methyl-2-propanol HCl salt (188 mg, 1.50 mmol) by the method of Example 20 to give the title compound as a yellow solid (205 mg, 56%). $\delta_H$ (DMSO-d$_6$) 10.77 (1H, br s), 8.00 (1H, br m), 7.83-7.57 (8H, m), 6.79 (1H, d, J 9.7 Hz), 6.29 (1H, d, J 9.7 Hz), 4.47 (1H, br s), 3.00 (2H, d, J 5.6 Hz), 1.05 (6H, s). LCMS (ES$^+$) RT 3.11 minutes, 496 (M+H)$^+$.

EXAMPLE 125

N-[3-(4-Fluoro-3-methylbenzoyl)-6-oxo-7-phenyl-6,7-dihydrothieno[2,3-b]pyridin-2-yl]-N'-(2-hydroxy-2-methylpropyl)urea From Example 50 (294 mg, 0.77 mmol) and 3-amino-2-methyl-2-propanol HCl salt (192 mg, 1.54 mmol) by the method of Example 20 to give the title compound as a yellow solid (251 mg, 66%). $\delta_H$ (DMSO-d$_6$) 10.57 (1H, s), 7.90 (1H, m), 7.68-7.53 (5H, m), 7.49-7.46 (2H, m), 7.32 (1H, t, J 9.0 Hz), 6.87 (1H, d, J 9.7 Hz), 6.30 (1H, d, J 9.7 Hz), 4.48 (1H, s), 2.98 (2H, d, J 5.6 Hz), 2.31 (3H, s), 1.03 (6H, s). LCMS (ES$^+$) RT 3.15 minutes, 494 (M+H)$^+$.

EXAMPLE 126

3-Benzoyl-2-nitro-7-phenylthieno[2,3-b]pyridin-6(7H)-one

From Intermediate 46 (20 g, 57 mmol) and benzaldehyde (6.90 ml, 68 mmol) by the method of Intermediate 56 to give the title compound as a brown solid (6.4 g, 30%). $\delta_H$ (DMSO-$d_6$) 7.98-7.46 (2H, m), 7.81-7.60 (9H, m), 6.67 (1H, d, J 9.7 Hz). LCMS (ES$^+$) RT 3.56 minutes, 377 (M+H)$^+$.

EXAMPLE 127

2-Amino-7-phenyl-3-[2-(trifluoromethoxy)benzoyl]thieno[2,3-b]pyridin-6(7H)-one

From Intermediate 85 by the method of Example 69 to give the title compound as a yellow solid. $\delta_H$ (DMSO-$d_6$) 8.69 (2H, s), 7.74-7.44 (9H, m), 6.16 (2H, m). LCMS (ES$^+$) RT 3.19 minutes, 431 (M+H)$^+$.

EXAMPLE 128

2-Amino-3-(3-fluorobenzoyl)-7-phenylthieno[2,3-b]pyridin-6(7H)-one

From Intermediate 86 by she method of Example 69 to give the title compound as a yellow solid. $\delta_H$ (DMSO-$d_6$) 8.32 (2H, s), 7.65-7.55 (4H, m), 7.48-7.34 (5H, m), 6.57 (1H, d, J 9.6 Hz), 6.21 (1H, d, J 9.6 Hz). LCMS (ES$^+$) RT 3.05 minutes, 365 (M+H)$^+$.

EXAMPLE 129

2-Amino-7-phenyl-3-(1,3-thiazol-2-ylcarbonyl)thieno[2,3-b]pyridin-6(7H)-one

From Intermediate 87 by the method of Example 130 to give the title compound as a yellow solid. $\delta_H$ (DMSO-$d_6$) 9.44 (2H, s), 8.34-8.24 (3H, m), 7.74-7.61 (5H, m), 6.49 (1H, d, J 9.6 Hz). LCMS (ES$^+$) RT 2.92 minutes, 354 (M+H)$^+$.

EXAMPLE 130

2-Amino-7-phenyl-3-(pyridin-2-ylcarbonyl)thieno[2,3-b]pyridin-6(7H)-one

A mixture of Intermediate 88 (1.0 g, 2.6 mmol) and palladium on charcoal (250 mg) in THF (150 ml) was stirred under a hydrogen atmosphere (balloon) at r.t. for 60 h. The catalyst was removed by filtration through Celite and the filtrate concentrated in vacuo. Purification by column chromatography (silica, 0 to 5% MeOH in DCM) gave an orange solid which was triturated with EtOAc to give the title compound as a yellow solid (284 mg, 31%). $\delta_H$ (DMSO-$d_6$) 8.65 (1H, d, J 4.4 Hz), 8.47 (2H, s), 8.05 (1H, t, J 7.6 Hz), 7.72 (1H d, J 7.6 Hz), 7.60-7.45 (6H, m), 6.43 (1H, d, J 9.6 Hz), 6.16 (1H, d, J 9.6 Hz). LCMS (ES$^+$) RT 2.60 minutes, 349 (M+H)$^+$.

EXAMPLE 131

2-Amino-7-(2-chlorophenyl)-3-(3-methylbenzoyl)thieno[2,3-b]pyridin-6(7H)-one

From Intermediate 89 (240 mg, 0.56 mmol) by the method of Example 69 to give the title compound as a yellow solid (190 mg, 85%). $\delta_H$ (DMSO-$d_6$) 8.25 (2H, br s), 7.80-7.62 (4H, m), 7.40-7.29 (4H, m), 6.60 (1H, d, J 8.9 Hz), 6.20 (1H, d, J 8.9 Hz), 2.38 (3H, s). LCMS (ES$^+$) RT 3.24 minutes, 395 (M+H)$^+$.

EXAMPLE 132

2-Amino-3-benzoyl-7-(2-fluorophenyl)thieno[2,3-b]pyridin-6(7H)-one

From Intermediate 92 (360 mg, 0.91 mmol) by the method of Example 69 to give the title compound (235 mg, 71%). $\delta_H$ (DMSO-$d_6$) 8.27 (2H, br s), 7.68-7.43 (9H, m), 6.59 (1H, d, J 9.7 Hz), 6.20 (1H, d, J 9.7 Hz). LCMS (ES$^+$) RT 3.05 minutes, 365 (M+H)$^+$.

EXAMPLE 133

2-Amino-3-(4-fluoro-3-methylbenzoyl)-7-(2-fluorophenyl)thieno[2,3-b]pyridin-6(7H)-one From Intermediate 93 (853 mg, 2.0 mmol) by the method of Example 69 to give the title compound as a yellow solid (268 mg, 34%). $\delta_H$ (DMSO-$d_6$) 8.20 (2H, br s), 7.72-7.67 (2H, m), 7.62-7.43 (4H, m), 7.34-7.28 (1H, m), 6.78 (1H, d, J 9.6 Hz), 6.30 (1H, d, J 9.6 Hz), 2.34 (3H, s). LCMS (ES$^+$) RT 3.26 minutes, 397 (M+H)$^+$.

EXAMPLE 134

2-Amino-7-(2-fluorophenyl)-3-(3-methylbenzoyl)thieno[2,3-b]pyridin-6(7H)-one

From Intermediate 94 (262 mg, 0.64 mmol) by the method of Example 69 to give the title compound as a yellow solid (215 mg, 89%). $\delta_H$ (DMSO-$d_6$) 8.29 (2H, br s), 7.73-7.67 (2H, m), 7.62-7.58 (1H, m), 7.56-7.44 (3H, m), 7.38-7.33 (2H, m), 6.64 (1H, d, J 9.7 Hz), 6.24 (1H, d, J 9.7 Hz), 2.54 (3H, s). LCMS (ES$^+$) RT 3.20 minutes, 380 (M+H)$^+$.

EXAMPLE 135

2-Amino-3-benzoyl-7-[6-(dimethylamino)pyridin-3-yl]thieno[2,3-b]pyridin-6(7H)-one hydrochloride A mixture of Intermediate 100 (100 mg, 0.26 mmol) and dimethylamine in MeOH (2M, 3 ml) was heated in a sealed tube in a microwave reactor at 140° C. at 150 p.s.i. for 1 h. Volatiles were removed in vacuo. Purification by chromatography (silica, 50% EtOAc in DCM then +2% EtOH) gave a sticky yellow solid which was lyophilised from water and 2M HCl (0.1 ml) to give the title compound as a pale brown solid (6 mg, 5%). $\delta_H$ (DMSO-$d_6$) 8.33 (1H, d, J 2.5 Hz), 7.90 (1H, dd, J 2.5, 9.8 Hz), 7.70-7.55 (7H, m), 7.15 (1H, d, J 9.4 Hz), 6.59 (1H, d J 9.6 Hz), 6.23 (1H, d, J 9.6 Hz), 3.26 (6H, s). LCMS (ES$^+$) RT 2.58 minutes, 391 (M+H)$^+$.

EXAMPLE 136

N-{3-[3-(Difluoromethoxy)benzoyl]-6-oxo-7-phenyl-6,7-dihydrothieno[2,3-b]pyridin-2-yl}acetamide From Example 99 by the method of Example 14 to give the title compound as a yellow solid. $\delta_H$ (DMSO-$d_6$) 10.98 (1H, s), 7.75-7.23 (9H, m), 7.23 (1H, t, J 73.7 Hz), 7.27 (1H, d, J 9.7 Hz), 6.42 (1H, d, J 9.7 Hz), 2.02 (3H, s). LCMS (ES$^+$) RT 3.33 minutes, 455 (M+H)$^+$.

EXAMPLE 137

N-[3-(3-Fluorobenzoyl)-6-oxo-7-phenyl-6,7-dihydrothieno[2,3-b]pyridin-2-yl]acetamide From Example 128 by the method of Example 14 to give the title compound as a yellow solid. $\delta_H$ (DMSO-$d_6$) 10.98 (1H, s), 7.69-7.50 (9H, m), 7.24 (1H, d, J 9.6 Hz), 6.42 (1H, d, J 9.6 Hz), 2.03 (3H, s). LCMS (ES$^+$) RT 3.26 minutes, 407 (M+H)$^+$.

EXAMPLE 138

N-[7-(2-Chlorophenyl)-3-(3-methylbenzoyl)-6-oxo-6,7-dihydrothieno[2,3-b]pyridin-2-yl]acetamide From Example 131 (150 mg, 0.38 mmol) by the method of Example 14 to give the title compound as a yellow solid (40 mg, 24%). $\delta_H$ (DMSO-$d_6$) 11.01 (1H, br s), 7.84-7.81 (1H, m), 7.73-7.61 (4H, m), 7.54-7.43 (3H, m), 7.22 (1H, d, J 9.7 Hz), 6.43 (1H, d, J 9.7 Hz), 2.40 (3H, s), 2.04 (3H, s). LCMS (ES$^+$) RT 3.49 minutes, 437 (M+H)$^+$.

EXAMPLE 139

N-[3-Benzoyl-7-(2-fluorophenyl)-6-oxo-6,7-dihydrothieno[2,3-b]pyridin-2-yl]acetamide From Example 132 (150 mg, 0.38 mmol) by the method of Example 14 to give the title compound as a yellow solid (40 mg, 24%). $\delta_H$ (DMSO-$d_6$) 11.03 (1H, br s), 7.79-7.48 (9H, m), 7.23 (1H, d, J 9.6 Hz), 6.55 (1H, d, J 9.6 Hz), 2.04 (3H, s). LCMS (ES$^+$) RT 3.28 minutes, 407 (M+H)$^+$.

EXAMPLE 140

N-[3-(4-Fluoro-3-methylbenzoyl)-7-(2-fluorophenyl)-6-oxo-6,7-dihydrothieno[2,3-b]pyridin-2-yl]acetamide From Example 133 (174 mg, 0.43 mmol) by the method of Example 14 to give the title compound as a yellow solid (108 mg, 57%). $\delta_H$ (DMSO-$d_6$) 11.00 (1H, br s), 7.82-7.80 (1H, m), 7.79-7.59 (4H, m), 7.58-7.50 (1H, m), 7.39-7.33 (2H, m), 6.48 (1H, d, J 9.6 Hz), 2.35 (3H, s), 2.06 (3H, s). LCMS (ES$^+$) RT 3.46 minutes, 439 (M+H)$^+$.

EXAMPLE 141

N-[7-(2-Fluorophenyl)-3-(3-methylbenzoyl)-6-oxo-6,7-dihydrothieno[2,3-b]pyridin-2-yl]acetamide From Example 134 (180 mg, 0.47 mmol) by the method of Example 14 to give the title compound as a yellow solid (193 mg, 90%). $\delta_H$ (DMSO-$d_6$) 11.06 (1H, s), 7.78-7.70 (2H, m), 7.65-7.47 (6H, m), 7.26 (1H, d, J 9.7 Hz), 6.46 (1H, d, J 9.7 Hz), 2.43 (3H, s), 2.08 (3H, s). LCMS (ES$^+$) RT 3.44 minutes, 421 (M+H)$^+$.

EXAMPLE 142

N-1-(3-Benzoyl-6-oxo-7-phenyl-6,7-dihydrothieno[2,3-b]pyridin-2-yl)glycinamide

From Intermediate 101 (160 mg, 0.50 mmol) by the method of Example 61 to give the title compound as a bright yellow powder (97 mg, 75%). $\delta_H$ (DMSO-$d_6$) 7.70-7.48 (10H, m), 7.32 (1H, d, J 9.6 Hz), 6.37 (1H, d, J 9.6 Hz), 6.11 (2H, br s), 3.23 (2H, s). LCMS (ES$^+$) RT 2.04 minutes, 404 (M+H)$^+$.

EXAMPLE 143

N-1-(3-Benzoyl-6-oxo-7-phenyl-6,7-dihydrothieno[2,3-b]pyridin-2-yl)-N-2-methylglycinamide From Intermediate 102 (160 mg, 0.50 mmol) by the method of Example 61 to give the title compound as a bright yellow powder (25 mg, 6%). $\delta_H$ (DMSO-$d_6$) 7.72-7.48 (11H, m), 7.22 (1H, d, J 9.6 Hz), 6.38 (1H, d, J 9.6 Hz), 3.27 (2H, s), 2.26 (3H, s). LCMS (ES$^+$) RT 2.15 minutes, 418 (M+H)$^+$.

EXAMPLE 144

N-1-(3-Benzoyl-6-oxo-7-phenyl-6,7-dihydrothieno[2,3-b]pyridin-2-yl)-N-2,N-2-dimethylglycinamide From Example 143 (200 mg, 0.48 mmol) by the method of Example 59 to give the title compound as a bright yellow solid (30 mg, 14%). $\delta_H$ (CDCl$_3$) 12.10 (1H, br s), 7.66-7.44 (8H, m), 7.34-7.33 (2H, m), 6.90 (1H, d, J 9.7 Hz), 6.35 (1H, d, J 9.7 Hz), 3.17 (2H, br s), 2.38 (6H, br s). LCMS (ES$^+$) RT 2.22 minutes, 432 (M+H)$^+$.

EXAMPLE 145

N-1-(3-Benzoyl-6-oxo-7-phenyl-6,7-dihydrothieno[2,3-b]pyridin-2-yl)-D-alaninamide hydrochloride From Intermediate 103 (180 mg, 0.34 mmol) by the method of Example 122 to give the title compound as a bright yellow powder (150 mg, 100%). $\delta_H$ (DMSO-$d_6$) 8.15 (2H, br s), 7.81-7.78 (2H, m), 7.74-7.54 (8H, m), 7.40 (1H, d, J 9.6 Hz), 6.48 (1H, d, J 9.6 Hz), 4.00-3.96 (1H, br m), 1.09 (3H, d, J 7.0 Hz). LCMS (ES$^+$) RT 2.13 minutes, 418 (M+H)$^+$.

EXAMPLE 146

N-1-(3-Benzoyl-6-oxo-7-phenyl-6,7-dihydrothieno[2,3-b]pyridin-2-yl)-beta-alaninamide hydrochloride From Intermediate 104 (760 mg, 1.40 mmol) by the method of Example 122 to give the title compound as a yellow solid (528 mg, 79%). $\delta_H$ (DMSO-$d_6$) 8.10-7.51 (13H, br m), 7.23 (1H, d, J 9.6 Hz), 6.42 (1H, d, J 9.6 Hz), 2.94 (2H, t, J 6.6 Hz), 2.69 (2H, t, J 6.6 Hz). LCMS (ES$^+$) RT 2.12 minutes, 418 (M+H)$^+$.

EXAMPLE 147

N-[3-Benzoyl-7-(cyclopropylmethyl)-6-oxo-6,7-dihydrothieno[2,3-b]pyridin-2-yl]piperidine-4-carboxamide hydrochloride From Intermediate 105 (50 mg, 0.09 mmol) by the method of Example 122 to give the title compound as a yellow solid (25 mg, 56%). $\delta_H$ (DMSO-$d_6$) 11.13 (1H, s), 8.80-8.40 (2H, m), 7.80-7.75 (3H, m), 7.72-7.65 (2H, m), 7.22 (1H, d, J 9.52 Hz), 6.40 (1H, d, J 9.52 Hz), 4.06 (2H, d, J 7 Hz), 2.90-2.80 (2H, m), 2.75-2.65 (1H, m), 1.90-1.65 (4H, m), 1.40-1.35 (1H, m), 0.62-0.51 (4H, m). LCMS (ES$^+$) RT 2.21 minutes, 436 (M+H)$^+$.

EXAMPLE 148

N-[3-(4-Fluoro-3-methylbenzoyl)-7-(2-fluorophenyl)-6-oxo-6,7-dihydrothieno[2,3-b]pyridin-2-yl]piperidine-4-carboxamide hydrochloride From Intermediate 106 (326 mg, 0.53 mmol) by the method of Example 122 to give the title compound as a yellow solid (244 mg, 84%). $\delta_H$ (DMSO-$d_6$) 11.10 (11H, s), 8.90-8.40 (2H, m), 7.81-7.61 (5H, m), 7.56-7.52 (1H, m), 7.44 (1H, d, J 9.6 Hz), 7.40-7.34 (1H, m), 6.53 (1H, d, J 9.6 Hz), 3.28-3.24 (2H, m), 2.90-2.84 (2H, m), 2.68-2.62 (1H, m), 2.54 (3H, s), 1.82-1.79 (2H, m), 1.70-1.61 (2H, m). LCMS (ES$^+$) RT 2.38 minutes, 508 (M+H)$^+$.

EXAMPLE 149

N-[3-(4-Fluoro-3-methylbenzoyl)-6-oxo-7-phenyl-6,7-dihydrothieno[2,3-b]pyridin-2-yl]piperidine-4-carboxamide From Intermediate 107 by the method of Example 122 to give the title compound as a yellow solid. $\delta_H$ (DMSO-$d_6$) 7.83 (1H, d, J 9.3 Hz), 7.64-7.53 (5H, m), 7.45-7.43 (2H, m), 7.18 (1H, t, J 9.3 Hz), 6.38 (1H, d, J 9.6 Hz), 3.32 (1H, br s), 2.97-2.87 (2H, m), 2.66-2.54 (2H, m), 2.26 (3H, s), 2.26-2.15 (1H, m), 1.58-1.48 (2H, m), 1.42-1.29 (2H, m). LCMS (ES$^+$) RT 2.29 minutes, 490 (M+H)$^+$.

EXAMPLE 150

N-[3-Benzoyl-7-(2-chlorophenyl)-6-oxo-6,7-dihydrothieno[2,3-b]pyridin-2-yl]-1-methylpiperidine-4-carboxamide From Example 122 (142 mg, 0.27 mmol) by the method of Example 59 to give the title compound as a yellow solid (40 mg, 29%). $\delta_H$ (DMSO-$d_6$) 10.87 (1H, br s), 7.84-7.53 (9H, m), 7.38 (1H, d, J 9.6 Hz), 6.45 (1H, d, J 9.6 Hz), 2.71-2.67 (2H, m), 2.29-2.20 (1H, m), 2.12 (3H, s), 1.91-1.80 (2H, m), 1.58-1.38 (4H, m). LCMS (ES$^+$) RT 2.33 minutes, 506 (M+1)$^+$.

EXAMPLE 151

N-[3-(4-Fluoro-3-methylbenzoyl)-7-(2-fluorophenyl)-6-oxo-6,7-dihydrothieno[2,3-b]pyridin-2-yl]-1-methylpiperidine-4-carboxamide From Example 148 (150 mg, 0.27 mmol) by the method of Example 59 to give the title compound as a light green solid (112 mg, 80%). $\delta_H$ (DMSO-$d_6$) 11.70 (1H, s), 7.55-7.48 (2H, m), 7.44-7.39 (1H, m), 7.35-7.29 (2H, m), 7.17-7.13 (1H, m), 7.02 (1H, d, J 9.7 Hz), 6.44 (1H, d, J 9.7 Hz), 3.08-2.90 (2H, m), 2.50-1.80 (13H, m). LCMS (ES$^+$) RT 2.39 minutes, 522 (M+H)$^+$.

EXAMPLE 152

N-(3-Benzoyl-6-oxo-7-phenyl-6,7-dihydrothieno[2,3-b]pyridin-2-yl)-D-prolinamide hydrochloride From Intermediate 108 (270 mg, 0.50 mmol) by the method of Example 122 to give the title compound as a yellow solid (190 mg, 86%). $\delta_H$ (DMSO-$d_6$) 11.47 (1H, s), 9.84 (1H, br s), 8.64 (1H, br s), 7.80 (2H, d, J 8.0 Hz), 7.73-7.53 (8H, m), 7.41 (1H, d, J 9.6 Hz), 6.48 (1H, d, J 9.6 Hz), 4.43-4.30 (1H, br m), 3.17-3.12 (2H, br m), 2.06-1.94 (1H, br m), 1.89-1.68 (2H, br m), 1.56-1.45 (1H, br m). LCMS (ES$^+$) RT 2.18 minutes, 444 (M+H)$^+$.

EXAMPLE 153

N-(3-Benzoyl-6-oxo-7-phenyl-6,7-dihydrothieno[2,3-b]pyridin-2-yl)-L-prolinamide hydrochloride From Intermediate 109 (760 mg, 1.40 mmol) by the method of Example 122 to give the title compound as a yellow solid (528 mg, 79%). $\delta_H$ (DMSO-$d_6$) 11.49 (1H, s), 9.88 (1H, br s), 8.66 (1H, br s), 7.82-7.79 (2H, m), 7.74-7.54 (8H, m), 7.42 (1H, d, J 9.6 Hz), 6.48 (1H, d, J 9.6 Hz), 4.35-4.30 (1H, br m), 3.17-3.13 (2H, m), 2.07-1.95 (1H, m), 1.88-1.68 (2H, m), 1.66-1.45 (1H, m). LCMS (ES$^+$) RT 2.18 minutes, 444 (M+H)$^+$.

EXAMPLE 154

N-(3-Benzoyl-6-oxo-7-phenyl-6,7-dihydrothieno[2,3-b]pyridin-2-yl)-1-methyl-L-prolinamide From the free base of Example 152 (120 mg, 0.27 mmol) by the method of Example 59 to give the title compound as a yellow solid (32 mg, 26%). $\delta_H$ (DMSO-$d_6$) 11.63 (1H, br s), 7.74-7.49 (10H, m), 7.14 (1H, d, J 9.7 Hz), 6.40 (1H, d, J 9.7 Hz), 3.08-2.98 (2H, m), 2.32-2.28 (4H, m), 2.20-2.07 (1H, m), 1.79-1.56 (3H, m). LCMS (ES$^+$) RT 2.27 minutes, 458 (M+H)$^+$.

EXAMPLE 155

N-(3-Benzoyl-6-oxo-7-phenyl-6,7-dihydrothieno[2,3-b]pyridin-2-yl)-1-methyl-D-prolinamide From the free base of Example 153 (173 mg, 0.39 mmol) by the method of Example 59 to give the title compound as a yellow solid (54 mg, 30%). $\delta_H$ (DMSO-$d_6$) 11.69 (1H, br s), 7.79-7.55 (10H, m), 7.20 (1H, d, J 9.7 Hz), 6.46 (1H, d, J 9.7 Hz), 3.14-3.04 (2H, m), 2.44-2.34 (4H, m), 2.26-2.12 (1H, m), 1.84-1.61 (3H, m). LCMS (ES$^+$) RT 2.28 minutes, 458 (M+H)$^+$.

EXAMPLE 156

N-(3-Benzoyl-6-oxo-7-phenyl-6,7-dihydrothieno[2,3-b]pyridin-2-yl)-N'-(2-hydroxyethyl)urea From Example 13 (300 mg, 0.87 mmol) and ethanolamine (106 mg, 1.74 mmol) by the method of Example 20 to give the title compound as a light brown solid (260 mg, 69%). $\delta_H$ (DMSO-$d_6$) 10.70 (1H, s), 8.05 (1H, br m), 7.71-7.55 (8H, m), 7.49-7.46 (2H, m), 6.74 (1H, d, J 9.7 Hz), 6.26 (1H, d, J 9.7 Hz), 4.72 (1H, t, J 5.2 Hz), 3.43-3.37 (2H, m), 3.14-3.08 (2H, m). LCMS (ES$^+$) RT 2.77 minutes, 434 (M+H)$^+$.

EXAMPLE 157

N-(3-Benzoyl-6-oxo-7-phenyl-6,7-dihydrothieno[2,3-b]pyridin-2-yl)-N'-[(3R)-1-methylpyrrolidin-3-yl]urea From Intermediate 111 (152 mg, 0.31 mmol) by the method of Example 59 to give the title compound as a yellow solid (9 mg, 6%). $\delta_H$ (DMSO-$d_6$) 10.69 (1H, s), 8.24 (1H, d, J 6.0 Hz), 7.67-7.55 (8H, m), 7.47 (2H, d, J 6.7 Hz), 6.71 (1H, d, J 9.6 Hz), 6.25 (1H, d, J 9.6 Hz), 4.01 (1H, br s), 2.64-2.56 (2H, m), 2.37-2.32 (2H, m), 2.26 (3H, s), 2.17-2.08 (1H, m), 1.52-1.50 (1H, m). LCMS (ES$^+$) RT 2.21 minutes, 473 (M+H)$^+$.

EXAMPLE 158

(3R)-N-(3-Benzoyl-6-oxo-7-phenyl-6,7-dihydrothieno[2,3-b]pyridin-2-yl)-3-(dimethylamino)pyrrolidine-1-carboxamide From Example 13 (250 mg, 0.72 mmol) and (R)-3-(dimethylamino)pyrrolidine (165 mg, 1.44 mmol) by the method of Example 20 to give the title compound as a yellow solid (75 mg, 21%). $\delta_H$ (CDCl$_3$) 11.75 (1H, s), 7.67-7.51 (8H, m), 7.43-7.40 (2H, m), 6.85 (1H, d, J 9.7 Hz), 6.38 (1H, d, J 9.7 Hz), 3.83-3.73 (2H, br m), 3.53 (1H, br m), 3.39-3.35 (1H, br m), 2.87 (1H, br s), 2.33 (6H, s), 2.25-2.20 (1H, br m), 2.05-1.98 (1H, br m). LCMS (ES$^+$) RT 2.20 minutes, 487 (M+H)$^+$.

EXAMPLE 159

(3S)-N-(3-Benzoyl-6-oxo-7-phenyl-6,7-dihydrothieno[2,3-b]pyridin-2-yl)-3-(dimethylamino)pyrrolidine-1-carboxamide From Example 13 (250 mg, 0.72 mmol) and (S)-3-(dimethylamino)pyrrolidine (165 mg, 1.44 mmol) by the method of Example 20 to give the title compound as a yellow solid (50 mg, 14%). $\delta_H$ (CDCl$_3$) 11.75 (1H, s), 7.67-7.50 (8H, m), 7.43-7.40 (2H, m), 6.85 (1H, d, J 9.7 Hz), 6.38 (1H, d, J 9.7 Hz), 3.83-3.73 (2H, br m), 3.54 (1H, br m), 3.41-3.35 (1H, br m), 2.89 (1H, br s), 2.34 (6H, s), 2.22-2.18 (1H, br m), 2.06-1.99 (1H, br m). LCMS (ES$^+$) RT 2.21 minutes, 487 (M+H)$^+$.

EXAMPLE 160

N-(3-Benzoyl-6-oxo-7-phenyl-6,7-dihydrothieno[2,3-b]pyridin-2-yl)-N'-[(3S)-pyrrolidin-3-yl]urea hydrochloride From Intermediate 112 (587 mg, 1.05 mmol) by the method of Example 122 to give the title compound as a yellow solid (378 mg, 73%). $\delta_H$ (DMSO-d$_6$) 10.76 (1H, s), 9.31 (1H, br s), 9.22 (1H, br s), 8.39 (1H, d, J 5.6 Hz), 7.71-7.55 (8H, m), 7.47 (2H, d, J 7.9 Hz), 6.72 (1H, d, J 9.7 Hz), 6.27 (1H, d, J 9.7 Hz), 4.16 (1H, d, J 5.0 Hz), 3.34-3.22 (3H, m), 3.01-3.00 (1H, m), 2.18-2.09 (1H, m), 1.84-1.78 (1H, m). LCMS (ES$^+$) RT 2.18 minutes, 459 (M+H)$^+$.

EXAMPLE 161

(3R)-3-Amino-N-(3-benzoyl-6-oxo-7-phenyl-6,7-dihydrothieno[2,3-b]pyridin-2-yl)pyrrolidine-1-carboxamide hydrochloride From Intermediate 113 (606 mg, 1.09 mmol) by the method of Example 122 to give the title compound as a yellow solid (339 mg, 63%). $\delta_H$ (DMSO-d$_6$) 11.02 (1H, s), 8.31 (3H, br m), 7.71-7.48 (10H, m), 6.90 (1H, d, J 9.7 Hz), 6.34 (1H, d, J 9.7 Hz), 3.83 (1H, br m), 3.53-3.38 (4H, br m), 2.27-2.09 (2H, br m). LCMS (ES$^+$) RT 2.17 minutes, 459 (M+H)$^+$.

EXAMPLE 162

(3S)-3-Amino-N-(3-benzoyl-6-oxo-7-phenyl-6,7-dihydrothieno[2,3-b]pyridin-2-yl)pyrrolidine-1-carboxamide hydrochloride From Intermediate 114 (618 mg, 1.10 mmol) by the method of Example 122 to give the title compound as a yellow solid (447 mg, 81%). $\delta_H$ (DMSO-d$_6$) 11.02 (1H, s), 8.32 (3H, br m), 7.72-7.48 (10H, m), 6.90 (1H, d, J 9.7 Hz), 6.34 (1H, d, J 9.7 Hz), 3.82 (1H, br m), 3.51-3.38 (4H, br m), 2.27-2.09 (2H, br m). LCMS (ES$^+$) RT 2.17 minutes, 459 (M+H)$^+$.

EXAMPLE 163

N-(3-Benzoyl-6-oxo-7-phenyl-6,7-dihydrothieno[2,3-b]pyridin-2-yl)-N'-[(3S)-1-methylpyrrolidin-3-yl]urea From Example 160 (274 mg, 0.55 mmol) by the method of Example 59 to give the title compound as a yellow solid (162 mg, 62%). $\delta_H$ (DMSO-d$_6$) 10.68 (1H, s), 8.23 (1H, d, J 7.0 Hz), 7.70-7.55 (8H, m), 7.49-7.46 (2H, m), 6.71 (1H, d, J 9.7 Hz), 6.25 (1H, d, J 9.7 Hz), 4.10-3.95 (1H, m), 2.62-2.55 (2H, m), 2.33-2.25 (2H, m), 2.22 (3H, s), 2.16-2.04 (1H, m), 1.50-1.44 (1H, m). LCMS (ES$^+$) RT 2.19 minutes, 473 (M+H)$^+$.

EXAMPLE 164

(3S)-N-(3-Benzoyl-6-oxo-7-phenyl-6,7-dihydrothieno[2,3-b]pyridin-2-yl)-3-(isopropylamino)pyrrolidine-1-carboxamide From Example 162 (100 mg, 0.20 mmol) and acetone following the method of Example 59 to give the title compound as a bright yellow solid (34 mg, 34%). $\delta_H$ (DMSO-d$_6$) 7.68-7.47 (11H, m), 7.02 (1H, br s), 6.32 (1H, d, J 9.7 Hz), 3.25-3.18 (3H, br m), 3.06-2.98 (1H, br m), 2.80-2.70 (1H, br m), 2.10-1.95 (1H, br m), 1.75-1.60 (1H, br m), 0.99-0.96 (6H, m). LCMS (ES$^+$) RT 2.23 minutes, 501 (M+H)$^+$.

EXAMPLE 165

N-[3-(4-Fluoro-3-methylbenzoyl)-6-oxo-7-phenyl-6,7-dihydrothieno[2,3-b]pyridin-2-yl]-N'-(1,1-dimethyl-2-hydroxyethyl)urea From Example 50 (340 mg, 0.90 mmol) and 2-amino-2-methyl-1-propanol (160 mg, 1.80 mmol) by the method of Example 20 to give the title compound as a yellow solid (240 mg, 54%). $\delta_H$ (DMSO-d$_6$) 10.51 (1H, s), 7.71 (1H, s), 7.67-7.46 (8H, m), 7.32 (1H, t, J 9.0 Hz), 6.82 (1H, d, J 9.6 Hz), 6.29 (1H, d, J 9.6 Hz), 4.79 (1H, t, J 5.6 Hz), 2.31 (3H, s), 1.14 (6H, s). LCMS (ES$^+$) RT 3.27 minutes, 494 (M+H)$^+$.

EXAMPLE 166

N-[3-(4-Fluoro-3-methylbenzoyl)-6-oxo-7-phenyl-6,7-dihydrothieno[2,3-b]pyridin-2-yl]-N'-[(3R)-pyrrolidin-3-yl]urea hydrochloride From Intermediate 115 (100 mg, 0.17 mmol) by the method of Example 122 to give the title compound as a yellow solid (80 mg, 90%). $\delta_H$ (DMSO-d$_6$) 10.62 (1H, s), 9.29 (1H, br s), 9.20 (1H, br s), 8.35 (1H, d, J 5.7 Hz), 7.68-7.47 (7H, m), 7.33 (1H, t, J 9.0 Hz), 6.85 (1H, d, J 9.7 Hz), 6.31 (1H, d, J 9.7 Hz), 4.16 (1H, dd, J 5.6, 11.1 Hz), 3.42-3.19 (2H, br m), 2.99-2.10 (1H, m), 2.32 (3H, s), 2.18-2.07 (1H, s), 1.86-1.76 (1H, m). LCMS (ES$^+$) RT 2.30 minutes, 491 (M+H)$^+$.

EXAMPLE 167

N-[3-(4-Fluoro-3-methylbenzoyl)-6-oxo-7-phenyl-6, 7-dihydrothieno[2,3-b]pyridin-2-yl]-N'-[(3R)-1-methylpyrrolidin-3-yl]urea From Example 166 (357 mg, 0.68 mmol) by the method of Example 59 to give the title compound as a yellow solid (192 mg, 56%). $\delta_H$ (DMSO-d$_6$) 10.53 (1H, s), 8.18 (1H, d, J 6.2 Hz), 7.66-7.52 (5H, m), 7.49-7.46 (2H, m), 7.32 (1H, t, J 9.0 Hz), 6.84 (1H, d, J 9.7 Hz), 6.30 (1H, d, J 9.7 Hz), 4.00 (1H, br s), 2.62-2.54 (2H, m), 2.31-2.22 (8H, m), 2.13-2.04 (1H, m), 1.49-1.43 (1H, m). LCMS (ES$^+$) RT 2.33 minutes, 505 (M+H)$^+$.

EXAMPLE 168

N-[(3R)-1-Ethylpyrrolidin-3-yl]-N'-[3-(4-fluoro-3-methylbenzoyl)-6-oxo-7-phenyl-6,7-dihydrothieno[2,3-b]pyridin-2-yl]urea Sodium cyanoborohydride (87 mg, 1.39 mmol) was added to a mixture of Example 166 (616 mg, 1.16 mmol) in EtOH (10 ml). Acetaldehyde (255 mg, 5.8 mmol) was added to the reaction mixture and it was stirred at r.t. for 16 h. 2M HCl(aq) (20 ml) was added, followed by NaOH(aq) (20 ml), and the mixture was extracted with DCM (2×20 ml). The combined organic extracts were dried (MgSO$_4$) and concentrated in vacuo. Purification by column chromatography (silica, 0-5% MeOH in DCM) gave the title compound as a yellow solid (250 mg, 42%). $\delta_H$ (DMSO-d$_6$) 10.54 (1H, s), 8.16 (1H, d, J 6.6 Hz), 7.68-7.45 (7H, m), 7.32 (1H, t, J 9.0 Hz), 6.83 (1H, d, J 9.6 Hz), 6.29 (1H, d, J 9.6 Hz), 3.99 (1H, br s), 2.66-2.53 (1H, m), 2.39-2.24 (8H, m), 2.14-2.05 (1H, m), 1.53-1.42 (1H, m), 0.99 (3H, t, J 7.2 Hz). LCMS (ES$^+$) RT 2.34 minutes, 519 (M+H)$^+$.

EXAMPLE 169

(3R)-3-(Dimethylamino)-N-[3-(4-fluoro-3-methylbenzoyl)-6-oxo-7-phenyl-6,7-dihydrothieno[2,3-b]pyridin-2-yl]pyrrolidine-1-carboxamide From Example 50 and (R)-3-(dimethylamino)pyrrolidine by the method of Example 20 to give the title compound as a yellow solid. $\delta_H$ (DMSO-d$_6$) 10.50 (1H, br d), 7.66-7.49 (7H, m), 7.31 (1H, t, J 8.9 Hz), 7.19 (1H, br s), 6.38 (1H, d, J 9.6 Hz), 3.41-3.25 (3H, m), 2.97 (1H, br s), 2.70 (1H, br s), 2.51 (6H, s), 2.30 (3H, s), 2.05 (1H, m), 1.71 (1H, br s). LCMS (ES$^+$) RT 2.30 minutes, 519 (M+H)$^+$.

EXAMPLE 170

(3S)-3-(Dimethylamino)-N-[3-(4-fluoro-3-methylbenzoyl)-6-oxo-7-phenyl-6,7-dihydrothieno[2,3-b]pyridin-2-yl]pyrrolidine-1-carboxamide From Example 50 and (S)-3-(dimethylamino)pyrrolidine by the method of Example 20 to give the title compound as a yellow solid. $\delta_H$ (DMSO-d$_6$) 10.50 (1H, br d), 7.67-7.49 (7H, m), 7.31 (1H, t, J 8.9 Hz), 7.18 (1H, br s), 6.38 (1H, d, J 9.6 Hz), 3.43-3.25 (3H, m), 2.97 (1H, br s), 2.70 (1H, br s), 2.51 (6H, s), 2.30 (3H, s), 2.04 (1H, m), 1.70 (1H, br s). LCMS (ES$^+$) RT 2.30 minutes, 519 (M+H)$^+$.

EXAMPLE 171

N-[3-(4-Fluoro-3-methylbenzoyl)-6-oxo-7-phenyl-6, 7-dihydrothieno[2,3-b]pyridin-2-yl]4-methylpiperazine-1-carboxamide From Example 50 and N-methylpiperazine by the method of Example 20 to give the title compound as a yellow solid. $\delta_H$ (DMSO-d$_6$) 10.51 (1H, br s), 7.65-7.30 (9H, m), 6.40 (1H, d, J 9.5 Hz), 3.32-3.05 (4H, m), 2.53-2.00 (10H, m). LCMS (ES$^+$) RT 2.29 minutes, 505 (M+H)$^+$.

EXAMPLE 172

N-[7-(2-Chlorophenyl)-3-(4-fluoro-3-methylbenzoyl)-6-oxo-6,7-dihydrothieno[2,3-b]pyridin-2-yl]-N'-(1,1-dimethyl-2-hydroxyethyl)urea From Example 120 (206 mg, 0.50 mmol) and 2-amino-2-methyl-1-propanol (0.096 ml, 1.0 mmol) by the method of Example 20 to give the title compound as a yellow solid (96 mg, 39%). $\delta_H$ (DMSO-d$_6$) 10.69 (1H, br s), 7.89-7.86 (1H, m), 7.79 (1H, s), 7.76-7.67 (6H, m), 7.60-7.55 (1H, m), 7.40 (1H, t, J 9.0 Hz), 6.92 (1H, d, J 9.7 Hz), 6.38 (1H, d, J 9.7 Hz), 4.85 (1H, t, J 5.6 Hz), 3.45-3.40 (2H, m), 2.38 (3H, d, J 1.3 Hz), 1.21 (4H, s). LCMS (ES$^+$) RT 3.37 minutes, 528 (M+H)$^+$.

EXAMPLE 173

N-[3-Benzoyl-7-(cyclopropylmethyl)-6-oxo-6,7-dihydrothieno[2,3-b]pyridin-2-yl]-N'-(1,1-dimethyl-2-hydroxyethyl)urea From Example 40 (87 mg, 0.27 mmol) and 2-amino-2-methyl-1-propanol (0.055 ml, 0.54 mmol) by the method of Example 20 to give the title compound as a yellow solid (45 mg, 38%). $\delta_H$ (DMSO-d$_6$) 10.70 (1H, s), 7.84 (1H, s), 7.71-7.65 (3H, m), 7.60-7.55 (2H, m), 6.65 (1H, d, J 9.5 Hz), 6.20 (1H, d, J 9.5 Hz), 4.88 (1H, t, J 5.65 Hz), 4.08 (2H, d, J 7 Hz), 3.45 (2H, d, J 5.6 Hz), 1.39-1.34 (1H, m), 1.27 (6H, s), 0.60-0.50 (4H, m). LCMS (ES$^+$) RT 3.15 minutes, 440 (M+H)$^+$.

EXAMPLE 174

N-[3-Benzoyl-7-(cyclopropylmethyl)-6-oxo-6,7-dihydrothieno[2,3-b]pyridin-2-yl]-N'-(2-hydroxy-2-methylpropyl)urea From Example 40 (147 mg, 0.45 mmol) and 2-amino-1,1-dimethylethanol hydrochloride salt (106 mg, 0.9 mmol) by the method of Example 20 to give the title compound as a yellow solid (19 mg, 10%). $\delta_H$ (DMSO-d$_6$) 10.78 (1H, s), 8.04 (1H, m), 7.72-7.67 (3H, m), 7.61-7.56 (2H, m), 6.70 (1H, d, J 9.6 Hz), 6.22 (1H, d, J 9.6 Hz), 4.55 (1H, s), 4.04 (2H, d, J 7 Hz), 3.13 (2H, d, J 5.5 Hz), 1.38-1.34 (1H, m), 1.13 (6H, s), 0.60-0.50 (4H, m). LCMS (ES$^+$) RT 3.02 minutes, 440 (M+H)$^+$.

EXAMPLE 175

3-Benzoyl-7-phenyl-2-(piperidin-4-ylamino)thieno[2,3-b]pyridin-6(7H)-one

From Intermediate 116 (123 mg, 0.23 mmol) by the method of Example 61 to give the title compound as a yellow solid (50 mg, 51%). δ$_H$ (DMSO-d$_6$) 9.63 (1H, d, J 8.6 Hz), 7.66-7.46 (11H, m), 6.53 (1H, d, J 9.7 Hz), 6.20 (1H, d, J 9.7 Hz), 3.28-3.19 (1H, m), 2.85 (2H, dd, J 3.7, 9.0 Hz), 2.28-2.12 (2H, m), 1.83 (2H, d, J 9.9 Hz), 1.42-1.31 (2H, m). LCMS (ES$^+$) RT 2.16 minutes, 430 (M+H)$^+$.

EXAMPLE 176

3-Benzoyl-2-[(1-methylpiperidin-4-yl)amino]-7-phenylthieno[2,3-b]pyridin-6(7H)-one From Example 175 (473 mg, 1.10 mmol) by the method of Example 59 to give the title compound as a yellow solid (220 mg, 45%). δ$_H$ (DMSO-d$_6$) 9.58 (1H, d, J 8.6 Hz), 7.79-7.46 (10H, m), 6.54 (1H, d, J 9.7 Hz), 6.21 (1H, d, J 9.7 Hz), 3.20-3.17 (1H, m), 2.58-2.55 (2H, m), 2.14 (3H, s), 2.08-2.05 (2H, m), 1.88-1.85 (2H, m), 1.63-1.56 (2H, m). LCMS (ES$^+$) RT 2.18 minutes, 444 (M+H)$^+$.

EXAMPLE 177

3-Benzoyl-7-phenyl-2-[(3R)-pyrrolidin-3-ylamino]thieno[2,3-b]pyridin-6(7H)-one

From Intermediate 117 (680 mg, 1.32 mmol) by the method of Example 122 to give the title compound as a yellow solid (366 mg, 67%). δ$_H$ (DMSO-d$_6$) 9.50 (1H, br s), 7.66-7.47 (10H, m), 6.55 (1H, d, J 9.7 Hz), 6.21 (1H, d, J 9.7 Hz), 3.95 (1H, br s), 3.78 (1H, br s) 3.04-2.96 (2H, m), 2.93-2.72 (2H, m), 2.13-2.01 (1H, m), 1.64-1.62 (1H, m). LCMS (ES$^+$) RT 1.36 minutes, 416 (M+H)$^+$.

EXAMPLE 178

3-Benzoyl-2-{[(3R)-1-methylpyrrolidin-3-yl]amino}-7-phenylthieno[2,3-b]pyridin-6(7H)-one hydrochloride From Example 177 (241 mg, 0.58 mmol) by the method of Example 59 to give the title compound as a yellow solid (25 mg, 9%). δ$_H$ (DMSO-d$_6$) 10.64 (1H, br s), 9.28-9.22 (1H, m), 7.64-7.48 (10H, m), 6.63-6.59 (1H, m), 6.25 (1H, d, J 9.6 Hz), 4.35-4.20 (1H, m), 4.06-3.82 (1H, m), 3.66-3.48 (2H, m), 3.39-2.95 (2H, m), 2.79 (3H, s), 2.32-1.93 (1H, m). LCMS (ES$^+$) RT 2.16 minutes, 430 (M+H)$^+$.

EXAMPLE 179

3-Benzoyl-7-phenyl-2-[(3S)-pyrrolidin-3-ylamino]thieno[2,3-b]pyridin-6(7H)-one

From Intermediate 118 (1.0 g, 2.0 mmol) by the method of Example 122 to give the title compound as a yellow solid (389 mg, 47%). δ$_H$ (DMSO-d$_6$) 9.48 (1H, br s), 7.65-7.48 (10H, m), 6.55 (1H, d, J 9.7 Hz), 6.22 (1H, d, J 9.7 Hz), 4.00 (1H, br s), 3.79 (1H, br S), 3.04-3.00 (1H, m), 2.69-2.90 (1H, m), 2.79-2.73 (2H, m), 2.12-2.03 (1H, m), 1.65 (1H, t, J 5.7 Hz). LCMS (ES$^+$) RT 2.14 minutes, 416 (M+H)$^+$.

EXAMPLE 180

3-Benzoyl-2-{[(3S)-1-methylpyrrolidin-3-yl]amino}-7-phenylthieno[2,3-b]pyridin-6(7H)-one From Example 179 (200 mg, 0.48 mmol) by the method of Example 59 to give the title compound as a yellow solid (134 mg, 65%). δ$_H$ (DMSO-d$_6$) 9.60 (1H, d, J 8.3 Hz), 7.65-7.36 (11H, m), 6.54 (1H, d, J 9.7 Hz), 6.21 (1H, d, J 9.7 Hz), 3.86 (1H, m), 2.84-2.73 (1H, m), 2.64-2.54 (1H, m), 2.26 (3H, s), 2.24-2.16 (2H, m), 2.04-1.60 (1H, m). LCMS (ES$^+$) RT 2.13 minutes, 430 (M+H)$^+$.

EXAMPLE 181

3-Benzoyl-2-[(3S)-3-(dimethylamino)pyrrolidin-1-yl]-7-phenylthieno[2,3-b]pyridin-6(7H)-one From Intermediate 36 (500 mg, 1.2 mmol) and (3S)-3-(dimethylamino)pyrrolidine (167 mg, 1.46 mmol) by the method of Example 55 to give the title compound as a yellow solid (163 mg, 30%). δ$_H$ (DMSO-d$_6$) 7.83 (2H, d, J 8.3 Hz), 7.72-7.55 (8H, m), 7.44 (1H, d, J 9.6 Hz), 6.44 (1H, d, J 9.6 Hz), 3.35-3.01 (3H, m), 2.73 (1H, br s), 2.07 (8H, br s), 1.69 (1H, br s). LCMS (ES$^+$) RT 2.12 minutes, 444 (M+H)$^+$.

EXAMPLE 182

2-(3-Aminoazetidin-1-yl)-3-benzoyl-7-phenylthieno[2,3-b]pyridin-6(7H)-one

From Intermediate 119 (1.0 g, 2.0 mmol) by the method of Example 61 to give the title compound as a yellow solid (437 mg, 54%). δ$_H$ (DMSO-d$_6$) 7.73-7.71 (2H, m), 7.67-7.44 (9H, m), 6.39 (1H, d, J 9.6 Hz), 3.66 (2H, t, J 7.7 Hz), 3.60-3.54 (1H, m), 3.20 (2H, dd, J 5.4, 8.2 Hz), 2.06 (2H, br s). LCMS (ES$^+$) RT 2.01 minutes, 402 (M+H)$^+$.

EXAMPLE 183

2-(4-Aminopiperidin-1-yl)-3-benzoyl-7-phenylthieno[2,3-b]pyridin-6(7H)-one

From Intermediate 120 (359 mg, 0.68 mmol) by the method of Example 61 to give the title compound as a yellow solid (190 mg, 65%). δ$_H$ (DMSO-d$_6$) 7.85 (1H, d, J 9.6 Hz), 7.80 (2H, d, J 8.0 Hz), 7.67-7.49 (8H, m), 6.50 (1H, d, J 9.6 Hz), 2.97 (2H, br d, J 11.3 Hz), 2.72-2.42 (3H, m), 1.62 (2H, br s), 1.32 (2H, br d, J 12.8 Hz), 0.68-0.58 (2H, m). LCMS (ES$^+$) RT 2.13 minutes, 430 (M+H)$^+$.

EXAMPLE 184

3-Benzoyl-2-[3-(dimethylamino)azetidin-1-yl]-7-phenylthieno[2,3-b]pyridin-6(7H)-one From Example 182 (186 mg, 0.46 mmol) by the method of Example 59 to give the title compound as a yellow solid (147 mg, 75%). δ$_H$ (DMSO-d$_6$) 7.79 (2H, d J 7.2 Hz), 7.73-7.54 (8H, m), 7.48 (1H, d, J 9.6 Hz), 6.44 (1H, d, J 9.6 Hz), 3.68-3.64 (2H, m), 3.42-3.39 (2H, m), 3.08 (1H, t, J 4.9 Hz), 1.98 (6H, s). LCMS (ES$^+$) RT 2.09 minutes, 430 (M+H)$^+$.

EXAMPLE 185

2-[(Azetidin-3-ylmethyl)amino]-3-benzoyl-7-phenylthieno[2,3-b]pyridin-6(7H)-one

From Intermediate 121 (494 mg, 0.96 mmol) by the method of Example 61 to give the title compound as a yellow solid (389 mg, 98%). δ$_H$ (DMSO-d$_6$) 9.54 (1H, br s), 7.66-7.47 (11H, m), 6.55 (1H, d, J 9.7 Hz), 6.21 (1H, d, J 9.7 Hz), 3.49 (2H, t, J 7.6 Hz), 3.41-3.38 (2H, m), 3.17-3.12 (2H, m), 2.87-2.79 (1H, m). LCMS (ES$^+$) RT 2.12 minutes, 416 (M+H)$^+$.

EXAMPLE 186

3-Benzoyl-2-{[(1-methylazetidin-3-yl)methyl]amino}-7-phenylthieno[2,3-b]pyridin-6(7H)-one From Example 185 (239 mg, 0.58 mmol) by the method of Example 59 to give the title compound as a yellow solid (109 mg, 44%). $\delta_H$ (DMSO-$d_6$) 9.53 (1H, t, J 5.1 Hz), 7.76-7.46 (10H, m), 6.56 (1H, d, J 9.7 Hz), 6.21 (1H, d, J 9.7 Hz), 3.36 (2H, t, J 6.0 Hz), 3.15 (2H, t, 7.0 Hz), 2.89-2.85 (2H, m), 2.59 (1H, t, J 6.0 Hz), 2.14 (3H, s). LCMS (ES$^+$) RT 2.13 minutes, 430 (M+H)$^+$.

EXAMPLE 187

3-Benzoyl-2-(morpholin-4-yl)-7-phenylthieno[2,3-b]pyridin-6(7H)-one

Example 126 (260 mg, 0.69 mmol) was added to morpholine (4 ml, 46.8 mmol), and the reaction mixture was heated in the microwave for 30 min at 160° C., at a pressure of 60 psi. NaHCO$_3$(aq) (10 ml) was added, and the mixture was extracted with DCM (2×20 ml). The combined organic extracts were dried (MgSO$_4$) and concentrated in vacuo. The crude product was purified by chromatography (silica, 10-50% EtOAc in DCM) to give the title compound as a yellow solid (200 mg, 70%). $\delta_H$ (DMSO-$d_6$) 7.86 (1H, d, J 9.6 Hz), 7.83-7.80 (2H, m), 7.69-7.51 (8H, m), 6.53 (1H, d, J 9.6 Hz), 3.06 (4H, t, J 4.5 Hz), 2.75 (4H, t, J 4.5 Hz). LCMS (ES$^+$) RT 3.37 minutes, 417 (M+H)$^+$.

EXAMPLE 188

3-Benzoyl-2-{[3-(dimethylamino)-2,2-dimethylpropyl]amino}-7-phenylthieno[2,3-b]pyridin-6(7H)-one Example 126 (250 mg, 0.66 mmol) was added to N,N,2,2-tetramethyl-1,3-propanediamine (4 ml, 25.1 mmol), and the reaction mixture was heated in the microwave for 30 min at 160° C., at a pressure of 60 psi. NaHCO$_3$(aq) (10 ml) was added, and the mixture was extracted with DCM (2×20 ml). The combined organic extracts were dried (MgSO$_4$) and concentrated in vacuo. The crude product was purified by chromatography (silica, 10-50% EtOAc in DCM) to give the title compound as a yellow solid (15 mg, 5%). $\delta_H$ (DMSO-$d_6$) 10.18 (1H, br s), 7.65-7.46 (10H, m), 6.55 (1H, d, J 9.7 Hz), 6.21 (1H, d, J 9.7 Hz), 3.05 (2H, t, J 5.2 Hz), 2.22 (8H, br s), 0.89 (6H, br s). LCMS (ES$^+$) RT 2.26 minutes, 460 (M+H)$^+$.

EXAMPLE 189

N-[3-(4-Fluoro-3-methylbenzoyl)-6-oxo-7-phenyl-6,7-dihydrothieno[2,3-b]pyridin-2-yl]-1-methylpiperidine-4-carboxamide From Example 149 (500 mg, 0.95 mmol) by the method of Example 59 to give the title compound as a yellow solid (45 mg, 9%). $\delta_H$ (DMSO-$d_6$) 10.78 (1H, s), 7.73-7.60 (5H, m), 7.50 (2H, d, J 6.6 Hz), 7.39 (1H, d, J 9.3 Hz), 7.31 (1H, t, J 9.0 Hz), 6.43 (1H, d, J 9.6 Hz), 2.70 (2H, br d, J 10.7 Hz), 2.29-2.24 (4H, m), 2.13 (3H, s), 1.97-1.78 (2H, m), 1.57-1.42 (4H, m). LCMS (ES$^+$) RT 2.28 minutes, 504.0 (M+H)$^+$.

EXAMPLE 190

2-(Azetidin-3-ylamino)-3-(4-fluoro-3-methylbenzoyl)-7-phenylthieno[2,3-b]pyridin-6(7H)-one From Intermediate 124 (309 mg, 0.58 mmol) by the method of Example 61 to give the title compound as a yellow solid (150 mg, 60%). $\delta_H$ (DMSO-$d_6$) 9.39 (1H, br s), 7.66-7.41 (7H, m), 7.30 (1H, t, J 9.0 Hz), 6.74 (1H, d, J 9.7 Hz), 6.29 (1H, d, J 9.7 Hz), 4.13 (1H, qn, J 6.6 Hz), 3.64 (2H, t, J 7.9 Hz), 3.45 (2H, t, J 7.4 Hz), 2.90 (1H, br s), 2.31 (3H, s). LCMS (ES$^+$) RT 2.229 minutes, 434 (M+H)$^+$.

EXAMPLE 191

3-(4-Fluoro-3-methylbenzoyl)-2-[(1-methylazetidin-3-yl)amino]-7-phenylthieno[2,3-b]pyridin-6(7H)-one From Example 190 (110 mg, 0.254 mmol) by the method of Example 59 to give the title compound as a yellow solid (84 mg, 74%). $\delta_H$ (DMSO-$d_6$) 9.31 (1H, d, J 7.9 Hz), 7.67-7.41 (7H, m), 7.30 (1H, t, J 9.0 Hz), 6.75 (1H, d, J 9.7 Hz), 6.29 (1H, d, J 9.7 Hz), 4.02-3.91 (1H, m), 3.63 (2H, t, J 8.2 Hz), 3.19 (2H, t, J 6.4 Hz), 2.28 (3H, s), 2.27 (3H, s). LCMS (ES$^+$) RT 2.242 minutes, 448 (M+H)$^+$.

EXAMPLE 192

3-(4-Fluoro-3-methylbenzoyl)-7-phenyl-2-(piperidin-4-ylamino)thieno[2,3-b]pyridin-6(7H)-one From Intermediate 125 (1.29 g, 2.3 mmol) by the method of Example 122 to give the title compound as a yellow solid (488 mg, 46%). $\delta_H$ (DMSO-$d_6$) 9.41 (1H, d, J 8.7 Hz), 7.66-7.55 (3H, m), 7.50-7.38 (4H, m), 7.28 (1H, t, J 9.0 Hz), 6.70 (1H, d, J 9.7 Hz), 6.26 (1H, d, J 9.7/Hz), 4.70 (1H, br s), 3.39-3.37 (I, m), 2.97-2.93 (2H, m), 2.64-2.57 (2H, m), 2.30 (3H, s). 1.90-1.87 (2H, m), 1.50-1.39 (2H, m). LCMS (ES$^+$) RT 2.26 minutes, 462 (M+H)$^+$.

EXAMPLE 193

3-(4-Fluoro-3-methylbenzoyl)-2-[(1-methylpiperidin-4-ylamino]-7-phenylthieno[2,3-b]pyridin-6(7H)-one From Example 192 (377 mg, 0.82 mmol) by the method of Example 59 to give the title compound as a yellow solid (200 mg, 51%). $\delta_H$ (DMSO-$d_6$) 9.45 (1H, d, J 8.6 Hz), 7.67-7.58 (3H, m), 7.56-7.46 (3H, m), 7.41-7.38 (1H, m), 7.28 (1H, t, J 9.0 Hz), 6.69 (1H, d, J 9.7 Hz), 6.26 (1H, d, J 9.7 Hz), 3.21-3.13 (1H, m), 2.57-2.49 (2H, m), 2.30 (3H, s), 2.12-2.03 (5H, m), 1.86-1.83 (2H, m), 1.62-1.50 (2H, m). LCMS (ES$^+$) RT 2.26 minutes, 476 (M+H)$^+$.

EXAMPLE 194

3-(4-Fluoro-3-methylbenzoyl)-7-phenyl-2-[(3R)-pyrrolidin-3-ylamino]thieno[2,3-b]pyridin-6(7H)-one From Intermediate 126 (642 mg, 1.17 mmol) by the method of Example 122 to give the title compound as a yellow solid (357 mg, 68%). $\delta_H$ (DMSO-$d_6$) 9.37 (1H, br s), 7.66-7.56 (3H, m), 7.50-7.37 (4H, m), 7.28 (1H, t, J 9.0 Hz), 6.69 (1H, d, J 9.7 Hz), 6.26 (1H, d, J 9.7 Hz), 3.74 (1H, br s), 3.39-3.31 (1H, m), 2.99-2.82 (2H, m), 2.75-2.30 (2H, m), 2.30 (3H, s), 2.09-1.97 (1H, m), 1.64-1.56 (1H, m). LCMS (ES$^+$) RT 2.24 minutes, 448 (M+H)$^+$.

EXAMPLE 195

3-(4-Fluoro-3-methylbenzoyl)-2-{[(3R)-1-methylpyrrolidin-3-yl]amino}-7-phenylthieno[2,3-b]pyridin-6(7H)-one From Example 194 (224 mg, 0.50 mmol) by the method of Example 59 to give the title compound as a yellow solid (140 mg, 61%). $\delta_H$ (DMSO-$d_6$) 9.48 (1H, d, J 8.3 Hz), 7.65-7.57 (3H, m), 7.49-7.47 (3H, m), 7.41-7.38 (1H, m), 7.29 (1H, t, J 9.0 Hz), 6.69 (1H, d, J 9.7 Hz), 6.27 (1H, d J 9.7 Hz), 3.86-3.80 (1H, m), 2.78-2.72 (1H, m), 2.59-2.45 (1H, m), 2.30 (3H, s), 2.28-2.13 (6H, m), 1.68-1.61 (1H, m). LCMS (ES$^+$) RT 2.24 minutes, 462 (M+H)$^+$.

EXAMPLE 196

3-(4-Fluoro-3-methylbenzoyl)-7-phenyl-2-[(3S)-pyrrolidin-3-ylamino]thieno[2,3-b]pyridin-6(7H)-one From Intermediate 127 (1.20 g, 2.19 mmol) by the method of Example 122 to give the title compound as a yellow solid (890 mg, 91%). $\delta_H$ (DMSO-$d_6$) 9.37 (1H, br s), 7.67-7.58 (3H, m), 7.50-7.47 (3H, m), 7.43-7.37 (1H, m), 7.32-7.26 (1H, m), 6.70 (1H, d, J 9.7 Hz), 6.27 (1H, d, J 9.7 Hz), 3.80-3.70 (1H, br m), 3.00-2.82 (2H, m), 2.75-2.64 (2H, m), 2.30 (3H, s), 2.09-1.98 (1H, m), 1.64-1.53 (1H, br m). LCMS (ES$^+$) RT 2.22 minutes, 448 (M+H)$^+$.

EXAMPLE 197

3-(4-Fluoro-3-methylbenzoyl)-2-{[(3S)-1-methylpyrrolidin-3-yl]amino}-7-phenylthieno[2,3-b]pyridin-6(7H)-one From Example 196 (600 mg, 1.34 mmol) by the method of Example 59 to give the title compound as a yellow solid (305 mg, 49%). $\delta_H$ (DMSO-$d_6$) 9.47 (1H, d, J 8.3 Hz), 7.67-7.56 (3H, m), 7.49-7.46 (3H, m), 7.42-7.37 (1H, m), 7.32-7.26 (1H, m), 6.69 (1H, d, J 9.7 Hz), 6.27 (1H, d, J 9.7 Hz), 3.84-3.79 (1H, br m), 2.77-2.72 (1H, m), 2.58 (1H, dd, J 9.7, 2.7 Hz), 2.31-2.16 (9H, m), 1.70-1.60 (1H, br m). LCMS (ES$^+$) RT 2.25 minutes, 462 (M+H)$^+$.

EXAMPLE 198

3-(3-Methylbenzoyl)-7-phenyl-2-(piperidin-4-ylamino)thieno[2,3-b]pyridin-6(7H)-one From Intermediate 128 (1.0 g 1.84 mmol) by the method of Example 122 to give the title compound as a yellow solid (423 mg, 52%). $\delta_H$ (DMSO-$d_6$) 9.56 (1H, d, J 8.6 Hz), 7.66-7.55 (3H, m), 7.49-7.40 (4H, m), 7.33-7.29 (2H, m), 6.58 (1H, d, J 9.7 Hz), 6.22 (1H, d, J 9.7 Hz), 3.32-3.26 (1H, br m), 2.94-2.89 (2H, br m), 2.61-2.56 (2H, br m), 2.38 (3H, s), 1.89-1.86 (2H, br m) 1.48-1.36 (2H, br m). LCMS (ES$^+$) RT 2.22 minutes, 444 (M+H)$^+$.

EXAMPLE 199

3-(3-Methylbenzoyl)-2-[(1-methylpiperidin-4-yl)amino]-7-phenylthieno[2,3-b]pyridin-6(7H)-one From Intermediate 123 (500 mg, 1.18 mmol) and 4-amino-1-methylpiperidine (161 mg, 3.60 mmol) by the method of Example 55 to give the title compound as a yellow solid (345 mg, 64%). $\delta_H$ (DMSO-$d_6$) 9.73 (1H, d, J 8.2 Hz), 7.56-7.48 (3H, m), 7.35-7.25 (6H, m), 6.67 (1H, d, J 9.7 Hz), 6.24 (1H, d, J 9.7 Hz), 3.10-3.05 (1H, br m), 2.66-2.61 (2H, br m), 2.34 (3H, s), 2.21 (3H, s), 2.15-2.10 (2H, br m), 1.97-1.91 (2H, br m), 1.70-1.58 (2H, br m). LCMS (ES$^+$) RT 2.22 minutes, 458 (M+H)$^+$.

EXAMPLE 200

2-(Azetidin-3-ylamino)-3-(3-methylbenzoyl)-7-phenylthieno[2,3-b]pyridin-6(7H)-one From Intermediate 129 (757 mg, 1.5 mmol) by the method of Example 61 to give the title compound as a yellow solid (273 mg, 45%). $\delta_H$ (DMSO-$d_6$) 9.52 (1H, br s), 7.65-7.56 (3H, m), 7.48-7.42 (4H, m), 7.38-7.32 (2H, m), 6.61 (1H, d, J 9.7 Hz), 6.53 (1H, d, J 9.7 Hz), 4.16-4.14 (1H, m), 3.71-3.67 (2H, m), 3.51-3.48 (2H, m), 2.39 (3H, s). LCMS (ES$^+$) RT 2.17 minutes, 416 (M+H)$^+$.

EXAMPLE 201

2-[(1-Methylazetidin-3-ylamino]-3-(3-methylbenzoyl-7-phenylthieno[2,3-b]pyridin-6(7H)-one From Example 200 (125 mg, 0.30 mmol) by the method of Example 59 to give the title compound as a yellow solid (60 mg, 47%). $\delta_H$ (DMSO-$d_6$) 9.53 (1H, d, J 7.6 Hz), 7.71-7.62 (3H, m), 7.54-7.41 (4H, m), 7.39-7.36 (2H, m), 6.67 (1H, d, J 9.7 Hz), 6.29 (1H, d, J 9.7 Hz), 3.94 (1H, dd, J 6.2, 13.3 Hz), 3.56 (2H, dd, J 6.6, 7.8 Hz), 3.04 (2H, dd, J 5.9, 7.7 Hz), 2.44 (3H, s), 2.26 (3H, s). LCMS (ES$^+$) RT 2.17 minutes, 430 (M+H)$^+$.

EXAMPLE 202

3-Benzoyl-7-phenyl-2-[(3R)-piperidin-3-ylamino]thieno[2,3-b]pyridin-6(7H)-one

From Intermediate 130 (892 mg, 1.7 mmol) by the method of Example 122 to give the title compound as a yellow solid (523 mg, 72%). $\delta_H$ (DMSO-$d_6$) 9.77 (1H, d, J 8.7 Hz), 7.65-7.46 (10H, m), 6.52 (1H, d, J 9.7 Hz), 6.20 (1H, d, J 9.7 Hz), 3.28-3.25 (2H, m), 2.86 (1H, dd, J 2.6, 11.7 Hz), 2.67-2.57 (3H, m), 1.79-1.75 (1H, m), 1.60-1.55 (2H, m), 1.40-1.37 (1H, m). LCMS (ES$^+$) RT 2.15 minutes, 430 (M+H)$^+$.

EXAMPLE 203

3-Benzoyl-2-{[(3R)-1-methylpiperidin-3-yl]-amino}-7-phenylthieno[2,3-b]pyridin-6(7H)-one From Example 202 (465 mg, 1.1 mmol) by the method of Example 59 to give the title compound as a yellow solid (120 mg, 25%). $\delta_H$ (DMSO-$d_6$) 9.83 (1H, d, J 8.6 Hz), 7.70-7.52 (10H, m), 6.60 (1H, d, J 9.7 Hz), 6.26 (1H, d, J 9.7 Hz), 3.51-3.44 (1H, m), 2.49-2.39 (3H, m), 2.22-2.15 (4H, m), 1.62-1.53 (4H, m). LCMS (ES$^+$) RT 2.15 minutes, 444 (M+H)$^+$.

EXAMPLE 204

3-Benzoyl-7-phenyl-2-[(3S)-piperidin-3-ylamino]thieno[2,3-b]pyridin-6(7H)-one

From Intermediate 131 (710 mg, 1.3 mmol) by the method of Example 122 to give the title compound as a yellow solid (460 mg, 80%). $\delta_H$ (DMSO-$d_6$) 9.77 (1H, d, J 8.8 Hz), 7.65-7.47 (10H, m), 6.52 (1H, d, J 9.7 Hz), 6.20 (1H, d, J 9.7 Hz), 3.26-3.20 (2H, m), 2.87 (1H, dd, J 2.6, 11.7 Hz), 2.68-2.55 (3H, m), 1.78-1.76 (1H, m), 1.61-1.55 (2H, m), 1.40-1.38 (1H, m). LCMS (ES$^+$) RT 2.15 minutes, 430 (M+H)$^+$.

EXAMPLE 205

3-Benzoyl-2-{[(3S)-1-methylpiperidin-3-yl]amino}-7-phenylthieno[2,3-b]pyridin-6(7H)-one From Example 204 (404 mg, 0.94 mmol) by the method of Example 59 to give the title compound as a yellow solid (60 mg, 14%). $\delta_H$ (DMSO-$d_6$) 9.83 (1H, d, J 8.6 Hz), 7.70-7.52 (10H, m), 6.60 (1H, d, J 9.7 Hz), 6.26 (1H, d, J 9.7 Hz), 3.53-3.44 (1H, m), 2.49-2.38 (3H, m), 2.22-2.15 (4H, m), 1.62-1.53 (4H, m). LCMS (ES$^+$) RT 2.16 minutes, 444 (M+H)$^+$.

EXAMPLE 206

3-Benzoyl-2-[(1-ethylazetidin-3-yl)amino]-7-phenylthieno[2,3-b]pyridin-6(7H)-one From Example 67 and acetaldehyde by the method of Example 168 to give the title compound as a yellow solid. $\delta_H$ (DMSO-$d_6$) 9.49 (1H, d, J 7.6 Hz), 7.67-7.45 (10H, m), 6.59 (1H, d, J 9.7 Hz), 6.23 (1H, d, J 9.7 Hz), 3.95 (1H, m), 3.48 (2H, t, J 6.7 Hz), 2.94 (2H, t, J 6.1 Hz), 2.37 (2H, q, J 7.1 Hz), 0.83 (3H, t, J 7.1 Hz). LCMS (ES$^+$) RT 2.09 minutes, 430 (M+H)$^+$.

EXAMPLE 207

3-Benzoyl-2-[(1-isopropylazetidin-3-yl)amino]-7-phenylthieno[2,3-b]pyridin-6(7H)-one From Example 67 and acetone by the method of Example 168 to give the title compound as a yellow solid. $\delta_H$ (DMSO-$d_6$) 9.46 (1H, d, J 7.6 Hz), 7.67-7.45 (10H, m), 6.58 (1H, d, J 9.7 Hz), 6.23 (1H, d, J 9.7 Hz), 3.85 (1H, m), 3.46 (2H, dd, J 6.6, 7.8 Hz), 2.94 (2H, t, J 6.4 Hz), 2.28 (1H, sept, J 6.1 Hz), 0.81 (6H, d, J 6.1 Hz). LCMS (ES$^+$) RT 2.14 minutes, 444 (M+E)$^+$.

EXAMPLE 208

3-Benzoyl-2-[(1-ethylpiperidin-4-yl)amino]-7-phenylthieno[2,3-b]pyridin-6(7H)-one From Example 175 (190 mg, 0.44 mmol) and acetaldehyde by the method of Example 168. Purification by column chromatography (silica, 0-10% MeOH in DCM) gave the title compound as a yellow solid (100 mg, 50%). $\delta_H$ (DMSO-$d_6$) 9.64 (1H, d, J 8.5 Hz), 7.72-7.51 (10H, m), 6.61 (1H, d, J 9.7 Hz), 6.27 (1H, d J 9.7 Hz), 3.28-3.24 (1H, br m), 2.70-2.65 (2H, br m), 2.38-2.33 (2H, br m), 2.18-2.12 (2H, br m), 1.97-1.92 (2H, br m), 1.66-1.56 (2H, br m), 1.03 (3H, t, J 7.1 Hz). LCMS (ES$^+$) RT 2.18 minutes, 458 (M+H)$^+$.

EXAMPLE 209

3-Benzoyl-2-[(1-isopropylpiperidin-4-yl)amino]-7-phenylthieno[2,3-b]pyridin-6(7H)-one From Example 175 (500 mg, 1.16 mmol) and acetone by the method of Example 168. Purification by column chromatography (silica, 0-5% i-PrOH then 10% MeOH in DCM) gave the title compound as a yellow solid (300 mg, 55%). $\delta_H$ (DMSO-$d_6$) 9.58 (1H, d, J 8.5 Hz), 7.67-7.46 (10H, m), 6.56 (1H, d, J 9.7 Hz), 6.21 (1H, d, J 9.7 Hz), 3.20-3.15 (1H, br m), 2.75-2.65 (3H, br m), 2.30-2.24 (2H, br m), 2.00-1.85 (2H, br m), 1.60-1.45 (2H, br m), 0.94 (6H, d, J 6.5 Hz). LCMS (ES$^+$) RT 2.25 minutes, 472 (M+H)$^+$.

EXAMPLE 210

3-Benzoyl-2-{[(3)-1-isopropylpyrrolidin-3-yl]amino}-7-phenylthieno[2,3-b]pyridin-6(7H)-one From Example 179 (500 mg, 1.20 mmol) and acetone by the method of Example 168. Purification by column chromatography (silica, 0%-15% i-PrOH in DCM) gave the title compound as a yellow solid (330 mg, 60%). $\delta_H$ (DMSO-$d_6$) 9.56 (1H, d, J 8.3 Hz), 7.67-7.46 (10H, m), 6.56 (1H, d, J 9.7 Hz), 6.22 (1H, d, J 9.7 Hz), 3.86-3.80 (1H, m), 2.84-2.77 (1H, m), 2.68-2.58 (2H, m), 2.40-2.15 (3H, m), 1.72-1.60 (1H, br m), 1.05-0.95 (6H, m). LCMS (ES$^+$) RT 2.23 minutes, 458 (M+H)$^+$.

EXAMPLE 211

2-[(trans-4-Aminocyclohexyl)amino]-3-benzoyl-7-phenylthieno[2,3-b]pyridin-6(7H)-one From Intermediate 132 and trifluoroacetic acid by the method of Example 61 to give the title compound as a yellow solid. $\delta_H$ (DMSO-$d_6$) 9.46 (1H, d, J 8.9 Hz), 7.76-7.22 (10H, m), 6.53 (1H, d, J 9.7 Hz), 6.21 (1H, d, J 9.7 Hz), 3.15 (1H, m), 3.01 (1H, m), 2.03-1.90 (4H, m), 1.55-1.32 (4H, m). (NH$_2$ not observed). LCMS (ES$^+$) RT 2.22 minutes, 444 (M+H)$^+$.

EXAMPLE 212

2-[(1-Ethylpiperidin-4-yl)amino]-3-(3-methylbenzoyl)-7-phenylthieno[2,3-b]pyridin-6(7H)-one From Example 198 and acetaldehyde by the method of Example 168 to give the title compound as a yellow solid. $\delta_H$ (DMSO-$d_6$) 9.41 (1H, d, J 6.8 Hz), 7.66-7.30 (9H, m), 6.61 (1H, d, J 9.7 Hz), 6.24 (1H, d, J 9.7 Hz), 3.50-2.50 (7H, m), 2.39 (3H, s), 2.00 (2H, m), 1.72 (2H, m), 1.24 (3H, t, J 7.2 Hz). LCMS (ES$^+$) RT 2.29 minutes, 472 (M+H)$^+$.

EXAMPLE 213

2-[(1-Isopropylpiperidin-4-ylamino]-3-(3-methylbenzoyl)-7-phenylthieno[2,3-b]pyridin-6(7H)-one From Example 198 and acetone by the method of Example 168 to give the title compound as a yellow solid. $\delta_H$ (DMSO-$d_6$) 9.54 (1H, br s), 7.65-7.29 (9H, m), 6.59 (1H, d, J 9.7 Hz), 6.23 (1H, d, J 9.7 Hz), 3.20 (1H, br s), 2.68 (3H, br s), 2.39 (3H, s), 2.33 (2H, m), 1.91 (2H, br s), 1.54 (2H, br s), 0.96 (6H, s). LCMS (ES$^+$) RT 2.33 minutes, 486 (M+H)$^+$.

EXAMPLE 214

3-(3-Methylbenzoyl)-7-phenyl-2-[(3S)-pyrrolidin-3-ylmino]thieno[2,3-b]pyridin-6(7H)-one From Intermediate 133 (1.30 g, 2.45 mmol) by the method of Example 122. Purification by column chromatography (silica, 0-15% MeOH in DCM, then reverse phase silica, 1:1

EtOH:H₂O) gave the title compound as a yellow solid (75 mg, 7%). $\delta_H$ (DMSO-d₆) 9.25 (1H, d, J 8.3 Hz), 8.90-8.70 (1H, br m), 7.67-7.31 (9H, m), 6.62 (1H, d, J 9.7 Hz), 6.25 (1H, d, J 9.7 Hz), 4.10-4.00 (1H, br m), 3.40-3.05 (4H, br m), 2.39 (3H, s), 2.36-2.21 (1H, br m), 1.97-1.85 (1H, br m). LCMS (ES⁺) RT 2.23 minutes, 430 (M+H)⁺.

EXAMPLE 215

3-(3-Methylbenzoyl)-2-{[(3S)-1-methylpyrrolidin-3-yl]amino}-7-phenylthieno[2,3-b]pyridin-6(7H)-one From Example 214 (430 mg, 1.00 mmol) and formaldehyde by the method of Example 59. Purification by column chromatography (silica, 0-20% i-PrOH in DCM) gave the title compound as a yellow solid (262 mg, 59%). $\delta_H$ (DMSO-d₆) 9.57 (1H, d, J 8.3 Hz), 7.65-7.57 (3H, m), 7.50-7.40 (4H, m), 7.32-7.28 (2H, m), 6.58 (1H, d, J 9.7 Hz), 6.22 (1H, d, J 9.7 Hz), 3.87-3.80 (1H, br m), 2.78-2.73 (1H, m), 2.59 (1H, dd, J 9.7, 2.7 Hz), 2.49-2.46 (1H, m), 2.38 (3H, s), 2.27-2.15 (5H, br m), 1.70-1.65 (1H, br m). LCMS (ES⁺) RT 2.24 minutes, 444 (M+H)⁺.

EXAMPLE 216

2-[(1-Ethylazetidin-3-yl)amino]-3-(4-fluoro-3-methylbenzoyl)-7-phenylthieno[2,3-b]pyridin-6(7H)-one From Example 190 (500 mg, 1.13 mmol) and acetaldehyde by the method of Example 168. Purification by column chromatography (silica, 0%-5% i-PrOH, 1% MeOH in DCM) gave the title compound as a yellow solid (256 mg, 48%). $\delta_H$ (CDCl₃) 9.49 (1H, d, J 7.4 Hz), 7.56-7.46 (3H, m), 7.39-7.30 (4H, m), 7.03 (1H, t, J 8.8 Hz), 6.75 (1H, d, J 9.7 Hz), 6.29 (1H, d, J 9.7 Hz), 3.92-3.81 (1H, m), 3.66 (2H, t, J 6.9 Hz), 2.86 (2H, t, J 6.9 Hz), 2.40 (2H, q, J 7.1 Hz), 2.27 (3H, d, J 1.8 Hz), 0.88 (3H, t, J 7.1 Hz). LCMS (ES⁺) RT 2.28 minutes, 462 (M+H)⁺.

EXAMPLE 217

3-(4-Fluoro-3-methylbenzoyl)-2-[(1-isopropylazetidin-3-yl)amino]-7-phenylthieno[2,3-b]pyridin-6 (7H)-one From Example 190 (500 mg, 1.13 mmol) and acetone by the method of Example 168. Purification by column chromatography (silica, 0%-5% i-PrOH, 1% MeOH in DCM) gave the title compound as a yellow solid (300 mg, 55%). $\delta_H$ (CDCl₃) 9.46 (1H, d, Hz), 6.28 (1H, d, J 9.7 Hz), 3.87-3.76 (1H, m), 3.66-3.61 (2H, m), 2.88-2.83 (2H, m), 2.27-2.22 (4H, m), 0.84 (6H, d, J 6.2 Hz). LCMS (ES⁺) RT 2.31 minutes, 476 (M+H)⁺.

EXAMPLE 218

2-[(1-Ethylpiperidin-4-yl)amino]-3-(4-fluoro-3-methylbenzoyl)-7-phenylthieno[2,3-b]pyridin-6(7H)-one From Example 192 (180 mg, 0.39 mmol) and acetaldehyde by the method of Example 168. Purification by column chromatography (silica, 0-10% MeOH in DCM) gave the title compound as a yellow solid (90 mg, 47%). $\delta_H$ MeOD-d₄) 7.58-7.49 (3H, br m), 7.36-7.27 (4H, m), 7.11-7.06 (1H, m), 6.76 (1H, d, J 9.6 Hz), 6.23 (1H, d, J 9.6 Hz), 3.18-3.15 (1H, br m), 2.80-2.70 (2H, br m), 2.35 (2H, q, J 7.2 Hz), 2.24 (3H, s), 2.16-2.09 (2H, br m), 1.96-1.91 (2H, br m), 1.63-1.51 (2H, br m), 0.99 (3H, t, J 7.2 Hz). LCMS (ES⁺) RT 3.45 minutes, 490 (M+H)⁺.

EXAMPLE 219

3-(4-Fluoro-3-methylbenzoyl)-2-[(1-isopropylpiperidin-4-yl)amino]-7-phenylthieno[2,3-b]pyridin-6 (7H)-one From Example 192 (490 mg, 1.06 mmol) and acetone by the method of Example 168. Purification by column chromatography (silica, 0-5% MeOH in DCM) gave the title compound as a yellow solid (200 mg, 37%). $\delta_H$ (DMSO-d₆) 9.45 (1H, d, J 8.6 Hz), 7.67-7.56 (3H, m), 7.50-7.39 (4H, m), 7.28 (1H, t, J 8.6 Hz), 6.70 (1H, d, J 9.7 Hz), 6.27 (1H, d, J 9.7 Hz), 3.18-3.12 (1H, br m), 2.71-2.61 (3H, br m), 2.31 (3H, s), 2.28-2.20 (2H, br m), 1.90-1.85 (2H, br m), 1.55-1.46 (2H, br m), 0.94 (3H, s), 0.92 (3H, s). LCMS (ES⁺) RT 3.40 minutes, 504 (M+H)⁺.

EXAMPLE 220

2-(Azetidin-3-ylamino)-3-benzoyl-7-(cyclopropylmethyl)thieno[2,3-b]pyridin-6(7H)-one From Intermediate 135 (901 mg, 1.88 mmol) and trifluoroacetic acid by the method of Example 61, to give the title compound as a yellow solid (491 mg, 69%). $\delta_H$ (DMSO-d₆) 9.34 (1H, d, J 8.4 Hz), 8.89 (br s, 7.65-7.5 (5H, m), 7.56 (1H, d, J 9.6 Hz), 6.16 (1H, d, J 9.6 Hz), 4.55-4.45 (1H, m), 4.32-4.26 (2H, m), 4.19-4.13 (2H, m), 3.93 (2H, d, J 7.0 Hz), 1.32-1.26 (1H, m), 0.54-0.48 (4H, m). LCMS (ES⁺) RT 2.15 minutes, 380 (M+H)⁺.

EXAMPLE 221

3-Benzoyl-7-(cyclopropylmethyl)-2-[(1-methylazetidin-3-yl)amino]thieno[2,3-b]pyridin 6(7H)-one From Example 220 (200 mg, 0.53 mmol) and formaldehyde by the method of Example 59, to give the title compound as a yellow solid (94 mg, 45%). $\delta_H$ (DMSO-d₆) 9.50 (1H, d, J 7.4 Hz), 7.64-7.56 (5H, m), 6.55 (1H, d, J 9.6 Hz), 6.19 (1H, d, J 9.6 Hz), 4.18-4.09 (1H, m), 3.98 (2H, d, J 7.0 Hz), 3.72 (2H, dd, J 6.6, 7.6 Hz), 3.11 (2H, dd, J 6.1, 7.5 Hz), 2.32 (3H, s), 1.38-1.29 (1H, m), 0.61-0.49 (4H, m). LCMS (ES⁺) RT 2.14 minutes, 394 (M+H)⁺.

EXAMPLE 222

2-(Azetidin-3-ylamino)-7-(cyclopropylmethyl)-3-(4-fluoro-3-methylbenzoyl)thieno[2,3-b]pyridin-6(7H)-one From Intermediate 137 (880 mg, 1.72 mmol) and trifluoroacetic acid by the method of Example 61 to give the title compound as a yellow solid (459 mg, 65%). $\delta_H$ (DMSO-d₆) 9.33 (1H, br s), 7.48 (1H, dd, J 1.6, 7.5 Hz), 7.42-7.37 (1H, m), 7.26 (1H, t, J 9.0 Hz), 6.65 (1H, d, J 9.6 Hz), 6.19 (1H, d, J 9.6 Hz), 4.48-4.27 (1H, m), 3.93 (2H, d, J 7.1 Hz), 3.77 (2H, dd, J 7.2, 8.6 Hz), 3.55 (2H, t, J 6.6), 2.28 (3H, s), 1.33-1.24 (1H, m), 0.56-0.47 (4H, m). LCMS (ES⁺) RT 2.29 minutes, 412 (M+H)⁺.

EXAMPLE 223

7-(Cyclopropylmethyl)-3-(4-fluoro-3-methylbenzoyl)-2-[(1-methylazetidin-3-yl)amino]thieno[2,3-b]pyridin-6(7H)-one From Example 222 (409 mg, 1.0 mmol) and formaldehyde by the method of Example 59 to give the title compound as a yellow solid (170 mg, 40%). $\delta_H$ (DMSO-$d_6$) 9.04 (1H, d, J 7.4 Hz), 7.24 (1H, dd, J 1.5, 7.4 Hz), 7.18-7.13 (1H, m), 7.02 (1H, t, J 9.0 Hz), 6.41 (1H, d, J 9.6 Hz), 5.95 (1H, d, J 9.6 Hz), 3.88-3.77 (1H, m), 3.69 (2H, d, J 7.0 Hz), 3.43 (2H, dd, J 6.5, 7.9 Hz), 2.81 (2H, dd, J 6.1, 7.8 Hz), 2.03 (6H, s), 1.12-0.98 (1H, m), 0.32-0.21 (4H, m). LCMS (ES$^+$) RT 2.28 minutes, 426 (M+H)$^+$.

EXAMPLE 224

3-(3-Methoxybenzoyl)-2-[(1-methylpiperidin-4-yl)amino]-7-phenylthieno[2,3-b]pyridin-6(7H)-one From Intermediate 138 and 4-amino-1-methylpiperidine by the method of Example 55 to give the title compound as a yellow solid. $\delta_H$ (DMSO-$d_6$) 9.62 (1H, d, J 8.6 Hz), 7.66-7.43 (6H, m), 7.14 (1H, dd, J 4.8, 6.6 Hz), 7.06 (2H, m), 6.59 (1H, d, J 9.7 Hz), 6.23 (1H, d, J 9.7 Hz), 3.81 (3H, s), 3.19 (1H, m), 3.51 (2H, m), 2.14 (3H, s), 2.09 (2H, m), 1.86 (2H, m), 1.57 (2H, m). LCMS (ES$^+$) RT 2.21 minutes, 474 (M+H)$^+$.

EXAMPLE 225

3-(3-Chloro-4-fluorobenzoyl)-2-[(1-methylpiperidin-4-yl)amino]-7-phenylthieno[2,3-b]pyridin-6(7H)-one From Intermediate 139 and 4-amino-1-methylpiperidine by the method of Example 55 to give the title compound as a yellow solid. $\delta_H$ (DMSO-$d_6$) 9.46 (1H, d, J 8.7 Hz), 7.77 (1H, d, J 7.4 Hz), 7.67-7.46 (7H, m), 6.75 (1H, d, J 9.7 Hz), 6.28 (1H, d, J 9.7 Hz), 3.19 (1H, m), 2.56 (2H, m), 2.14 (3H, s), 2.10 (2H, m), 1.85 (2H, m), 1.59 (2H, m). LCMS (ES$^+$) RT 2.30 minutes, 496 (M+H)$^+$.

EXAMPLE 226

2-Amino-3-benzoyl-7-(2,6-difluorophenyl)thieno[2,3-b]pyridin-6(7H)-one

From Intermediate 144 (3.55 g, 8.62 mmol) by the method of Example 69 to give the title compound as a yellow solid (2.18 g, 45%). $\delta_H$ (DMSO-$d_6$) 8.32 (2H, br s), 7.81-7.73 (1H, m), 7.62-7.47 (7H, m), 6.63 (1H, d, J 9.8 Hz), 6.25 (1H, d, J 9.8 Hz). LCMS (ES$^+$) RT 3.09 minutes, 383 (M+H)$^+$.

EXAMPLE 227

2-(Azetidin-3-ylamino)-3-benzoyl-7-(2,6-difluorophenyl)thieno[2,3-b]pyridin-6(7H)-one From Intermediate 146 (800 mg, 1.49 mmol) by the method of Example 61 to give the title compound as a yellow solid (420 mg, 65%). $\delta_H$ (DMSO-$d_6$) 9.56 (1H, br s), 7.83-7.73 (1H, m), 7.62-7.47 (8H, m), 6.69 (1H, d, J 9.8 Hz), 6.31 (1H, d, J 9.8 Hz), 4.21-4.16 (1H, m), 3.75-3.65 (2H, m), 3.51-3.46 (2H, m). LCMS (ES$^+$) RT 2.23 minutes, 438 (M+H)$^+$.

EXAMPLE 228

3-Benzoyl-7-(2,6-difluorophenyl)-2-[(1-methylazetidin-3-yl)amino]thieno[2,3-b]pyridin-6(7H)-one From Example 227 (275 mg, 0.63 mmol) and formaldehyde by the method of Example 59 to give the title compound as a yellow solid (90 mg, 32%). $\delta_H$ (DMSO-$d_6$) 9.49 (1H, d, J 7.7 Hz), 7.83-7.73 (1H, m), 7.65-7.47 (7H, m), 6.69 (1H, d, J 9.8 Hz), 6.31 (1H, d, J 9.8 Hz), 4.00-3.89 (1H, m), 3.55 (2H, dd, J 6.6, 8.0 Hz), 3.03 (2H, J 6.6, 7.8 Hz), 2.23 (3H, s). LCMS (ES$^+$) RT 2.26 minutes, 452 (M+H)$^+$.

EXAMPLE 229

2-Amino-7-(2,6-difluorophenyl)-3-(4-fluoro-3-methylbenzoyl)thieno[2,3-b]pyridin-6(7H)-one From Intermediate 148 (4.31 g, 9.71 mmol) by the method of Example 69 to give the title compound as a yellow solid (3.27 g, 82%). $\delta_H$ (DMSO-$d_6$) 8.19 (2H, br s), 7.81-7.71 (1H, m), 7.54-7.40 (4H, m), 7.27 (1H, t, J 9.0 Hz), 6.81 (1H, d, J 9.7 Hz), 6.30 (1H, d, J 9.7 Hz), 2.30 (3H, s). LCMS (ES$^+$) RT 3.37 minutes, 415 (M+H)$^+$.

EXAMPLE 230

N-[7-(2,6-Difluorophenyl)-3-(4-fluoro-3-methylbenzoyl)-6-oxo-6,7-dihydrothieno[2,3-b]pyridin-2-yl]-1-methylpiperidine-4-carboxamide From Example 229 (500 mg, 1.20 mmol) and 1-methylpiperidine 4-carboxylic acid hydrochloride (431 mg, 2.40 mmol) by the method of Intermediate 103 to give the title compound as a yellow solid (250 mg, 39%). $\delta_H$ (DMSO-$d_6$) 10.73 (1H, br s), 7.84-7.72 (2H, m), 7.65-7.48 (4H, m), 7.28 (1H, t, J 9.0 Hz), 6.50 (1H, d, J 9.7 Hz), 2.73 (2H, br d, J 11.3 Hz), 2.29-2.18 (7H, m), 2.08-1.85 (2H, m), 1.58-1.40 (4H, m). LCMS (ES$^+$) RT 2.39 minutes, 540 (M+H)$^+$.

EXAMPLE 231

7-(2,6-Difluorophenyl)-3-(4-fluoro-3-methylbenzoyl)-2-[(1-methylpiperidin-4-yl)amino]thieno[2,3-b]pyridin-6(7H)-one From Intermediate 149 (400 mg, 0.84 mmol) and 4-amino-1-methylpiperidine (115 mg, 1.01 mmol) by the method of Example 55 to give the title compound as an orange solid (120 mg, 28%). $\delta_H$ (DMSO-$d_6$) 9.50 (1H, d, J 8.5 Hz), 7.88-7.78 (1H, m), 7.58-7.46 (4H, m), 7.34 (1H, t, J 9.0 Hz), 6.85 (1H, d, J 9.8 Hz), 6.40 (1H, d, J 9.8 Hz), 3.28-3.25 (1H, m), 2.64-2.59 (2H, m), 2.36 (3H, s), 2.19-2.10 (5H, m), 1.94-1.91 (2H, m), 1.68-1.58 (2H, m). LCMS (ES$^+$) RT 2.37 minutes, 512 (M+H)$^+$.

EXAMPLE 232

2-(Azetidin-3-ylamino)-3-benzoyl-7-(4-methylphenyl)thieno[2,3-b]pyridin-6(7H)-one From Intermediate 151 (557 mg, 1.08 mmol) by the method of Example 61 to give the title compound as a yellow solid (316 mg, 71%). δ$_H$ (DMSO-d$_6$) 9.56 (1H, br s), 7.61-7.53 (5H, m), 7.41 (2H, d, J 8.2 Hz), 7.33 (2H, d, J 8.2 Hz), 6.57 (1H, d, J 9.7 Hz), 6.21 (1H, d, J 9.7 Hz), 4.17-4.13 (1H, m), 3.68-3.63 (2H, m), 3.47-3.42 (2H, m), 2.42 (3H, s). LCMS (ES$^+$) RT 2.21 minutes, 416 (M+H)$^+$.

EXAMPLE 233

3-Benzoyl-2-[(1-methylazetidin-3-yl)amino]-7-(4-methylphenyl)thieno[2,3-b]pyridin-6(7H)-one From Example 232 (244 mg, 0.59 mmol) and formaldehyde by the method of Example 59 to give the title compound as a yellow solid (140 mg, 55%). δ$_H$ (DMSO-d$_6$) 9.50 (1H, d, J 7.7 Hz), 7.64-7.51 (5H, m), 7.41 (2H, d, J 8.1 Hz), 7.32 (2H, dd, J 1.9, 6.5 Hz), 6.57 (1H, d, J 9.7 Hz), 6.21 (1H, d, J 9.7 Hz), 3.95-3.84 (1H, m), 3.51 (2H, dd, J 6.5, 7.9 Hz), 2.98 (2H, dd, J 5.8, 7.9 Hz), 2.42 (3H, s), 2.21 (3H, s). LCMS (ES$^+$) RT 2.23 minutes, 430 (M+H)$^+$.

EXAMPLE 234

2-Amino-3-(4-fluoro-3-methylbenzoyl)-7-(4-methylphenyl)thieno[2,3-b]pyridin-6(7H)-one From Intermediate 156 (4.6 g, 11.0 mmol) by the method of Example 69 to give the title compound as a yellow solid (1.67 g, 39%). δ$_H$ (DMSO-d$_6$) 8.12 (2H, s), 7.50 (1H, d, J 7.4 Hz), 7.42-7.24 (6H, m), 6.68 (1H, d, J 9.6 Hz), 6.20 (1H, d, J 9.6 Hz), 2.41 (3H, s), 2.30 (3H, s). LCMS (ES$^+$) RT 3.31 minutes, 393 (M+H)$^+$.

EXAMPLE 235

2-(Azetidin-3-ylamino)-3-(4-fluoro-3-methylbenzoyl)-7-(4-methylbenzoyl)thieno[2,3-b]pyridin-6(7H)-one From Intermediate 158 (824 mg, 1.51 mmol) by the method of Example 61 to give the title compound as a yellow solid (280 mg, 42%). δ$_H$ (DMSO-d$_6$) 9.39 (1H, br s), 7.51 (1H, d, J 7.5 Hz), 7.41 (3H, d, J 8.2 Hz), 7.34-7.26 (3H, m), 6.72 (1H, d, J 9.7 Hz), 6.26 (1H, d, J 9.7 Hz), 4.15 (1H, t, J 6.5 Hz), 3.69 (2H, t, J 7.7 Hz), 3.48 (2H, t, J 7.7 Hz), 2.42 (3H, s), 2.30 (3H, s). LCMS (ES$^+$) RT 2.28 minutes, 448 (M+H)$^+$.

EXAMPLE 236

3-(4-Fluoro-3-methylbenzoyl)-2-[(1-methylazetidin-3-yl)amino]-7-(4-methylphenyl thieno[2,3-b]pyridin-6(7H)-one From Example 235 (238 mg, 0.53 mmol) and formaldehyde by the method of Example 59 to give the title compound as a yellow solid (150 mg, 61%). δ$_H$ (DMSO-d$_6$) 9.35 (1H, d, J 7.6 Hz), 7.51 (1H, d, J 7.5 Hz), 7.42 (3H, d, J 8.0 Hz), 7.34-7.27 (3H, m), 6.72 (1H, d, J 9.7 Hz) 6.26 (1H, d, J 9.7 Hz), 3.90-3.86 (1H, m, 3.50 (2H, dd, J 6.6, 7.7 Hz), 2.99-2.95 (2H, m), 2.42 (3H, s), 2.31 (3H, s), 2.20 (3H, s). LCMS (ES$^+$) RT 2.30 minutes, 462 (M+H)$^+$.

EXAMPLE 237

2-Amino-3-(4-fluoro-3-methylbenzoyl)-7-(4-fluorophenyl)thieno[2,3-b]pyridin-6(7H)-one From Intermediate 165 (4.2 g, 9.9 mmol) by the method of Example 69 to give the title compound as a yellow solid (3.46 g, 89%). δ$_H$ (DMSO-d$_6$) 8.13 (2H, br s), 7.59-7.38 (6H, m), 7.27 (1H, t, J 9.0 Hz), 6.70 (1H, d, J 9.6 Hz), 6.22 (1H, d, J 9.6 Hz), 2.30 (3H, s). LCMS (ES$^+$) RT 3.22 minutes, 397 (M+H)$^+$.

EXAMPLE 238

2-Amino-3-benzoyl-7-(4-fluorophenyl)thieno[2,3-b]pyridin-6(7H)-one

From Intermediate 163 (2.80 g, 7.1 mmol) by the method of Example 69 to give the title compound as a yellow solid (1.96 g, 76%). δ$_H$ (DMSO-d$_6$) 8.24 (2H, br s), 7.60-7.42 (9H, m), 6.54 (1H, d, J 9.7 Hz), 6.1.7 (1H, d, J 9.7 Hz). LCMS (ES$^+$) RT 3.02 minutes, 365 (M+H)$^+$.

EXAMPLE 239

3-Benzoyl-7-(4-fluorophenyl)-2-[(1-methylpiperidin-4-yl)amino]thieno[2,3-b]pyridin-6(7H)-one From Intermediate 166 (400 mg, 0.93 mmol) and 4-amino-1-methylpiperidine (12 mg, 1.12 mmol) by the method of Example 55 to give the title compound as a pale yellow solid (220 mg, 51%). δ$_H$ (DMSO-d$_6$) 9.57 (1H, br d, J 8.7 Hz), 7.61-7.43 (9H, m), 6.55 (1H, d, J 9.7 Hz), 6.21 (1H, d, J 9.7 Hz), 3.22-3.19 (1H, m), 2.59-2.54 (2H, m), 2.13 (3H, s), 2.10-2.05 (2H, m), 1.90-1.85 (2H, m), 1.63-1.53 (2H, m). LCMS (ES$^+$) RT 2.20 minutes, 462 (M+H)$^+$.

EXAMPLE 240

2-(Azetidin-3-ylamino)-7-(2,6-difluorophenyl)-3-(4-fluoro-3-methylbenzoyl)thieno[2,3-b]pyridin-6(7H)-one From Intermediate 169 (929 mg, 1.63 mmol) by the method of Example 61 to give the title compound as a yellow solid (650 mg, 85%). δ$_H$ (DMSO-d$_6$) 9.25 (1H, br s), 7.82-7.72 (1H, m), 7.55-7.42 (4H, m), 7.29 (1H, t, J 9.0 Hz), 6.85 (1H, d, J 9.8 Hz), 6.36 (1H, d, J 9.8 Hz), 4.18 (1H, t, J 6.8 Hz), 3.72 (2H, t, J 7.4 Hz), 2.53 (2H, t, J 7.0 Hz), 2.31 (3H, d, J 1.5 Hz). LCMS (ES$^+$) RT 2.34 minutes, 470 (M+H)$^+$.

EXAMPLE 241

3-(4-Fluoro-3-methylbenzoyl)-7-(4-fluorophenyl)-2-[(1-methylpiperidin-4-yl)amino]thieno[2,3-b]pyridin-6(7H)-one From Intermediate 167 and 4-amino-1-methylpiperidine (128 mg, 1.12 mmol) by the method of Example 55 to give the title compound as an orange solid (380 mg, 44%). δ$_H$ (DMSO-d$_6$) 9.43 (1H, d, J 8.5 Hz), 7.59-7.54 (1H, m), 7.50-7.34 (5H, m), 7.28 (1H, t, J 9.0 Hz), 6.70 (1H, d, J 9.7 Hz), 6.26 (1H, d, J 9.7 Hz), 3.20-3.13 (1H, m), 2.57-2.51 (2H, m), 2.30 (3H, d, J 1.4 Hz), 2.13 (3H, s), 2.07-2.05 (2H, m), 1.86 (2H, br d, J 9.8 Hz), 1.61-1.52 (2H, m). LCMS (ES$^+$) RT 2.31 minutes, 494 (M+H)$^+$.

Biological Assays

The following assays and animal models can be used to demonstrate the potency and selectivity of the compounds according to the invention. In each assay an $IC_{50}$ value was determined for each test compound and represents the concentration of compound necessary to achieve 50% inhibition.

Preparation of Activated Human p38α for Inhibitor Assays

Purification of Human p38α

Human p38α, incorporating an N-terminal $(His)_6$ tag, was expressed in baculovirus-infected High-Five™ cells (nitrogen) according to the manufacturer's instructions. The cells were harvested 72 h post-infection and lysed in phosphate-buffered saline (PBS) containing 1% (w/v) β-octylglucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after a wash with 15 mM imidazole in PBS) and directly applied to a HiTrap Q™ column (AP Biotech). Bound protein was eluted using a 20 column volume, 0 to 1 M NaCl gradient. Fractions containing (His)6-p38 MAPK were aliquoted and stored at −70° C. prior to their activation.

Preparation of GST-MKK6EE-Containing Lysates

E. coli (BL21 pLysS) expressing the constitutively-activated form of human MKK6 fused with an N-terminal glutathione-S-transferase tag (GST-MKK6EE) were harvested by centrifugation and frozen at −70° C. Cells were lysed by resuspension in ⅒th the culture volume of PBS containing Complete, EDTA-free™ protease inhibitors followed by sonication on ice for 4×15 sec. Cell debris was removed by centrifugation at 35,000×g and the resultant supernatant stored in aliquots at −70° C.

Activation of (His)6-p38 MAPK 0.45 ml of purified (His)6-p38 MAPK was incubated with 50 μl of the GST-MKK6EE-containing lysate for 30 min at 23° C. in the presence of 1 mM β-glycerophosphate, 10 mM $MgCl_2$ and 9 mM ATP. The extent of activation was monitored by mass spectrometric detection of the doubly-phosphorylated form of (His)6-p38 MAPK, which routinely comprised greater than 90% of the final (His)6-p38 MAPK preparation. The activated (His)6-p38 MAPK was then diluted ×10 in PBS and repurified using the method described above. The concentration of purified, activated (His)6-p38 MAPK was measured by UV absorbance at 280 nm using A280, 0.1%=1.2 and the preparation stored in aliquots at −70° C. prior to its use in inhibitor assays.

p38 MAPK Inhibition Assays

Inhibition of Phosphorylation of Biotinylated Myelin Basic Protein (MBP)

The inhibition of p38 MAPK-catalysed phosphorylation of biotinylated MBP is measured using a DELFIA-based format. The assay was performed in a buffer comprising 20 mM CREPES (pH 7.4), 5 mM $MgCl_2$ and 3 mM DTT. For a typical $IC_{50}$ determination, biotinylated MBP (2.5 μM) was incubated at room temperature in a streptavidin-coated microtitre plate together with activated gst-p38 MAPK (10 nM) and ATP (1 μM) in the presence of a range of inhibitor concentrations (final concentration of DMSO is 2 percent). After fifteen minutes the reaction was terminated by the addition of EDTA (75 mM). The microtitre plate was then washed with Tris-buffered saline (TBS), prior to the addition of 100 μl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature. $IC_{50}$ values are determined from the plot of $\log_{10}$[inhibitor concentration] (x-axis) versus percentage inhibition of the fluorescence generated by a control sample in the absence of inhibitor (y-axis).

Purification of Human Peripheral Blood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400×g for 35 min over a Ficoll-paque gradient (Amersham-Pharmacia Biotech, UK). Cells at the interface were removed and washed once followed by a low speed spin (250×g) to remove platelets. Cells were then resuspended in DMEM containing 10% FCS, penicillin 100 units $ml^{-1}$, streptomycin 50 μg $ml^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, pre-warmed to 37° C. and transferred to plates containing PBMC. PBMC and inhibitors were incubated together for 30 min prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 μl. Inhibitor was incubated with whole blood for 30 min prior to the addition of LPS.

LPS Stimulation of PBMC

PBMC were resuspended at a density of $2 \times 10^5$ cells/well in flat-bottomed 96-well tissue culture treated plates. After the addition of inhibitor cells were stimulated with an optimal dose of LPS (E. coli strain B5:055, Sigma, at a final concentration of 1 $\mu gml^{-1}$) and incubated at 37° C. in 5% $CO_2$/95% air for 18 hours. TNF-α levels were measured from cell-free supernatants by sandwich ELISA (BioSource #CHC1751).

LPS Stimulation of Whole Blood

Whole blood was taken by venous puncture using heparinised vacutainers (Becton Dickinson), and 500 μl of blood aliquoted into each well of a 24-well tissue culture treated plate. After the addition of inhibitor cells were stimulated with an optimal dose of LPS (E. coli strain B5:055, Sigma, at a final concentration of 1 $\mu gml^{-1}$) and incubated at 37° C. without $CO_2$ for 18 hours. TNF-α levels were measured from cell-free supernatants by sandwich ELISA (BioSource #CHC1751).

Rat LPS-Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNF-α by commercial ELISA.

Rat CIA

Female Lewis rats (180-200 g) are anaesthetised with Isofluor and immunised i.d. at the base of the tail with 2×100 μl of emulsion containing 4 mg/ml bovine collagen II in 0.01 M acetic acid and Freund's Incomplete Adjuvant at a ratio of 1:1. A polyarthritis develops with onset from about 13 days post-sensitisation. The disease is mainly confined to the ankles and is quantified by plethysmometry. Results are expressed as change in paw volume over time.

CONCLUSION

In the p38 MAPK inhibitor assays described above, the compounds of the Examples have $IC_{50}$ values of around 2 μM and below. The compounds of the invention are clearly potent inhibitors of p38 MAP kinase, especially p38α kinase.

The invention claimed is:
1. A compound of formula (I), or a pharmaceutically acceptable salt thereof:

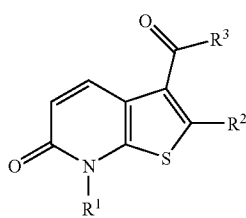

(I)

wherein
R$^1$ represents an optionally substituted ($C_{3-7}$ cycloalkyl) methyl, or aryl group;
R$^2$ represents hydrogen, nitro, cyano, —$CO_2R^a$, —$CONR^bR^c$, —$NR^bR^c$, —$NR^dCOR^a$, —$NR^dCO_2R^a$, —$NR^dCONR^bR^c$, —$NR^dSO_2R^a$ or —$NR^dCONHNHSO_2R^a$;
R$^3$ represents an optionally substituted aryl group;
wherein the optional substituents on R$^1$ and R$^3$ are selected from the group consisting of halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, $C_{1-6}$ alkylamino, di($C_{1-6}$)-alkylamino, aminocarbonyl, and $C_{2-6}$ alkoxycarbony;
R$^a$ represents hydrogens $C_{1-6}$ alkyl optionally substituted by amino, $C_{1-6}$ alkylamino or di($C_{1-6}$)alkylamino; or $C_{3-7}$ heterocycloalkyl optionally substituted by $C_{1-6}$ alkyl;
R$^b$ represents hydrogens $C_{1-6}$ alkyl optionally substituted by hydroxy, amino, $C_{1-6}$ alkylamino, di($C_{1-6}$)alkylamino or $C_{3-7}$ heterocycloalkyl; $C_{2-6}$ alkenyl; $C_{3-7}$ cycloalkyl optionally substituted by amino, $C_{1-6}$ alkylamino or di($C_{1-6}$)alkylamino; or $C_{3-7}$ heterocycloalkyl optionally substituted by $C_{1-6}$ alkyl; and
R$^c$ represents hydrogen or $C_{1-6}$ alkyl; or
R$^b$ and R$^c$, when taken together with the nitrogen atom to which they are attached, represent azetidin-1-yl optionally substituted by hydroxy, amino, $C_{1-6}$ alkylamino or di($C_{1-6}$) alkylamino; pyrrolidin-1-yl optionally substituted by hydroxy, hydroxymethyl, amino, $C_{1-6}$ alkylamino or di($C_{1-6}$)alkylamino; piperidin-1-yl optionally substituted by hydroxy, amino, $C_{1-6}$ alkylamino or di($C_{1-6}$)alkylamino; piperazin-1-yl optionally substituted by $C_{1-6}$ alkyl; or morpholin-4-yl; and
R$^d$ represents hydrogen or $C_{1-6}$ alkyl.

2. A compound as claimed in claim 1 wherein R$^1$ represents cyclopropylmethyl, phenyl, fluorophenyl, chlorophenyl, difluorophenyl, methylphenyl.

3. A compound as claimed in claim 1 wherein R$^3$ represents phenyl, fluorophenyl, difluorophenyl, chlorophenyl, (chloro)(fluoro)phenyl, bromophenyl, cyanophenyl, methylphenyl, (fluoro)(methyl)phenyl, dimethylphenyl, trifluoromethylphenyl, methoxyphenyl, (ethoxy)(methyl)phenyl, difluoromethoxy-phenyl, or trifluoromethoxy-phenyl.

4. A compound as claimed in claim 1 represented by formula (IIA) or a pharmaceutically acceptable salt thereof:

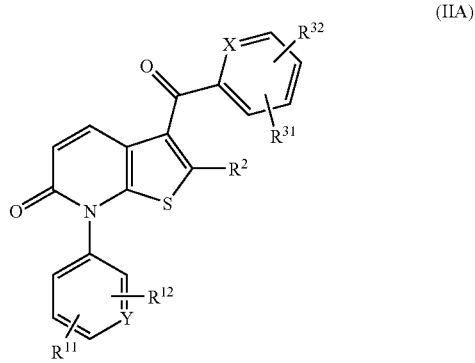

(IIA)

wherein
X represents CH;
Y represents CH; and
R$^{11}$, R$^{12}$, R$^{31}$ and R$^{32}$ each independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylsulphonyl, amino, $C_{1-6}$ alkylamino, di($C_{1-6}$)alkylamino, aminocarbonyl or $C_{2-6}$ alkoxycarbonyl.

5. A compound as claimed in claim 1 wherein R$^2$ represents —$NR^bR^c$.

6. A compound as claimed in claim 1 represented by formula (IIB) or a pharmaceutically acceptable salt thereof:

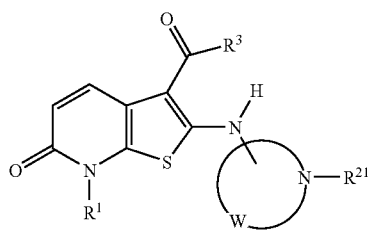

(IIB)

wherein
W represents the residue of an azetidine, pyrrolidine or piperidine ring; and
R$^{21}$ represents hydrogen or $C_{1-6}$ alkyl.

7. A compound as claimed in claim 6 wherein R$^{21}$ represents methyl.

8. A compound as claimed in claim 1 that is:
Ethyl 3-(3-methylbenzoyl)-6-oxo-7-phenyl-6,7-dihydrothieno[2,3-b]pyridine-2-carboxylate;
3-(3-Methylbenzoyl)-6-oxo-7-phenyl-6,7-dihydrothieno[2,3-b]pyridine-2-carboxylic acid;
tert-Butyl[3-(3-methylbenzoyl)-6-oxo-7-phenyl-6,7-dihydrothieno[2,3-b]pyridin-2-yl]carbamate,
2-Amino-3-(3-methylbenzoyl)-7-phenylthieno[2,3-b]pyridin-6(7H)-one;
3-(3-Methylbenzoyl)-6-oxo-7-phenyl-6,7-dihydrothieno[2,3-b]pyridine-2-carbonitrile;
3-(3-Methylbenzoyl)-6-oxo-7-phenyl-6,7-dihydrothieno[2,3-b]pyridine-2-carboxamide;

2-(Azetidin-1-ylcarbonyl)-3-(3-methylbenzoyl)-7-phenylthieno[2,3-b]pyridin-6(7H)-one;
3-(3-Methylbenzoyl)-7-phenyl-2-(piperidin-1-yl)thieno[2,3-b]pyridin-6(7H)-one;
3-(3-Methylbenzoyl)-7-phenylthieno[2,3-b]pyridin-6(7H)-one;
Ethyl 3-benzoyl-6-oxo-7-phenyl-6,7-dihydrothieno[2,3-b]pyridine-2-carboxylate;
3-Benzoyl-6-oxo-7-phenyl-6,7-dihydrothieno[2,3-b]pyridine-2-carboxylic acid;
tert-Butyl(3-benzoyl-6-oxo-7-phenyl-6,7-dihydrothieno[2,3-b]pyridin-2-yl)carbamate;
2-Amino-3-benzoyl-7-phenylthieno[2,3-b]pyridin-6(7H)-one;
N-(3-Benzoyl-6-oxo-7-phenyl-6,7-dihydrothieno[2,3-b]pyridin-2-yl)acetamide;
N-[3-(3-Methylbenzoyl)-6-oxo-7-phenyl-6,7-dihydrothieno[2,3-b]pyridin-2-yl]acetamide;
N-(3-Benzoyl-6-oxo-7-phenyl-6,7-dihydrothieno[2,3-b]pyridin-2-yl)methanesulfonamide;
N-[3-(3-Methylbenzoyl)-6-oxo-7-phenyl-6,7-dihydrothieno[2,3-b]pyridin-2-yl]methanesulfonamide;
2-(Azetidin-1-yl)-3-(3-methylbenzoyl)-7-phenylthieno[2,3-b]pyridin-6(7H)-one;
N-(3-Benzoyl-6-oxo-7-phenyl-6,7-dihydrothieno[2,3-b]pyridin-2-yl)piperidine-4-carboxamide;
N'-(3-Benzoyl-6-oxo-7-phenyl-6,7-dihydrothieno[2,3-b]pyridin-2-yl)-N,N-dimethylurea;
N-(2-Hydroxy-2-methylpropyl)-N'-[3-(3-methylbenzoyl)-6-oxo-7-phenyl-6,7-dihydrothieno[2,3-b]pyridin-2-yl]urea;
4-Methyl-N-[3-(3-methylbenzoyl)-6-oxo-7-phenyl-6,7-dihydrothieno[2,3-b]pyridin-2-yl]piperazine-1-carboxamide;
N-[3-(3-Methylbenzoyl)-6-oxo-7-phenyl-6,7-dihydrothieno[2,3-b]pyridin-2-yl]urea;
N,N-Dimethyl-N'-[3-(3-methylbenzoyl)-6-oxo-7-phenyl-6,7-dihydrothieno[2,3-b]pyridin-2-yl]urea;
N-[3-(3-Methylbenzoyl)-6-oxo-7-phenyl-6,7-dihydrothieno[2,3-b]pyridin-2-yl]azetidine-1-carboxamide;
N-Allyl-N'-[3-(3-methylbenzoyl)-6-oxo-7-phenyl-6,7-dihydrothieno[2,3-b]pyridin-2-yl]urea;
(2R)-2-(Hydroxymethyl)-N-[3-(3-methylbenzoyl)-6-oxo-7-phenyl-6,7-dihydrothieno[2,3-b]pyridin-2-yl]pyrrolidine-1-carboxamide;
N-(1-Ethylpyrrolidin-3-yl)-N'-[3-(3-methylbenzoyl)-6-oxo-7-phenyl-6,7-dihydrothieno[2,3-b]pyridin-2-yl]urea;
N-[3-(3-Methylbenzoyl)-6-oxo-7-phenyl-6,7-dihydrothieno[2,3-b]pyridin-2-yl]-2-(methylsulfonyl)hydrazinecarboxamide;
3-Benzoyl-N-methyl-6-oxo-7-phenyl-6,7-dihydrothieno[2,3-b]pyridine-2-carboxamide;
2-(Azetidin-1-ylcarbonyl)-3-benzoyl-7-phenylthieno[2,3-b]pyridin-6(7H)-one;
3-Benzoyl-N-(1,1-dimethyl-2-hydroxyethyl)-6-oxo-7-phenyl-6,7-dihydrothieno[2,3-b]pyridine-2-carboxamide;
3-Benzoyl-N,N-dimethyl-6-oxo-7-phenyl-6,7-dihydrothieno[2,3-b]pyridine-2-carboxamide;
3-Benzoyl-2-{[(2S)-2-(hydroxymethyl)pyrrolidin-1-yl]carbonyl}-7-phenylthieno[2,3-b]pyridin-6(7H)-one;
3-Benzoyl-2-(morpholin-4-ylcarbonyl)-7-phenylthieno[2,3-b]pyridin-6(7H)-one;
3-Benzoyl-7-phenyl-2-(pyrrolidin-1-ylcarbonyl)thieno[2,3-b]pyridin-6(7H)-one;
3-Benzoyl-6-oxo-7-phenyl-6,7-dihydrothieno[2,3-b]pyridine-2-carbonitrile;
3-Benzoyl-6-oxo-7-phenyl-6,7-dihydrothieno[2,3-b]pyridine-2-carboxamide;
Ethyl 3-benzoyl-7-(cyclopropylmethyl)-6-oxo-6,7-dihydrothieno[2,3-b]pyridine-2-carboxylate;
2-Amino-3-benzoyl-7-(cyclopropylmethyl)thieno[2,3-b]pyridin-6(7H)-one;
3-Benzoyl-7-(2-chlorophenyl)-6-oxo-6,7-dihydrothieno[2,3-b]pyridine-2-carbonitrile;
2-Amino-3-benzoyl-7-(2-chlorophenyl)thieno[2,3-b]pyridin-6(7H)-one;
3-(3-Chlorobenzoyl)-6-oxo-7-phenyl-6,7-dihydrothieno[2,3-b]pyridine-2-carboxamide;
Ethyl 3-(3-chlorobenzoyl)-6-oxo-7-phenyl-6,7-dihydrothieno[2,3-b]pyridine-2-carboxylate;
2-Amino-3-(3-chlorobenzoyl)-7-phenylthieno[2,3-b]pyridin-6(7H)-one;
N-[3-(3-Chlorobenzoyl)-6-oxo-7-phenyl-6,7-dihydrothieno[2,3-b]pyridin-2-yl]acetamide;
3-(2,4-Difluorobenzoyl)-6-oxo-7-phenyl-6,7-dihydrothieno[2,3-b]pyridine-2-carboxamide;
3-(4-Fluoro-3-methylbenzoyl)-6-oxo-7-phenyl-6,7-dihydrothieno[2,3-b]pyridine-2-carboxamide;
Ethyl 3-(4-fluoro-3-methylbenzoyl)-6-oxo-7-phenyl-6,7-dihydrothieno[2,3-b]pyridine-2-carboxylate;
2-Amino-3-(4-fluoro-3-methylbenzoyl)-7-phenylthieno[2,3-b]pyridin-6(7H)-one;
2-Amino-3-(4-ethoxy-3-methylbenzoyl)-7-phenylthieno[2,3-b]pyridin-6(7H)-one;
3-(3-Chloro-4-fluorobenzoyl)-6-oxo-7-phenyl-6,7-dihydrothieno[2,3-b]pyridine-2-carboxamide,
3-Benzoyl-2-(dimethylamino)-7-phenylthieno[2,3-b]pyridin-6(7H)-one;
3-Benzoyl-7-phenylthieno[2,3-b]pyridin-6(7H)-one;
2-Amino-7-phenyl-3-[3-(trifluoromethyl)benzoyl]thieno[2,3-b]pyridin-6(7H)-one;
N-{6-Oxo-7-phenyl-3-[3-(trifluoromethyl)benzoyl]-6,7-dihydrothieno[2,3-b]pyridin-2-yl}acetamide,
N-(3-Benzoyl-6-oxo-7-phenyl-6,7-dihydrothieno[2,3-b]pyridin-2-yl)-1-methylpiperidine-4-carboxamide,
N-(3-Benzoyl-6-oxo-7-phenyl-6,7-dihydrothieno[2,3-b]pyridin-2-yl)-1-ethylpiperidine-4-carboxamide;
N-{6-Oxo-7-phenyl-3-[3-(trifluoromethyl)benzoyl]-6,7-dihydrothieno[2,3-b]pyridin-2-yl}piperidine-4-carboxamide;
N-[3-(3-Chlorobenzoyl)-6-oxo-7-phenyl-6,7-dihydrothieno[2,3-b]pyridin-2-yl]piperidine-4-carboxamide;
3-Benzoyl-2-[(3R)-3-hydroxypyrrolidin-1-yl]-7-phenylthieno[2,3-b]pyridin-6(7H)-one;
3-Benzoyl-7-phenyl-2-{[2-(piperidin-1-yl)ethyl]amino}thieno[2,3-b]pyridin-6(7H)-one;
3-Benzoyl-7-phenyl-2-{[2-(pyrrolidin-1-yl)ethyl]amino}thieno[2,3-b]pyridin-6(7H)-one;
3-Benzoyl-7-phenyl-2-(piperidin-3-ylamino)thieno[2,3-b]pyridin-6(7H)-one;
2-(Azetidin-3-ylamino)-3-benzoyl-7-phenylthieno[2,3-b]pyridin-6(7H)-one;
3-Benzoyl-2-[(1-methylazetidin-3-yl)amino]-7-phenylthieno[2,3-b]pyridin-6(7H)-one;
2-Amino-3-(3-methoxybenzoyl)-7-phenylthieno[2,3-b]pyridin-6(7H)-one;
2-Amino-3-(2-chlorobenzoyl)-7-phenylthieno[2,3-b]pyridin-6(7H)-one,
2-Amino-3-(3-chloro-4-fluorobenzoyl)-7-phenylthieno[2,3-b]pyridin-6(7H)-one;

3-[(2-Amino-6-oxo-7-phenyl-6,7-dihydrothieno[2,3-b]
pyridin-3-yl)carbonyl]benzonitrile;
2-Amino-3-(2-fluorobenzoyl)-7-phenylthieno[2,3-b]pyridin-6(7H)-one,
2-Amino-3-(4-chlorobenzoyl)-7-phenylthieno[2,3-b]pyridin-6(7H)-one;
2-Amino-3-(4-fluorobenzoyl)-7-phenylthieno[2,3-b]pyridin-6(7H)-one,
2-Amino-3-(3-bromobenzoyl)-7-phenylthieno[2,3-b]pyridin-6(7H)-one,
2-Amino-3-(2,4-difluorobenzoyl)-7-phenylthieno[2,3-b]pyridin-6(7H)-one,
2-Amino-7-phenyl-3-[3-(trifluoromethoxy)benzoyl]thieno[2,3-b]pyridin-6(7H)-one,
2-Amino-3-(3,4-dimethylbenzoyl)-7-phenylthieno[2,3-b]pyridin-6(7H)-one;
2-Amino-3-(2-methoxybenzoyl)-7-phenylthieno[2,3-b]pyridin-6(7H)-one;
2-[(2-Amino-6-oxo-7-phenyl-6,7-dihydrothieno[2,3-b]pyridin-3-yl)carbonyl]benzonitrile;
2-Amino-3-Benzoyl-7-(4-methylphenyl)thieno[2,3-b]pyridin-6(7H)-one;
N-[3-Benzoyl-7-(2-chlorophenyl)-6-oxo-6,7-dihydrothieno[2,3-b]pyridin-2-yl]acetamide;
N-[3-(3-Chloro-4-fluorobenzoyl)-6-oxo-7-phenyl-6,7-dihydrothieno[2,3-b]pyridin-2-yl]acetamide;
N-[3-Benzoyl-7-(cyclopropylmethyl)-6-oxo-6,7-dihydrothieno[2,3-b]pyridin-2-yl]acetamide;
N-[3-(2-Fluorobenzoyl)-6-oxo-7-phenyl-6,7-dihydrothieno[2,3-b]pyridin-2-yl]acetamide;
N-[3-(4-Fluoro-3-methylBenzoyl)-6-oxo-7-phenyl-6,7-dihydrothieno[2,3-b]pyridin-2-yl]acetamide;
N-[3-(4-Fluorobenzoyl)-6-oxo-7-phenyl-6,7-dihydrothieno[2,3-b]pyridin-2-yl]acetamide;
N-[3-(3-MethoxyBenzoyl)-6-oxo-7-phenyl-6,7-dihydrothieno[2,3-b]pyridin-2-yl]acetamide;
N-[3-(3-BromoBenzoyl)-6-oxo-7-phenyl-6,7-dihydrothieno[2,3-b]pyridin-2-yl]acetamide;
2-Amino-7-phenyl-3-[4-(trifluoromethyl)benzoyl]thieno[2,3-b]pyridin-6(7H)-one;
4-[(2-Amino-6-oxo-7-phenyl-6,7-dihydrothieno[2,3-b]pyridin-3-yl)carbonyl]benzonitrile;
2-Amino-3-(4-methoxybenzoy1)-7-phenylthieno[2,3-b]pyridin-6(7H)-one;
2-Amino-7-phenyl-3-[4-(trifluoromethoxy)benzoyl]thieno[2,3-b]pyridin-6(7H)-one,
2-Amino-3-(2-methylbenzoyl)-7-phenylthieno[2,3-b]pyridin-6(7H)-one,
2-Amino-3-(4-methylbenzoyl)-7-phenylthieno[2,3-b]pyridin-6(7H)-one:
2-Amino-7-phenyl-3-[2-(trifluoromethyl)benzoyl]thieno[2,3-b]pyridin-6(7H)-one;
2-Amino-3-[3-(difluoromethoxy)benzoyl]-7-phenylthieno[2,3-b]pyridin-6(7H)-one;
2-Amino-3-[4-(difluorometholy)benzoyl]phenylthieno[2,3-b]pyridin-6(7H)-one;
2-Amino-3-[2-(difluoromethoxy)benzoyl]-7-phenylthieno[2,3-b]pyridin-6(7H)-one,
N-{6-Oxo-7-phenyl-3-[3-(trifluoromethoxy)benzoyl]-6,7-dihydrothieno[2,3-b]pyridin-2-yl}acetamide;
N-[3-(3,4-Dimethylbenzoyl)-6-oxo-7-phenyl-6,7-dihydrothieno[2,3-b]pyridin-2-yl]acetamide;
N-[3-(2-Methoxybenzoyl)-6-oxo-7-phenyl-6,7-dihydrothieno[2,3-b]pyridin-2-yl]acetamide;
N-[3-(2-Cyanobenzoyl)-6-oxo-7-phenyl-6,7-dihydrothieno[2,3-b]pyridin-2-yl]acetamide;
N-[3-(2-Chlorobenzoyl)-6-oxo-7-phenyl-6,7-dihydrothieno[2,3-b]pyridin-2-yl]acetamide;
N-[3-(2-Methylbenzoyl)-6-oxo-7-phenyl-6,7-dihydrothieno[2,3-b]pyridin-2-yl]acetamide;
N-[3-(4-Methylbenzoyl)-6-oxo-7-phenyl-6,7-dihydrothieno[2,3-b]pyridin-2-yl]acetamide;
N-(3-Benzoyl-6-oxo-7-phenyl-6,7-dihydrothieno[2,3-b]pyridin-2-yl)-N'- 92-hydroxy-2-hydroxy-1,1-dimethylethyl)urea;
N-(3-Benzol-6-oxo-7-phenyl-6,7-dihydrothieno[2,3-b]pyridin-2-yl)-N-(2-hydroxy-2-methylpropyl)urea;
N-(3-Benzoyl-6-oxo-7-phenyl-6,7-dihydrothieno[2,3-b]pyridin-2-yl)-N'-(2-hydroxy-1,1-dimethylethyl)urea;
N-(3-Benzoyl-6-oxo-7-phenyl-6,7-dihydrothieno[2,3-b]pyridin-2-yl)-4-methylpiperazine-1-carboxamide;
(3R)-N-(3-Benzoyl-6-oxo-7-phenyl-6,7-dihydrothieno[2,3-b]pyridin-2-yl)-3-hydroxypyrrolidine-1-carboxamide;
2-Amino-7-(cyclopropylmethyl)-3-(4-fluoro-3-methylbenzoyl)thieno[2,3-b]pyridin-6(7H)-one;
N-[7-(Cyclopropylmethyl)-3-(4-fluoro-3-methylbenzoyl)-6-oxo-6,7-dihydrothieno[2,3-b]pyridin-2-yl]acetamide,
N-[7-(Cyclopropylmethyl)-3-(4-fluoro-3-methylbenzoyl)-6-oxo-6,7-dihydrothieno[2,3-b]pyridin-2-yl]-N'-(2-hydroxy-2-methylpropyl)urea;
N-[7-(Cyclopropylmethyl)-3-(4-fluoro-3-methylbenzoyl)-6-oxo-6,7-dihydrothieno[2,3-b]pyridin-2-yl]-N'-(2-hydroxy-1,1-dimethylethyl)urea;
7-(2-Chlorophenyl)-3-(4-fluoro-3-methylbenzoyl)-2-nitrothieno[2,3-b]pyridin-6(7H)-one;
2-Amino-7-(2-chlorophenyl)-3-(4-fluoro-3-methylbenzoyl)thieno[2,3-b]pyridin-6(7H)-one;
N-[7-(2-Chlorophenyl)-3-(4-fluoro-3-methylbenzoyl)-6-oxo-6,7-dihydrothieno[2,3-b]pyridin-2-yl]acetamide,
N-[3-Benzoyl-7-(2-chlorophenyl)-6-oxo-6,7-dihydrothieno[2,3-b]pyridin-2-yl]piperidine-4-carboxamide hydrochloride;
N-[3-Benzoyl-7-(2-chlorophenyl)-6-oxo-6,7-dihydrothieno[2,3-b]pyridin-2-yl]-N'-(2-hydroxy-1,1-dimethylethyl)urea;
N-[3-Benzoyl-7-(2-chlorophenyl)-6-oxo-6,7-dihydrothieno[2,3-b]pyridin-2-yl]-N'-(2-hydroxy-2-methylpropyl)urea;
N-[3-(4-Fluoro-3-methylbenzoyl)-6-oxo-7-phenyl-6,7-dihydrothieno[2,3-b]pyridin-2-yl]-N'-(2-hydroxy-2-methylpropyl)urea,
3-Benzoyl-2-nitro-7-phenylthieno[2,3-b]pyridin-6(7H)-one;
2-Amino-7-phenyl-3-[2-(trifluoromethoxy)benzoyl]thieno[2,3-b]pyridin-6(7H)-one;
2-Amino-3-(3-fluorobenzoyl)-7-phenylthieno[2,3-b]pyridin-6(7H)-one;
2-Amino-7-(2-chlorophenyl)-3-(3-methylbenzoyl)thieno[2,3-b]pyridin-6(7H)-one,
2-Amino-3-benzoyl-7-(2-fluorophenyl)thieno[2,3-b]pyridin-6(7H)-one; 2-Amino-3-(4-fluoro-3-methylbenzoyl)-7-(2-fluorophenyl)thieno[2,3-b]pyridin-6(7H)-one;
2-Amino-7-(2-fluorophenyl)-3-(3-methylbenzoyl)thieno[2,3-b]pyridin-6(7H)-one;
N-{3-[(Difluoromethoxy)benzoyl]-6-oxo-7-phenyl-6,7-dihydrothieno[2,3-b]pyridin-2-yl}acetamide;
N-[3-(3-Fluorobenzoyl)-6-oxo-7-phenyl-6,7-dihydrothieno[2,3-b]pyridin-2-yl]acetamide;
N-[7-(2-Chlorophenyl)-3-(3-methylbenzoyl)-6-oxo-6,7-dihydrothieno[2,3-b]pyridin-2-yl]acetamide;

N-[3-Benzoyl-7-(2-fluorophenyl)-6-oxo-6,7-dihydrothieno[2,3-b]pyridin-2-yl]acetamide;
N-[3-(4-Fluoro-3-methylbenzoyl)-7-(2-fluorophenyl)-6-oxo-6,7-dihydrothieno[2,3-b]pyridin-2-yl]acetamide;
N-[7-(2-Fluorophenyl)-3-(3-methylbenzoyl)-6-oxo-6,7-dihydrothieno[2,3-b]pyridin-2-yl]acetamide;
N-1-(3-Benzoyl-6-oxo-7-phenyl-6,7-dihydrothieno[2,3-b]pyridin-2-yl)glycinamide;
N-1-(3-Benzoyl-6-oxo-7-phenyl-6,7-dihydrothieno[2,3-b]pyridin-2-yl)-N-2-methylglycinamide,
N-1-(3-Benzoyl-6-oxo-7-phenyl-6,7-dihydrothieno[2,3-b]pyridin-2-yl)-N-2,N-2-dimethylglycinamide;
N-1-(3-Benzoyl-6-oxo-7-phenyl-6,7-dihydrothieno[2,3-b]pyridin-2-yl)-D-alaninamide hydrochloride;
N-1-(3-Benzoyl-6-oxo-7-phenyl-6,7-dihydrothieno[2,3-b]pyridin-2-yl)-beta-alaninamide hydrochloride;
N-[3-Benzoyl-7-(cyclopropylmethyl)-6-oxo-6,7-dihydrothieno[2,3-b]pyridin-2-yl]piperidine-4-carboxamide hydrochloride,
N-[3-(4-Fluoro-3-methylbenzoyl)-7-(2-fluorophenyl)-6-oxo-6,7-dihydrothieno[2,3-b]pyridin-2-yl]piperidine-4-carboxamide hydrochloride;
N-[3-(4-Fluoro-3-methylbenzoyl)-6-oxo-7-phenyl-6,7-dihydrothieno[2,3-b]pyridin-2-yl]piperidine-4-carboxamide;
N-[3-Benzoyl-7-(2-chlorophenyl)-6-oxo-6,7-dihydrothieno[2,3-b]pyridin-2-yl]-1-methylpiperidine-4-carboxamide;
N-[3-(4-Fluoro-3-methylbenzoyl)-7-(2-fluorophenyl)-6-oxo-6,7-dihydrothieno[2,3-b]pyridin-2-yl]-1-methylpiperidine-4-carboxamide;
N-(3-Benzoyl-6-oxo-7-phenyl-6,7-dihydrothieno[2,3-b]pyridin-2-yl)-D-prolinamide hydrochloride;
N-(3-Benzoyl-6-oxo-7-phenyl-6,7-dihydrothieno[2,3-b]pyridin-2-yl)-L-prolinamide hydrochloride;
N-(3-Benzoyl-6-oxo-7-phenyl-6,7-dihydrothieno[2,3-b]pyridin-2-yl)-1-methyl-L-prolinamide;
N-(3-Benzoyl-6-oxo-7-phenyl-6,7-dihydrothieno[2,3-b]pyridin-2-yl)-1-methyl-D-prolinamide,
N-(3-Benzoyl-6-oxo-7-phenyl-6,7-dihydrothieno[2,3-b]pyridin-2-yl)-N'-(2-hydroxyethyl)urea;
N-(3-Benzoyl-6-oxo-7-phenyl-6,7-dihydrothieno[2,3-b]pyridin-2-yl)-N'-[(3R)-1-methylpyrrolidin-3-yl]urea;
(3R)-N-(3-Benzoyl-6-oxo-7-phenyl-6,7-dihydrothieno[2,3-b]pyridin-2-yl)-3-(dimethylamino)pyrrolidine-1-carboxamide:
(3S)-N-(3-Benzoyl-6-oxo-7-phenyl-6,7-dihydrothieno[2,3-b]pyridin-2-yl)-3-(dimethylamino)pyrrolidine-1-carboxamide;
N-(3-Benzoyl-6-oxo-7-phenyl-6,7-dihydrothieno[2,3-b]pyridin-2-yl)-N'-[(3S)-pyrrolidin-3-yl]urea hydrochloride;
(3R)-3-Amino-N-(3-benzoyl-6-oxo-7-phenyl-6,7-dihydrothieno[2,3-b]pyridin-2-yl)pyrrolidine-1-carboxamide hydrochloride;
(3S)-3-Amino-N-(3-benzoyl-6-oxo-7-phenyl-6,7-dihydrothieno[2,3-b]pyridin-2-yl)pyrrolidine-1-carboxamide hydrochloride;
N-(3-Benzoyl-6-oxo-7-phenyl-6,7-dihydrothieno[2,3-b]pyridin-2-yl)-N'-[(3S)-1-methylpyrrolidin-3-yl]urea;
(3S)-N-(3-Benzoyl-6-oxo-7-phenyl-6,7-dihydrothieno[2,3-b]pyridin-2-yl)-3-(isopropylamino)pyrrolidine-1-carboxamide;
N-[3-(4-Fluoro-3-methylbenzoyl)-6-oxo-7-phenyl-6,7-dihydrothieno[2,3-b]pyridin-2-yl]-N'-(1,1-dimethyl-2-hydroxyethyl)urea;
N-[3-(4-Fluoro-3-methylbenzoyl)-6-oxo-7-phenyl-6,7-dihydrothieno[2,3-b]pyridin-2-yl]-N'-[(3R)-pyrrolidin-3-yl]urea hydrochloride;
N-[3-(4-Fluoro-3-methylbenzoyl)-6-oxo-7-phenyl-6,7-dihydrothieno[2,3-b]pyridin-2-yl]-N'-[(3R)-1-methylpyrrolidin-3-yl]urea;
N-[(3R)-1-Ethylpyrrolidin-3-yl]-N'-[3-(4-fluoro-3-methylbenzoyl)-6-oxo-7-phenyl-6,7-dihydrothieno[2,3-b]pyridin-2-yl]urea;
(3R)-3-(Dimethylamino)-N-[3-(4-fluoro-3-methylbenzoyl)-6-oxo-7-phenyl-6,7-dihydrothieno[2,3-b]pyridin-2-yl]pyrrolidine-1-carboxamide;
(3S)-3-(Dimethylamino)-N-[3-(4-fluoro-3-methylbenzoyl)-6-oxo-7-phenyl-6,7-dihydrothieno[2,3-b]pyridin-2-yl]pyrrolidine-1-carboxamide;
N-[3-(4-Fluoro-3-methylbenzoyl)-6-oxo-7-phenyl-6,7-dihydrothieno[2,3-b]pyridin-2-yl]-4-methylpiperazine-1-carboxamide;
N-[7-(2-Chlorophenyl)-3-(4-fluoro-3-methylbenzoyl)-6-oxo-6,7-dihydrothieno[2,3-b]pyridin-2-yl]-N'-(1,1-dimethyl-2-hydroxyethyl)urea;
N-[3-Benzoyl-7-(cyclopropylmethyl)-6-oxo-6,7-dihydrothieno[2,3-b]pyridin-2-yl]-N'-(1,1-dimethyl-2-hydroxyethyl)urea;
N-[3-Benzoyl-7-(cyclopropylmethyl)-6-oxo-6,7-dihydrothieno[2,3-b]pyridin-2-yl]-N'-(2-hydroxy-2-methylpropyl)urea,
3-Benzoyl-7-phenyl-2-(piperidin-4-ylamino)thieno[2,3-b]pyridin-6(7H)-one,
3-Benzoyl-2-[(1-methylpiperidin-4-yl)amino]-7-phenylthieno[2,3-b]pyridin-6(7H)-one;
3-Benzoyl-7-phenyl-2-[(3R)-pyrrolidin-3-ylamino]thieno[2,3-b]pyridin-6(7H)-one;
3-Benzoyl-2-{[(3R)-1-methylpyrrolidin-3-yl]amino}-7-phenylthieno[2,3-b]pyridin-6(7H)-one hydrochloride;
3-Benzoyl-7-phenyl-2-[(3S)-pyrrolidin-3-ylamino]thieno[2,3-b]pyridin-6(7H)-one;
3-Benzoyl-2-{[(3S)-1-methylpyrrolidin-3-yl]amino}-7-phenylthieno[2,3-b]pyridin-6(7H)-one;
3-Benzoyl-2-[(3S)-3-(dimethylamino)pyrrolidin-1-yl]-7-phenylthieno[2,3-b]pyridin-6(7H)-one;
2-(3-Aminoazetidin-1-yl)-3-benzoyl-7-phenylthieno[2,3-b]pyridin-6(7H)-one,
2-(4-Aminopiperidin-1-yl)-3-benzoyl-7-phenylthieno[2,3-b]pyridin-6(7H)-one;
3-Benzoyl-2-[3-(dimethylamino)azetidin-1-yl]-7-phenylthieno[2,3-b]pyridin-6(7H)-one;
2-[(Azetidin-3-ylmethyl)amino]-3-benzoyl-7-phenylthieno[2,3-b]pyridin-6(7H)-one;
3-Benzoyl-2-{[(1-methylazetidin-3-yl)methyl]amino}-7-phenylthieno[2,3-b]pyridin-6(7H)-one;
3-Benzoyl-2-(morpholin-4-yl)-7-phenylthieno[2,3-b]pyridin-6(7H)-one,
3-Benzoyl-2-{[3-(dimethylamino)-2,2-dimethylpropyl]amino}-7-phenylthieno[2,3-b]pyridin-6(7H)-one;
N-[3-(4-Fluoro-3-methylbenzoyl)-6-oxo-7-phenyl-6,7-dihydrothieno[2,3-b]pyridin-2-yl]-1-methylpiperidine-4-carboxamide,
2-(Azetidin-3-ylamino)-3-(4-fluoro-3-methylbenzoyl)-7-phenylthieno[2,3-b]pyridin-6(7H)-one;
3-(4-Fluoro-3-methylbenzoyl)-2-[(1-methylazetidin-3-yl)amino]-7-phenylthieno[2,3-b]pyridin-6(7H)-one;
3-(4-Fluoro-3-methylbenzoyl)-7-phenyl-2-(piperidin-4-ylamino)thieno[2,3-b]pyridin-6(7H)-one;
3-(4-Fluoro-3-methylbenzoyl)-2-[(1-methylpiperidin-4-yl)amino]-7-phenylthieno[2,3-b]pyridin-6(7H)-one;

3-(4-Fluoro-3-methylbenzoyl)-7-phenyl-2-[(3R)-pyrrolidin-3-ylamino]thieno[2,3-b]pyridin-6(7H)-one;
3-(4-Fluoro-3-methylbenzoyl)-2-{[(3R)-1-methylpyrrolidin-3-yl]amino}-7-phenylthieno[2,3-b]pyridin-6(7H)-one;
3-(4-Fluoro-3-methylbenzoyl)-7-phenyl-2-[(3S)-pyrrolidin-3-ylamino]thieno[2,3-b]pyridin-6(7H)-one;
3-(4-Fluoro-3-methylbenzoyl)-2-{[(3S)-1-methylpyrrolidin-3-yl]amino}-7-phenylthieno[2,3-b]pyridin-6(7H)-one,
3-(3-Methylbenzoyl)-7-phenyl-2-(piperidin-4-ylamino)thieno[2,3-b]pyridin-6(7H)-one,
3-(3-Methylbenzoyl)-2-[(1-methylpiperidin-4-yl)amino]-7-phenylthieno[2,3-b]pyridin-6(7H)-one;
2-(Azetidin-3-ylamino)-3-(3-methylbenzoyl)-7-phenylthieno[2,3-b]pyridin-6(7H)-one;
2-[(1-Methylazetidin-3-yl)amino]-3-(3-methylbenzoyl)-7-phenylthieno[2,3-b]pyridin-6(7H)-one;
3-Benzoyl-7-phenyl-2-[(3R)-piperidin-3-ylamino]thieno[2,3-b]pyridin-6(7H)-one;
3-Benzoyl-2-{[(3R)-1-methylpiperidin-3-yl]amino}-7-phenylthieno[2,3-b]pyridin-6(7H)-one;
3-Benzoyl-7-phenyl-2-[(3S)-piperidin-3-ylamino]thieno[2,3-b]pyridin-6(7H)-one;
3-Benzoyl-2-{[(3S)-1-methylpiperidin-3-yl]amino}-7-phenylthieno[2,3-b]pyridin-6(7H)-one;
3-Benzoyl-2-[(1-ethylazetidin-3-yl)amino]-7-phenylthieno[2,3-b]pyridin-6(7H)-one;
3-Benzoyl-2-[(1-isopriopylazeidin-3-yl)amino]-7-phenylthieno[2,3-b]pyridin-6(7)-one;
3-Benzoyl-2[(1-ethylpiperidin-4-yl)amino]-7-phenylthieno[2,3-b]pyridin-6(7H)-one;
3-Benzoyl-2-[(1-isopropylazetidin-4-yl)amino]-7-phenylthieno[2,3-b]pyridin-6(7H)-one;
3-Benzoyl-2-{[(3S)-1-isopropylpyrrolidin-3-yl)amino]-7-phenylthieno[2,3-b]pyridin-6(7H)-one;
2-[(trans-4-Aminocyclohexyl)amino]-3-benzoyl-7-phenylthieno[2,3-b]pyridin-6(7H)-one;
2-[(1-Ethylpiperidin-4-yl)amino]-3-(3-methylbenzoyl)-7-phenylthieno[2,3-b]pyridin-6(7H)-one;
2-[(1-Isopropylpiperidin-4-yl)amino]-3-(3-methylbenzoyl)-7-phenylthieno[2,3-b]pyridin-6(7H)-one;
3-(3-Methylbenzoyl)-7-phenyl-2-[(3S)-pyrrolidin-3-ylamino]thieno[2,3-b]pyridin-6(7H)-one,
3-(3-Methylbenzoyl)-2-{[(3S)-1-methylpyrrolidin-3-yl]amino}-7-phenylthieno[2,3-b]pyridin-6(7H)-one;
2-[(1-Ethylazetidin-3-yl)amino]-3-(4-fluoro-3-methylbenzoyl)-7-phenylthieno[2,3-b]pyridin-6(7H)-one;
3-(4-Fluoro-3-methylbenzoyl)-2-[(1-isopropylazetidin-3-yl)amino]-7-phenylthieno[2,3-b]pyridin-6(7H)-one;
3-Benzoyl-7-(cyclopropylmethyl)-2-[(1-methylazetidin-3-yl)amino]thieno[2,3-b]pyridin-6(7H)-one,
2-(Azetidin-3-ylamino)-7-(cyclopropylmethyl)-3-(4-fluoro-3-methylbenzoyl)thieno[2,3-b]pyridin-6(7H)-one;
7-(Cyclopropylmethyl)-3-(4-fluoro-3-methylbenzoyl)-2-[(1-methylazetidin-3-yl)amino]thieno[2,3-b]pyridin-6(7H)-one;
3-(3-Methoxybenzoyl)-2-[(1-methylpiperidin-4-yl)amino]-7-phenylthieno[2,3-b]pyridin-6(7H)-one;
3-(3-Chloro-4-fluorobenzoyl)-2-[(1-methylpiperidin-4-yl)amino]-7-phenylthieno[2,3-b]pyridin-6(7H)-one;
2-Amino-3-benzoyl-7-(2,6-difluorophenyl)thieno[2,3-b]pyridin-6(7H)-one;
2-(Azetidin-3-ylamino)-3-benzoyl-7-(2,6-difluorophenyl)thieno[2,3-b]pyridin-6(7H)-one,
3-Benzoyl-7-(2,6-difluorophenyl)-2-[(1-methylazetidin-3-yl)amino]thieno[2,3-b]pyridin-6(7H)-one;
2-Amino-7-(2,6-difluorophenyl)-3-(4-fluoro-3-methylbenzoyl)thieno[2,3-b]pyridin-6(7H)-one;
N-[7-(2,6-Difluorophenyl)-3-(4-fluoro-3-methylbenzoyl)-6-oxo-6,7-dihydrothieno[2,3-b]pyridin-2-yl]-1-methylpiperidine-4-carboxamide;
7-(2,6-Difluorophenyl)-3-(4-fluoro-3-methylbenzoyl)-2-[(1-methylpiperidin-4-yl)amino]thieno[2,3-b]pyridin-6(7H)-one;
2-(Azetidin-3-ylamino)-3-benzoyl-7-(4-methylphenyl)thieno[2,3-b]pyridin-6(7H)-one;
3-Benzoyl-2-[(1-methylazetidin-3-yl)amino]-7-(4-methylphenyl)thieno[2,3-b]pyridin-6(7H)-one;
2-Amino-3-(4-fluoro-3-methylbenzoyl)-7-(4-methylphenyl)thieno[2,3-b]pyridin-6(7H)-one;
2-(Azetidin-3-ylamino)-3-(4-fluoro-3-methylbenzoyl)-7-(4-methylphenyl)thieno[2,3-b]pyridin-6(7H)-one;
3-(4-Fluoro-3-methylbenzoyl)-2-[(1-methylazetidin-3-yl)amino]-7-(4-methylphenyl)thieno[2,3-b]pyridin-6(7H)-one;
2-Amino-3-(4-fluoro-3-methylbenzoyl)-7-(4-fluorophenyl)thieno[2,3-b]pyridin-6(7H)-one;
2-Amino-3-benzoyl-7-(4-fluorophenyl)thieno[2,3-b]pyridin-6(7H)-one;
3-Benzoyl-7-(4-fluorophenyl)-2-[(1-methylpiperidin-4-yl)amino]thieno[2,3-b]pyridin-6(7H)-one,
2-(Azetidin-3-ylamino)-7-(2,6-difluorophenyl)-3-(4-fluoro-3-methylbenzoyl)thieno[2,3-b]pyridin-6(7H)-one; or
3-(4-Fluoro-3-methylbenzoyl)-7-(4-fluorophenyl)-2-[(1-methylpiperidin-4-yl)amino]thieno[2,3-b]pyridin-6(7H)-one.

9. A pharmaceutical composition comprising a compound as claimed in claim 1, or a pharmaceutically acceptable salt thereof, in association with a pharmaceutically acceptable carrier.

* * * * *